(12) United States Patent
Steinitz et al.

(10) Patent No.: US 8,969,524 B2
(45) Date of Patent: Mar. 3, 2015

US008969524B2

(54) FVIII PEPTIDES FOR IMMUNE TOLERANCE INDUCTION AND IMMUNODIAGNOSTICS

(75) Inventors: Katharina Nora Steinitz, Siegenfeld (AT); Paula Maria Wilhelmina van Helden, DV Den Bosch (NL); Birgit Maria Reipert, Deutsch-Wagram (AT); Hans-Peter Schwarz, Vienna (AT); Hartmut Ehrlich, Vienna (AT)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 326 days.

(21) Appl. No.: 13/283,452

(22) Filed: Oct. 27, 2011

(65) Prior Publication Data

US 2012/0135019 A1    May 31, 2012

Related U.S. Application Data

(60) Provisional application No. 61/407,402, filed on Oct. 27, 2010, provisional application No. 61/467,894, filed on Mar. 25, 2011, provisional application No. 61/502,476, filed on Jun. 29, 2011.

(51) Int. Cl.
*A61K 38/37* (2006.01)
*C07K 14/745* (2006.01)
*G01N 33/50* (2006.01)

(52) U.S. Cl.
CPC .............. *A61K 38/37* (2013.01); *G01N 33/505* (2013.01)
USPC ........... 530/383; 530/300; 530/324; 530/325; 530/338; 435/69.6; 424/185.1

(58) Field of Classification Search
None
See application file for complete search history.

(56) References Cited

U.S. PATENT DOCUMENTS

2005/0256304 A1*  11/2005  Jones et al. .................. 530/383
2010/0168018 A1    7/2010  Pikal et al.

FOREIGN PATENT DOCUMENTS

| WO | WO 03/087161 A1 | 10/2003 |
| WO | WO 2009/071666 A1 | 6/2009 |
| WO | WO 2009071886 A1 * | 6/2009 |
| WO | WO 2009/095646 A2 | 8/2009 |

OTHER PUBLICATIONS

Heinz et al., "Factor VIII-eGFP fusion proteins with preserved functional activity for the analysis of the early secretory pathway of factor VIII", Thromb Haemost, 2009, pp. 925-935.*
Toole et al., "A large region (≈95 kDa) of human factor VIII is dispensable for in vitro procoagulant activity", PNAS, 1986, pp. 5939-5942.*
Moreira, "Coagulation factor VIIIc [Ateles Belzebuth chamek]; GenBank Accession No. AAD16965.1"; Direct Submission; Nov. 16, 1998; Genetics Section, Instituto Nacional de Cancer, Brazil, p. 1; obtained from www.ncbi.nlm.nih.gov/protein/AAD16965.1 on Apr. 7, 2014.*
Ay, B. et al., "Sorting and Pooling Strategy: A Novel Tool to Map a Virus Proteome for CD8 T-Cell Epitopes," *Peptide Science*, 2007, vol. 88, No. 1, pp. 64-75.
Hay, C.R.M. et al., "HLA Class II Profile: A Weak Determinant of Factor VIII Inhibitor Development in Severe Haemophilia A," *Thrombosis and Haemostasis*, 1997, vol. 77, No, 2, pp. 234-237.
International Search Report mailed on Mar. 9, 2012, for International Patent Application No. PCT/US2011/058165 filed Oct. 27, 2011, 3 pages.
Jones, E.Y. et al., "MHC class II proteins and disease: a structural perspective," *Immunology*, Apr. 2006, vol. 6, pp. 271-282.
Oldenburg, J. et al., "HLA Genotype of Patients with Severe Haemophilia A due to Intron 22 Inversion with and without Inhibitors of Factor VIII," *Thrombosis and Haemostasis*, 1997, vol. 77, No, 2, pp. 238-242.
Pavlova, A. et al., "Impact of polymorphisms of the major histocompatibility complex class II, interleukin-10, tumor necrosis factor-α and cytotoxic T-lymphocyte antigen-4 genes on inhibitor development in severe hemophilia A," *Journal of Thrombosis and Haemostasis*, 2009, vol. 7, pp. 2006-2015.
Reipert, B.M. et al., "Opportunities and limitations of mouse models humanized for HLA class II antigens," *Journal of Thrombosis and Haemostasis*, 2009, vol. 7 (Suppl. 1), pp. 92-97.

* cited by examiner

*Primary Examiner* — Karlheinz R Skowronek
*Assistant Examiner* — Lianko Garyu
(74) *Attorney, Agent, or Firm* — Morgan, Lewis & Bockius LLP

(57) ABSTRACT

The present invention is related to peptides that can be used to reduce the immune response against FVIII or to induce tolerance to human FVIII in patients with, e.g., hemophilia A. Furthermore, the peptides can be used for immunodiagnostic purposes to detect FVIII-specific CD4+ T cells to monitor patients with hemophilia A during replacement therapy and during immune tolerance induction therapy.

20 Claims, No Drawings

FVIII PEPTIDES FOR IMMUNE TOLERANCE INDUCTION AND IMMUNODIAGNOSTICS

CROSS-REFERENCES TO RELATED APPLICATIONS

The present application claims priority to U.S. Provisional Patent Application Ser. No. 61/407,402, filed on Oct. 27, 2010, U.S. Provisional Patent Application Ser. No. 61/467,894, filed on Mar. 25, 2011, and U.S. Provisional Patent Application Ser. No. 61/502,476, filed on Jun. 29, 2011, the disclosures of which are hereby incorporated by reference in their entireties for all purposes.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Factor VIII (FVIII) is a protein found in blood plasma that acts as a cofactor in the cascade of reactions leading to blood coagulation. Hemophilia A is caused by a reduction or deficiency of functional FVIII protein and is one of the most common bleeding disorders that affects about 1 in 5000-10000 men. Clinical symptoms in hemophilia are frequent muscle and joint bleeds, and trauma can even lead to life threatening situations. Currently, effective treatments for hemophilia include replacing the missing FVIII protein using intravenous application of recombinant or plasma derived FVIII products. Such preparations are generally administered either in response to a bleeding episode (on-demand therapy) or at frequent, regular intervals to prevent uncontrolled bleeding (prophylaxis). Unfortunately, the appearance of neutralizing anti-FVIII antibodies (FVIII inhibitors) is a major complication during replacement therapy with FVIII products. Approximately 25% of the patients receiving treatment develop this immunity to FVIII protein, thus making further control of bleeding very difficult.

The cause for this immune response to FVIII protein has not been fully elucidated, but the specifics of a patient's immune system can affect their response to therapy. Normally, the immune system develops a tolerance to certain antigens, e.g., "self" antigens. This feature is important because, otherwise, if a self antigen is recognized as a foreign antigen, autoimmune disease results. Hemophilia A patients, in particular, have a genetic defect in their FVIII gene, which causes the immune system to not recognize the administered FVIII protein as a "self" antigen. Thus, when FVIII protein is administered during coagulation factor replacement therapy, the patient's immune system recognizes the FVIII protein as a foreign antigen or an altered self protein and develops anti-FVIII antibodies accordingly.

The FVIII inhibitors, i.e., anti-FVIII antibodies are produced by plasma cells derived from FVIII specific B cells. B cells need the help of activated CD4+ T-cells to proliferate and differentiate into anti-FVIII antibody producing plasma cells. For example, FVIII protein is recognized by B and T lymphocytes in different ways. The induction of anti-FVIII antibodies is T helper cell dependent. B cells recognize whole protein epitopes via their specific B cell receptor. T-cells on the other hand, recognize proteins in the form of processed peptides complexed with an MHC class II molecule presented on the surface of an antigen presenting cell. Each CD4+ T-cell clone recognizes only one specific peptide-MHC complex. For presenting the peptides to the T-cells, MHC class II molecules have an open binding groove that allows peptides of various lengths to fit in and be presented on the surface of a cell. Moreover, the MHC class II protein contains four binding pockets that differ for the various haplotypes (Jones et al., *Nature Rev. Immunol.* 6:271-282 (2006)). Only specific amino acids fit into these binding pockets, and the minimal size of binding peptides is nine amino acids. Notably, different MHC class II haplotypes can present different peptides. Thus, it is likely that a patient's MHC class II haplotype influences the risk of developing anti-FVIII antibodies. Indeed, several studies have shown that there is a correlation of the human MHC class II haplotype HLA-DRB1*1501 with an increased risk for anti-FVIII antibody development (Pavlova et al., *J. Thromb. Haemost.* 7:2006-2015 (2009); Oldenburg et al., *Thromb. Haemost.* 77:238-242 (1997); Hay et al., *Thromb. Haemost.* 77:234-237 (1997)).

Certain approaches have been explored to address the challenges associated with treating hemophilia by administration of FVIII protein. For example, WO 03/087161 discloses modified FVIII proteins, in which the immune characteristics of the FVIII protein are modified by reducing or removing the number of potential T-cell epitopes present on the protein. A number of regions that include T-cell epitopes along the FVIII protein were identified, including, e.g., $FVIII^{2030-2044}$. According to the disclosure, removal of such regions could be used to provide functional FVIII protein that did not induce production of anti-FVIII antibodies. WO 09/071,886 also discloses specific regions of FVIII protein that were predicted to give rise to HLA-DR2 binding peptides that are involved in a patient's immune response, such as, e.g., $FVIII^{475-495}$ $FVIII^{542-562}$, $FVIII^{1785-1805}$, and $FVIII^{2158-2178}$. The peptides were identified for possible use in inducing immune tolerance in a patient.

While there have been advances in identifying regions of FVIII protein involved in the immune response, there is still a need to identify other regions of FVIII protein that can be used for developing other therapeutic peptides and methodologies that can, for example, be used to treat patients having hemophilia A.

BRIEF SUMMARY OF THE INVENTION

The present invention is based on the identification of regions of FVIII protein related to the immune response against FVIII molecules. More specifically, a FVIII peptide including the region of FVIII protein can be used to induce tolerance to human FVIII in patients with, e.g., hemophilia A. Furthermore, the FVIII peptides can be used for immunodiagnostic purposes to monitor patients with hemophilia A during replacement therapy and during immune tolerance induction therapy.

In one aspect, the present invention provides a method of inducing an immune tolerance to FVIII in a subject in need thereof, the method comprising a step of: administering to the subject a therapeutically effective amount of a peptide having an amino acid sequence consisting of: $(R^1)_x$—P—$(R^2)_y$, wherein: P is an amino acid sequence having at least 85% identity to at least nine consecutive amino acids of a sequence selected from SEQ ID NOS:10, 68, 344, and 740; $R^1$ is an amino acid sequence consisting of from 1 to 80 amino acids;

$R^2$ is an amino acid sequence consisting of from 1 to 80 amino acids; and each of x and y are independently zero or one.

In one embodiment of the methods provided above, P is an amino acid sequence having at least 90% identity to a sequence of at least nine consecutive amino acids of SEQ ID NO:10.

In one embodiment of the methods provided above, P is an amino acid sequence identical to a sequence of at least nine consecutive amino acids of SEQ ID NO:10.

In one embodiment of the methods provided above, P is an amino acid sequence having at least 90% identity to a sequence of at least nine consecutive amino acids of SEQ ID NO:68.

In one embodiment of the methods provided above, P is an amino acid sequence having at least 95% identity to a sequence of at least nine consecutive amino acids of SEQ ID NO:68.

In one embodiment of the methods provided above, P is an amino acid sequence identical to a sequence of at least nine consecutive amino acids of SEQ ID NO:68.

In one embodiment of the methods provided above, P is an amino acid sequence having at least 85% identity to a sequence of at least nine consecutive amino acids of SEQ ID NO:344.

In one embodiment of the methods provided above, P is an amino acid sequence having at least 90% identity to a sequence of at least nine consecutive amino acids of SEQ ID NO:344.

In one embodiment of the methods provided above, P is an amino acid sequence having at least 95% identity to a sequence of at least nine consecutive amino acids of SEQ ID NO:344.

In one embodiment of the methods provided above, P is an amino acid sequence identical to a sequence of at least nine consecutive amino acids of SEQ ID NO:344.

In one embodiment of the methods provided above, P is an amino acid sequence having at least 85% identity to a sequence of at least nine consecutive amino acids of SEQ ID NO:740.

In one embodiment of the methods provided above, P is an amino acid sequence having at least 90% identity to a sequence of at least nine consecutive amino acids of SEQ ID NO:740.

In one embodiment of the methods provided above, P is an amino acid sequence having at least 95% identity to a sequence of at least nine consecutive amino acids of SEQ ID NO:740.

In one embodiment of the methods provided above, P is an amino acid sequence identical to a sequence of at least nine consecutive amino acids of SEQ ID NO:740.

In one embodiment of the methods provided above, x and y are both zero.

In one embodiment of the methods provided above, x is one and y is zero.

In one embodiment of the methods provided above, x is zero and y is one.

In one embodiment of the methods provided above, x and y are both zero.

In one embodiment of the methods provided above, the peptide consists of from 9 to 100 amino acids.

In one embodiment of the methods provided above, the peptide consists of from 9 to 50 amino acids.

In one embodiment of the methods provided above, the peptide consists of from 9 to 25 amino acids.

In one embodiment of the methods provided above, administration of the pharmaceutical composition prevents development of anti-FVIII antibodies in the subject.

In one embodiment of the methods provided above, administration of the pharmaceutical composition reduces an amount anti-FVIII antibodies present in the subject.

In one aspect, the present invention provides a peptide consisting of the amino acid sequence: $(R^1)_x$—P—$(R^2)_y$, wherein: P is an amino acid sequence having at least 85% identity to a sequence of at least nine consecutive amino acids of a sequence selected from SEQ ID NOS:10, 68, 159, 250, 344, 477, 568, 659, and 740; $R^1$ is an amino acid sequence consisting of from 1 to 80 amino acids; $R^2$ is an amino acid sequence consisting of from 1 to 80 amino acids; and each of x and y are independently zero or one.

In one embodiment of the peptides provided above, P is an amino acid sequence having at least 90% identity to a sequence of at least nine consecutive amino acids of SEQ ID NO:10.

In one embodiment of the peptides provided above, P is an amino acid sequence identical to a sequence of at least nine consecutive amino acids of SEQ ID NO:10.

In one embodiment of the peptides provided above, P is an amino acid sequence having at least 90% identity to a sequence of at least nine consecutive amino acids of SEQ ID NO:68.

In one embodiment of the peptides provided above, P is an amino acid sequence having at least 95% identity to a sequence of at least nine consecutive amino acids of SEQ ID NO:68.

In one embodiment of the peptides provided above, P is an amino acid sequence identical to a sequence of at least nine consecutive amino acids of SEQ ID NO:68.

In one embodiment of the peptides provided above, P is an amino acid sequence having at least 85% identity to a sequence of at least nine consecutive amino acids of SEQ ID NO:344.

In one embodiment of the peptides provided above, P is an amino acid sequence having at least 90% identity to a sequence of at least nine consecutive amino acids of SEQ ID NO:344.

In one embodiment of the peptides provided above, P is an amino acid sequence having at least 95% identity to a sequence of at least nine consecutive amino acids of SEQ ID NO:344.

In one embodiment of the peptides provided above, P is an amino acid sequence identical to a sequence of at least nine consecutive amino acids of SEQ ID NO:344.

In one embodiment of the peptides provided above, P is an amino acid sequence having at least 85% identity to a sequence of at least nine consecutive amino acids of SEQ ID NO:740.

In one embodiment of the peptides provided above, P is an amino acid sequence having at least 90% identity to a sequence of at least nine consecutive amino acids of SEQ ID NO:740.

In one embodiment of the peptides provided above, P is an amino acid sequence having at least 95% identity to a sequence of at least nine consecutive amino acids of SEQ ID NO:740.

In one embodiment of the peptides provided above, P is an amino acid sequence identical to a sequence of at least nine consecutive amino acids of SEQ ID NO:740.

In one embodiment of the peptides provided above, x and y are both zero.

In one embodiment of the peptides provided above, x is one and y is zero.

In one embodiment of the peptides provided above, x is zero and y is one.

In one embodiment of the peptides provided above, x and y are both zero.

In one embodiment of the peptides provided above, the peptide consists of from 9 to 100 amino acids.

In one embodiment of the peptides provided above, the peptide consists of from 9 to 50 amino acids.

In one embodiment of the peptides provided above, the peptide consists of from 9 to 25 amino acids.

In one aspect, the present invention provides a composition comprising a peptide as described herein.

In one embodiment of the compositions provided above, the composition is formulated for pharmaceutical administration.

In one embodiment of the compositions provided above, the composition further comprises a second polypeptide, the second polypeptide consisting of the amino acid sequence: $(R^1)_x$—P—$(R^2)_y$, wherein: P is an amino acid sequence having at least 85% identity to a sequence of at least nine consecutive amino acids of a sequence selected from SEQ ID NOS:10, 68, 159, 250, 477, 568, 659, and 740; $R^1$ is an amino acid sequence consisting of from 1 to 80 amino acids; $R^2$ is an amino acid sequence consisting of from 1 to 80 amino acids; and each of x and y are independently zero or one.

In one aspect, the present invention provides a method of making a FVIII peptide, the method comprising the steps of: a) providing a culture of cells comprising a polynucleotide that encodes a FVIII peptide according to any one of claims 24 to 41; and b) expressing the peptide in the culture of cells.

In one aspect, the present invention provides a method of identifying a FVIII peptide-specific T cell, the method comprising: a) combining a plurality of CD4+ T cells with a peptide complexed with a MHC class II multimer, wherein the peptide is a FVIII peptide according to any one of claims 24 to 41; and b) identifying at least one of the members of the plurality of CD4+ T cells that is specific for the peptide complexed with the MHC class II multimer.

In one embodiment of the methods provided above, the MHC class II multimer is a MHC class II tetramer.

In one embodiment of the methods provided above, the peptide or MHC class II multimer further comprises a detectable moiety.

In one embodiment of the methods provided above, the method further comprises isolating at least one CD4+ T cell that is specific for the peptide.

In one embodiment of the methods provided above, the CD4+ T cell is isolated using flow cytometry.

In one aspect, the present invention provides a fusion protein comprising a FVIII peptide as provided herein and a second peptide.

In one embodiment of the methods provided above, the second peptide is a reporter peptide.

In one embodiment of the methods provided above, the fusion protein is encoded by a nucleic acid.

In one embodiment of the methods provided above, the FVIII peptide is chemically linked to the second peptide.

In one aspect, the FVIII peptides provided herein are used to induce immune tolerance towards human FVIII for the prevention of FVIII inhibitor development.

In one aspect, the FVIII peptides provided herein are used to induce tolerance towards human FVIII for the treatment of patients with established FVIII inhibitors.

In one aspect, the FVIII peptides provided herein are used to generate reagents suitable for direct staining of FVIII specific T cells (e.g., MHC class II multimers or MHC class II tetramers) in immune monitoring of patients during replacement therapy or during immune tolerance induction therapy.

In one aspect, the FVIII peptides provided herein are used to identify antigen specific T cells. In one embodiment, these reagents can be used to track FVIII specific T cells in in vitro and in ex vivo settings. In another embodiment, these reagents can be used to isolate and further characterize FVIII specific T cells. In one embodiment, fluorescent activated cell sorting (FACS) or single cell PCR can be used for these purposes.

In one aspect, the FVIII peptides provided herein are used for immune monitoring of FVIII specific T cells during immune tolerance induction therapy.

In one aspect, the FVIII peptides provided herein are used for immune monitoring of FVIII specific T cells during FVIII treatment.

In one aspect, the FVIII peptides provided herein are used for immunodiagnostics of FVIII specific T cells during clinical development of new immune modulators for the prevention of FVIII inhibitors.

BRIEF DESCRIPTION OF THE DRAWINGS

Not applicable.

DETAILED DESCRIPTION OF THE INVENTION

I. Introduction

The present invention is related to Factor VIII (FVIII) peptides that can be used to induce tolerance to FVIII protein in, for example, patients with hemophilia A. Furthermore, the peptides can be used for immunodiagnostic purposes to monitor FVIII-specific T cells in patients with hemophilia A during replacement therapy and during immune tolerance induction therapy.

The present invention is based in-part on the discovery that several regions of FVIII, specifically $FVIII^{102-122}$, $FVIII^{246-266}$, and $FVIII^{1401-1424}$, are involved in the immune response mounted against FVIII protein during Factor VIII replacement therapy or connected with acquired hemophilia. The amino acid sequences of the regions identified are TVVITLKNMASHPVSLHAVGV (SEQ ID NO:740), AWPKMHTVNGYVNRSLPGLIG (SEQ ID NO:68), and QANRSPLPIAKVSSFPSIRPIYLT (SEQ ID NO:344), respectively. It is believed that the present invention provides for the first time identification of these FVIII protein regions and their relationship to the immune response to FVIII protein.

Peptides of the present invention include peptides having at least a portion of the regions $FVIII^{102-122}$, $FVIII^{246-266}$, and $FVIII^{1401-1424}$ that complexes with a MHC class II molecule to produce a T cell epitope capable of being recognized by T cells involved in a patient's immune response. In some embodiments, the peptides include at least nine contiguous amino acids that correspond to nine contiguous amino acids in $FVIII^{102-122}$, $FVIII^{246-266}$, or $FVIII^{1401-1424}$. As described further below, the peptides provided herein also include peptides longer than nine amino acids in length as well as variants of the $FVIII^{102-122}$, $FVIII^{246-266}$, and $FVIII^{1401-1424}$ sequences. Such an identification of the peptides of the present invention can have implications in improving and advancing therapeutic strategies designed to treat diseases related to blood coagulation, such as hemophilia A.

II. Definitions

The term "Factor VIII protein" or "FVIII protein" refers to any FVIII molecule which has at least a portion of the B domain intact, and which exhibits biological activity that is associated with native human FVIII protein. The FVIII molecule can be full-length FVIII. The FVIII molecule may also be a conservatively modified variant of native FVIII. The FVIII protein can be derived from human plasma or be produced by recombinant engineering techniques. Additional characterization of FVIII protein can be, e.g., found at paragraphs [0042]-[0055] in US 2010/0168018, which is incorporated by reference herein.

The term "Factor VIII peptide" or "FVIII peptide" refers to the peptides described herein that include an amino acid sequence corresponding to a region of FVIII protein discovered to be important in an immune response against FVIII. A FVIII peptide includes at least nine amino acids that complex with a MHC class II protein for presentation to T cells involved in the immune response. Additional amino acids can be present on either end of the at least nine amino acid core of the peptide. In some embodiments, a FVIII peptide can include a sequence identical to the particular region of native human FVIII protein. In other embodiments, a FVIII peptide can be a conservatively modified variant of a region of FVIII protein. As described further herein, a FVIII peptide can be characterized by a certain percent identity, e.g., 85% identical, relative to the sequence of a region of native human FVIII protein.

The term "amino acid" refers to naturally occurring and non-natural amino acids, including amino acid analogs and amino acid mimetics that function in a manner similar to the naturally occurring amino acids. Naturally occurring amino acids include those encoded by the genetic code, as well as those amino acids that are later modified, e.g., hydroxyproline, y-carboxyglutamate, and O-phosphoserine. Naturally occurring amino acids can include, e.g., D- and L-amino acids. The amino acids used herein can also include non-natural amino acids. Amino acid analogs refer to compounds that have the same basic chemical structure as a naturally occurring amino acid, i.e., any carbon that is bound to a hydrogen, a carboxyl group, an amino group, and an R group, e.g., homoserine, norleucine, methionine sulfoxide, or methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given peptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of ordinary skill in the art will recognize that individual substitutions, deletions or additions to a nucleic acid or peptide sequence that alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M). See, e.g., Creighton, *Proteins* (1984).

The terms "identical" or percent "identity," in the context of two or more nucleic acids or peptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection.

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Augsburger & Hoag, *Pharmaceutical Dosage Forms* (vols. 1-3, 3rd Ed. 2008); Lloyd, *The Art, Science and Technology of Pharmaceutical Compounding* (3rd Ed., 2008); Pickar, *Dosage Calculations* (8th Ed., 2007); and *Remington: The Science and Practice of Pharmacy*, 21st Ed., 2005, Gennaro, Ed., Lippincott, Williams & Wilkins).

III. FVIII Peptides

The present invention relates to FVIII peptides that correspond to regions of FVIII protein involved in an immune response against FVIII. In one aspect, the present invention provides a FVIII peptide consisting of a consecutive sequence of nine amino acids that is at least 85% identical to nine consecutive amino acids in one of the following amino acid sequences: AWPKMHTVNGYVNRSLPGLIG (SEQ ID NO:68); QANRSPLPIAKVSSFPSIRPIYLT (SEQ ID NO:344); or TVVITLKNMASHPVSLHAVGV (SEQ ID NO:740), wherein the peptide consists of from 9 to 180 amino acids.

In a specific embodiment, the FVIII peptide has the sequence: $(R^1)_x$—P—$(R^2)_y$, wherein P is an amino acid sequence having at least 85% identity to a sequence of at least nine consecutive amino acids of a sequence selected from SEQ ID NOS:68, 344, and 740, $R^1$ is an amino acid sequence consisting of from 1 to 80 amino acids; $R^2$ is an amino acid sequence consisting of from 1 to 80 amino acids; and each of x and y are independently zero or one. In one embodiment, $R^1$ is an amino acid sequence consisting of from 1 to 40 amino acids, and $R^2$ is an amino acid sequence consisting of from 1 to 40 amino acids.

In one embodiment, $R^1$ and $R^2$ are separately or both amino acid sequences consisting of from 1 to 80 amino acids. In another embodiment, $R^1$ and $R^2$ are separately or both amino acid sequences consisting of from 1 to 70 amino acids. In another embodiment, $R^1$ and $R^2$ are separately or both amino acid sequences consisting of from 1 to 60 amino acids. In another embodiment, $R^1$ and $R^2$ are separately or both amino acid sequences consisting of from 1 to 50 amino acids. In another embodiment, $R^1$ and $R^2$ are separately or both amino acid sequences consisting of from 1 to 40 amino acids. In another embodiment, $R^1$ and $R^2$ are separately or both amino acid sequences consisting of from 1 to 30 amino acids. In another embodiment, $R^1$ and $R^2$ are separately or both amino acid sequences consisting of from 1 to 20 amino acids. In another embodiment, $R^1$ and $R^2$ are separately or both amino acid sequences consisting of from 1 to 10 amino acids. In another embodiment, $R^1$ and $R^2$ are separately or both amino acid sequences consisting of from 1 to 5 amino acids. In yet other embodiment, $R^1$ and $R^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In one embodiment, the FVIII peptide consists of from 9 to 150 amino acids. In another embodiment, the FVIII peptide consists of from 9 to 100 amino acids. In another embodiment, the FVIII peptide consists of from 9 to 50 amino acids. In another embodiment, the FVIII peptide consists of from 9 to 25 amino acids. In yet other embodiments, the FVIII peptide consists of from 9 to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, or 180 amino acids.

Generally, the FVIII peptides of the present invention can include any sequence of amino acids present in the identified region of $FVIII^{102-122}$, $FVIII^{246-266}$, or $FVIII^{1401-1424}$, or a modified variant that can, for example, have a retained function similar or identical to $FVIII^{102-122}$, $FVIII^{246-266}$, or $FVIII^{1401-1424}$. In particular, the FVIII peptides of the present invention include a sequence of amino acids that includes a T cell epitope. The FVIII peptides include a sequence of at least nine amino acids that can range in percent identity relative to the amino acid sequence AWPKMHTVNGYVNRSLPGLIG (SEQ ID NO:68); QANRSPLPIAKVSSFPSIRPIYLT (SEQ ID NO:344); or TVVITLKNMASHPVSLHAVGV (SEQ ID NO:740). For example, a FVIII peptides can have nine amino acids that are identical or at least 50%, 60%, 70%, 80%, or 85% percent identical to any of nine consecutive amino acids in $FVIII^{102-122}$, $FVIII^{246-266}$, or $FVIII^{1401-1424}$.

In another group of embodiments, the FVIII peptides can have amino acid sequences greater than nine amino acids, in which the amino acid sequences include a region that can be identical or at least 50%, 55%, 60%, 65%, 70%, 75%, 80%, 85%, 90%, 91%, 92%, 93%, 94%, 95%, 96%, 97%, 98%, or 99% percent identical to the sequence of consecutive amino acids in $FVIII^{102-122}$, $FVIII^{246-266}$, or $FVIII^{1401-1424}$. One of ordinary skill in the art will appreciate that known mutagenesis techniques, such as alanine substitution, can be used to identify modified variants that retain the function of the $FVIII^{102-122}$, $FVIII^{246-266}$, or $FVIII^{1401-1424}$ region.

In addition, the FVIII peptides can further include additional sequences of amino acids on either end of the core sequence of the FVIII peptides discussed above. The additional sequences are designated $(R^1)_x$ and $(R^2)_y$. In certain embodiments, $R^1$ and $R^2$ can range from 1 to about 80 amino acids in length. Alternatively, $R^1$ and $R^2$ can range from 1 to about 40 amino acids in length. In certain embodiments, each of the subscripts x and y are independently zero or one. In some embodiments, both x and y can be zero. In other embodiments, x can be one and y can be zero. In yet other embodiments, x can be zero and y can be one. In another embodiment, both x and y are one. Additional amino acids on either end can be added for a variety of reasons, including increased stability of the peptides, improved binding to MHC class II molecules and/or T cells, as well as other aspects that will be appreciated by one of ordinary skill in the art.

In one embodiment, the present invention provides a polypeptide having the sequence $(R^1)_x$—P—$(R^2)_y$, wherein P is an amino acid sequence having at least 85% identity to a sequence of at least nine consecutive amino acids of a Factor VIII region identified in Table 1, $R^1$ is an amino acid sequence consisting of from 1 to 80 amino acids, and $R^2$ is an amino acid sequence consisting of from 1 to 80 amino acids, wherein each of x and y are independently zero or one. Alternatively, $R^1$ and $R^2$ can range from 1 to about 40 amino acids in length. In one embodiment, P is an amino acid sequence having at least 90% identity to a sequence of at least nine consecutive amino acids of a Factor VIII region identified in Table 1. In another embodiment, P is an amino acid sequence having at least 95% identity to a sequence of at least nine consecutive amino acids of a Factor VIII region identified in Table 1. In some embodiments, both x and y can be zero. In other embodiments, x can be one and y can be zero. In other embodiments, x can be zero and y can be one. In yet another embodiment, both x and y can be one. In one embodiment, the FVIII peptide consists of from 9 to 150 amino acids. In another embodiment, the FVIII peptide consists of from 9 to 100 amino acids. In another embodiment, the FVIII peptide consists of from 9 to 50 amino acids. In another embodiment, the FVIII peptide consists of from 9 to 25 amino acids.

TABLE 1

Regions of FVIII including T-cell epitopes

| Regions including T cell epitopes | Amino Acid Sequence |
|---|---|
| $FVIII^{102-119}$ | TVVITLKNMASHPVSLHA (SEQ ID NO: 10) |
| $FVIII^{246-266}$ | AWPKMHTVNGYVNRSLPGLIG (SEQ ID NO: 68) |

TABLE 1-continued

Regions of FVIII including T-cell epitopes

| Regions including T cell epitopes | Amino Acid Sequence | |
|---|---|---|
| FVIII$^{474-494}$ | GEVGDTLLIIFKNQASRPYNI | (SEQ ID NO: 159) |
| FVIII$^{540-560}$ | PTKSDPRCLTRYYSSFVNMER | (SEQ ID NO: 250) |
| FVIII$^{1401-1424}$ | QANRSPLPIAKVSSFPSIRPIYLT | (SEQ ID NO: 344) |
| FVIII$^{1785-1805}$ | EVEDNIMVTFRNQASRPYSFY | (SEQ ID NO: 477) |
| FVIII$^{2025-2045}$ | LHAGMSTLFLVYSNKCQTPLG | (SEQ ID NO: 568) |
| FVIII$^{2169-2180}$ | NPPIIARYIRLHPTHYSIRST | (SEQ ID NO: 659) |
| FVIII$^{102-122}$ | TVVITLKNMASHPVSLHAVGV | (SEQ ID NO: 740) |

As described above, the FVIII peptides of the present invention can include any sequence of amino acids present in the identified region of FVIII$^{1401-1424}$ or a modified variant that can, for example, have a retained function similar or identical to FVIII$^{1401-1424}$. In certain embodiments, the peptides can cover the whole B-domain of human FVIII protein. The present invention also can include other FVIII peptides that include a peptide having a sequence of at least nine amino acids that can range in percent identity relative to any one of the following amino acid sequences: GEVGDTLLIIFKNQASRPYNI (FVIII$^{474-494}$; SEQ ID NO:159), PTKSDPRCLTRYYSSFVNMER (FVIII$^{540-560}$; SEQ ID NO:250), EVEDNIMVTFRNQASRPYSFY (FVIII$^{1785-1805}$; SEQ ID NO:477), LHAGMSTLFLVYSNKCQTPLG (FVIII$^{2025-2045}$; SEQ ID NO:568), NPPIIARYIRLHPTHYSIRST (FVIII$^{2160-2180}$; SEQ ID NO:659), TVVITLKNMASHPVSLHA (FVIII$^{102-119}$; SEQ ID NO:10), AWPKMHTVNGYVNRSLPGLIG (FVIII$^{246-266}$; SEQ ID NO:68), and TVVITLKNMASHPVSLHAVGV (FVIII$^{102-122}$; SEQ ID NO:740).

For example, the FVIII peptides having nine amino acids that are identical or at least 50%, 60%, 70%, 80%, or 85% percent identical to any of nine consecutive amino acids in FVIII$^{474-494}$, FVIII$^{540-560}$, FVIII$^{1785-1805}$, FVIII$^{2025-2045}$, FVIII$^{2160-2180}$, FVIII$^{102-119}$, FVIII$^{246-266}$, or FVIII$^{102-122}$. In another group of embodiments, the FVIII peptides can have amino acid sequences greater than nine amino acids, in which the amino acid sequences can be identical or at least 50%, 55%, 60%, 65%, 70%, 75%, 80%, 85%, 90%, 91%, 92%, 93%, 94%, 95%, 96%, 97%, 98%, or 99% percent identical to any of nine consecutive amino acids in FVIII$^{474-494}$, FVIII$^{540-560}$, FVIII$^{1785-1805}$, FVIII$^{2025-2045}$, FVIII$^{2160-2180}$, FVIII$^{102-119}$, FVIII$^{246-266}$, or FVIII$^{102-122}$. One of ordinary skill in the art will appreciate that known mutagenesis techniques, such as alanine substitution, can be used to identify modified variants that retain the function of the FVIII$^{474-494}$, FVIII$^{540-560}$, FVIII$^{1785-1805}$, FVIII$^{2025-2045}$, FVIII$^{2160-2180}$, FVIII$^{102-119}$, FVIII$^{246-266}$, or FVIII$^{102-122}$ regions. The FVIII peptides disclosed here can be made using methods described above with respect to the FVIII peptides relating to FVIII$^{1401-1424}$.

A. Factor VIII$^{102-119}$ Peptides

In one embodiment, the present invention provides a polypeptide having the sequence $(R^1)_x$—P—$(R^2)_y$, wherein P is an amino acid sequence having at least 85% identity to a sequence of at least nine consecutive amino acids of a Factor VIII$^{102-119}$ peptide having the sequence: TVVITLKNMASHPVSLHA (SEQ ID NO:10), $R^1$ is an amino acid sequence consisting of from 1 to 80 amino acids, and $R^2$ is an amino acid sequence consisting of from 1 to 80 amino acids, wherein each of x and y are independently zero or one.

In one embodiment, P is an amino acid sequence having at least 90% identity to a sequence of at least nine consecutive amino acids of a Factor VIII$^{102-119}$ peptide having the sequence: TVVITLKNMASHPVSLHA (SEQ ID NO:10). In one embodiment, P is an amino acid sequence having at least 85% identity to a sequence selected from SEQ ID NOS:1 to 55 (SEQ ID NO:10). In one embodiment, P is an amino acid sequence having at least 90% identity to a sequence selected from SEQ ID NOS:1 to 55. In one embodiment, P is an amino acid sequence selected from SEQ ID NOS:1 to 55. In some embodiments, both x and y can be zero. In other embodiments, x can be one and y can be zero. In other embodiments, x can be zero and y can be one. In yet another embodiment, both x and y can be one.

In one embodiment, $R^1$ and $R^2$ are separately or both amino acid sequences consisting of from 1 to 80 amino acids. In another embodiment, $R^1$ and $R^2$ are separately or both amino acid sequences consisting of from 1 to 70 amino acids. In another embodiment, $R^1$ and $R^2$ are separately or both amino acid sequences consisting of from 1 to 60 amino acids. In another embodiment, $R^1$ and $R^2$ are separately or both amino acid sequences consisting of from 1 to 50 amino acids. In another embodiment, $R^1$ and $R^2$ are separately or both amino acid sequences consisting of from 1 to 40 amino acids. In another embodiment, $R^1$ and $R^2$ are separately or both amino acid sequences consisting of from 1 to 30 amino acids. In another embodiment, $R^1$ and $R^2$ are separately or both amino acid sequences consisting of from 1 to 20 amino acids. In another embodiment, $R^1$ and $R^2$ are separately or both amino acid sequences consisting of from 1 to 10 amino acids. In another embodiment, $R^1$ and $R^2$ are separately or both amino acid sequences consisting of from 1 to 5 amino acids. In yet other embodiment, $R^1$ and $R^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In certain embodiments, $R^1$ is an amino acid sequence consisting of from 1 to 40 amino acids, and $R^2$ is an amino acid sequence consisting of from 1 to 40 amino acids. In one embodiment, the FVIII peptide consists of from 9 to 150 amino acids. In another embodiment, the FVIII peptide consists of from 9 to 100 amino acids. In another embodiment, the FVIII peptide consists of from 9 to 50 amino acids. In another embodiment, the FVIII peptide consists of from 9 to 25 amino acids. In yet other embodiments, the FVIII peptide consists of from 9 to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, or 180 amino acids.

TABLE 2

Exemplary FVIII$^{102-119}$ Peptides

| Peptide | Sequence | SEQ ID NO: |
|---|---|---|
| FVIII$^{102-119}$-1 | TVVITLKNM | 1 |
| FVIII$^{102-119}$-2 | TVVITLKNMA | 2 |
| FVIII$^{102-119}$-3 | TVVITLKNMAS | 3 |
| FVIII$^{102-119}$-4 | TVVITLKNMASH | 4 |
| FVIII$^{102-119}$-5 | TVVITLKNMASHP | 5 |
| FVIII$^{102-119}$-6 | TVVITLKNMASHPV | 6 |
| FVIII$^{102-119}$-7 | TVVITLKNMASHPVS | 7 |
| FVIII$^{102-119}$-8 | TVVITLKNMASHPVSL | 8 |
| FVIII$^{102-119}$-9 | TVVITLKNMASHPVSLH | 9 |
| FVIII$^{102-119}$-10 | TVVITLKNMASHPVSLHA | 10 |
| FVIII$^{102-119}$-11 | VVITLKNMA | 11 |
| FVIII$^{102-119}$-12 | VVITLKNMAS | 12 |
| FVIII$^{102-119}$-13 | VVITLKNMASH | 13 |
| FVIII$^{102-119}$-14 | VVITLKNMASHP | 14 |
| FVIII$^{102-119}$-15 | VVITLKNMASHPV | 15 |
| FVIII$^{102-119}$-16 | VVITLKNMASHPVS | 16 |
| FVIII$^{102-119}$-17 | VVITLKNMASHPVSL | 17 |
| FVIII$^{102-119}$-18 | VVITLKNMASHPVSLH | 18 |
| FVIII$^{102-119}$-19 | VVITLKNMASHPVSLHA | 19 |
| FVIII$^{102-119}$-20 | VITLKNMAS | 20 |
| FVIII$^{102-119}$-21 | VITLKNMASH | 21 |
| FVIII$^{102-119}$-22 | VITLKNMASHP | 22 |
| FVIII$^{102-119}$-23 | VITLKNMASHPV | 23 |
| FVIII$^{102-119}$-24 | VITLKNMASHPVS | 24 |
| FVIII$^{102-119}$-25 | VITLKNMASHPVSL | 25 |
| FVIII$^{102-119}$-26 | VITLKNMASHPVSLH | 26 |
| FVIII$^{102-119}$-27 | VITLKNMASHPVSLHA | 27 |
| FVIII$^{102-119}$-28 | ITLKNMASH | 28 |
| FVIII$^{102-119}$-29 | ITLKNMASHP | 29 |
| FVIII$^{102-119}$-30 | ITLKNMASHPV | 30 |
| FVIII$^{102-119}$-31 | ITLKNMASHPVS | 31 |
| FVIII$^{102-119}$-32 | ITLKNMASHPVSL | 32 |
| FVIII$^{102-119}$-33 | ITLKNMASHPVSLH | 33 |
| FVIII$^{102-119}$-34 | ITLKNMASHPVSLHA | 34 |
| FVIII$^{102-119}$-35 | TLKNMASHP | 35 |
| FVIII$^{102-119}$-36 | TLKNMASHPV | 36 |
| FVIII$^{102-119}$-37 | TLKNMASHPVS | 37 |
| FVIII$^{102-119}$-38 | TLKNMASHPVSL | 38 |
| FVIII$^{102-119}$-39 | TLKNMASHPVSLH | 39 |
| FVIII$^{102-119}$-40 | TLKNMASHPVSLHA | 40 |
| FVIII$^{102-119}$-41 | LKNMASHPV | 41 |
| FVIII$^{102-119}$-42 | LKNMASHPVS | 42 |
| FVIII$^{102-119}$-43 | LKNMASHPVSL | 43 |
| FVIII$^{102-119}$-44 | LKNMASHPVSLH | 44 |
| FVIII$^{102-119}$-45 | LKNMASHPVSLHA | 45 |
| FVIII$^{102-119}$-46 | KNMASHPVS | 46 |
| FVIII$^{102-119}$-47 | KNMASHPVSL | 47 |
| FVIII$^{102-119}$-48 | KNMASHPVSLH | 48 |
| FVIII$^{102-119}$-49 | KNMASHPVSLHA | 49 |
| FVIII$^{102-119}$-50 | NMASHPVSL | 50 |
| FVIII$^{102-119}$-51 | NMASHPVSLH | 51 |
| FVIII$^{102-119}$-52 | NMASHPVSLHA | 52 |
| FVIII$^{102-119}$-53 | MASHPVSLH | 53 |
| FVIII$^{102-119}$-54 | MASHPVSLHA | 54 |
| FVIII$^{102-119}$-55 | ASHPVSLHA | 55 |

B. Factor VIII$^{246-266}$ Peptides

In one embodiment, the present invention provides a polypeptide having the sequence $(R^1)_x$—P—$(R^2)_y$, wherein P is an amino acid sequence having at least 85% identity to a sequence of at least nine consecutive amino acids of a Factor VIII$^{246-266}$ peptide having the sequence: AWPKMHTVNGYVNRSLPGLIG (SEQ ID NO:68), $R^1$ is an amino acid sequence consisting of from 1 to 80 amino acids, and $R^2$ is an amino acid sequence consisting of from 1 to 80 amino acids, wherein each of x and y are independently zero or one.

In one embodiment, P is an amino acid sequence having at least 90% identity to a sequence of at least nine consecutive amino acids of a Factor VIII$^{246-266}$ peptide having the sequence: AWPKMHTVNGYVNRSLPGLIG (SEQ ID NO:68). In one embodiment, P is an amino acid sequence having at least 95% identity to a sequence of at least nine consecutive amino acids of a Factor VIII$^{246-266}$ peptide having the sequence: AWPKMHTVNGYVNRSLPGLIG (SEQ ID NO:68). In one embodiment, P is an amino acid sequence having at least 85% identity to a sequence selected from SEQ ID NOS:56 to 146. In one embodiment, P is an amino acid sequence having at least 90% identity to a sequence selected from SEQ ID NOS:56 to 146. In one embodiment, P is an amino acid sequence having at least 95% identity to a sequence selected from SEQ ID NOS:56 to 146. In one embodiment, P is an amino acid sequence selected from SEQ ID NOS:56 to 146. In some embodiments, both x and y can be zero. In other embodiments, x can be one and y can be zero. In other embodiments, x can be zero and y can be one. In yet another embodiment, both x and y can be one.

In one embodiment, $R^1$ and $R^2$ are separately or both amino acid sequences consisting of from 1 to 80 amino acids. In another embodiment, $R^1$ and $R^2$ are separately or both amino acid sequences consisting of from 1 to 70 amino acids. In another embodiment, $R^1$ and $R^2$ are separately or both amino acid sequences consisting of from 1 to 60 amino acids. In another embodiment, $R^1$ and $R^2$ are separately or both amino acid sequences consisting of from 1 to 50 amino acids. In another embodiment, $R^1$ and $R^2$ are separately or both amino acid sequences consisting of from 1 to 40 amino acids. In another embodiment, $R^1$ and $R^2$ are separately or both amino acid sequences consisting of from 1 to 30 amino acids. In another embodiment, $R^1$ and $R^2$ are separately or both amino acid sequences consisting of from 1 to 20 amino acids. In another embodiment, $R^1$ and $R^2$ are separately or both amino acid sequences consisting of from 1 to 10 amino acids. In another embodiment, $R^1$ and $R^2$ are separately or both amino acid sequences consisting of from 1 to 5 amino acids. In yet other embodiment, $R^1$ and $R^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In one embodiment, the FVIII peptide consists of from 9 to 150 amino acids. In another embodiment, the FVIII peptide consists of from 9 to 100 amino acids. In another embodiment, the FVIII peptide consists of from 9 to 50 amino acids. In another embodiment, the FVIII peptide consists of from 9 to 25 amino acids. In yet other embodiments, the FVIII peptide consists of from 9 to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, or 180 amino acids.

TABLE 3

Exemplary $FVIII^{246-266}$ Peptides

| Peptide | Sequence | SEQ ID NO: |
|---|---|---|
| $FVIII^{246-266}$-1 | AWPKMHTVN | 56 |
| $FVIII^{246-266}$-2 | AWPKMHTVNG | 57 |
| $FVIII^{246-266}$-3 | AWPKMHTVNGY | 58 |
| $FVIII^{246-266}$-4 | AWPKMHTVNGYV | 59 |
| $FVIII^{246-266}$-5 | AWPKMHTVNGYVN | 60 |
| $FVIII^{246-266}$-6 | AWPKMHTVNGYVNR | 61 |
| $FVIII^{246-266}$-7 | AWPKMHTVNGYVNRS | 62 |
| $FVIII^{246-266}$-8 | AWPKMHTVNGYVNRSL | 63 |

TABLE 3-continued

Exemplary $FVIII^{246-266}$ Peptides

| Peptide | Sequence | SEQ ID NO: |
|---|---|---|
| $FVIII^{246-266}$-9 | AWPKMHTVNGYVNRSLP | 64 |
| $FVIII^{246-266}$-10 | AWPKMHTVNGYVNRSLPG | 65 |
| $FVIII^{246-266}$-11 | AWPKMHTVNGYVNRSLPGL | 66 |
| $FVIII^{246-266}$-12 | AWPKMHTVNGYVNRSLPGLI | 67 |
| $FVIII^{246-266}$-13 | AWPKMHTVNGYVNRSLPGLIG | 68 |
| $FVIII^{246-266}$-14 | WPKMHTVNG | 69 |
| $FVIII^{246-266}$-15 | WPKMHTVNGY | 70 |
| $FVIII^{246-266}$-16 | WPKMHTVNGYV | 71 |
| $FVIII^{246-266}$-17 | WPKMHTVNGYVN | 72 |
| $FVIII^{246-266}$-18 | WPKMHTVNGYVNR | 73 |
| $FVIII^{246-266}$-19 | WPKMHTVNGYVNRS | 74 |
| $FVIII^{246-266}$-20 | WPKMHTVNGYVNRSL | 75 |
| $FVIII^{246-266}$-21 | WPKMHTVNGYVNRSLP | 76 |
| $FVIII^{246-266}$-22 | WPKMHTVNGYVNRSLPG | 77 |
| $FVIII^{246-266}$-23 | WPKMHTVNGYVNRSLPGL | 78 |
| $FVIII^{246-266}$-24 | WPKMHTVNGYVNRSLPGLI | 79 |
| $FVIII^{246-266}$-25 | WPKMHTVNGYVNRSLPGLIG | 80 |
| $FVIII^{246-266}$-26 | PKMHTVNGY | 81 |
| $FVIII^{246-266}$-27 | PKMHTVNGYV | 82 |
| $FVIII^{246-266}$-28 | PKMHTVNGYVN | 83 |
| $FVIII^{246-266}$-29 | PKMHTVNGYVNR | 84 |
| $FVIII^{246-266}$-30 | PKMHTVNGYVNRS | 85 |
| $FVIII^{246-266}$-31 | PKMHTVNGYVNRSL | 86 |
| $FVIII^{246-266}$-32 | PKMHTVNGYVNRSLP | 87 |
| $FVIII^{246-266}$-33 | PKMHTVNGYVNRSLPG | 88 |
| $FVIII^{246-266}$-34 | PKMHTVNGYVNRSLPGL | 89 |
| $FVIII^{246-266}$-35 | PKMHTVNGYVNRSLPGLI | 90 |
| $FVIII^{246-266}$-36 | PKMHTVNGYVNRSLPGLIG | 91 |
| $FVIII^{246-266}$-37 | KMHTVNGY | 92 |
| $FVIII^{246-266}$-38 | KMHTVNGYVN | 93 |
| $FVIII^{246-266}$-39 | KMHTVNGYVNR | 94 |
| $FVIII^{246-266}$-40 | KMHTVNGYVNRS | 95 |
| $FVIII^{246-266}$-41 | KMHTVNGYVNRSL | 96 |
| $FVIII^{246-266}$-42 | KMHTVNGYVNRSLP | 97 |
| $FVIII^{246-266}$-43 | KMHTVNGYVNRSLPG | 98 |
| $FVIII^{246-266}$-44 | KMHTVNGYVNRSLPGL | 99 |
| $FVIII^{246-266}$-45 | KMHTVNGYVNRSLPGLI | 100 |
| $FVIII^{246-266}$-46 | KMHTVNGYVNRSLPGLIG | 101 |

TABLE 3-continued

Exemplary FVIII$^{246-266}$ Peptides

| Peptide | Sequence | SEQ ID NO: |
|---|---|---|
| FVIII$^{246-266}$-47 | MHTVNGYVN | 102 |
| FVIII$^{246-266}$-48 | MHTVNGYVNR | 103 |
| FVIII$^{246-266}$-49 | MHTVNGYVNRS | 104 |
| FVIII$^{246-266}$-50 | MHTVNGYVNRSL | 105 |
| FVIII$^{246-266}$-51 | MHTVNGYVNRSLP | 106 |
| FVIII$^{246-266}$-52 | MHTVNGYVNRSLPG | 107 |
| FVIII$^{246-266}$-53 | MHTVNGYVNRSLPGL | 108 |
| FVIII$^{246-266}$-54 | MHTVNGYVNRSLPGLI | 109 |
| FVIII$^{246-266}$-55 | MHTVNGYVNRSLPGLIG | 110 |
| FVIII$^{246-266}$-56 | HTVNGYVNR | 111 |
| FVIII$^{246-266}$-57 | HTVNGYVNRS | 112 |
| FVIII$^{246-266}$-58 | HTVNGYVNRSL | 113 |
| FVIII$^{246-266}$-59 | HTVNGYVNRSLP | 114 |
| FVIII$^{246-266}$-60 | HTVNGYVNRSLPG | 115 |
| FVIII$^{246-266}$-61 | HTVNGYVNRSLPGL | 116 |
| FVIII$^{246-266}$-62 | HTVNGYVNRSLPGLI | 117 |
| FVIII$^{246-266}$-63 | HTVNGYVNRSLPGLIG | 118 |
| FVIII$^{246-266}$-64 | TVNGYVNRS | 119 |
| FVIII$^{246-266}$-65 | TVNGYVNRSL | 120 |
| FVIII$^{246-266}$-66 | TVNGYVNRSLP | 121 |
| FVIII$^{246-266}$-67 | TVNGYVNRSLPG | 122 |
| FVIII$^{246-266}$-68 | TVNGYVNRSLPGL | 123 |
| FVIII$^{246-266}$-69 | TVNGYVNRSLPGLI | 124 |
| FVIII$^{246-266}$-70 | TVNGYVNRSLPGLIG | 125 |
| FVIII$^{246-266}$-71 | VNGYVNRSL | 126 |
| FVIII$^{246-266}$-72 | VNGYVNRSLP | 127 |
| FVIII$^{246-266}$-73 | VNGYVNRSLPG | 128 |
| FVIII$^{246-266}$-74 | VNGYVNRSLPGL | 129 |
| FVIII$^{246-266}$-75 | VNGYVNRSLPGLI | 130 |
| FVIII$^{246-266}$-76 | VNGYVNRSLPGLIG | 131 |
| FVIII$^{246-266}$-77 | NGYVNRSLP | 132 |
| FVIII$^{246-266}$-78 | NGYVNRSLPG | 133 |
| FVIII$^{246-266}$-79 | NGYVNRSLPGL | 134 |
| FVIII$^{246-266}$-80 | NGYVNRSLPGLI | 135 |
| FVIII$^{246-266}$-81 | NGYVNRSLPGLIG | 136 |
| FVIII$^{246-266}$-82 | GYVNRSLPG | 137 |
| FVIII$^{246-266}$-83 | GYVNRSLPGL | 138 |
| FVIII$^{246-266}$-84 | GYVNRSLPGLI | 139 |
| FVIII$^{246-266}$-85 | GYVNRSLPGLIG | 140 |
| FVIII$^{246-266}$-86 | YVNRSLPGL | 141 |
| FVIII$^{246-266}$-87 | YVNRSLPGLI | 142 |
| FVIII$^{246-266}$-88 | YVNRSLPGLIG | 143 |
| FVIII$^{246-266}$-89 | VNRSLPGLI | 144 |
| FVIII$^{246-266}$-90 | VNRSLPGLIG | 145 |
| FVIII$^{246-266}$-91 | NRSLPGLIG | 146 |

C. Factor VIII$^{474-494}$ Peptides

In one embodiment, the present invention provides a polypeptide having the sequence $(R^1)_x$—P—$(R^2)_y$, wherein P is an amino acid sequence having at least 85% identity to a sequence of at least nine consecutive amino acids of a Factor VIII$^{474-494}$ peptide having the sequence: GEVGDTLLIFKNQASRPYNI (SEQ ID NO:159), $R^1$ is an amino acid sequence consisting of from 1 to 80 amino acids, and $R^2$ is an amino acid sequence consisting of from 1 to 80 amino acids, wherein each of x and y are independently zero or one.

In one embodiment, P is an amino acid sequence having at least 90% identity to a sequence of at least nine consecutive amino acids of a Factor VIII$^{474-494}$ peptide having the sequence: GEVGDTLLIIFKNQASRPYNI (SEQ ID NO:159). In one embodiment, P is an amino acid sequence having at least 95% identity to a sequence of at least nine consecutive amino acids of a Factor VIII$^{474-494}$ peptide having the sequence: GEVGDTLLIIFKNQASRPYNI (SEQ ID NO:159). In one embodiment, P is an amino acid sequence having at least 85% identity to a sequence selected from SEQ ID NOS:147 to 237. In one embodiment, P is an amino acid sequence having at least 90% identity to a sequence selected from SEQ ID NOS:147 to 237. In one embodiment, P is an amino acid sequence having at least 95% identity to a sequence selected from SEQ ID NOS:147 to 237. In one embodiment, P is an amino acid sequence selected from SEQ ID NOS:147 to 237. In some embodiments, both x and y can be zero. In other embodiments, x can be one and y can be zero. In other embodiments, x can be zero and y can be one. In yet another embodiment, both x and y can be one.

In certain embodiments, $R^1$ is an amino acid sequence consisting of from 1 to 40 amino acids, and $R^2$ is an amino acid sequence consisting of from 1 to 40 amino acids. In one embodiment, the FVIII peptide consists of from 9 to 150 amino acids. In another embodiment, the FVIII peptide consists of from 9 to 100 amino acids. In another embodiment, the FVIII peptide consists of from 9 to 50 amino acids. In another embodiment, the FVIII peptide consists of from 9 to 25 amino acids. In yet other embodiments, the FVIII peptide consists of from 9 to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, or 180 amino acids.

TABLE 4

Exemplary FVIII$^{474-494}$ Peptides

| Peptide | Sequence | SEQ ID NO: |
|---|---|---|
| FVIII$^{474-494}$-1 | GEVGDTLLI | 147 |
| FVIII$^{474-494}$-2 | GEVGDTLLII | 148 |
| FVIII$^{474-494}$-3 | GEVGDTLLIIF | 149 |
| FVIII$^{474-494}$-4 | GEVGDTLLIIFK | 150 |
| FVIII$^{474-494}$-5 | GEVGDTLLIIFKN | 151 |
| FVIII$^{474-494}$-6 | GEVGDTLLIIFKNQ | 152 |
| FVIII$^{474-494}$-7 | GEVGDTLLIIFKNQA | 153 |
| FVIII$^{474-494}$-8 | GEVGDTLLIIFKNQAS | 154 |
| FVIII$^{474-494}$-9 | GEVGDTLLIIFKNQASR | 155 |
| FVIII$^{474-494}$-10 | GEVGDTLLIIFKNQASRP | 156 |
| FVIII$^{474-494}$-11 | GEVGDTLLIIFKNQASRPY | 157 |
| FVIII$^{474-494}$-12 | GEVGDTLLIIFKNQASRPYN | 158 |
| FVIII$^{474-494}$-13 | GEVGDTLLIIFKNQASRPYNI | 159 |
| FVIII$^{474-494}$-14 | EVGDTLLII | 160 |
| FVIII$^{474-494}$-15 | EVGDTLLIIF | 161 |
| FVIII$^{474-494}$-16 | EVGDTLLIIFK | 162 |
| FVIII$^{474-494}$-17 | EVGDTLLIIFKN | 163 |
| FVIII$^{474-494}$-18 | EVGDTLLIIFKNQ | 164 |
| FVIII$^{474-494}$-19 | EVGDTLLIIFKNQA | 165 |
| FVIII$^{474-494}$-20 | EVGDTLLIIFKNQAS | 166 |
| FVIII$^{474-494}$-21 | EVGDTLLIIFKNQASR | 167 |
| FVIII$^{474-494}$-22 | EVGDTLLIIFKNQASRP | 168 |
| FVIII$^{474-494}$-23 | EVGDTLLIIFKNQASRPY | 169 |
| FVIII$^{474-494}$-24 | EVGDTLLIIFKNQASRPYN | 170 |
| FVIII$^{474-494}$-25 | EVGDTLLIIFKNQASRPYNI | 171 |
| FVIII$^{474-494}$-26 | VGDTLLIIF | 172 |
| FVIII$^{474-494}$-27 | VGDTLLIIFK | 173 |
| FVIII$^{474-494}$-28 | VGDTLLIIFKN | 174 |
| FVIII$^{474-494}$-29 | VGDTLLIIFKNQ | 175 |
| FVIII$^{474-494}$-30 | VGDTLLIIFKNQA | 176 |
| FVIII$^{474-494}$-31 | VGDTLLIIFKNQAS | 177 |
| FVIII$^{474-494}$-32 | VGDTLLIIFKNQASR | 178 |
| FVIII$^{474-494}$-33 | VGDTLLIIFKNQASRP | 179 |
| FVIII$^{474-494}$-34 | VGDTLLIIFKNQASRPY | 180 |
| FVIII$^{474-494}$-35 | VGDTLLIIFKNQASRPYN | 181 |
| FVIII$^{474-494}$-36 | VGDTLLIIFKNQASRPYNI | 182 |
| FVIII$^{474-494}$-37 | GDTLLIIFK | 183 |
| FVIII$^{474-494}$-38 | GDTLLIIFKN | 184 |
| FVIII$^{474-494}$-39 | GDTLLIIFKNQ | 185 |
| FVIII$^{474-494}$-40 | GDTLLIIFKNQA | 186 |
| FVIII$^{474-494}$-41 | GDTLLIIFKNQAS | 187 |
| FVIII$^{474-494}$-42 | GDTLLIIFKNQASR | 188 |
| FVIII$^{474-494}$-43 | GDTLLIIFKNQASRP | 189 |
| FVIII$^{474-494}$-44 | GDTLLIIFKNQASRPY | 190 |
| FVIII$^{474-494}$-45 | GDTLLIIFKNQASRPYN | 191 |
| FVIII$^{474-494}$-46 | GDTLLIIFKNQASRPYNI | 192 |
| FVIII$^{474-494}$-47 | DTLLIIFKN | 193 |
| FVIII$^{474-494}$-48 | DTLLIIFKNQ | 194 |
| FVIII$^{474-494}$-49 | DTLLIIFKNQA | 195 |
| FVIII$^{474-494}$-50 | DTLLIIFKNQAS | 196 |
| FVIII$^{474-494}$-51 | DTLLIIFKNQASR | 197 |
| FVIII$^{474-494}$-52 | DTLLIIFKNQASRP | 198 |
| FVIII$^{474-494}$-53 | DTLLIIFKNQASRPY | 199 |
| FVIII$^{474-494}$-54 | DTLLIIFKNQASRPYN | 200 |
| FVIII$^{474-494}$-55 | DTLLIIFKNQASRPYNI | 201 |
| FVIII$^{474-494}$-56 | TLLIIFKNQ | 202 |
| FVIII$^{474-494}$-57 | TLLIIFKNQA | 203 |
| FVIII$^{474-494}$-58 | TLLIIFKNQAS | 204 |
| FVIII$^{474-494}$-59 | TLLIIFKNQASR | 205 |
| FVIII$^{474-494}$-60 | TLLIIFKNQASRP | 206 |
| FVIII$^{474-494}$-61 | TLLIIFKNQASRPY | 207 |
| FVIII$^{474-494}$-62 | TLLIIFKNQASRPYN | 208 |
| FVIII$^{474-494}$-63 | TLLIIFKNQASRPYNI | 209 |
| FVIII$^{474-494}$-64 | LLIIFKNQA | 210 |
| FVIII$^{474-494}$-65 | LLIIFKNQAS | 211 |
| FVIII$^{474-494}$-66 | LLIIFKNQASR | 212 |
| FVIII$^{474-494}$-67 | LLIIFKNQASRP | 213 |
| FVIII$^{474-494}$-68 | LLIIFKNQASRPY | 214 |
| FVIII$^{474-494}$-69 | LLIIFKNQASRPYN | 215 |
| FVIII$^{474-494}$-70 | LLIIFKNQASRPYNI | 216 |
| FVIII$^{474-494}$-71 | LIIFKNQAS | 217 |
| FVIII$^{474-494}$-72 | LIIFKNQASR | 218 |
| FVIII$^{474-494}$-73 | LIIFKNQASRP | 219 |
| FVIII$^{474-494}$-74 | LIIFKNQASRPY | 220 |
| FVIII$^{474-494}$-75 | LIIFKNQASRPYN | 221 |
| FVIII$^{474-494}$-76 | LIIFKNQASRPYNI | 222 |

TABLE 4-continued

Exemplary FVIII$^{474-494}$ Peptides

| Peptide | Sequence | SEQ ID NO: |
|---|---|---|
| FVIII$^{474-494}$-77 | IIFKNQASR | 223 |
| FVIII$^{474-494}$-78 | IIFKNQASRP | 224 |
| FVIII$^{474-494}$-79 | IIFKNQASRPY | 225 |
| FVIII$^{474-494}$-80 | IIFKNQASRPYN | 226 |
| FVIII$^{474-494}$-81 | IIFKNQASRPYNI | 227 |
| FVIII$^{474-494}$-82 | IFKNQASRP | 228 |
| FVIII$^{474-494}$-83 | IFKNQASRPY | 229 |
| FVIII$^{474-494}$-84 | IFKNQASRPYN | 230 |
| FVIII$^{474-494}$-85 | IFKNQASRPYNI | 231 |
| FVIII$^{474-494}$-86 | FKNQASRPY | 232 |
| FVIII$^{474-494}$-87 | FKNQASRPYN | 233 |
| FVIII$^{474-494}$-88 | FKNQASRPYNI | 234 |
| FVIII$^{474-494}$-89 | KNQASRPYN | 235 |
| FVIII$^{474-494}$-90 | KNQASRPYNI | 236 |
| FVIII$^{474-494}$-91 | NQASRPYNI | 237 |

D. Factor VIII$^{540-560}$ Peptides

In one embodiment, the present invention provides a polypeptide having the sequence $(R^1)_x$—P—$(R^2)_y$, wherein P is an amino acid sequence having at least 85% identity to a sequence of at least nine consecutive amino acids of a Factor VIII$^{540-560}$ peptide having the sequence: PTKSDPRCLTRYYSSFVNMER (SEQ ID NO:250), $R^1$ is an amino acid sequence consisting of from 1 to 80 amino acids, and $R^2$ is an amino acid sequence consisting of from 1 to 80 amino acids, wherein each of x and y are independently zero or one.

In one embodiment, P is an amino acid sequence having at least 90% identity to a sequence of at least nine consecutive amino acids of a Factor VIII$^{540-560}$ peptide having the sequence: PTKSDPRCLTRYYSSFVNMER (SEQ ID NO:250). In one embodiment, P is an amino acid sequence having at least 95% identity to a sequence of at least nine consecutive amino acids of a Factor VIII$^{540-560}$ peptide having the sequence: PTKSDPRCLTRYYSSFVNMER (SEQ ID NO:250). In one embodiment, P is an amino acid sequence having at least 85% identity to a sequence selected from SEQ ID NOS:238 to 328. In one embodiment, P is an amino acid sequence having at least 90% identity to a sequence selected from SEQ ID NOS:238 to 328. In one embodiment, P is an amino acid sequence having at least 95% identity to a sequence selected from SEQ ID NOS:238 to 328. In one embodiment, P is an amino acid sequence selected from SEQ ID NOS:238 to 328. In some embodiments, both x and y can be zero. In other embodiments, x can be one and y can be zero. In other embodiments, x can be zero and y can be one. In yet another embodiment, both x and y can be one.

In one embodiment, $R^1$ and $R^2$ are separately or both amino acid sequences consisting of from 1 to 80 amino acids. In another embodiment, $R^1$ and $R^2$ are separately or both amino acid sequences consisting of from 1 to 70 amino acids. In another embodiment, $R^1$ and $R^2$ are separately or both amino acid sequences consisting of from 1 to 60 amino acids. In another embodiment, $R^1$ and $R^2$ are separately or both amino acid sequences consisting of from 1 to 50 amino acids. In another embodiment, $R^1$ and $R^2$ are separately or both amino acid sequences consisting of from 1 to 40 amino acids. In another embodiment, $R^1$ and $R^2$ are separately or both amino acid sequences consisting of from 1 to 30 amino acids. In another embodiment, $R^1$ and $R^2$ are separately or both amino acid sequences consisting of from 1 to 20 amino acids. In another embodiment, $R^1$ and $R^2$ are separately or both amino acid sequences consisting of from 1 to 10 amino acids. In another embodiment, $R^1$ and $R^2$ are separately or both amino acid sequences consisting of from 1 to 5 amino acids. In yet other embodiment, $R^1$ and $R^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In one embodiment, the FVIII peptide consists of from 9 to 150 amino acids. In another embodiment, the FVIII peptide consists of from 9 to 100 amino acids. In another embodiment, the FVIII peptide consists of from 9 to 50 amino acids. In another embodiment, the FVIII peptide consists of from 9 to 25 amino acids. In yet other embodiments, the FVIII peptide consists of from 9 to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, or 180 amino acids.

TABLE 5

Exemplary FVIII$^{540-560}$ Peptides

| Peptide | Sequence | SEQ ID NO: |
|---|---|---|
| FVIII$^{540-560}$-1 | PTKSDPRCL | 238 |
| FVIII$^{540-560}$-2 | PTKSDPRCLT | 239 |
| FVIII$^{540-560}$-3 | PTKSDPRCLTR | 240 |
| FVIII$^{540-560}$-4 | PTKSDPRCLTRY | 241 |
| FVIII$^{540-560}$-5 | PTKSDPRCLTRYY | 242 |
| FVIII$^{540-560}$-6 | PTKSDPRCLTRYYS | 243 |
| FVIII$^{540-560}$-7 | PTKSDPRCLTRYYSS | 244 |
| FVIII$^{540-560}$-8 | PTKSDPRCLTRYYSSF | 245 |
| FVIII$^{540-560}$-9 | PTKSDPRCLTRYYSSFV | 246 |
| FVIII$^{540-560}$-10 | PTKSDPRCLTRYYSSFVN | 247 |
| FVIII$^{540-560}$-11 | PTKSDPRCLTRYYSSFVNM | 248 |
| FVIII$^{540-560}$-12 | PTKSDPRCLTRYYSSFVNME | 249 |
| FVIII$^{540-560}$-13 | PTKSDPRCLTRYYSSFVNMER | 250 |
| FVIII$^{540-560}$-14 | TKSDPRCLT | 251 |
| FVIII$^{540-560}$-15 | TKSDPRCLTR | 252 |
| FVIII$^{540-560}$-16 | TKSDPRCLTRY | 253 |
| FVIII$^{540-560}$-17 | TKSDPRCLTRYY | 254 |
| FVIII$^{540-560}$-18 | TKSDPRCLTRYYS | 255 |

TABLE 5-continued

Exemplary FVIII$^{540-560}$ Peptides

| Peptide | Sequence | SEQ ID NO: |
|---|---|---|
| FVIII$^{540-560}$-19 | TKSDPRCLTRYYSS | 256 |
| FVIII$^{540-560}$-20 | TKSDPRCLTRYYSSF | 257 |
| FVIII$^{540-560}$-21 | TKSDPRCLTRYYSSFV | 258 |
| FVIII$^{540-560}$-22 | TKSDPRCLTRYYSSFVN | 259 |
| FVIII$^{540-560}$-23 | TKSDPRCLTRYYSSFVNM | 260 |
| FVIII$^{540-560}$-24 | TKSDPRCLTRYYSSFVNME | 261 |
| FVIII$^{540-560}$-25 | TKSDPRCLTRYYSSFVNMER | 262 |
| FVIII$^{540-560}$-26 | KSDPRCLTR | 263 |
| FVIII$^{540-560}$-27 | KSDPRCLTRY | 264 |
| FVIII$^{540-560}$-28 | KSDPRCLTRYY | 265 |
| FVIII$^{540-560}$-29 | KSDPRCLTRYYS | 266 |
| FVIII$^{540-560}$-30 | KSDPRCLTRYYSS | 267 |
| FVIII$^{540-560}$-31 | KSDPRCLTRYYSSF | 268 |
| FVIII$^{540-560}$-32 | KSDPRCLTRYYSSFV | 269 |
| FVIII$^{540-560}$-33 | KSDPRCLTRYYSSFVN | 270 |
| FVIII$^{540-560}$-34 | KSDPRCLTRYYSSFVNM | 271 |
| FVIII$^{540-560}$-35 | KSDPRCLTRYYSSFVNME | 272 |
| FVIII$^{540-560}$-36 | KSDPRCLTRYYSSFVNMER | 273 |
| FVIII$^{540-560}$-37 | SDPRCLTRY | 274 |
| FVIII$^{540-560}$-38 | SDPRCLTRYY | 275 |
| FVIII$^{540-560}$-39 | SDPRCLTRYYS | 276 |
| FVIII$^{540-560}$-40 | SDPRCLTRYYSS | 277 |
| FVIII$^{540-560}$-41 | SDPRCLTRYYSSF | 278 |
| FVIII$^{540-560}$-42 | SDPRCLTRYYSSFV | 279 |
| FVIII$^{540-560}$-43 | SDPRCLTRYYSSFVN | 280 |
| FVIII$^{540-560}$-44 | SDPRCLTRYYSSFVNM | 281 |
| FVIII$^{540-560}$-45 | SDPRCLTRYYSSFVNME | 282 |
| FVIII$^{540-560}$-46 | SDPRCLTRYYSSFVNMER | 283 |
| FVIII$^{540-560}$-47 | DPRCLTRYY | 284 |
| FVIII$^{540-560}$-48 | DPRCLTRYYS | 285 |
| FVIII$^{540-560}$-49 | DPRCLTRYYSS | 286 |
| FVIII$^{540-560}$-50 | DPRCLTRYYSSF | 287 |
| FVIII$^{540-560}$-51 | DPRCLTRYYSSFV | 288 |
| FVIII$^{540-560}$-52 | DPRCLTRYYSSFVN | 289 |
| FVIII$^{540-560}$-53 | DPRCLTRYYSSFVNM | 290 |
| FVIII$^{540-560}$-54 | DPRCLTRYYSSFVNME | 291 |
| FVIII$^{540-560}$-55 | DPRCLTRYYSSFVNMER | 292 |
| FVIII$^{540-560}$-56 | PRCLTRYYS | 293 |
| FVIII$^{540-560}$-57 | PRCLTRYYSS | 294 |
| FVIII$^{540-560}$-58 | PRCLTRYYSSF | 295 |
| FVIII$^{540-560}$-59 | PRCLTRYYSSFV | 296 |
| FVIII$^{540-560}$-60 | PRCLTRYYSSFVN | 297 |
| FVIII$^{540-560}$-61 | PRCLTRYYSSFVNM | 298 |
| FVIII$^{540-560}$-62 | PRCLTRYYSSFVNME | 299 |
| FVIII$^{540-560}$-63 | PRCLTRYYSSFVNMER | 300 |
| FVIII$^{540-560}$-64 | RCLTRYYSS | 301 |
| FVIII$^{540-560}$-65 | RCLTRYYSSF | 302 |
| FVIII$^{540-560}$-66 | RCLTRYYSSFV | 303 |
| FVIII$^{540-560}$-67 | RCLTRYYSSFVN | 304 |
| FVIII$^{540-560}$-68 | RCLTRYYSSFVNM | 305 |
| FVIII$^{540-560}$-69 | RCLTRYYSSFVNME | 306 |
| FVIII$^{540-560}$-70 | RCLTRYYSSFVNMER | 307 |
| FVIII$^{540-560}$-71 | CLTRYYSSF | 308 |
| FVIII$^{540-560}$-72 | CLTRYYSSFV | 309 |
| FVIII$^{540-560}$-73 | CLTRYYSSFVN | 310 |
| FVIII$^{540-560}$-74 | CLTRYYSSFVNM | 311 |
| FVIII$^{540-560}$-75 | CLTRYYSSFVNME | 312 |
| FVIII$^{540-560}$-76 | CLTRYYSSFVNMER | 313 |
| FVIII$^{540-560}$-77 | LTRYYSSFV | 314 |
| FVIII$^{540-560}$-78 | LTRYYSSFVN | 315 |
| FVIII$^{540-560}$-79 | LTRYYSSFVNM | 316 |
| FVIII$^{540-560}$-80 | LTRYYSSFVNME | 317 |
| FVIII$^{540-560}$-81 | LTRYYSSFVNMER | 318 |
| FVIII$^{540-560}$-82 | TRYYSSFVN | 319 |
| FVIII$^{540-560}$-83 | TRYYSSFVNM | 320 |
| FVIII$^{540-560}$-84 | TRYYSSFVNME | 321 |
| FVIII$^{540-560}$-85 | TRYYSSFVNMER | 322 |
| FVIII$^{540-560}$-86 | RYYSSFVNM | 323 |
| FVIII$^{540-560}$-87 | RYYSSFVNME | 324 |
| FVIII$^{540-560}$-88 | RYYSSFVNMER | 325 |
| FVIII$^{540-560}$-89 | YYSSFVNME | 326 |
| FVIII$^{540-560}$-90 | YYSSFVNMER | 327 |
| FVIII$^{540-560}$-91 | YSSFVNMER | 328 |

E. Factor VIII$^{1401-1424}$ Peptides

In one embodiment, the present invention provides a polypeptide having the sequence $(R^1)_x$—P—$(R^2)_y$, wherein P is an amino acid sequence having at least 85% identity to a sequence of at least nine consecutive amino acids of a Factor VIII$^{1401-1424}$ peptide having the sequence: QANRSPLPIAKVSSFPSIRPIYLT (SEQ ID NO:344), R$^1$ is an amino acid sequence consisting of from 1 to 80 amino acids, and R$^2$ is an amino acid sequence consisting of from 1 to 80 amino acids, wherein each of x and y are independently zero or one.

In one embodiment, P is an amino acid sequence having at least 90% identity to a sequence of at least nine consecutive amino acids of a Factor VIII$^{1401-1424}$ peptide having the sequence: QANRSPLPIAKVSSFPSIRPIYLT (SEQ ID NO:344). In one embodiment, P is an amino acid sequence having at least 95% identity to a sequence of at least nine consecutive amino acids of a Factor VIII$^{1401-1424}$ peptide having the sequence: QANRSPLPIAKVSSFPSIRPIYLT (SEQ ID NO:344). In one embodiment, P is an amino acid sequence having at least 85% identity to a sequence selected from SEQ ID NOS:329 to 464. In one embodiment, P is an amino acid sequence having at least 90% identity to a sequence selected from SEQ ID NOS:329 to 464. In one embodiment, P is an amino acid sequence having at least 95% identity to a sequence selected from SEQ ID NOS:329 to 464. In one embodiment, P is an amino acid sequence selected from SEQ ID NOS:329 to 464. In some embodiments, both x and y can be zero. In other embodiments, x can be one and y can be zero. In other embodiments, x can be zero and y can be one. In yet another embodiment, both x and y can be one.

In one embodiment, R$^1$ and R$^2$ are separately or both amino acid sequences consisting of from 1 to 80 amino acids. In another embodiment, R$^1$ and R$^2$ are separately or both amino acid sequences consisting of from 1 to 70 amino acids. In another embodiment, R$^1$ and R$^2$ are separately or both amino acid sequences consisting of from 1 to 60 amino acids. In another embodiment, R$^1$ and R$^2$ are separately or both amino acid sequences consisting of from 1 to 50 amino acids. In another embodiment, R$^1$ and R$^2$ are separately or both amino acid sequences consisting of from 1 to 40 amino acids. In another embodiment, R$^1$ and R$^2$ are separately or both amino acid sequences consisting of from 1 to 30 amino acids. In another embodiment, R$^1$ and R$^2$ are separately or both amino acid sequences consisting of from 1 to 20 amino acids. In another embodiment, R$^1$ and R$^2$ are separately or both amino acid sequences consisting of from 1 to 10 amino acids. In another embodiment, R$^1$ and R$^2$ are separately or both amino acid sequences consisting of from 1 to 5 amino acids. In yet other embodiment, R$^1$ and R$^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In one embodiment, the FVIII peptide consists of from 9 to 150 amino acids. In another embodiment, the FVIII peptide consists of from 9 to 100 amino acids. In another embodiment, the FVIII peptide consists of from 9 to 50 amino acids. In another embodiment, the FVIII peptide consists of from 9 to 25 amino acids. In yet other embodiments, the FVIII peptide consists of from 9 to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, or 180 amino acids.

TABLE 6

Exemplary FVIII$^{1401-1424}$ Peptides

| Peptide | Sequence | SEQ ID NO: |
|---|---|---|
| FVIII$^{1401-1424}$-1 | QANRSPLPI | 329 |
| FVIII$^{1401-1424}$-2 | QANRSPLPIA | 330 |
| FVIII$^{1401-1424}$-3 | QANRSPLPIAK | 331 |
| FVIII$^{1401-1424}$-4 | QANRSPLPIAKV | 332 |
| FVIII$^{1401-1424}$-5 | QANRSPLPIAKVS | 333 |
| FVIII$^{1401-1424}$-6 | QANRSPLPIAKVSS | 334 |
| FVIII$^{1401-1424}$-7 | QANRSPLPIAKVSSF | 335 |
| FVIII$^{1401-1424}$-8 | QANRSPLPIAKVSSFP | 336 |
| FVIII$^{1401-1424}$-9 | QANRSPLPIAKVSSFPS | 337 |
| FVIII$^{1401-1424}$-10 | QANRSPLPIAKVSSFPSI | 338 |
| FVIII$^{1401-1424}$-11 | QANRSPLPIAKVSSFPSIR | 339 |
| FVIII$^{1401-1424}$-12 | QANRSPLPIAKVSSFPSIRP | 340 |
| FVIII$^{1401-1424}$-13 | QANRSPLPIAKVSSFPSIRPI | 341 |
| FVIII$^{1401-1424}$-14 | QANRSPLPIAKVSSFPSIRPIY | 342 |
| FVIII$^{1401-1424}$-15 | QANRSPLPIAKVSSFPSIRPIYL | 343 |
| FVIII$^{1401-1424}$-16 | QANRSPLPIAKVSSFPSIRPIYLT | 344 |
| FVIII$^{1401-1424}$-17 | ANRSPLPIA | 345 |
| FVIII$^{1401-1424}$-18 | ANRSPLPIAK | 346 |
| FVIII$^{1401-1424}$-19 | ANRSPLPIAKV | 347 |
| FVIII$^{1401-1424}$-20 | ANRSPLPIAKVS | 348 |
| FVIII$^{1401-1424}$-21 | ANRSPLPIAKVSS | 349 |
| FVIII$^{1401-1424}$-22 | ANRSPLPIAKVSSF | 350 |
| FVIII$^{1401-1424}$-23 | ANRSPLPIAKVSSFP | 351 |
| FVIII$^{1401-1424}$-24 | ANRSPLPIAKVSSFPS | 352 |
| FVIII$^{1401-1424}$-25 | ANRSPLPIAKVSSFPSI | 353 |
| FVIII$^{1401-1424}$-26 | ANRSPLPIAKVSSFPSIR | 354 |
| FVIII$^{1401-1424}$-27 | ANRSPLPIAKVSSFPSIRP | 355 |
| FVIII$^{1401-1424}$-28 | ANRSPLPIAKVSSFPSIRPI | 356 |
| FVIII$^{1401-1424}$-29 | ANRSPLPIAKVSSFPSIRPIY | 357 |
| FVIII$^{1401-1424}$-30 | ANRSPLPIAKVSSFPSIRPIYL | 358 |
| FVIII$^{1401-1424}$-31 | ANRSPLPIAKVSSFPSIRPIYLT | 359 |
| FVIII$^{1401-1424}$-32 | NRSPLPIAK | 360 |
| FVIII$^{1401-1424}$-33 | NRSPLPIAKV | 361 |
| FVIII$^{1401-1424}$-34 | NRSPLPIAKVS | 362 |
| FVIII$^{1401-1424}$-35 | NRSPLPIAKVSS | 363 |
| FVIII$^{1401-1424}$-36 | NRSPLPIAKVSSF | 364 |
| FVIII$^{1401-1424}$-37 | NRSPLPIAKVSSFP | 365 |
| FVIII$^{1401-1424}$-38 | NRSPLPIAKVSSFPS | 366 |

TABLE 6-continued

Exemplary FVIII^1401-1424 Peptides

| Peptide | Sequence | SEQ ID NO: |
|---|---|---|
| FVIII^1401-1424-39 | NRSPLPIAKVSSFPSI | 367 |
| FVIII^1401-1424-40 | NRSPLPIAKVSSFPSIR | 368 |
| FVIII^1401-1424-41 | NRSPLPIAKVSSFPSIRP | 369 |
| FVIII^1401-1424-42 | NRSPLPIAKVSSFPSIRPI | 370 |
| FVIII^1401-1424-43 | NRSPLPIAKVSSFPSIRPIY | 371 |
| FVIII^1401-1424-44 | NRSPLPIAKVSSFPSIRPIYL | 372 |
| FVIII^1401-1424-45 | NRSPLPIAKVSSFPSIRPIYLT | 373 |
| FVIII^1401-1424-46 | RSPLPIAKV | 374 |
| FVIII^1401-1424-47 | RSPLPIAKVS | 375 |
| FVIII^1401-1424-48 | RSPLPIAKVSS | 376 |
| FVIII^1401-1424-49 | RSPLPIAKVSSF | 377 |
| FVIII^1401-1424-50 | RSPLPIAKVSSFP | 378 |
| FVIII^1401-1424-51 | RSPLPIAKVSSFPS | 379 |
| FVIII^1401-1424-52 | RSPLPIAKVSSFPSI | 380 |
| FVIII^1401-1424-53 | RSPLPIAKVSSFPSIR | 381 |
| FVIII^1401-1424-54 | RSPLPIAKVSSFPSIRP | 382 |
| FVIII^1401-1424-55 | RSPLPIAKVSSFPSIRPI | 383 |
| FVIII^1401-1424-56 | RSPLPIAKVSSFPSIRPIY | 384 |
| FVIII^1401-1424-57 | RSPLPIAKVSSFPSIRPIYL | 385 |
| FVIII^1401-1424-58 | RSPLPIAKVSSFPSIRPIYLT | 386 |
| FVIII^1401-1424-59 | SPLPIAKVS | 387 |
| FVIII^1401-1424-60 | SPLPIAKVSS | 388 |
| FVIII^1401-1424-61 | SPLPIAKVSSF | 389 |
| FVIII^1401-1424-62 | SPLPIAKVSSFP | 390 |
| FVIII^1401-1424-63 | SPLPIAKVSSFPS | 391 |
| FVIII^1401-1424-64 | SPLPIAKVSSFPSI | 392 |
| FVIII^1401-1424-65 | SPLPIAKVSSFPSIR | 393 |
| FVIII^1401-1424-66 | SPLPIAKVSSFPSIRP | 394 |
| FVIII^1401-1424-67 | SPLPIAKVSSFPSIRPI | 395 |
| FVIII^1401-1424-68 | SPLPIAKVSSFPSIRPIY | 396 |
| FVIII^1401-1424-69 | SPLPIAKVSSFPSIRPIYL | 397 |
| FVIII^1401-1424-70 | SPLPIAKVSSFPSIRPIYLT | 398 |
| FVIII^1401-1424-71 | PLPIAKVSS | 399 |
| FVIII^1401-1424-72 | PLPIAKVSSF | 400 |
| FVIII^1401-1424-73 | PLPIAKVSSFP | 401 |
| FVIII^1401-1424-74 | PLPIAKVSSFPS | 402 |
| FVIII^1401-1424-75 | PLPIAKVSSFPSI | 403 |
| FVIII^1401-1424-76 | PLPIAKVSSFPSIR | 404 |
| FVIII^1401-1424-77 | PLPIAKVSSFPSIRP | 405 |
| FVIII^1401-1424-78 | PLPIAKVSSFPSIRPI | 406 |
| FVIII^1401-1424-79 | PLPIAKVSSFPSIRPIY | 407 |
| FVIII^1401-1424-80 | PLPIAKVSSFPSIRPIYL | 408 |
| FVIII^1401-1424-81 | PLPIAKVSSFPSIRPIYLT | 409 |
| FVIII^1401-1424-82 | LPIAKVSSF | 410 |
| FVIII^1401-1424-83 | LPIAKVSSFP | 411 |
| FVIII^1401-1424-84 | LPIAKVSSFPS | 412 |
| FVIII^1401-1424-85 | LPIAKVSSFPSI | 413 |
| FVIII^1401-1424-86 | LPIAKVSSFPSIR | 414 |
| FVIII^1401-1424-87 | LPIAKVSSFPSIRP | 415 |
| FVIII^1401-1424-88 | LPIAKVSSFPSIRPI | 416 |
| FVIII^1401-1424-89 | LPIAKVSSFPSIRPIY | 417 |
| FVIII^1401-1424-90 | LPIAKVSSFPSIRPIYL | 418 |
| FVIII^1401-1424-91 | LPIAKVSSFPSIRPIYLT | 419 |
| FVIII^1401-1424-92 | PIAKVSSFP | 420 |
| FVIII^1401-1424-93 | PIAKVSSFPS | 421 |
| FVIII^1401-1424-94 | PIAKVSSFPSI | 422 |
| FVIII^1401-1424-95 | PIAKVSSFPSIR | 423 |
| FVIII^1401-1424-96 | PIAKVSSFPSIRP | 424 |
| FVIII^1401-1424-97 | PIAKVSSFPSIRPI | 425 |
| FVIII^1401-1424-98 | PIAKVSSFPSIRPIY | 426 |
| FVIII^1401-1424-99 | PIAKVSSFPSIRPIYL | 427 |
| FVIII^1401-1424-100 | PIAKVSSFPSIRPIYLT | 428 |
| FVIII^1401-1424-101 | IAKVSSFPS | 429 |
| FVIII^1401-1424-102 | IAKVSSFPSI | 430 |
| FVIII^1401-1424-103 | IAKVSSFPSIR | 431 |
| FVIII^1401-1424-104 | IAKVSSFPSIRP | 432 |
| FVIII^1401-1424-105 | IAKVSSFPSIRPI | 433 |
| FVIII^1401-1424-106 | IAKVSSFPSIRPIY | 434 |
| FVIII^1401-1424-107 | IAKVSSFPSIRPIYL | 435 |
| FVIII^1401-1424-108 | IAKVSSFPSIRPIYLT | 436 |
| FVIII^1401-1424-109 | AKVSSFPSI | 437 |
| FVIII^1401-1424-110 | AKVSSFPSIR | 438 |
| FVIII^1401-1424-111 | AKVSSFPSIRP | 439 |
| FVIII^1401-1424-112 | AKVSSFPSIRPI | 440 |
| FVIII^1401-1424-113 | AKVSSFPSIRPIY | 441 |

TABLE 6-continued

Exemplary FVIII[1401-1424] Peptides

| Peptide | Sequence | SEQ ID NO: |
|---|---|---|
| FVIII[1401-1424]-114 | AKVSSFPSIRPIYL | 442 |
| FVIII[1401-1424]-115 | AKVSSFPSIRPIYLT | 443 |
| FVIII[1401-1424]-116 | KVSSFPSIR | 444 |
| FVIII[1401-1424]-117 | KVSSFPSIRP | 445 |
| FVIII[1401-1424]-118 | KVSSFPSIRPI | 446 |
| FVIII[1401-1424]-119 | KVSSFPSIRPIY | 447 |
| FVIII[1401-1424]-120 | KVSSFPSIRPIYL | 448 |
| FVIII[1401-1424]-121 | KVSSFPSIRPIYLT | 449 |
| FVIII[1401-1424]-122 | VSSFPSIRP | 450 |
| FVIII[1401-1424]-123 | VSSFPSIRPI | 451 |
| FVIII[1401-1424]-124 | VSSFPSIRPIY | 452 |
| FVIII[1401-1424]-125 | VSSFPSIRPIYL | 453 |
| FVIII[1401-1424]-126 | VSSFPSIRPIYLT | 454 |
| FVIII[1401-1424]-127 | SSFPSIRPI | 455 |
| FVIII[1401-1424]-128 | SSFPSIRPIY | 456 |
| FVIII[1401-1424]-129 | SSFPSIRPIYL | 457 |
| FVIII[1401-1424]-130 | SSFPSIRPIYLT | 458 |
| FVIII[1401-1424]-131 | SFPSIRPIY | 459 |
| FVIII[1401-1424]-132 | SFPSIRPIYL | 460 |
| FVIII[1401-1424]-133 | SFPSIRPIYLT | 461 |
| FVIII[1401-1424]-134 | FPSIRPIYL | 462 |
| FVIII[1401-1424]-135 | FPSIRPIYLT | 463 |
| FVIII[1401-1424]-136 | PSIRPIYLT | 464 |

F. Factor VIII[1785-1805] Peptides

In one embodiment, the present invention provides a polypeptide having the sequence $(R^1)_x$—P—$(R^2)_y$, wherein P is an amino acid sequence having at least 85% identity to a sequence of at least nine consecutive amino acids of a Factor VIII[1785-1805] peptide having the sequence: EVEDNIMVT-FRNQASRPYSFY (SEQ ID NO:477), $R^1$ is an amino acid sequence consisting of from 1 to 80 amino acids, and $R^2$ is an amino acid sequence consisting of from 1 to 80 amino acids, wherein each of x and y are independently zero or one. In one embodiment, P is an amino acid sequence having at least 90% identity to a sequence of at least nine consecutive amino acids of a Factor VIII[1785-1805] peptide having the sequence: EVED-NIMVTFRNQASRPYSFY (SEQ ID NO:477).

In one embodiment, P is an amino acid sequence having at least 95% identity to a sequence of at least nine consecutive amino acids of a Factor VIII[1785-1805] peptide having the sequence: EVEDNIMVTFRNQASRPYSFY (SEQ ID NO:477). In one embodiment, P is an amino acid sequence having at least 85% identity to a sequence selected from SEQ ID NOS:465 to 555. In one embodiment, P is an amino acid sequence having at least 90% identity to a sequence selected from SEQ ID NOS:465 to 555. In one embodiment, P is an amino acid sequence having at least 95% identity to a sequence selected from SEQ ID NOS:465 to 555. In one embodiment, P is an amino acid sequence selected from SEQ ID NOS:465 to 555. In some embodiments, both x and y can be zero. In other embodiments, x can be one and y can be zero. In other embodiments, x can be zero and y can be one. In yet another embodiment, both x and y can be one.

In one embodiment, $R^1$ and $R^2$ are separately or both amino acid sequences consisting of from 1 to 80 amino acids. In another embodiment, $R^1$ and $R^2$ are separately or both amino acid sequences consisting of from 1 to 70 amino acids. In another embodiment, $R^1$ and $R^2$ are separately or both amino acid sequences consisting of from 1 to 60 amino acids. In another embodiment, $R^1$ and $R^2$ are separately or both amino acid sequences consisting of from 1 to 50 amino acids. In another embodiment, $R^1$ and $R^2$ are separately or both amino acid sequences consisting of from 1 to 40 amino acids. In another embodiment, $R^1$ and $R^2$ are separately or both amino acid sequences consisting of from 1 to 30 amino acids. In another embodiment, $R^1$ and $R^2$ are separately or both amino acid sequences consisting of from 1 to 20 amino acids. In another embodiment, $R^1$ and $R^2$ are separately or both amino acid sequences consisting of from 1 to 10 amino acids. In another embodiment, $R^1$ and $R^2$ are separately or both amino acid sequences consisting of from 1 to 5 amino acids. In yet other embodiment, $R^1$ and $R^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In one embodiment, the FVIII peptide consists of from 9 to 150 amino acids. In another embodiment, the FVIII peptide consists of from 9 to 100 amino acids. In another embodiment, the FVIII peptide consists of from 9 to 50 amino acids. In another embodiment, the FVIII peptide consists of from 9 to 25 amino acids. In yet other embodiments, the FVIII peptide consists of from 9 to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, or 180 amino acids.

TABLE 7

Exemplary FVIII[1785-1805] Peptides

| Peptide | Sequence | SEQ ID NO: |
|---|---|---|
| FVIII[1785-1805]-1 | EVEDNIMVT | 465 |
| FVIII[1785-1805]-2 | EVEDNIMVTF | 466 |
| FVIII[1785-1805]-3 | EVEDNIMVTFR | 467 |
| FVIII[1785-1805]-4 | EVEDNIMVTFRN | 468 |
| FVIII[1785-1805]-5 | EVEDNIMVTFRNQ | 469 |
| FVIII[1785-1805]-6 | EVEDNIMVTFRNQA | 470 |
| FVIII[1785-1805]-7 | EVEDNIMVTFRNQAS | 471 |
| FVIII[1785-1805]-8 | EVEDNIMVTFRNQASR | 472 |

TABLE 7-continued

Exemplary FVIII$^{1785-1805}$ Peptides

| Peptide | Sequence | SEQ ID NO: |
|---|---|---|
| FVIII$^{1785-1805}$-9 | EVEDNIMVTFRNQASRP | 473 |
| FVIII$^{1785-1805}$-10 | EVEDNIMVTFRNQASRPY | 474 |
| FVIII$^{1785-1805}$-11 | EVEDNIMVTFRNQASRPYS | 475 |
| FVIII$^{1785-1805}$-12 | EVEDNIMVTFRNQASRPYSF | 476 |
| FVIII$^{1785-1805}$-13 | EVEDNIMVTFRNQASRPYSFY | 477 |
| FVIII$^{1785-1805}$-14 | VEDNIMVTF | 478 |
| FVIII$^{1785-1805}$-15 | VEDNIMVTFR | 479 |
| FVIII$^{1785-1805}$-16 | VEDNIMVTFRN | 480 |
| FVIII$^{1785-1805}$-17 | VEDNIMVTFRNQ | 481 |
| FVIII$^{1785-1805}$-18 | VEDNIMVTFRNQA | 482 |
| FVIII$^{1785-1805}$-19 | VEDNIMVTFRNQAS | 483 |
| FVIII$^{1785-1805}$-20 | VEDNIMVTFRNQASR | 484 |
| FVIII$^{1785-1805}$-21 | VEDNIMVTFRNQASRP | 485 |
| FVIII$^{1785-1805}$-22 | VEDNIMVTFRNQASRPY | 486 |
| FVIII$^{1785-1805}$-23 | VEDNIMVTFRNQASRPYS | 487 |
| FVIII$^{1785-1805}$-24 | VEDNIMVTFRNQASRPYSF | 488 |
| FVIII$^{1785-1805}$-25 | VEDNIMVTFRNQASRPYSFY | 489 |
| FVIII$^{1785-1805}$-26 | EDNIMVTFR | 490 |
| FVIII$^{1785-1805}$-27 | EDNIMVTFRN | 491 |
| FVIII$^{1785-1805}$-28 | EDNIMVTFRNQ | 492 |
| FVIII$^{1785-1805}$-29 | EDNIMVTFRNQA | 493 |
| FVIII$^{1785-1805}$-30 | EDNIMVTFRNQAS | 494 |
| FVIII$^{1785-1805}$-31 | EDNIMVTFRNQASR | 495 |
| FVIII$^{1785-1805}$-32 | EDNIMVTFRNQASRP | 496 |
| FVIII$^{1785-1805}$-33 | EDNIMVTFRNQASRPY | 497 |
| FVIII$^{1785-1805}$-34 | EDNIMVTFRNQASRPYS | 498 |
| FVIII$^{1785-1805}$-35 | EDNIMVTFRNQASRPYSF | 499 |
| FVIII$^{1785-1805}$-36 | EDNIMVTFRNQASRPYSFY | 500 |
| FVIII$^{1785-1805}$-37 | DNIMVTFRN | 501 |
| FVIII$^{1785-1805}$-38 | DNIMVTFRNQ | 502 |
| FVIII$^{1785-1805}$-39 | DNIMVTFRNQA | 503 |
| FVIII$^{1785-1805}$-40 | DNIMVTFRNQAS | 504 |
| FVIII$^{1785-1805}$-41 | DNIMVTFRNQASR | 505 |
| FVIII$^{1785-1805}$-42 | DNIMVTFRNQASRP | 506 |
| FVIII$^{1785-1805}$-43 | DNIMVTFRNQASRPY | 507 |
| FVIII$^{1785-1805}$-44 | DNIMVTFRNQASRPYS | 508 |
| FVIII$^{1785-1805}$-45 | DNIMVTFRNQASRPYSF | 509 |
| FVIII$^{1785-1805}$-46 | DNIMVTFRNQASRPYSFY | 510 |
| FVIII$^{1785-1805}$-47 | NIMVTFRNQ | 511 |
| FVIII$^{1785-1805}$-48 | NIMVTFRNQA | 512 |
| FVIII$^{1785-1805}$-49 | NIMVTFRNQAS | 513 |
| FVIII$^{1785-1805}$-50 | NIMVTFRNQASR | 514 |
| FVIII$^{1785-1805}$-51 | NIMVTFRNQASRP | 515 |
| FVIII$^{1785-1805}$-52 | NIMVTFRNQASRPY | 516 |
| FVIII$^{1785-1805}$-53 | NIMVTFRNQASRPYS | 517 |
| FVIII$^{1785-1805}$-54 | NIMVTFRNQASRPYSF | 518 |
| FVIII$^{1785-1805}$-55 | NIMVTFRNQASRPYSFY | 519 |
| FVIII$^{1785-1805}$-56 | IMVTFRNQA | 520 |
| FVIII$^{1785-1805}$-57 | IMVTFRNQAS | 521 |
| FVIII$^{1785-1805}$-58 | IMVTFRNQASR | 522 |
| FVIII$^{1785-1805}$-59 | IMVTFRNQASRP | 523 |
| FVIII$^{1785-1805}$-60 | IMVTFRNQASRPY | 524 |
| FVIII$^{1785-1805}$-61 | IMVTFRNQASRPYS | 525 |
| FVIII$^{1785-1805}$-62 | IMVTFRNQASRPYSF | 526 |
| FVIII$^{1785-1805}$-63 | IMVTFRNQASRPYSFY | 527 |
| FVIII$^{1785-1805}$-64 | MVTFRNQAS | 528 |
| FVIII$^{1785-1805}$-65 | MVTFRNQASR | 529 |
| FVIII$^{1785-1805}$-66 | MVTFRNQASRP | 530 |
| FVIII$^{1785-1805}$-67 | MVTFRNQASRPY | 531 |
| FVIII$^{1785-1805}$-68 | MVTFRNQASRPYS | 532 |
| FVIII$^{1785-1805}$-69 | MVTFRNQASRPYSF | 533 |
| FVIII$^{1785-1805}$-70 | MVTFRNQASRPYSFY | 534 |
| FVIII$^{1785-1805}$-71 | VTFRNQASR | 535 |
| FVIII$^{1785-1805}$-72 | VTFRNQASRP | 536 |
| FVIII$^{1785-1805}$-73 | VTFRNQASRPY | 537 |
| FVIII$^{1785-1805}$-74 | VTFRNQASRPYS | 538 |
| FVIII$^{1785-1805}$-75 | VTFRNQASRPYSF | 539 |
| FVIII$^{1785-1805}$-76 | VTFRNQASRPYSFY | 540 |
| FVIII$^{1785-1805}$-77 | TFRNQASRP | 541 |
| FVIII$^{1785-1805}$-78 | TFRNQASRPY | 542 |
| FVIII$^{1785-1805}$-79 | TFRNQASRPYS | 543 |
| FVIII$^{1785-1805}$-80 | TFRNQASRPYSF | 544 |
| FVIII$^{1785-1805}$-81 | TFRNQASRPYSFY | 545 |
| FVIII$^{1785-1805}$-82 | FRNQASRPY | 546 |
| FVIII$^{1785-1805}$-83 | FRNQASRPYS | 547 |
| FVIII$^{1785-1805}$-84 | FRNQASRPYSF | 548 |

TABLE 7-continued

Exemplary FVIII$^{1785-1805}$ Peptides

| Peptide | Sequence | SEQ ID NO: |
|---|---|---|
| FVIII$^{1785-1805}$-85 | FRNQASRPYSFY | 549 |
| FVIII$^{1785-1805}$-86 | RNQASRPYS | 550 |
| FVIII$^{1785-1805}$-87 | RNQASRPYSF | 551 |
| FVIII$^{1785-1805}$-88 | RNQASRPYSFY | 552 |
| FVIII$^{1785-1805}$-89 | NQASRPYSF | 553 |
| FVIII$^{1785-1805}$-90 | NQASRPYSFY | 554 |
| FVIII$^{1785-1805}$-91 | QASRPYSFY | 555 |

G. Factor VIII$^{2025-2045}$ Peptides

In one embodiment, the present invention provides a polypeptide having the sequence $(R^1)_x$—P—$(R^2)_y$, wherein P is an amino acid sequence having at least 85% identity to a sequence of at least nine consecutive amino acids of a Factor VIII$^{2025-2045}$ peptide having the sequence: LHAGMSTLFLVYSNKCQTPLG (SEQ ID NO:568), $R^1$ is an amino acid sequence consisting of from 1 to 80 amino acids, and $R^2$ is an amino acid sequence consisting of from 1 to 80 amino acids, wherein each of x and y are independently zero or one.

In one embodiment, P is an amino acid sequence having at least 90% identity to a sequence of at least nine consecutive amino acids of a Factor VIII$^{2025-2045}$ peptide having the sequence: LHAGMSTLFLVYSNKCQTPLG (SEQ ID NO:568). In one embodiment, P is an amino acid sequence having at least 95% identity to a sequence of at least nine consecutive amino acids of a Factor VIII$^{2025-2045}$ peptide having the sequence: LHAGMSTLFLVYSNKCQTPLG (SEQ ID NO:568). In one embodiment, P is an amino acid sequence having at least 85% identity to a sequence selected from SEQ ID NOS:556 to 646. In one embodiment, P is an amino acid sequence having at least 90% identity to a sequence selected from SEQ ID NOS:556 to 646. In one embodiment, P is an amino acid sequence having at least 95% identity to a sequence selected from SEQ ID NOS:556 to 646. In one embodiment, P is an amino acid sequence selected from SEQ ID NOS:556 to 646. In some embodiments, both x and y can be zero. In other embodiments, x can be one and y can be zero. In other embodiments, x can be zero and y can be one. In yet another embodiment, both x and y can be one.

In one embodiment, $R^1$ and $R^2$ are separately or both amino acid sequences consisting of from 1 to 80 amino acids. In another embodiment, $R^1$ and $R^2$ are separately or both amino acid sequences consisting of from 1 to 70 amino acids. In another embodiment, $R^1$ and $R^2$ are separately or both amino acid sequences consisting of from 1 to 60 amino acids. In another embodiment, $R^1$ and $R^2$ are separately or both amino acid sequences consisting of from 1 to 50 amino acids. In another embodiment, $R^1$ and $R^2$ are separately or both amino acid sequences consisting of from 1 to 40 amino acids. In another embodiment, $R^1$ and $R^2$ are separately or both amino acid sequences consisting of from 1 to 30 amino acids. In another embodiment, $R^1$ and $R^2$ are separately or both amino acid sequences consisting of from 1 to 20 amino acids. In another embodiment, $R^1$ and $R^2$ are separately or both amino acid sequences consisting of from 1 to 10 amino acids. In another embodiment, $R^1$ and $R^2$ are separately or both amino acid sequences consisting of from 1 to 5 amino acids. In yet other embodiment, $R^1$ and $R^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In one embodiment, the FVIII peptide consists of from 9 to 150 amino acids. In another embodiment, the FVIII peptide consists of from 9 to 100 amino acids. In another embodiment, the FVIII peptide consists of from 9 to 50 amino acids. In another embodiment, the FVIII peptide consists of from 9 to 25 amino acids. In yet other embodiments, the FVIII peptide consists of from 9 to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, or 180 amino acids.

TABLE 8

Exemplary FVIII$^{2025-2045}$ Peptides

| Peptide | Sequence | SEQ ID NO: |
|---|---|---|
| FVIII$^{2025-2045}$-1 | LHAGMSTLF | 556 |
| FVIII$^{2025-2045}$-2 | LHAGMSTLFL | 557 |
| FVIII$^{2025-2045}$-3 | LHAGMSTLFLV | 558 |
| FVIII$^{2025-2045}$-4 | LHAGMSTLFLVY | 559 |
| FVIII$^{2025-2045}$-5 | LHAGMSTLFLVYS | 560 |
| FVIII$^{2025-2045}$-6 | LHAGMSTLFLVYSN | 561 |
| FVIII$^{2025-2045}$-7 | LHAGMSTLFLVYSNK | 562 |
| FVIII$^{2025-2045}$-8 | LHAGMSTLFLVYSNKC | 563 |
| FVIII$^{2025-2045}$-9 | LHAGMSTLFLVYSNKCQ | 564 |
| FVIII$^{2025-2045}$-10 | LHAGMSTLFLVYSNKCQT | 565 |
| FVIII$^{2025-2045}$-11 | LHAGMSTLFLVYSNKCQTP | 566 |
| FVIII$^{2025-2045}$-12 | LHAGMSTLFLVYSNKCQTPL | 567 |
| FVIII$^{2025-2045}$-13 | LHAGMSTLFLVYSNKCQTPLG | 568 |
| FVIII$^{2025-2045}$-14 | HAGMSTLFL | 569 |
| FVIII$^{2025-2045}$-15 | HAGMSTLFLV | 570 |
| FVIII$^{2025-2045}$-16 | HAGMSTLFLVY | 571 |
| FVIII$^{2025-2045}$-17 | HAGMSTLFLVYS | 572 |
| FVIII$^{2025-2045}$-18 | HAGMSTLFLVYSN | 573 |
| FVIII$^{2025-2045}$-19 | HAGMSTLFLVYSNK | 574 |
| FVIII$^{2025-2045}$-20 | HAGMSTLFLVYSNKC | 575 |
| FVIII$^{2025-2045}$-21 | HAGMSTLFLVYSNKCQ | 576 |
| FVIII$^{2025-2045}$-22 | HAGMSTLFLVYSNKCQT | 577 |
| FVIII$^{2025-2045}$-23 | HAGMSTLFLVYSNKCQTP | 578 |
| FVIII$^{2025-2045}$-24 | HAGMSTLFLVYSNKCQTPL | 579 |
| FVIII$^{2025-2045}$-25 | HAGMSTLFLVYSNKCQTPLG | 580 |

TABLE 8-continued

Exemplary FVIII$^{2025-2045}$ Peptides

| Peptide | Sequence | SEQ ID NO: |
|---|---|---|
| FVIII$^{2025-2045}$-26 | AGMSTLFLV | 581 |
| FVIII$^{2025-2045}$-27 | AGMSTLFLVY | 582 |
| FVIII$^{2025-2045}$-28 | AGMSTLFLVYS | 583 |
| FVIII$^{2025-2045}$-29 | AGMSTLFLVYSN | 584 |
| FVIII$^{2025-2045}$-30 | AGMSTLFLVYSNK | 585 |
| FVIII$^{2025-2045}$-31 | AGMSTLFLVYSNKC | 586 |
| FVIII$^{2025-2045}$-32 | AGMSTLFLVYSNKCQ | 587 |
| FVIII$^{2025-2045}$-33 | AGMSTLFLVYSNKCQT | 588 |
| FVIII$^{2025-2045}$-34 | AGMSTLFLVYSNKCQTP | 589 |
| FVIII$^{2025-2045}$-35 | AGMSTLFLVYSNKCQTPL | 590 |
| FVIII$^{2025-2045}$-36 | AGMSTLFLVYSNKCQTPLG | 591 |
| FVIII$^{2025-2045}$-37 | GMSTLFLVY | 592 |
| FVIII$^{2025-2045}$-38 | GMSTLFLVYS | 593 |
| FVIII$^{2025-2045}$-39 | GMSTLFLVYSN | 594 |
| FVIII$^{2025-2045}$-40 | GMSTLFLVYSNK | 595 |
| FVIII$^{2025-2045}$-41 | GMSTLFLVYSNKC | 596 |
| FVIII$^{2025-2045}$-42 | GMSTLFLVYSNKCQ | 597 |
| FVIII$^{2025-2045}$-43 | GMSTLFLVYSNKCQT | 598 |
| FVIII$^{2025-2045}$-44 | GMSTLFLVYSNKCQTP | 599 |
| FVIII$^{2025-2045}$-45 | GMSTLFLVYSNKCQTPL | 600 |
| FVIII$^{2025-2045}$-46 | GMSTLFLVYSNKCQTPLG | 601 |
| FVIII$^{2025-2045}$-47 | MSTLFLVYS | 602 |
| FVIII$^{2025-2045}$-48 | MSTLFLVYSN | 603 |
| FVIII$^{2025-2045}$-49 | MSTLFLVYSNK | 604 |
| FVIII$^{2025-2045}$-50 | MSTLFLVYSNKC | 605 |
| FVIII$^{2025-2045}$-51 | MSTLFLVYSNKCQ | 606 |
| FVIII$^{2025-2045}$-52 | MSTLFLVYSNKCQT | 607 |
| FVIII$^{2025-2045}$-53 | MSTLFLVYSNKCQTP | 608 |
| FVIII$^{2025-2045}$-54 | MSTLFLVYSNKCQTPL | 609 |
| FVIII$^{2025-2045}$-55 | MSTLFLVYSNKCQTPLG | 610 |
| FVIII$^{2025-2045}$-56 | STLFLVYSN | 611 |
| FVIII$^{2025-2045}$-57 | STLFLVYSNK | 612 |
| FVIII$^{2025-2045}$-58 | STLFLVYSNKC | 613 |
| FVIII$^{2025-2045}$-59 | STLFLVYSNKCQ | 614 |
| FVIII$^{2025-2045}$-60 | STLFLVYSNKCQT | 615 |
| FVIII$^{2025-2045}$-61 | STLFLVYSNKCQTP | 616 |
| FVIII$^{2025-2045}$-62 | STLFLVYSNKCQTPL | 617 |
| FVIII$^{2025-2045}$-63 | STLFLVYSNKCQTPLG | 618 |
| FVIII$^{2025-2045}$-64 | TLFLVYSNK | 619 |
| FVIII$^{2025-2045}$-65 | TLFLVYSNKC | 620 |
| FVIII$^{2025-2045}$-66 | TLFLVYSNKCQ | 621 |
| FVIII$^{2025-2045}$-67 | TLFLVYSNKCQT | 622 |
| FVIII$^{2025-2045}$-68 | TLFLVYSNKCQTP | 623 |
| FVIII$^{2025-2045}$-69 | TLFLVYSNKCQTPL | 624 |
| FVIII$^{2025-2045}$-70 | TLFLVYSNKCQTPLG | 625 |
| FVIII$^{2025-2045}$-71 | LFLVYSNKC | 626 |
| FVIII$^{2025-2045}$-72 | LFLVYSNKCQ | 627 |
| FVIII$^{2025-2045}$-73 | LFLVYSNKCQT | 628 |
| FVIII$^{2025-2045}$-74 | LFLVYSNKCQTP | 629 |
| FVIII$^{2025-2045}$-75 | LFLVYSNKCQTPL | 630 |
| FVIII$^{2025-2045}$-76 | LFLVYSNKCQTPLG | 631 |
| FVIII$^{2025-2045}$-77 | FLVYSNKCQ | 632 |
| FVIII$^{2025-2045}$-78 | FLVYSNKCQT | 633 |
| FVIII$^{2025-2045}$-79 | FLVYSNKCQTP | 634 |
| FVIII$^{2025-2045}$-80 | FLVYSNKCQTPL | 635 |
| FVIII$^{2025-2045}$-81 | FLVYSNKCQTPLG | 636 |
| FVIII$^{2025-2045}$-82 | LVYSNKCQT | 637 |
| FVIII$^{2025-2045}$-83 | LVYSNKCQTP | 638 |
| FVIII$^{2025-2045}$-84 | LVYSNKCQTPL | 639 |
| FVIII$^{2025-2045}$-85 | LVYSNKCQTPLG | 640 |
| FVIII$^{2025-2045}$-86 | VYSNKCQTP | 641 |
| FVIII$^{2025-2045}$-87 | VYSNKCQTPL | 642 |
| FVIII$^{2025-2045}$-88 | VYSNKCQTPLG | 643 |
| FVIII$^{2025-2045}$-89 | YSNKCQTPL | 644 |
| FVIII$^{2025-2045}$-90 | YSNKCQTPLG | 645 |
| FVIII$^{2025-2045}$-91 | SNKCQTPLG | 646 |

H. Factor VIII$^{2160-2180}$ Peptides

In one embodiment, the present invention provides a polypeptide having the sequence $(R^1)_x$—P—$(R^2)_y$, wherein P is an amino acid sequence having at least 85% identity to a sequence of at least nine consecutive amino acids of a Factor VIII$^{2160-2180}$ peptide having the sequence: NPPIIARYIRLHPTHYSIRST (SEQ ID NO:659), $R^1$ is an amino acid sequence consisting of from 1 to 80 amino acids, and $R^2$ is an amino acid sequence consisting of from 1 to 80 amino acids, wherein each of x and y are independently zero or one.

In one embodiment, P is an amino acid sequence having at least 90% identity to a sequence of at least nine consecutive amino acids of a Factor VIII$^{2160-2180}$ peptide having the sequence: NPPIIARYIRLHPTHYSIRST (SEQ ID NO:659). In one embodiment, P is an amino acid sequence having at least 95% identity to a sequence of at least nine consecutive amino acids of a Factor VIII$^{2160-2180}$ peptide having the sequence: NPPIIARYIRLHPTHYSIRST (SEQ ID NO:659). In one embodiment, P is an amino acid sequence having at least 85% identity to a sequence selected from SEQ ID NOS: 647 to 737. In one embodiment, P is an amino acid sequence having at least 90% identity to a sequence selected from SEQ ID NOS:647 to 737. In one embodiment, P is an amino acid sequence having at least 95% identity to a sequence selected from SEQ ID NOS:647 to 737. In one embodiment, P is an amino acid sequence selected from SEQ ID NOS:647 to 737. In some embodiments, both x and y can be zero. In other embodiments, x can be one and y can be zero. In other embodiments, x can be zero and y can be one. In yet another embodiment, both x and y can be one.

In one embodiment, $R^1$ and $R^2$ are separately or both amino acid sequences consisting of from 1 to 80 amino acids. In another embodiment, $R^1$ and $R^2$ are separately or both amino acid sequences consisting of from 1 to 70 amino acids. In another embodiment, $R^1$ and $R^2$ are separately or both amino acid sequences consisting of from 1 to 60 amino acids. In another embodiment, $R^1$ and $R^2$ are separately or both amino acid sequences consisting of from 1 to 50 amino acids. In another embodiment, $R^1$ and $R^2$ are separately or both amino acid sequences consisting of from 1 to 40 amino acids. In another embodiment, $R^1$ and $R^2$ are separately or both amino acid sequences consisting of from 1 to 30 amino acids. In another embodiment, $R^1$ and $R^2$ are separately or both amino acid sequences consisting of from 1 to 20 amino acids. In another embodiment, $R^1$ and $R^2$ are separately or both amino acid sequences consisting of from 1 to 10 amino acids. In another embodiment, $R^1$ and $R^2$ are separately or both amino acid sequences consisting of from 1 to 5 amino acids. In yet other embodiment, $R^1$ and $R^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In one embodiment, the FVIII peptide consists of from 9 to 150 amino acids. In another embodiment, the FVIII peptide consists of from 9 to 100 amino acids. In another embodiment, the FVIII peptide consists of from 9 to 50 amino acids. In another embodiment, the FVIII peptide consists of from 9 to 25 amino acids. In yet other embodiments, the FVIII peptide consists of from 9 to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, or 180 amino acids.

TABLE 9

Exemplary $FVIII^{2160-2180}$ Peptides

| Peptide | Sequence | SEQ ID NO: |
|---|---|---|
| $FVIII^{2160-2180}$-1 | NPPIIARYI | 647 |
| $FVIII^{2160-2180}$-2 | NPPIIARYIR | 648 |
| $FVIII^{2160-2180}$-3 | NPPIIARYIRL | 649 |
| $FVIII^{2160-2180}$-4 | NPPIIARYIRLH | 650 |

TABLE 9-continued

Exemplary $FVIII^{2160-2180}$ Peptides

| Peptide | Sequence | SEQ ID NO: |
|---|---|---|
| $FVIII^{2160-2180}$-5 | NPPIIARYIRLHP | 651 |
| $FVIII^{2160-2180}$-6 | NPPIIARYIRLHPT | 652 |
| $FVIII^{2160-2180}$-7 | NPPIIARYIRLHPTH | 653 |
| $FVIII^{2160-2180}$-8 | NPPIIARYIRLHPTHY | 654 |
| $FVIII^{2160-2180}$-9 | NPPIIARYIRLHPTHYS | 655 |
| $FVIII^{2160-2180}$-10 | NPPIIARYIRLHPTHYSI | 656 |
| $FVIII^{2160-2180}$-11 | NPPIIARYIRLHPTHYSIR | 657 |
| $FVIII^{2160-2180}$-12 | NPPIIARYIRLHPTHYSIRS | 658 |
| $FVIII^{2160-2180}$-13 | NPPIIARYIRLHPTHYSIRST | 659 |
| $FVIII^{2160-2180}$-14 | PPIIARYIR | 660 |
| $FVIII^{2160-2180}$-15 | PPIIARYIRL | 661 |
| $FVIII^{2160-2180}$-16 | PPIIARYIRLH | 662 |
| $FVIII^{2160-2180}$-17 | PPIIARYIRLHP | 663 |
| $FVIII^{2160-2180}$-18 | PPIIARYIRLHPT | 664 |
| $FVIII^{2160-2180}$-19 | PPIIARYIRLHPTH | 665 |
| $FVIII^{2160-2180}$-20 | PPIIARYIRLHPTHY | 666 |
| $FVIII^{2160-2180}$-21 | PPIIARYIRLHPTHYS | 667 |
| $FVIII^{2160-2180}$-22 | PPIIARYIRLHPTHYSI | 668 |
| $FVIII^{2160-2180}$-23 | PPIIARYIRLHPTHYSIR | 669 |
| $FVIII^{2160-2180}$-24 | PPIIARYIRLHPTHYSIRS | 670 |
| $FVIII^{2160-2180}$-25 | PPIIARYIRLHPTHYSIRST | 671 |
| $FVIII^{2160-2180}$-26 | PIIARYIRL | 672 |
| $FVIII^{2160-2180}$-27 | PIIARYIRLH | 673 |
| $FVIII^{2160-2180}$-28 | PIIARYIRLHP | 674 |
| $FVIII^{2160-2180}$-29 | PIIARYIRLHPT | 675 |
| $FVIII^{2160-2180}$-30 | PIIARYIRLHPTH | 676 |
| $FVIII^{2160-2180}$-31 | PIIARYIRLHPTHY | 677 |
| $FVIII^{2160-2180}$-32 | PIIARYIRLHPTHYS | 678 |
| $FVIII^{2160-2180}$-33 | PIIARYIRLHPTHYSI | 679 |
| $FVIII^{2160-2180}$-34 | PIIARYIRLHPTHYSIR | 680 |
| $FVIII^{2160-2180}$-35 | PIIARYIRLHPTHYSIRS | 681 |
| $FVIII^{2160-2180}$-36 | PIIARYIRLHPTHYSIRST | 682 |
| $FVIII^{2160-2180}$-37 | IIARYIRLH | 683 |
| $FVIII^{2160-2180}$-38 | IIARYIRLHP | 684 |
| $FVIII^{2160-2180}$-39 | IIARYIRLHPT | 685 |
| $FVIII^{2160-2180}$-40 | IIARYIRLHPTH | 686 |
| $FVIII^{2160-2180}$-41 | IIARYIRLHPTHY | 687 |
| $FVIII^{2160-2180}$-42 | IIARYIRLHPTHYS | 688 |

TABLE 9-continued
Exemplary FVIII²¹⁶⁰⁻²¹⁸⁰ Peptides

| Peptide | Sequence | SEQ ID NO: |
|---|---|---|
| FVIII²¹⁶⁰⁻²¹⁸⁰-43 | IIARYIRLHPTHYSI | 689 |
| FVIII²¹⁶⁰⁻²¹⁸⁰-44 | IIARYIRLHPTHYSIR | 690 |
| FVIII²¹⁶⁰⁻²¹⁸⁰-45 | IIARYIRLHPTHYSIRS | 691 |
| FVIII²¹⁶⁰⁻²¹⁸⁰-46 | IIARYIRLHPTHYSIRST | 692 |
| FVIII²¹⁶⁰⁻²¹⁸⁰-47 | IARYIRLHP | 693 |
| FVIII²¹⁶⁰⁻²¹⁸⁰-48 | IARYIRLHPT | 694 |
| FVIII²¹⁶⁰⁻²¹⁸⁰-49 | IARYIRLHPTH | 695 |
| FVIII²¹⁶⁰⁻²¹⁸⁰-50 | IARYIRLHPTHY | 696 |
| FVIII²¹⁶⁰⁻²¹⁸⁰-51 | IARYIRLHPTHYS | 697 |
| FVIII²¹⁶⁰⁻²¹⁸⁰-52 | IARYIRLHPTHYSI | 698 |
| FVIII²¹⁶⁰⁻²¹⁸⁰-53 | IARYIRLHPTHYSIR | 699 |
| FVIII²¹⁶⁰⁻²¹⁸⁰-54 | IARYIRLHPTHYSIRS | 700 |
| FVIII²¹⁶⁰⁻²¹⁸⁰-55 | IARYIRLHPTHYSIRST | 701 |
| FVIII²¹⁶⁰⁻²¹⁸⁰-56 | ARYIRLHPT | 702 |
| FVIII²¹⁶⁰⁻²¹⁸⁰-57 | ARYIRLHPTH | 703 |
| FVIII²¹⁶⁰⁻²¹⁸⁰-58 | ARYIRLHPTHY | 704 |
| FVIII²¹⁶⁰⁻²¹⁸⁰-59 | ARYIRLHPTHYS | 705 |
| FVIII²¹⁶⁰⁻²¹⁸⁰-60 | ARYIRLHPTHYSI | 706 |
| FVIII²¹⁶⁰⁻²¹⁸⁰-61 | ARYIRLHPTHYSIR | 707 |
| FVIII²¹⁶⁰⁻²¹⁸⁰-62 | ARYIRLHPTHYSIRS | 708 |
| FVIII²¹⁶⁰⁻²¹⁸⁰-63 | ARYIRLHPTHYSIRST | 709 |
| FVIII²¹⁶⁰⁻²¹⁸⁰-64 | RYIRLHPTH | 710 |
| FVIII²¹⁶⁰⁻²¹⁸⁰-65 | RYIRLHPTHY | 711 |
| FVIII²¹⁶⁰⁻²¹⁸⁰-66 | RYIRLHPTHYS | 712 |
| FVIII²¹⁶⁰⁻²¹⁸⁰-67 | RYIRLHPTHYSI | 713 |
| FVIII²¹⁶⁰⁻²¹⁸⁰-68 | RYIRLHPTHYSIR | 714 |
| FVIII²¹⁶⁰⁻²¹⁸⁰-69 | RYIRLHPTHYSIRS | 715 |
| FVIII²¹⁶⁰⁻²¹⁸⁰-70 | RYIRLHPTHYSIRST | 716 |
| FVIII²¹⁶⁰⁻²¹⁸⁰-71 | YIRLHPTHY | 717 |
| FVIII²¹⁶⁰⁻²¹⁸⁰-72 | YIRLHPTHYS | 718 |
| FVIII²¹⁶⁰⁻²¹⁸⁰-73 | YIRLHPTHYSI | 719 |
| FVIII²¹⁶⁰⁻²¹⁸⁰-74 | YIRLHPTHYSIR | 720 |
| FVIII²¹⁶⁰⁻²¹⁸⁰-75 | YIRLHPTHYSIRS | 721 |
| FVIII²¹⁶⁰⁻²¹⁸⁰-76 | YIRLHPTHYSIRST | 722 |
| FVIII²¹⁶⁰⁻²¹⁸⁰-77 | IRLHPTHYS | 723 |
| FVIII²¹⁶⁰⁻²¹⁸⁰-78 | IRLHPTHYSI | 724 |
| FVIII²¹⁶⁰⁻²¹⁸⁰-79 | IRLHPTHYSIR | 725 |
| FVIII²¹⁶⁰⁻²¹⁸⁰-80 | IRLHPTHYSIRS | 726 |
| FVIII²¹⁶⁰⁻²¹⁸⁰-81 | IRLHPTHYSIRST | 727 |
| FVIII²¹⁶⁰⁻²¹⁸⁰-82 | RLHPTHYSI | 728 |
| FVIII²¹⁶⁰⁻²¹⁸⁰-83 | RLHPTHYSIR | 729 |
| FVIII²¹⁶⁰⁻²¹⁸⁰-84 | RLHPTHYSIRS | 730 |
| FVIII²¹⁶⁰⁻²¹⁸⁰-85 | RLHPTHYSIRST | 731 |
| FVIII²¹⁶⁰⁻²¹⁸⁰-86 | LHPTHYSIR | 732 |
| FVIII²¹⁶⁰⁻²¹⁸⁰-87 | LHPTHYSIRS | 733 |
| FVIII²¹⁶⁰⁻²¹⁸⁰-88 | LHPTHYSIRST | 734 |
| FVIII²¹⁶⁰⁻²¹⁸⁰-89 | HPTHYSIRS | 735 |
| FVIII²¹⁶⁰⁻²¹⁸⁰-90 | HPTHYSIRST | 736 |
| FVIII²¹⁶⁰⁻²¹⁸⁰-91 | PTHYSIRST | 737 |

I. Factor VIII¹⁰²⁻¹²² Peptides

In one embodiment, the present invention provides a polypeptide having the sequence $(R^1)_x$—P—$(R^2)_y$, wherein P is an amino acid sequence having at least 85% identity to a sequence of at least nine consecutive amino acids of a Factor VIII¹⁰²⁻¹²² peptide having the sequence: TVVITLKNMASHPVSLHAVGV (SEQ ID NO:740), $R^1$ is an amino acid sequence consisting of from 1 to 80 amino acids, and $R^2$ is an amino acid sequence consisting of from 1 to 80 amino acids, wherein each of x and y are independently zero or one.

In one embodiment, P is an amino acid sequence having at least 90% identity to a sequence of at least nine consecutive amino acids of a Factor VIII¹⁰²⁻¹²² peptide having the sequence: TVVITLKNMASHPVSLHAVGV (SEQ ID NO:740). In one embodiment, P is an amino acid sequence having at least 95% identity to a sequence of at least nine consecutive amino acids of a Factor VIII¹⁰²⁻¹²² peptide having the sequence: TVVITLKNMASHPVSLHAVGV (SEQ ID NO:740).

In the context of the present invention, FVIII¹⁰²⁻¹²² peptides also include FVIII¹⁰²⁻¹¹⁹ peptides. Accordingly, In one embodiment, P is an amino acid sequence having at least 85% identity to a sequence selected from SEQ ID NOS:1 to 55 and 738 to 773. In one embodiment, P is an amino acid sequence having at least 90% identity to a sequence selected from SEQ ID NOS:1 to 55 and 738 to 773. In one embodiment, P is an amino acid sequence having at least 95% identity to a sequence selected from SEQ ID NOS:1 to 55 and 738 to 773. In one embodiment, P is an amino acid sequence selected from SEQ ID NOS:1 to 55 and 738 to 773. In some embodiments, both x and y can be zero. In other embodiments, x can be one and y can be zero. In other embodiments, x can be zero and y can be one. In yet another embodiment, both x and y can be one.

In one embodiment, $R^1$ and $R^2$ are separately or both amino acid sequences consisting of from 1 to 80 amino acids. In another embodiment, $R^1$ and $R^2$ are separately or both amino acid sequences consisting of from 1 to 70 amino acids. In another embodiment, $R^1$ and $R^2$ are separately or both amino acid sequences consisting of from 1 to 60 amino acids. In another embodiment, $R^1$ and $R^2$ are separately or both amino acid sequences consisting of from 1 to 50 amino acids. In another embodiment, $R^1$ and $R^2$ are separately or both amino acid sequences consisting of from 1 to 40 amino acids. In another embodiment, $R^1$ and $R^2$ are separately or both amino acid sequences consisting of from 1 to 30 amino acids. In another embodiment, $R^1$ and $R^2$ are separately or both amino acid sequences consisting of from 1 to 20 amino acids. In another embodiment, $R^1$ and $R^2$ are separately or both amino acid sequences consisting of from 1 to 10 amino acids. In another embodiment, $R^1$ and $R^2$ are separately or both amino acid sequences consisting of from 1 to 5 amino acids. In yet other embodiment, $R^1$ and $R^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In one embodiment, the FVIII peptide consists of from 9 to 150 amino acids. In another embodiment, the FVIII peptide consists of from 9 to 100 amino acids. In another embodiment, the FVIII peptide consists of from 9 to 50 amino acids. In another embodiment, the FVIII peptide consists of from 9 to 25 amino acids. In yet other embodiments, the FVIII peptide consists of from 9 to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, or 180 amino acids.

TABLE 10

Exemplary FVIII$^{102-122}$ Peptides

| Peptide | Sequence | SEQ ID NO: |
|---|---|---|
| FVIII$^{102-122}$-738 | TVVITLKNMASHPVSLHAV | 738 |
| FVIII$^{102-122}$-739 | TVVITLKNMASHPVSLHAVG | 739 |
| FVIII$^{102-122}$-740 | TVVITLKNMASHPVSLHAVGV | 740 |
| FVIII$^{102-122}$-741 | VVITLKNMASHPVSLHAV | 741 |
| FVIII$^{102-122}$-742 | VVITLKNMASHPVSLHAVG | 742 |
| FVIII$^{102-122}$-743 | VVITLKNMASHPVSLHAVGV | 743 |
| FVIII$^{102-122}$-744 | VITLKNMASHPVSLHAV | 744 |
| FVIII$^{102-122}$-745 | VITLKNMASHPVSLHAVG | 745 |
| FVIII$^{102-122}$-746 | VITLKNMASHPVSLHAVGV | 746 |
| FVIII$^{102-122}$-747 | ITLKNMASHPVSLHAV | 747 |
| FVIII$^{102-122}$-748 | ITLKNMASHPVSLHAVG | 748 |
| FVIII$^{102-122}$-749 | ITLKNMASHPVSLHAVGV | 749 |
| FVIII$^{102-122}$-750 | TLKNMASHPVSLHAV | 750 |
| FVIII$^{102-122}$-751 | TLKNMASHPVSLHAVG | 751 |
| FVIII$^{102-122}$-752 | TLKNMASHPVSLHAVGV | 752 |
| FVIII$^{102-122}$-753 | LKNMASHPVSLHAV | 753 |
| FVIII$^{102-122}$-754 | LKNMASHPVSLHAVG | 754 |
| FVIII$^{102-122}$-755 | LKNMASHPVSLHAVGV | 755 |

TABLE 10-continued

Exemplary FVIII$^{102-122}$ Peptides

| Peptide | Sequence | SEQ ID NO: |
|---|---|---|
| FVIII$^{102-122}$-756 | KNMASHPVSLHAV | 756 |
| FVIII$^{102-122}$-757 | KNMASHPVSLHAVG | 757 |
| FVIII$^{102-122}$-758 | KNMASHPVSLHAVGV | 758 |
| FVIII$^{102-122}$-759 | NMASHPVSLHAV | 759 |
| FVIII$^{102-122}$-760 | NMASHPVSLHAVG | 760 |
| FVIII$^{102-122}$-761 | NMASHPVSLHAVGV | 761 |
| FVIII$^{102-122}$-762 | MASHPVSLHAV | 762 |
| FVIII$^{102-122}$-763 | MASHPVSLHAVG | 763 |
| FVIII$^{102-122}$-764 | MASHPVSLHAVGV | 764 |
| FVIII$^{102-122}$-765 | ASHPVSLHAV | 765 |
| FVIII$^{102-122}$-766 | ASHPVSLHAVG | 766 |
| FVIII$^{102-122}$-767 | ASHPVSLHAVGV | 767 |
| FVIII$^{102-122}$-768 | SHPVSLHAV | 768 |
| FVIII$^{102-122}$-769 | SHPVSLHAVG | 769 |
| FVIII$^{102-122}$-770 | SHPVSLHAVGV | 770 |
| FVIII$^{102-122}$-771 | HPVSLHAVG | 771 |
| FVIII$^{102-122}$-772 | HPVSLHAVGV | 772 |
| FVIII$^{102-122}$-773 | PVSLHAVGV | 773 |

IV. Methods of Producing FVIII Peptides

In another aspect, the present invention further relates to methods for producing FVIII peptides. In some embodiments, the FVIII peptides of the present invention can be produced using solid phase (e.g., Fmoc or t-Boc) or liquid phase synthesis techniques generally known in the art. See, e.g., Chan & White, Eds., Fmoc Solid Phase Peptide Synthesis: A Practical Approach (Oxford University Press, 2000); Benoiton, Chemistry of Peptide Synthesis (CRC Press, 2005); Howl, Peptide Synthesis and Applications (Humana Press, 2010).

In one embodiment, the present invention includes a method of making a FVIII peptide, the method comprising: a) synthesizing a peptide using solid phase or liquid phase synthesis techniques, the FVIII peptide having the sequence: $(R^1)_x$—P—$(R^2)_y$, wherein P is an amino acid sequence having at least 85% identity to a sequence of at least nine consecutive amino acids of a sequence selected from SEQ ID NOS:68, 344, and 740, R1 is an amino acid sequence consisting of from 1 to 80 amino acids; R2 is an amino acid sequence consisting of from 1 to 80 amino acids; and each of x and y are independently zero or one. In one embodiment, $R^1$ is an amino acid sequence consisting of from 1 to 40 amino acids, and $R^2$ is an amino acid sequence consisting of from 1 to 40 amino acids. In certain embodiments, the peptides can cover the whole B-domain of human FVIII protein.

In one embodiment, $R^1$ and $R^2$ are separately or both amino acid sequences consisting of from 1 to 80 amino acids. In another embodiment, $R^1$ and $R^2$ are separately or both amino acid sequences consisting of from 1 to 70 amino acids. In another embodiment, $R^1$ and $R^2$ are separately or both amino acid sequences consisting of from 1 to 60 amino acids. In another embodiment, $R^1$ and $R^2$ are separately or both amino acid sequences consisting of from 1 to 50 amino acids. In another embodiment, $R^1$ and $R^2$ are separately or both amino acid sequences consisting of from 1 to 40 amino acids. In another embodiment, $R^1$ and $R^2$ are separately or both amino acid sequences consisting of from 1 to 30 amino acids. In another embodiment, $R^1$ and $R^2$ are separately or both amino acid sequences consisting of from 1 to 20 amino acids. In another embodiment, $R^1$ and $R^2$ are separately or both amino acid sequences consisting of from 1 to 10 amino acids. In another embodiment, $R^1$ and $R^2$ are separately or both amino acid sequences consisting of from 1 to 5 amino acids. In yet other embodiment, $R^1$ and $R^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In other embodiments, the peptides can be produced using recombinant techniques. In one embodiment, the present invention includes a method of making a FVIII peptide, the method comprising the steps of: a) providing a culture of cells comprising a vector that encodes a FVIII peptide, the FVIII peptide having the sequence: $(R^1)_x$—P—$(R^2)_y$, wherein P is an amino acid sequence having at least 85% identity to a sequence of at least nine consecutive amino acids of a sequence selected from SEQ ID NOS:68, 344, and 740, R1 is an amino acid sequence consisting of from 1 to 80 amino acids; R2 is an amino acid sequence consisting of from 1 to 80 amino acids; and each of x and y are independently zero or one. In one embodiment, $R^1$ is an amino acid sequence consisting of from 1 to 40 amino acids, and $R^2$ is an amino acid sequence consisting of from 1 to 40 amino acids. In certain embodiments, the peptides can cover the whole B-domain of human FVIII protein.

In one embodiment, $R^1$ and $R^2$ are separately or both amino acid sequences consisting of from 1 to 80 amino acids. In another embodiment, $R^1$ and $R^2$ are separately or both amino acid sequences consisting of from 1 to 70 amino acids. In another embodiment, $R^1$ and $R^2$ are separately or both amino acid sequences consisting of from 1 to 60 amino acids. In another embodiment, $R^1$ and $R^2$ are separately or both amino acid sequences consisting of from 1 to 50 amino acids. In another embodiment, $R^1$ and $R^2$ are separately or both amino acid sequences consisting of from 1 to 40 amino acids. In another embodiment, $R^1$ and $R^2$ are separately or both amino acid sequences consisting of from 1 to 30 amino acids. In another embodiment, $R^1$ and $R^2$ are separately or both amino acid sequences consisting of from 1 to 20 amino acids. In another embodiment, $R^1$ and $R^2$ are separately or both amino acid sequences consisting of from 1 to 10 amino acids. In another embodiment, $R^1$ and $R^2$ are separately or both amino acid sequences consisting of from 1 to 5 amino acids. In yet other embodiment, $R^1$ and $R^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In one embodiment, the present invention provides a method for making a FVIII peptide, the method comprising the steps of: a) providing a culture of cells comprising a polynucleotide that encodes a FVIII peptide, the peptide having the sequence: $(R^1)_x$—P—$(R^2)_y$, wherein P is an amino acid sequence having at least 85% identity to a sequence of at least nine consecutive amino acids of a sequence selected from SEQ ID NOS:10, 68, 159, 250, 344, 477, 568, 659, and 740, R1 is an amino acid sequence consisting of from 1 to 80 amino acids; R2 is an amino acid sequence consisting of from 1 to 80 amino acids; and each of x and y are independently zero or one; and b) expressing the peptide in the culture of cells.

In one embodiment, $R^1$ and $R^2$ are separately or both amino acid sequences consisting of from 1 to 80 amino acids. In another embodiment, $R^1$ and $R^2$ are separately or both amino acid sequences consisting of from 1 to 70 amino acids. In another embodiment, $R^1$ and $R^2$ are separately or both amino acid sequences consisting of from 1 to 60 amino acids. In another embodiment, $R^1$ and $R^2$ are separately or both amino acid sequences consisting of from 1 to 50 amino acids. In another embodiment, $R^1$ and $R^2$ are separately or both amino acid sequences consisting of from 1 to 40 amino acids. In another embodiment, $R^1$ and $R^2$ are separately or both amino acid sequences consisting of from 1 to 30 amino acids. In another embodiment, $R^1$ and $R^2$ are separately or both amino acid sequences consisting of from 1 to 20 amino acids. In another embodiment, $R^1$ and $R^2$ are separately or both amino acid sequences consisting of from 1 to 10 amino acids. In another embodiment, $R^1$ and $R^2$ are separately or both amino acid sequences consisting of from 1 to 5 amino acids. In yet other embodiment, $R^1$ and $R^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In one embodiment of the methods for producing FVIII peptides, the FVIII peptide consists of from 9 to 150 amino acids. In another embodiment, the FVIII peptide consists of from 9 to 100 amino acids. In another embodiment, the FVIII peptide consists of from 9 to 50 amino acids. In another embodiment, the FVIII peptide consists of from 9 to 25 amino acids. In yet other embodiments, the FVIII peptide consists of from 9 to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, or 180 amino acids.

The FVIII peptides of the present invention can be produced by expression in a suitable prokaryotic or eukaryotic host system. Examples of eukaryotic cells include, without limitation, mammalian cells, such as CHO, COS, HEK 293, BHK, SK-Hep, and HepG2; insect cells, for example SF9 cells, SF21 cells, S2 cells, and High Five cells; and yeast cells, for example *Saccharomyces* or *Schizosaccharomyces* cells. In one embodiment, the FVIII peptides can be expressed in bacterial cells, yeast cells, insect cells, avian cells, mammalian cells, and the like. In some embodiments, the peptides can be expressed in a human cell line, a hamster cell line, or a murine cell line. In one particular embodiment, the cell line is a CHO, BHK, or HEK cell line.

A wide variety of vectors can be used for the expression of the FVIII peptides and can be selected from eukaryotic and prokaryotic expression vectors. The vectors will include a nucleotide sequence necessary for expression of at least one of the FVIII peptides disclosed herein. Examples of vectors for prokaryotic expression include plasmids such as pRSET, pET, pBAD, etc., wherein the promoters used in prokaryotic expression vectors include lac, trc, trp, recA, araBAD, etc. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

In some embodiments of the present invention, the nucleic acid sequences for producing the FVIII peptides further include other sequences suitable for a controlled expression of a protein such as promoter sequences, enhancers, TATA boxes, transcription initiation sites, polylinkers, restriction sites, poly-A-sequences, protein processing sequences, selection markers, and the like which are generally known to a person of ordinary skill in the art.

The culture media used for the cells producing the FVIII peptides can be based on a suitable basal medium well known in the art, e.g., DMEM, Ham's F12, Medium 199, McCoy, or RPMI. The basal medium can include a number of ingredients, including amino acids, vitamins, organic and inorganic salts, and sources of carbohydrate. Each ingredient can be present in an amount that supports the cultivation of a cell, such amounts being generally known to a person skilled in the art. The medium can include auxiliary substances, such as buffer substances, e.g., sodium bicarbonate, antioxidants, stabilizers to counteract mechanical stress, or protease inhibitors. If necessary, a non-ionic surfactant such as copolymers and/or mixtures of polyethylene glycols and polypropylene glycols can be added.

In some embodiments, the culture medium is free of exogenously added protein. "Protein free" and related terms refers to protein that is from a source exogenous to or other than the cells in the culture, which naturally shed proteins during growth. In another embodiment, the culture medium is polypeptide free. In another embodiment, the culture medium is serum free. In another embodiment the culture medium is animal protein free. In another embodiment the culture medium is animal component free. In another embodiment, the culture medium contains protein, e.g., animal protein from serum such as fetal calf serum. In another embodiment, the culture has recombinant proteins exogenously added. In another embodiment, the proteins are from a certified pathogen free animal.

Methods of preparing animal protein-free and chemically defined culture mediums are known in the art, for example in US 2008/0009040 and US 2007/0212770, which are both incorporated herein for all purposes. In one embodiment, the culture medium used in the methods described herein is animal protein-free or oligopeptide-free medium. In certain embodiments, the culture medium may be chemically defined. The term "chemically defined" as used herein shall mean, that the medium does not comprise any undefined supplements, such as, for example, extracts of animal components, organs, glands, plants, or yeast. Accordingly, each component of a chemically defined medium is accurately defined.

In certain embodiments, the methods of the present invention can include the use of a cell-culture system operated in, for example, batch-mode, semi-batch mode, fed-batch mode, or continuous mode. A batch culture can be a large scale cell culture in which a cell inoculum is cultured to a maximum density in a tank or fermenter, and harvested and processed as a batch. A fed-batch culture can be a batch culture which is supplied with either fresh nutrients (e.g., growth-limiting substrates) or additives (e.g., precursors to products). A continuous culture can be a suspension culture that is continuously supplied with nutrients by the inflow of fresh medium, wherein the culture volume is usually constant. Similarly, continuous fermentation can refer to a process in which cells or micro-organisms are maintained in culture in the exponential growth phase by the continuous addition of fresh medium that is exactly balanced by the removal of cell suspension from the bioreactor. Furthermore, the stirred-tank reactor system can be used for suspension, perfusion, chemostatic, and/or microcarrier cultures. Generally, the stirred-tank reactor system can be operated as any conventional stirred-tank reactor with any type of agitator such as a Rushton, hydrofoil, pitched blade, or marine.

In certain embodiments, the cell-culture methods of the invention can include the use of a microcarrier. In some embodiments, the cell-cultures of the embodiments can be performed in large bioreactors under conditions suitable for providing high volume-specific culture surface areas to achieve high cell densities and protein expression. One means for providing such growth conditions is to use microcarriers for cell-culture in stirred tank bioreactors. The concept of cell-growth on microcarriers was first described by van Wezel (van Wezel, A. L., *Nature* 216:64-5 (1967)) and allows for cell attachment on the surface of small solid particles suspended in the growth medium. These methods provide for high surface-to-volume ratios and thus allow for efficient nutrient utilization. Furthermore, for expression of secreted proteins in eukaryotic cell lines, the increased surface-to-volume ratio allows for higher levels of secretion and thus higher protein yields in the supernatant of the culture. Finally, these methods allow for the easy scale-up of eukaryotic expression cultures.

The cells expressing FVIII peptides can be bound to a spherical or a porous microcarrier during cell culture growth. The microcarrier can be a microcarrier selected from the group of microcarriers based on dextran, collagen, plastic, gelatine and cellulose and others. It is also possible to grow the cells to a biomass on spherical microcarriers and subculture the cells when they have reached final fermenter biomass and prior to production of the expressed protein on a porous microcarrier or vice versa. Suitable spherical microcarriers can include smooth surface microcarriers, such as Cytodex™ 1, Cytodex™ 2, and Cytodex™ 3 (GE Healthcare) and macroporous microcarriers such as Cytopore™ 1, Cytopore™ 2, Cytoline™ 1, and Cytoline™ 2 (GE Healthcare).

One of ordinary skill in the art will appreciate that the FVIII peptides produced by the synthetic and/or recombinant methods described above can include natural and/or non-natural amino acids, including amino acid analogs and/or amino acid mimetics.

V. Factor FVIII Peptide Compositions for Inducing Immune Tolerance

In another aspect, the FVIII peptides disclosed herein can be included in a pharmaceutical composition. In one embodiment, the present invention provides a pharmaceutical composition comprising a Factor $VIII^{246-266}$ peptide, Factor $VIII^{1401-1424}$ peptide, or Factor $VIII^{102-122}$ peptide, as described herein.

In one embodiment, the pharmaceutical composition comprises a Factor $VIII^{246-266}$ peptide as described herein. In another embodiment, the pharmaceutical composition further comprises a FVIII$^{474-494}$ peptide, FVIII$^{540-560}$ peptide, FVIII$^{1785-1805}$ peptide, FVIII$^{2025-2045}$ peptide, FVIII$^{2160-2180}$ peptide, FVIII$^{102-119}$ peptide, FVIII$^{1401-1424}$ peptide, FVIII$^{102-122}$ peptide, or second FVIII$^{246-266}$ peptide, as described herein.

In another embodiment, the pharmaceutical composition comprises a Factor VIII$^{1401-1424}$ peptide as described herein. In another embodiment, the pharmaceutical composition further comprises a FVIII$^{474-494}$ peptide, FVIII$^{540-560}$ peptide, FVIII$^{1785-1805}$ peptide, FVIII$^{2025-2045}$ peptide, FVIII$^{2160-2180}$ peptide, FVIII$^{102-119}$ peptide, FVIII$^{246-266}$ peptide, FVIII$^{102-122}$ peptide, or second FVIII$^{1401-1424}$ peptide, as described herein.

In another embodiment, the pharmaceutical composition comprises a Factor VIII$^{102-122}$ peptide as described herein. In another embodiment, the pharmaceutical composition further comprises a FVIII$^{474-494}$ peptide, FVIII$^{540-560}$ peptide, FVIII$^{1785-1805}$ peptide, FVIII$^{2025-2045}$ peptide, FVIII$^{2160-2180}$ peptide, FVIII$^{102-119}$ peptide, FVIII$^{246-266}$ peptide, FVIII$^{1401-1424}$ peptide, or second FVIII$^{102-122}$ peptide, as described herein.

In a specific embodiment, the present invention provides a pharmaceutical composition comprising a peptide having the sequence: $(R^1)_x$—P—$(R^2)_y$, wherein P is an amino acid sequence having at least 85% identity to a sequence of at least nine consecutive amino acids of a sequence selected from SEQ ID NOS:68, 344, and 740, $R^1$ is an amino acid sequence consisting of from 1 to 80 amino acids; $R^2$ is an amino acid sequence consisting of from 1 to 80 amino acids; and each of x and y are independently zero or one. In one embodiment, $R^1$ is an amino acid sequence consisting of from 1 to 40 amino acids, and $R^2$ is an amino acid sequence consisting of from 1 to 40 amino acids.

In one embodiment, $R^1$ and $R^2$ are separately or both amino acid sequences consisting of from 1 to 80 amino acids. In another embodiment, $R^1$ and $R^2$ are separately or both amino acid sequences consisting of from 1 to 70 amino acids. In another embodiment, $R^1$ and $R^2$ are separately or both amino acid sequences consisting of from 1 to 60 amino acids. In another embodiment, $R^1$ and $R^2$ are separately or both amino acid sequences consisting of from 1 to 50 amino acids. In another embodiment, $R^1$ and $R^2$ are separately or both amino acid sequences consisting of from 1 to 40 amino acids. In another embodiment, $R^1$ and $R^2$ are separately or both amino acid sequences consisting of from 1 to 30 amino acids. In another embodiment, $R^1$ and $R^2$ are separately or both amino acid sequences consisting of from 1 to 20 amino acids. In another embodiment, $R^1$ and $R^2$ are separately or both amino acid sequences consisting of from 1 to 10 amino acids. In another embodiment, $R^1$ and $R^2$ are separately or both amino acid sequences consisting of from 1 to 5 amino acids. In yet other embodiment, $R^1$ and $R^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In one embodiment, the FVIII peptide consists of from 9 to 150 amino acids. In another embodiment, the FVIII peptide consists of from 9 to 100 amino acids. In another embodiment, the FVIII peptide consists of from 9 to 50 amino acids. In another embodiment, the FVIII peptide consists of from 9 to 25 amino acids. In yet other embodiments, the FVIII peptide consists of from 9 to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, or 180 amino acids.

In a specific embodiment, the pharmaceutical composition further comprises a second polypeptide, the second polypeptide having the sequence: $(R^1)_x$—P—$(R^2)_y$, wherein P is an amino acid sequence having at least 85% identity to a sequence of at least nine consecutive amino acids of a sequence selected from SEQ ID NOS:10, 68, 159, 250, 344, 477, 568, 659, and 740, $R^1$ is an amino acid sequence consisting of from 1 to 80 amino acids; $R^2$ is an amino acid sequence consisting of from 1 to 80 amino acids; and each of x and y are independently zero or one. In one embodiment, $R^1$ is an amino acid sequence consisting of from 1 to 40 amino acids, and $R^2$ is an amino acid sequence consisting of from 1 to 40 amino acids.

In one embodiment, $R^1$ and $R^2$ are separately or both amino acid sequences consisting of from 1 to 80 amino acids. In another embodiment, $R^1$ and $R^2$ are separately or both amino acid sequences consisting of from 1 to 70 amino acids. In another embodiment, $R^1$ and $R^2$ are separately or both amino acid sequences consisting of from 1 to 60 amino acids. In another embodiment, $R^1$ and $R^2$ are separately or both amino acid sequences consisting of from 1 to 50 amino acids. In another embodiment, $R^1$ and $R^2$ are separately or both amino acid sequences consisting of from 1 to 40 amino acids. In another embodiment, $R^1$ and $R^2$ are separately or both amino acid sequences consisting of from 1 to 30 amino acids. In another embodiment, $R^1$ and $R^2$ are separately or both amino acid sequences consisting of from 1 to 20 amino acids. In another embodiment, $R^1$ and $R^2$ are separately or both amino acid sequences consisting of from 1 to 10 amino acids. In another embodiment, $R^1$ and $R^2$ are separately or both amino acid sequences consisting of from 1 to 5 amino acids. In yet other embodiment, $R^1$ and $R^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In one embodiment, the second FVIII peptide consists of from 9 to 150 amino acids. In another embodiment, the second FVIII peptide consists of from 9 to 100 amino acids. In another embodiment, the second FVIII peptide consists of from 9 to 50 amino acids. In another embodiment, the second FVIII peptide consists of from 9 to 25 amino acids. In yet other embodiments, the second FVIII peptide consists of from 9 to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, or 180 amino acids.

A. Administration

To administer compositions to a human or test animal, in one aspect, the compositions can include one or more pharmaceutically acceptable carriers. The phrases "pharmaceutically" or "pharmacologically" acceptable refer to molecular entities and compositions that are stable, inhibit protein or peptide degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like.

The pharmaceutical compositions can be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Dosages and frequency of administration will depend upon various factors generally appreciated by those of skill in the art, including, e.g., the severity of a patient's hemophilia and/or whether immune tolerance is more effectively induced using larger or smaller doses. Typical daily doses may range from about 0.01 to 100 mg/kg. Doses in the range of 0.07-700 mg FVIII peptide per week may be effective and well tolerated, although even higher weekly doses may be appropriate and/or well tolerated. The principal determining factor in defining the appropriate dose is the amount of a particular FVIII peptide necessary to be therapeutically effective in a particular context. Repeated administrations may be required in order to achieve longer lasting immune tolerance. Single or multiple administrations of the compositions can be carried out with the dose levels and pattern being selected by the treating physician.

In one aspect, compositions of the invention can be administered by bolus. As another example, a FVIII peptide can be administered as a one-time dose. Those of ordinary skill in the art will readily optimize effective dosages and administration regimens as determined by good medical practice and the clinical condition of the individual patient. The frequency of dosing depends on the route of administration. The optimal pharmaceutical composition is determined by one skilled in the art depending upon the route of administration and desired dosage. See e.g., Remington: The Science and Practice of Pharmacy (Remington the Science and Practice of Pharmacy), 21st Ed. (2005, Lippincott Williams & Wilkins) the disclosure of which is hereby incorporated by reference. Such compositions influence the physical state, stability, rate of in vivo release, and rate of in vivo clearance of the administered agents. Depending on the route of administration, a suitable dose is calculated according to body weight, body surface area or organ size. Appropriate dosages may be ascertained through use of established assays for determining blood level dosages in conjunction with appropriate dose-response data. The final dosage regimen is determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors.

In some embodiments, the compositions comprising a FVIII peptide disclosed herein are lyophilized prior to administration. Lyophilization is carried out using techniques common in the art and should be optimized for the composition being developed, as described, e.g., in Tang et al., *Pharm Res.* 21:191-200, (2004) and Chang et al., *Pharm Res.* 13:243-9 (1996). Methods of preparing pharmaceutical compositions can include one or more of the following steps: adding a stabilizing agent to the mixture prior to lyophilizing, adding at least one agent selected from a bulking agent, an osmolarity regulating agent, and a surfactant to the mixture prior to lyophilization. A lyophilized formulation is, in one aspect, at least comprised of one or more of a buffer, a bulking agent, and a stabilizer. In this aspect, the utility of a surfactant is evaluated and selected in cases where aggregation during the lyophilization step or during reconstitution becomes an issue. An appropriate buffering agent is included to maintain the formulation within stable zones of pH during lyophilization.

The standard reconstitution practice for lyophilized material is to add back a volume of pure water or sterile water for injection (WFI) (typically equivalent to the volume removed during lyophilization), although dilute solutions of antibacterial agents are sometimes used in the production of pharmaceuticals for parenteral administration. Accordingly, methods are provided for preparation of reconstituted FVIII peptide compositions comprising the step of adding a diluent to a lyophilized FVIII peptide compositions.

In some embodiments, the lyophilized material may be reconstituted as an aqueous solution. A variety of aqueous carriers, e.g., sterile water for injection, water with preservatives for multi dose use, or water with appropriate amounts of surfactants (for example, an aqueous suspension that contains the active compound in admixture with excipients suitable for the manufacture of aqueous suspensions). In various aspects, such excipients are suspending agents, for example and without limitation, sodium carboxymethylcellulose, methylcellulose, hydroxypropylmethylcellulose, sodium alginate, polyvinylpyrrolidone, gum tragacanth and gum acacia; dispersing or wetting agents are a naturally-occurring phosphatide, for example and without limitation, lecithin, or condensation products of an alkylene oxide with fatty acids, for example and without limitation, polyoxyethylene stearate, or condensation products of ethylene oxide with long chain aliphatic alcohols, for example and without limitation, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example and without limitation, polyethylene sorbitan monooleate. In various aspects, the aqueous suspensions also contain one or more preservatives, for example and without limitation, ethyl, or n-propyl, p-hydroxybenzoate.

VI. Methods of Treatment

The present invention further relates to methods of treating a patient having a disease associated with the FVIII protein, such as hemophilia A or acquired hemophilia. Such methods can include administration of at least one of the FVIII peptides disclosed herein. In particular, the pharmaceutical compositions including at least one of the FVIII peptides can be administered to induce immune tolerance to FVIII protein in a patient.

In some embodiments, the methods for inducing an immune tolerance to FVIII can include preventing FVIII inhibitor development after administration of FVIII. The term "preventing" refers to allowing no substantially detectable immune response to FVIII. For example, a patient prior to administration of FVIII protein may not have any detectable anti-FVIII antibodies. However, after administration therapy with FVIII protein the level of detectable anti-FVIII antibodies can increase if a FVIII peptide is not administered to induce immune tolerance. The administration of the FVIII peptides disclosed herein can induce immune tolerance, thereby treating a patient having hemophilia.

In other embodiments, the methods for inducing an immune tolerance to FVIII protein can include treating patients already having established FVIII inhibitors. In these embodiments, administration of the FVIII peptide can reduce or eliminate the presence of anti-FVIII antibodies. The term "reduce" means a partial reduction in an immune response to FVIII protein. In certain embodiments, reducing the immune response can include a 10%, 20%, 30%, 40%, 50%, 60%, 70%, 80%, or 90% reduction in the immune response as compared to the level of the immune response in a patient prior to administration of the FVIII peptide. For example, the percentage reduction can be analyzed by measuring the amount of anti-FVIII antibodies present in the blood prior to and after administration of the FVIII peptide, using standard methods for determining the amount of FVIII antibodies present. In other embodiments, reduction of the immune response can include measuring reduced levels of CD4+ T cells specific for FVIII or FVIII specific B cells secreting FVIII antibodies, or a combination of all three, the T cells, B cells, and the anti-FVIII antibodies. Immune cells, such as T cells and B specific for FVIII can be isolated using methods generally known in the art.

In one aspect, the present invention includes a method of inducing immune tolerance to FVIII in a subject, the method comprising a step of administering to the subject a therapeutically effective amount of a pharmaceutical composition comprising a FVIII peptide as described herein. In a specific embodiment, the FVIII peptide is a Factor VIII$^{246-266}$ peptide, Factor VIII$^{1401-1424}$ peptide, or Factor VIII$^{102-122}$ peptide, as described herein.

In one embodiment, the method comprises a step of administering to the subject a therapeutically effective amount of a pharmaceutical composition comprising a Factor VIII$^{246-266}$ peptide as described herein. In another embodiment, the pharmaceutical composition further comprises a FVIII$^{474-494}$ peptide, FVIII$^{540-560}$ peptide, FVIII$^{1785-1805}$ peptide, FVIII$^{2025-2045}$ peptide, FVIII$^{2160-2180}$ peptide, FVIII$^{102-119}$ peptide, FVIII$^{1401-1424}$ peptide, FVIII$^{102-122}$ peptide, or second FVIII$^{246-266}$ peptide, as described herein.

In another embodiment, the method comprises a step of administering to the subject a therapeutically effective amount of a pharmaceutical composition comprising a Factor VIII$^{1401-1424}$ peptide as described herein. In another embodiment, the pharmaceutical composition further comprises a FVIII$^{474-494}$ peptide, FVIII$^{540-560}$ peptide, FVIII$^{1785-1805}$ peptide, FVIII$^{2025-2045}$ peptide, FVIII$^{2160-2180}$ peptide, FVIII$^{102-119}$ peptide, FVIII$^{246-266}$ peptide, FVIII$^{102-122}$ peptide, or second FVIII$^{1401-1424}$ peptide, as described herein.

In another embodiment, the method comprises a step of administering to the subject a therapeutically effective amount of a pharmaceutical composition comprising a Factor VIII$^{102-122}$ peptide as described herein. In another embodiment, the pharmaceutical composition further comprises a FVIII$^{474-494}$ peptide, FVIII$^{540-560}$ peptide, FVIII$^{1785-1805}$ peptide, FVIII$^{2025-2045}$ peptide, FVIII$^{2160-2180}$ peptide, FVIII$^{102-119}$ peptide, FVIII$^{246-266}$ peptide, FVIII$^{1401-1424}$ peptide, or second FVIII$^{102-122}$ peptide, as described herein.

In one embodiment, the present invention provides a method for inducing an immune tolerance to a FVIII protein, the method comprising administering to the subject a therapeutically effective amount of a pharmaceutical composition comprising a peptide having the sequence: $(R^1)_x$—P—$(R^2)_y$, wherein P is an amino acid sequence having at least 85% identity to a sequence of at least nine consecutive amino acids of a sequence selected from SEQ ID NOS:68, 344, and 740, R1 is an amino acid sequence consisting of from 1 to 80 amino acids; R2 is an amino acid sequence consisting of from 1 to 80 amino acids; and each of x and y are independently zero or one; thereby inducing an immune tolerance to FVIII protein in the subject. In certain embodiments, $R^1$ is an amino acid sequence consisting of from 1 to 40 amino acids, and $R^2$ is an amino acid sequence consisting of from 1 to 40 amino acids.

In one embodiment, $R^1$ and $R^2$ are separately or both amino acid sequences consisting of from 1 to 80 amino acids. In another embodiment, $R^1$ and $R^2$ are separately or both amino acid sequences consisting of from 1 to 70 amino acids. In another embodiment, $R^1$ and $R^2$ are separately or both amino acid sequences consisting of from 1 to 60 amino acids. In another embodiment, $R^1$ and $R^2$ are separately or both amino acid sequences consisting of from 1 to 50 amino acids. In another embodiment, $R^1$ and $R^2$ are separately or both amino acid sequences consisting of from 1 to 40 amino acids. In another embodiment, $R^1$ and $R^2$ are separately or both amino acid sequences consisting of from 1 to 30 amino acids. In another embodiment, $R^1$ and $R^2$ are separately or both amino acid sequences consisting of from 1 to 20 amino acids. In another embodiment, $R^1$ and $R^2$ are separately or both amino acid sequences consisting of from 1 to 10 amino acids. In another embodiment, $R^1$ and $R^2$ are separately or both amino acid sequences consisting of from 1 to 5 amino acids. In yet other embodiment, $R^1$ and $R^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In one embodiment, the FVIII peptide consists of from 9 to 150 amino acids. In another embodiment, the FVIII peptide consists of from 9 to 100 amino acids. In another embodiment, the FVIII peptide consists of from 9 to 50 amino acids. In another embodiment, the FVIII peptide consists of from 9 to 25 amino acids. In yet other embodiments, the FVIII peptide consists of from 9 to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, or 180 amino acids.

The methods of inducing immune tolerance can further include combination therapies in which several peptides can be administered to induce immune tolerance. In one embodiment, the method of inducing immune tolerance further comprises administering a therapeutically effective amount of at least a second peptide having the sequence: $(R^1)_x$—P—$(R^2)_y$, wherein P is an amino acid sequence having at least 85% identity to a sequence of at least nine consecutive amino acids of a sequence selected from SEQ ID NOS:10, 68, 159, 250, 344, 477, 568, 659, and 740, R1 is an amino acid sequence consisting of from 1 to 80 amino acids; R2 is an amino acid sequence consisting of from 1 to 80 amino acids; and each of x and y are independently zero or one; thereby inducing an immune tolerance to FVIII protein in the subject. In certain embodiments, $R^1$ is an amino acid sequence consisting of from 1 to 40 amino acids, and $R^2$ is an amino acid sequence consisting of from 1 to 40 amino acids. In a particular embodiment, the second peptide consists of from 9 to 80 amino acids. In another particular embodiment, any additional amino acids in the second peptide are natural amino acids. In another particular embodiment, the second peptide consists of from 9 to 40 amino acids in length. In a specific embodiment, the second peptide consists of from 9 to 80 amino acids in length and any additional amino acids in the second peptide are natural amino acids.

In one embodiment, $R^1$ and $R^2$ are separately or both amino acid sequences consisting of from 1 to 80 amino acids. In another embodiment, $R^1$ and $R^2$ are separately or both amino acid sequences consisting of from 1 to 70 amino acids. In another embodiment, $R^1$ and $R^2$ are separately or both amino acid sequences consisting of from 1 to 60 amino acids. In another embodiment, $R^1$ and $R^2$ are separately or both amino acid sequences consisting of from 1 to 50 amino acids. In another embodiment, $R^1$ and $R^2$ are separately or both amino acid sequences consisting of from 1 to 40 amino acids. In another embodiment, $R^1$ and $R^2$ are separately or both amino acid sequences consisting of from 1 to 30 amino acids. In another embodiment, $R^1$ and $R^2$ are separately or both amino acid sequences consisting of from 1 to 20 amino acids. In another embodiment, $R^1$ and $R^2$ are separately or both amino acid sequences consisting of from 1 to 10 amino acids. In another embodiment, $R^1$ and $R^2$ are separately or both amino acid sequences consisting of from 1 to 5 amino acids. In yet other embodiment, $R^1$ and $R^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In one embodiment, the second FVIII peptide consists of from 9 to 150 amino acids. In another embodiment, the FVIII peptide consists of from 9 to 100 amino acids. In another embodiment, the FVIII peptide consists of from 9 to 50 amino acids. In another embodiment, the FVIII peptide consists of from 9 to 25 amino acids. In yet other embodiments, the FVIII peptide consists of from 9 to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, or 180 amino acids.

In a specific embodiment of method for inducing an immune tolerance, wherein the administered pharmaceutical composition comprises a peptide where P is an amino acid sequence having at least 85% identity to a sequence of at least nine consecutive amino acids of SEQ ID NO:68, 344, or 740, the composition further comprises a second polypeptide, the second polypeptide having the sequence: $(R^1)_x$—P—$(R^2)_y$, wherein P is an amino acid sequence having at least 85% identity to a sequence of at least nine consecutive amino acids of a sequence selected from SEQ ID NOS:10, 68, 159, 250, 344, 477, 568, 659, and 740, $R^1$ is an amino acid sequence consisting of from 1 to 80 amino acids; $R^2$ is an amino acid sequence consisting of from 1 to 80 amino acids; and each of x and y are independently zero or one.

In one embodiment, $R^1$ and $R^2$ are separately or both amino acid sequences consisting of from 1 to 80 amino acids. In another embodiment, $R^1$ and $R^2$ are separately or both amino acid sequences consisting of from 1 to 70 amino acids. In another embodiment, $R^1$ and $R^2$ are separately or both amino acid sequences consisting of from 1 to 60 amino acids. In another embodiment, $R^1$ and $R^2$ are separately or both amino acid sequences consisting of from 1 to 50 amino acids. In another embodiment, $R^1$ and $R^2$ are separately or both amino acid sequences consisting of from 1 to 40 amino acids. In another embodiment, $R^1$ and $R^2$ are separately or both amino acid sequences consisting of from 1 to 30 amino acids. In another embodiment, $R^1$ and $R^2$ are separately or both amino acid sequences consisting of from 1 to 20 amino acids. In another embodiment, $R^1$ and $R^2$ are separately or both amino acid sequences consisting of from 1 to 10 amino acids. In another embodiment, $R^1$ and $R^2$ are separately or both amino acid sequences consisting of from 1 to 5 amino acids. In yet other embodiment, $R^1$ and $R^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In one aspect, the present invention provides the use of a FVIII peptide as described herein for the manufacture of a medicament for the treatment of an immune response generated against FVIII replacement therapy. In a specific embodiment, the FVIII peptide is a $FVIII^{1401-1424}$ peptide. In a related aspect, the present invention provides the use of a FVIII peptide as described herein for the manufacture of a medicament for the prevention of an immune response generated against FVIII replacement therapy. In a specific embodiment, the FVIII peptide is a $FVIII^{1401-1424}$ peptide.

In one aspect, the present invention provides a FVIII peptide for use as a medicament. In a specific embodiment, the invention provides a polypeptide having the sequence $(R^1)_x$—P—$(R^2)_y$, wherein P is an amino acid sequence having at least 85% identity to a sequence of at least nine consecutive amino acids of a Factor $VIII^{1401-1424}$ peptide having the sequence: QANRSPLPIAKVSSFPSIRPIYLT (SEQ ID NO:344), $R^1$ is an amino acid sequence consisting of from 1 to 80 amino acids, and $R^2$ is an amino acid sequence consisting of from 1 to 80 amino acids, wherein each of x and y are independently zero or one for use as a medicament.

In one aspect, the present invention provides a FVIII peptide for the treatment of an immune response generated against FVIII replacement therapy. In a specific embodiment, the invention provides a polypeptide having the sequence $(R^1)_x$—P—$(R^2)_y$, wherein P is an amino acid sequence having at least 85% identity to a sequence of at least nine consecutive amino acids of a Factor $VIII^{1401-1424}$ peptide having the sequence: QANRSPLPIAKVSSFPSIRPIYLT (SEQ ID NO:344), $R^1$ is an amino acid sequence consisting of from 1 to 80 amino acids, and $R^2$ is an amino acid sequence consisting of from 1 to 80 amino acids, wherein each of x and y are independently zero or one for the treatment of an immune response generated against FVIII replacement therapy.

In one aspect, the present invention provides a FVIII peptide for the prevention of an immune response generated against FVIII replacement therapy. In a specific embodiment, the invention provides a polypeptide having the sequence $(R^1)_x$—P—$(R^2)_y$, wherein P is an amino acid sequence having at least 85% identity to a sequence of at least nine consecutive amino acids of a Factor $VIII^{1401-1424}$ peptide having the sequence: QANRSPLPIAKVSSFPSIRPIYLT (SEQ ID NO:344), $R^1$ is an amino acid sequence consisting of from 1 to 80 amino acids, and $R^2$ is an amino acid sequence consisting of from 1 to 80 amino acids, wherein each of x and y are independently zero or one for the prevention of an immune response generated against FVIII replacement therapy.

VII. Immunodiagnostics

In one aspect, the present invention provides a method for monitoring FVIII replacement therapy or FVIII immune tolerance induction therapy in a subject in need thereof by identifying the presence or level of a FVIII inhibitory antibody or CD4+ T cell that is specific for FVIII in a biological sample taken from the subject.

In one embodiment, the method comprises a method for monitoring FVIII replacement therapy in a subject in need thereof, the method comprising: contacting a biological sample from the subject with a FVIII$^{246-266}$ peptide, FVIII$^{1401-1424}$ peptide, or FVIII$^{102-122}$ peptide, as described herein; and detecting a complex formed between the FVIII peptide and a FVIII inhibitory antibody present in the sample. In one embodiment, the method comprises determining the level of FVIII inhibitory antibody in the sample. In yet another embodiment, the method comprises determining the level of a FVIII inhibitory antibody in at least two samples taken from the subject at different times, and comparing the levels of FVIII inhibitory antibody between the two samples, wherein an increase in the level of antibody over time is indicative of the formation of an immune response against FVIII administered to the subject during the course of the FVIII replacement therapy.

In another embodiment, the method comprises a method for monitoring FVIII immune tolerance induction therapy in a subject in need thereof, the method comprising: contacting a biological sample from the subject with a FVIII$^{246-266}$ peptide, FVIII$^{1401-1424}$ peptide, or FVIII$^{102-122}$ peptide, as described herein; and detecting a complex formed between the FVIII peptide and a FVIII inhibitory antibody present in the sample. In one embodiment, the method comprises determining the level of FVIII inhibitory antibody in the sample. In yet another embodiment, the method comprises determining the level of a FVIII inhibitory antibody in at least two samples taken from the subject at different times, and comparing the levels of FVIII inhibitory antibody between the two samples, wherein an decrease in the level of antibody over time is indicative of the formation of immune tolerance to FVIII protein in the subject.

In one embodiment, the method comprises a method for monitoring FVIII replacement therapy in a subject in need thereof, the method comprising: contacting a biological sample from the subject with a FVIII$^{246-266}$ peptide, FVIII$^{1401-1424}$ peptide, or FVIII$^{102-122}$ peptide, as described herein; and detecting a complex formed between the FVIII peptide and a CD4+ T cell specific for FVIII present in the sample. In one embodiment, the method comprises determining the level of CD4+ T cell specific for FVIII in the sample. In yet another embodiment, the method comprises determining the level of a CD4+ T cell specific for FVIII in at least two samples taken from the subject at different times, and comparing the levels of CD4+ T cell specific for FVIII between the two samples, wherein an increase in the level of antibody over time is indicative of the formation of an immune response against FVIII administered to the subject during the course of the FVIII replacement therapy. In a specific embodiment, the FVIII peptide is complexed with a MHC class II multimer.

In another embodiment, the method comprises a method for monitoring FVIII immune tolerance induction therapy in a subject in need thereof, the method comprising: contacting a biological sample from the subject with a FVIII$^{246-266}$ peptide, FVIII$^{1401-1424}$ peptide, or FVIII$^{102-122}$ peptide, as described herein; and detecting a complex formed between the FVIII peptide and a CD4+ T cell specific for FVIII present in the sample. In one embodiment, the method comprises determining the level of CD4+ T cell specific for FVIII in the sample. In yet another embodiment, the method comprises determining the level of a CD4+ T cell specific for FVIII in at least two samples taken from the subject at different times, and comparing the levels of CD4+ T cell specific for FVIII between the two samples, wherein an decrease in the level of antibody over time is indicative of the formation of immune tolerance to FVIII protein in the subject. In a specific embodiment, the FVIII peptide is complexed with a MHC class II multimer.

As will be appreciated by one of ordinary skill in the art, immune monitoring can be used, for example, to facilitate treatment of patients with hemophilia. For example, immune monitoring can be used to identify whether administration of the peptides and/or compositions of the present invention is preventing or reducing an immune response to a FVIII product. Dosage amounts and/or dosage intervals can be optimized by immune monitoring. In some embodiments, administration dosages can be tailored specifically based on results from immune monitoring of prevention or reduction of anti-FVIII antibodies. In addition, dosing intervals as well as dosage amounts can be determined for a particular patient or group of patients.

A. Methods of Identifying FVIII-Specific T Cells

In another aspect, the present invention includes methods of identifying antigen-specific T cells, more specifically T cells that are specific for FVIII protein and the FVIII peptides described herein. Such methods can, for example, be used for immunodiagnostics, such as immune monitoring of a patient. In one embodiment, the present invention includes a method of identifying FVIII peptide-specific T cells, the method comprising a) combining a plurality of CD4$^+$ T cells with a FVIII peptide complexed with a MHC class II multimer, the FVIII peptide having the sequence: $(R^1)_x$—P—$(R^2)_y$, wherein P is an amino acid sequence having at least 85% identity to a sequence of at least nine consecutive amino acids of a sequence selected from SEQ ID NOS:68, 344, and 740, R1 is an amino acid sequence consisting of from 1 to 80 amino acids; R2 is an amino acid sequence consisting of from 1 to 80 amino acids; and each of x and y are independently zero or one; and b) identifying at least one of the members of the plurality of CD4$^+$ T cells that is specific for the peptide complexed with the MHC class II multimer. In some embodiments, $R^1$ is an amino acid sequence consisting of from 1 to 40 amino acids, and $R^2$ is an amino acid sequence consisting of from 1 to 40 amino acids.

In certain embodiments, the FVIII peptides disclosed herein can be used to generate reagents suitable for direct staining of FVIII specific T cells. For example, the MHC class II multimers that present the FVIII peptides of the present invention can include a variety of forms, such as a MHC class II tetramer. These MHC class II molecules can be further modified to include a diagnostic agent. Alternatively, the FVIII peptides that complex with the MHC class II multimers can include a diagnostic agent. The diagnostic agents (i.e., a detectable moiety) used in the present invention can include those generally known in the art for immune monitoring. For example, FVIII-specific T cells can be identified and/or isolated based on detection of a diagnostic agent associated with a FVIII peptide described herein that is presented by an MHC class II tetramer. Suitable diagnostic agents can include a fluorescent agent, a chemiluminescent agent, a radioactive agent, a contrast agent, and the like. Suitable fluorescence agents include those typically used in flow cytometry and can include but are not limited to fluorescein isothiocyanate, R-Phycoerythrin, Texas Red, Cy3, Cy5, Cy5.5, Cy7, and derivatives thereof.

In certain embodiments, the FVIII peptide can be used to re-stimulate CD4$^+$ FVIII-specific T cells in vitro. In these embodiments, the re-stimulation of the T cells could be monitored by detection of proliferation, secretion of cytokines or chemokines, or the up- or down-regulation of certain activation markers that are known to those skilled in the art.

In some embodiments, detection of the diagnostic agent can be used to identify and/or isolate T cells specific for the FVIII peptides disclosed herein. For example, the reagents above (e.g., peptide, MHC class II tetramer, and diagnostic agent) can be used to track FVIII-specific T cells in vitro or ex vivo. In certain embodiments, the T cells can be further isolated and characterized using various techniques generally known in the art, such as flow cytometry, e.g., fluorescence activated cell sorting (FACS), and/or PCR, e.g., single cell PCR.

To carry out immune monitoring analyses, T cells that bind the FVIII peptide-MHC class II multimer complex include CD4$^+$ T cells and can be isolated from a patient using a variety of methods generally known in the art. For example, T cells can be isolated and purified from a patient's blood, organs or other tissue. Isolation and identification of the FVIII specific T cells can be used for a variety of immunodiagnostic applications. In certain embodiments, the FVIII peptides or associated reagents can be used for immune monitoring of FVIII-specific T cells during clinical development of a new FVIII product. In other embodiments, the FVIII peptides can be used for immune monitoring of FVIII-specific T cells during immune tolerance induction therapy. In yet other embodiments, the FVIII peptides can be used for immune monitoring of FVIII-specific T cells during FVIII treatment.

VIII. Kits of the Invention

The present invention also provides kits to facilitate and/or standardize use of compositions provided by the present invention, as well as facilitate the methods of the present invention. Materials and reagents to carry out these various methods can be provided in kits to facilitate execution of the methods. As used herein, the term "kit" is used in reference to a combination of articles that facilitate a process, assay, analysis or manipulation.

Kits can contain chemical reagents (e.g., FVIII peptides or polynucleotides encoding FVIII peptides) as well as other components. In addition, kits of the present invention can also include, for example but are not limited to, apparatus and reagents for sample collection and/or purification, apparatus and reagents for product collection and/or purification, reagents for bacterial cell transformation, reagents for eukaryotic cell transfection, previously transformed or transfected host cells, sample tubes, holders, trays, racks, dishes, plates, instructions to the kit user, solutions, buffers or other chemical reagents, suitable samples to be used for standardization, normalization, and/or control samples. Kits of the present invention can also be packaged for convenient storage and safe shipping, for example, in a box having a lid.

In some embodiments, for example, kits of the present invention can provide a FVIII peptide of the invention, a polynucleotide vector (e.g., a plasmid) encoding a FVIII peptide of the invention, bacterial cell strains suitable for propagating the vector, and reagents for purification of expressed fusion proteins. Alternatively, a kit of the present invention can provide the reagents necessary to conduct mutagenesis of a FVIII peptide in order to generate a conservatively modified variant of the FVIII peptide.

A kit can contain one or more compositions of the invention, for example, one or a plurality of FVIII peptides or one or a plurality of polynucleotides that encode the FVIII peptides. Alternatively, a kit can contain reagents (e.g., peptide, MHC class II tetramer, and diagnostic agent) for carrying out immune monitoring of a patient.

A kit of the invention also can contain one or a plurality of recombinant nucleic acid molecules, which encode the FVIII peptides, which can be the same or different, and can further include, for example, an operatively linked second polynucleotide containing or encoding a restriction endonuclease recognition site or a recombinase recognition site, or any polypeptide of interest. In addition, the kit can contain instructions for using the components of the kit, particularly the compositions of the invention that are contained in the kit.

IX. Specific Embodiments

In one embodiment, the present invention provides a FVIII peptide consisting of a consecutive sequence of nine amino acids that is at least 85% identical to nine consecutive amino acids in the following amino acid sequence: QANRSPLPI-AKVSSFPSIRPIYLT (SEQ ID NO:344), and the peptide has the formula: (R1)$_x$-peptide-(R2)$_y$, wherein R1 is an amino acid sequence consisting of from 1 to 80 amino acids; R2 is an amino acid sequence consisting of from 1 to 80 amino acids; and each of the subscripts x and y are independently zero or one.

In one embodiment, R$^1$ and R$^2$ are separately or both amino acid sequences consisting of from 1 to 80 amino acids. In another embodiment, R$^1$ and R$^2$ are separately or both amino acid sequences consisting of from 1 to 70 amino acids. In another embodiment, R$^1$ and R$^2$ are separately or both amino acid sequences consisting of from 1 to 60 amino acids. In another embodiment, R$^1$ and R$^2$ are separately or both amino acid sequences consisting of from 1 to 50 amino acids. In another embodiment, R$^1$ and R$^2$ are separately or both amino acid sequences consisting of from 1 to 40 amino acids. In another embodiment, R$^1$ and R$^2$ are separately or both amino acid sequences consisting of from 1 to 30 amino acids. In another embodiment, R$^1$ and R$^2$ are separately or both amino acid sequences consisting of from 1 to 20 amino acids. In another embodiment, R$^1$ and R$^2$ are separately or both amino acid sequences consisting of from 1 to 10 amino acids. In another embodiment, R$^1$ and R$^2$ are separately or both amino acid sequences consisting of from 1 to 5 amino acids. In yet other embodiment, R$^1$ and R$^2$ are separately or both amino acid sequences consisting of from 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In a specific embodiment of the peptides described above, x and y are both zero.

In a specific embodiment of the peptides described above, x is one and y is zero.

In a specific embodiment of the peptides described above, x is zero and y is one.

In a specific embodiment of the peptides described above, x and y are both one.

In a specific embodiment of the peptides described above, the consecutive sequence of nine amino acids is identical to nine consecutive amino acids in the amino acid sequence: QANRSPLPIAKVSSFPSIRPIYLT (SEQ ID NO:344).

In one embodiment, the present invention provides a pharmaceutical composition comprising a FVIII peptide consisting of a consecutive sequence of nine amino acids that is at least 85% identical to nine consecutive amino acids in the following amino acid sequence: QANRSPLPIAKVSSFP-SIRPIYLT (SEQ ID NO:344), and the peptide has the formula: (R1)$_x$-peptide-(R2)$_y$, wherein R1 is an amino acid sequence consisting of from 1 to 80 amino acids; R2 is an amino acid sequence consisting of from 1 to 80 amino acids; and each of the subscripts x and y are independently zero or one.

In a specific embodiment of the compositions described above, x and y are both zero.

In a specific embodiment of the compositions described above, x is one and y is zero.

In a specific embodiment of the compositions described above, x is zero and y is one.

In a specific embodiment of the compositions described above, x and y are both one.

In a specific embodiment of the compositions described above, the composition further comprises at least one peptide consisting of a consecutive sequence of nine amino acids that is at least 85% identical to nine consecutive amino acids in an amino acid sequence independently selected from the group consisting of GEVGDTLLIIFKNQASRPYNI (SEQ ID NO:159), PTKSDPRCLTRYYSSFVNMER (SEQ ID NO:250), EVEDNIMVTFRNQASRPYSFY (SEQ ID NO:477), LHAGMSTLFLVYSNKCQTPLG (SEQ ID NO:568), NPPIIARYIRLHPTHYSIRST (SEQ ID NO:659), TVVITLKNMASHPVSLHA (SEQ ID NO:10), AWPKMHTVNGYVNRSLPGLIG (SEQ ID NO:68), and TVVITLKNMASHPVSLHAVGV (SEQ ID NO:740), wherein the at least one peptide is a maximum of 80 amino acids in length and wherein any additional amino acids in the at least one peptide are natural amino acids.

In one embodiment, the present invention provides a method of inducing an immune tolerance to FVIII in a subject, the method comprising a step of administering to the subject a therapeutically effective amount of a pharmaceutical composition comprising a FVIII peptide consisting of a consecutive sequence of nine amino acids that is at least 85% identical to nine consecutive amino acids in the following amino acid sequence: QANRSPLPIAKVSSFPSIRPIYLT (SEQ ID NO: 344), and the peptide has the formula: $(R1)_x$-peptide-$(R2)_y$, wherein R1 is an amino acid sequence consisting of from 1 to 80 amino acids; R2 is an amino acid sequence consisting of from 1 to 80 amino acids; each of the subscripts x and y are independently zero or one; and thereby inducing an immune tolerance to FVIII protein in the subject.

In a specific embodiment of the methods described above, the pharmaceutical composition further comprises at least one peptide consisting of a consecutive sequence of nine amino acids that is at least 85% identical to nine consecutive amino acids in an amino acid sequence independently selected from the group consisting of GEVGDTLLIIFKNQASRPYNI (SEQ ID NO:159), PTKSDPRCLTRYYSSFVNMER (SEQ ID NO:250), EVEDNIMVTFRNQASRPYSFY (SEQ ID NO:477), LHAGMSTLFLVYSNKCQTPLG (SEQ ID NO:568), NPPIIARYIRLHPTHYSIRST (SEQ ID NO:659), TVVITLKNMASHPVSLHA (SEQ ID NO:10), AWPKMHTVNGYVNRSLPGLIG (SEQ ID NO:68), and TVVITLKNMASHPVSLHAVGV (SEQ ID NO:740), wherein the at least one peptide is a maximum of 80 amino acids in length and wherein any additional amino acids in the at least one peptide are natural amino acids.

In a specific embodiment of the methods described above, administration of the pharmaceutical composition prevents development anti-FVIII antibodies in the subject.

In a specific embodiment of the methods described above, administration of the pharmaceutical composition reduces an amount anti-FVIII antibodies present in the subject.

In a specific embodiment of the methods described above, x and y are both zero.

In a specific embodiment of the methods described above, x is one and y is zero.

In a specific embodiment of the methods described above, x is zero and y is one.

In a specific embodiment of the methods described above, x and y are both one.

In one embodiment, the present invention provides a method of making a FVIII peptide, the method comprising the steps of: a) providing a culture of cells comprising a vector that encodes a FVIII peptide consisting of a consecutive sequence of nine amino acids that is at least 85% identical to nine consecutive amino acids in the following amino acid sequence: QANRSPLPIAKVSSFPSIRPIYLT (SEQ ID NO: 344), and the peptide has the formula: $(R1)_x$-peptide-$(R2)_y$, wherein R1 is an amino acid sequence consisting of from 1 to 80 amino acids; R2 is an amino acid sequence consisting of from 1 to 80 amino acids; each of the subscripts x and y are independently zero or one; and b) expressing the peptide in the culture of cells.

In a specific embodiment of the methods described above, x and y are both zero.

In a specific embodiment of the methods described above, x is one and y is zero.

In a specific embodiment of the methods described above, x is zero and y is one.

In a specific embodiment of the methods described above, x and y are both one.

In one embodiment, the present invention provides a method of making a FVIII peptide, the method comprising: a) synthesizing a peptide using solid phase or liquid phase synthesis techniques, the peptide consisting of a consecutive sequence of nine amino acids that is at least 85% identical to nine consecutive amino acids in the following amino acid sequence: QANRSPLPIAKVSSFPSIRPIYLT (SEQ ID NO: 344), and the peptide has the formula: $(R1)_x$-peptide-$(R2)_y$, wherein R1 is an amino acid sequence consisting of from 1 to 80 amino acids; R2 is an amino acid sequence consisting of from 1 to 80 amino acids; and each of the subscripts x and y are independently zero or one.

In a specific embodiment of the methods described above, x and y are both zero.

In a specific embodiment of the methods described above, x is one and y is zero.

In a specific embodiment of the methods described above, x is zero and y is one.

In a specific embodiment of the methods described above, x and y are both one.

In one embodiment, the present invention provides a method of identifying FVIII peptide-specific T cells, the method comprising: a) combining a plurality of CD4+ T cells with a FVIII peptide complexed with a MHC class II multimer, the FVIII peptide consisting of a consecutive sequence of nine amino acids that is at least 85% identical to nine consecutive amino acids in the following amino acid sequence: QANRSPLPIAKVSSFPSIRPIYLT (SEQ ID NO: 344), and the peptide has the formula: $(R1)_x$-peptide-$(R2)_y$, wherein R1 is an amino acid sequence consisting of from 1 to 80 amino acids; R2 is an amino acid sequence consisting of from 1 to 80 amino acids; each of the subscripts x and y are independently zero or one; and b) identifying at least one of the members of the plurality of CD4+ T cells that is specific for the peptide complexed with the MHC class II multimer.

In a specific embodiment of the methods described above, the MHC class II multimer is a MHC class II tetramer.

In a specific embodiment of the methods described above, the peptide or MHC class II multimer further comprises a diagnostic agent.

In a specific embodiment of the methods described above, the diagnostic agent identifies the at least one member of the plurality of CD4+ T cells that is specific for the peptide.

In a specific embodiment of the methods described above, the method further comprises isolating the at least one member of the plurality of CD4+ T cells that is specific for the peptide based on detection of the diagnostic agent.

In a specific embodiment of the methods described above, the at least one member of the plurality of CD4+ T cells is isolated with flow cytometry.

In a specific embodiment of the methods described above, x and y are both zero.

In a specific embodiment of the methods described above, x is one and y is zero.

In a specific embodiment of the methods described above, x is zero and y is one.

In a specific embodiment of the methods described above, x and y are both one.

The present invention will now be further illustrated in the following examples, without being limited thereto.

X. Examples

Example 1

To better mimic the human MHC class II molecule for identifying FVIII peptides, a mouse model was developed for hemophilia A with a chimeric MHC class II molecule carrying a human HLA-DRB1*1501 specific binding site. This mouse was backcrossed to a mouse carrying a complete knock out of all murine MHC class II genes (Reipert et al., *J. Thromb. Haemost.* 7 Suppl. 1:92-97 (2009)). In this new transgenic mouse model, all CD4+ T cell responses are driven by the human MHC class II molecule. This mouse model was used to identify FVIII peptides presented by HLA-DRB1*1501 that drive anti-FVIII immune responses in these mice.

Materials and Methods

FVIII: Recombinant human FVIII (rFVIII) was produced as an albumin free bulk product (Baxter Neuchatel) and clinical sucrose formulated FVIII product (Advate, Baxter, Westlake Village, Calif.).

Hemophilic HLA-DRB15 E17 mice: HLA-DRB1*1501$^{+/-}$ E17$^{-/-}$ mice as described in Reipert et al., *J. Thromb. Haemost.* 7 Suppl. 1:92-97 (2009). Mice were all male and aged 8 to 12 weeks at the beginning of the experiment.

Immunization with human recombinant FVIII: HLA-DRB1*1501$^{+/-}$ E17$^{-/-}$ mice received between 4 and 8 intravenous or subcutaneous doses of 0.2 µg or 1 µg human rFVIII at weekly intervals. rFVIII was diluted in the original formulation buffer or Dulbecco phosphate buffered saline containing calcium and magnesium (DPBS; Sigma Aldrich, St. Louis, Mo., USA).

Cell preparation: Spleens were obtained 3 to 7 days after the last immunization with rFVIII. Spleen cells were minced and passed through a 70 µm cell strainer (Becton Dickinson, Franklin Lakes, N.J.). Single cells were collected in culture medium: RPMI 1640 medium (Gibco, Invitrogen, Life Technologies, Carlsbad, Calif.) supplemented with 10% preselected fetal calf serum (FCS; Hyclone, Logan, Utah), 2 mM L-glutamine, 100 U/mL penicillin/streptomycin (both from Gibco), and $5\times10^{-5}$ M mercaptoethanol (Sigma-Aldrich). Erythrocytes were lysed using hypotonic buffer (pH 7.2) composed of 0.15 M ammonium chloride, 10 mM potassium bicarbonate (both from Merck, Darmstadt, Germany) and 0.1 mM ethylene-diaminetetraacetic acid (Sigma-Aldrich). Cells were washed and counted using a Coulter Counter Z1.

Generation of T-Cell Hybridomas for Identifying FVIII Peptides

In vitro re-stimulation of spleen cells with human rFVIII: Spleen cells were re-stimulated in the presence of 20 µg/ml human FVIII in culture medium at a concentration of $1.5\times10^6$ cells/ml for 3 or 10 days. The culture medium for the 10 day cultures was renewed after 6 days.

Fusion of mouse T cells with BW cells: In vitro re-stimulated spleen cell cultures and BW cells (α-β-) were washed twice with serum free culture medium and then combined at a ratio of 1:3 to 1:10 (T cells:BW cells). The BW cell line was derived from a mouse AKR/J T cell lymphoma. These cells had no T cell receptors on their surface (α-β-) and therefore any T cell receptor after fusion with mouse spleen cells is derived from the fusion partner. After a third washing step, the supernatant was removed. Fusion conditions were achieved by the addition of 1 ml polyethyleneglycol (PEG; 50% Hybi-Max, Sigma-Aldrich) within 45 seconds. After another 45 seconds of incubation, subsequently 50 ml serum free medium were added to prevent the toxic effect of PEG. Cells were centrifuged at 1300 rpm for 5 minutes without a break to form a very firm pellet. The supernatant was discarded and 50 ml new serum free medium were added very slowly aiming not to dislocate the pellet. The tube was inverted slowly until the cells were re-suspended and centrifuged as before. This was done twice to remove the remaining PEG. The last washing step was done with culture medium. Cells were then diluted and cultured in 96 well plates. The culture medium was changed for selection medium (HAT medium supplement, Sigma Aldrich) after 48 hours and growing clones were selected. Selection medium was kept for 2 weeks, afterwards the medium was subsequently changed back to normal culture medium.

Peptide specificity of FVIII-specific T cell hybridomas: T cell hybridomas were tested for their antigen specificity. For this purpose, $1\times10^5$ cells were co-cultured with antigen presenting cells. We used either $5\times10^4$ Mgar cells (expressing HLA-DRB1*1501) or $1\times10^5$ whole spleen cells derived from naïve HLA-DRB1*1501-E17 mice. Cells were incubated with 10 µg/ml human rFVIII or with 1 µg/ml peptide/peptide pools for 24 hours at 37° C., 5% $CO_2$. The supernatants were collected and IL-2 release into the culture supernatant was measured using an IL-2 ELISA (BioLegend, San Diego, Calif.) or IL-2 Bio-Plex (Bio-Rad Laboratories, Hercules, Calif.) according to the manufacturers protocol. IL-2 release $\geq$20 pg/ml in the presence but not absence of FVIII (or peptides) was considered positive, or alternatively a 10 fold increase in IL-2 release in the presence of FVIII compared to the absence of FVIII was considered positive.

Subcloning of T cell hybridomas: To assure that each clone represents only one type of T cell, hybridoma all clones were sub-cloned. Hybridoma clones were diluted to a limiting dilution of 0.3 cells/well and co-cultured with 200 feeder cells/well. Feeder cells were produced by Mitomycin C treatment of the fusion partner cells, BW cells. $2\times10^8$ BW cells were treated with 0.1 mg Mitomycin C from *Streptomyces caespitosus* (Sigma Aldrich) for 10 minutes at room temperature and 25 minutes at 37° C., 5% $CO_2$ in the incubator. Five growing subclones per clone were selected and tested for their FVIII specificity.

FVIII peptide pools used to specify specificities of T cell hybridomas: FVIII peptide pools were produced using the SPOT synthesis method as described by Ay et al. (*Biopolymers* 88:64-75 (2007)). Briefly, 15 mer peptides were synthesized on two identical cellulose membranes. Membranes were cut into vertical and horizontal stripes. Peptides were released from the membrane stripes and used as peptide pools in specificity tests as described above. Peptides were dissolved in DMSO (Hybrimax, Sigma Aldrich) and further diluted with PBS.

Results

181 FVIII specific hybridoma clones were produced. These clones were screened against a peptide library spanning the whole human FVIII. 15 mer peptides offset by three amino acids were used. Using this approach, six different FVIII regions that contained peptides bound to HLA-DRB1*1501 were identified. We found two peptide domains within the A1 domain, two peptides within the A2 domain, one within the B domain, two within the A3 domain and one peptide domain within the C1 domain of human FVIII. FVIII peptide$^{1401-1424}$ has not been described before (Table 11). Peptides FVIII$^{474-494}$, FVIII$^{545-559}$, FVIII$^{1788-1802}$ and FVIII$^{2161-2175}$ were already identified in WO 09/071,886, which used computer prediction programs followed by the T cell hybridoma technology. Peptide FVIII$^{2636-2644}$ was disclosed in WO 03/087161. Peptide FVIII$^{2161-2186}$ was already published by Jacquemin et al., Blood 101(4):1351-8 (2003).

TABLE 11

Regions of FVIII including T-cell epitopes

| Regions including T cell epitopes | Amino Acid Sequence | Disclosures |
|---|---|---|
| FVIII$^{102-122}$ | TVVITLKNMASHPVSLHAVGV (SEQ ID NO: 740) | FVIII$^{107-121}$ disclosed in WO 2003/087161<br>FVIII$^{100-118}$ disclosed in WO/2009/095646 |
| FVIII$^{246-266}$ | AWPKMHTVNGYVNRSLPGLIG (SEQ ID NO: 68) | FVIII$^{253-268}$ disclosed in WO/2009/095646 |
| FVIII$^{474-494}$ | GEVGDTLLIIFKNQASRPYNI (SEQ ID NO: 159) | FVIII$^{475-495}$ Disclosed in WO 2009/071886<br>FVIII$^{477-495}$ disclosed in WO/2009/095646 |
| FVIII$^{540-560}$ | PTKSDPRCLTRYYSSFVNMER (SEQ ID NO: 250) | FVIII$^{542-562}$ Disclosed in WO 2009/071886<br>FVIII$^{545-569}$ disclosed in WO/2009/095646 |
| FVIII$^{1401-1424}$ | QANRSPLPIAKVSSFPSIRPIYLT (SEQ ID NO: 344) | A peptide of the present invention |
| FVIII$^{1785-1805}$ | EVEDNIMVTFRNQASRPYSFY (SEQ ID NO: 477) | FVIII$^{1785-1805}$ Disclosed in WO 2009/071886<br>FVIII$^{1787-1805}$ disclosed in WO/2009/095646 |
| FVIII$^{2025-2045}$ | LHAGMSTLFLVYSNKCQTPLG (SEQ ID NO: 568) | FVIII$^{2030-2044}$ Disclosed in WO 2003/087161 |
| FVIII$^{2160-2180}$ | NPPIIARYIRLHPTHYSIRST (SEQ ID NO: 659) | FVIII$^{2158-2178}$ Disclosed in WO 2009/071886 and FVIII$^{2161-2180}$ Jacquemin et al., supra.<br>FVIII$^{2164-2183}$ Disclosed in WO 2003/087161<br>FVIII$^{2164-2188}$ disclosed in WO/2009/095646 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An immunogenic peptide consisting of the amino acid sequence:

$$(R^1)_x-P-(R^2)_y,$$

wherein:

P is an amino acid sequence having at least 90% and not more than 99% identity to SEQ ID NO:344;

$R^1$ is an amino acid sequence consisting of from 1 to 80 amino acids;

$R^2$ is an amino acid sequence consisting of from 1 to 80 amino acids; and each of x and y are independently zero or one.

2. The immunogenic peptide of claim 1, wherein x and y are both zero.

3. The immunogenic peptide of claim 1, wherein x is one and y is zero.

4. The immunogenic peptide of claim 1, wherein x is zero and y is one.

5. The immunogenic peptide of claim 1, wherein x and y are both one.

6. The immunogenic peptide of claim 1, wherein the peptide consists of from 24 to 100 amino acids.

7. The immunogenic peptide of claim 6, wherein the peptide consists of from 24 to 50 amino acids.

8. The immunogenic peptide of claim 6, wherein the peptide consists of 24 amino acids.

9. A composition comprising an immunogenic peptide according to claim 1.

10. The composition of claim 9, wherein the composition is formulated for pharmaceutical administration.

11. The composition of claim 9, wherein the composition further comprises a second polypeptide, the second polypeptide consisting of the amino acid sequence:

$$(R^1)_x-P-(R^2)_y,$$

wherein:

P is an amino acid sequence having at least 85% identity to at least nine consecutive amino acids of a sequence selected from SEQ ID NOS:10, 68, 159, 250, 344, 477, 568, 659, and 740;

$R^1$ is an amino acid sequence consisting of from 1 to 80 amino acids;

$R^2$ is an amino acid sequence consisting of from 1 to 80 amino acids; and each of x and y are independently zero or one.

12. A method of inducing an immune tolerance to FVIII in a subject in need thereof, the method comprising a step of:

administering to the subject a therapeutically effective amount of a peptide according to claim 1.

13. A method of making a FVIII peptide, the method comprising the steps of:
   a) providing a culture of cells comprising a polynucleotide that encodes a FVIII peptide according to claim 1; and
   b) expressing the peptide in the culture of cells.

14. A method of identifying a FVIII peptide-specific T cell, the method comprising:
   a) combining a plurality of $CD4^+$ T cells with a peptide complexed with a MHC class II multimer, wherein the peptide is a FVIII peptide according to claim 1; and
   b) identifying at least one of the members of the plurality of $CD4^+$ T cells that is specific for the peptide complexed with the MHC class II multimer.

15. The method of claim 14, wherein the MHC class II multimer is a MHC class II tetramer.

16. The method of claim 14, wherein the peptide or MHC class II multimer further comprises a detectable moiety.

17. The method of claim 14, further comprising isolating the at least one $CD4^+$ T cells that is specific for the peptide.

18. The method of claim 17, wherein the $CD4^{4+}$ T cells is isolated using flow cytometry.

19. A fusion protein comprising:
   an immunogenic Factor VIII peptide according to claim 1; and
   a second peptide.

20. The fusion protein of claim 19, wherein the second peptide is a reporter peptide.

* * * * *

SEQUENCE LISTING

<160> NUMBER OF SEQ ID NOS: 773

<210> SEQ ID NO 1
<211> LENGTH: 9
<212> TYPE: PRT
<213> ORGANISM: Homo sapiens

<400> SEQUENCE: 1

Thr Val Val Ile Thr Leu Lys Asn Met
1               5

<210> SEQ ID NO 2
<211> LENGTH: 10
<212> TYPE: PRT
<213> ORGANISM: Homo sapiens

<400> SEQUENCE: 2

Thr Val Val Ile Thr Leu Lys Asn Met Ala
1               5                   10

<210> SEQ ID NO 3
<211> LENGTH: 11
<212> TYPE: PRT
<213> ORGANISM: Homo sapiens

<400> SEQUENCE: 3

Thr Val Val Ile Thr Leu Lys Asn Met Ala Ser
1               5                   10

<210> SEQ ID NO 4
<211> LENGTH: 12
<212> TYPE: PRT
<213> ORGANISM: Homo sapiens

<400> SEQUENCE: 4

Thr Val Val Ile Thr Leu Lys Asn Met Ala Ser His
1               5                   10

<210> SEQ ID NO 5
<211> LENGTH: 13
<212> TYPE: PRT
<213> ORGANISM: Homo sapiens

<400> SEQUENCE: 5

Thr Val Val Ile Thr Leu Lys Asn Met Ala Ser His Pro
1               5                   10

<210> SEQ ID NO 6
<211> LENGTH: 14
<212> TYPE: PRT
<213> ORGANISM: Homo sapiens

<400> SEQUENCE: 6

Thr Val Val Ile Thr Leu Lys Asn Met Ala Ser His Pro Val
1               5                   10

<210> SEQ ID NO 7
<211> LENGTH: 15
<212> TYPE: PRT
<213> ORGANISM: Homo sapiens

<400> SEQUENCE: 7

Thr Val Val Ile Thr Leu Lys Asn Met Ala Ser His Pro Val Ser
1               5                   10                  15

<210> SEQ ID NO 8
<211> LENGTH: 16
<212> TYPE: PRT
<213> ORGANISM: Homo sapiens

<400> SEQUENCE: 8

```
Thr Val Val Ile Thr Leu Lys Asn Met Ala Ser His Pro Val Ser Leu
1               5                   10                  15
```

<210> SEQ ID NO 9
<211> LENGTH: 17
<212> TYPE: PRT
<213> ORGANISM: Homo sapiens

<400> SEQUENCE: 9

```
Thr Val Val Ile Thr Leu Lys Asn Met Ala Ser His Pro Val Ser Leu
1               5                   10                  15
His
```

<210> SEQ ID NO 10
<211> LENGTH: 18
<212> TYPE: PRT
<213> ORGANISM: Homo sapiens

<400> SEQUENCE: 10

```
Thr Val Val Ile Thr Leu Lys Asn Met Ala Ser His Pro Val Ser Leu
1               5                   10                  15
His Ala
```

<210> SEQ ID NO 11
<211> LENGTH: 9
<212> TYPE: PRT
<213> ORGANISM: Homo sapiens

<400> SEQUENCE: 11

```
Val Val Ile Thr Leu Lys Asn Met Ala
1               5
```

<210> SEQ ID NO 12
<211> LENGTH: 10
<212> TYPE: PRT
<213> ORGANISM: Homo sapiens

<400> SEQUENCE: 12

```
Val Val Ile Thr Leu Lys Asn Met Ala Ser
1               5                   10
```

<210> SEQ ID NO 13
<211> LENGTH: 11
<212> TYPE: PRT
<213> ORGANISM: Homo sapiens

<400> SEQUENCE: 13

```
Val Val Ile Thr Leu Lys Asn Met Ala Ser His
1               5                   10
```

<210> SEQ ID NO 14
<211> LENGTH: 12
<212> TYPE: PRT
<213> ORGANISM: Homo sapiens

<400> SEQUENCE: 14

```
Val Val Ile Thr Leu Lys Asn Met Ala Ser His Pro
1               5                   10
```

<210> SEQ ID NO 15
<211> LENGTH: 13
<212> TYPE: PRT
<213> ORGANISM: Homo sapiens

<400> SEQUENCE: 15

Val Val Ile Thr Leu Lys Asn Met Ala Ser His Pro Val
1               5                   10

<210> SEQ ID NO 16
<211> LENGTH: 14
<212> TYPE: PRT
<213> ORGANISM: Homo sapiens

<400> SEQUENCE: 16

Val Val Ile Thr Leu Lys Asn Met Ala Ser His Pro Val Ser
1               5                   10

<210> SEQ ID NO 17
<211> LENGTH: 15
<212> TYPE: PRT
<213> ORGANISM: Homo sapiens

<400> SEQUENCE: 17

Val Val Ile Thr Leu Lys Asn Met Ala Ser His Pro Val Ser Leu
1               5                   10                  15

<210> SEQ ID NO 18
<211> LENGTH: 16
<212> TYPE: PRT
<213> ORGANISM: Homo sapiens

<400> SEQUENCE: 18

Val Val Ile Thr Leu Lys Asn Met Ala Ser His Pro Val Ser Leu His
1               5                   10                  15

<210> SEQ ID NO 19
<211> LENGTH: 17
<212> TYPE: PRT
<213> ORGANISM: Homo sapiens

<400> SEQUENCE: 19

Val Val Ile Thr Leu Lys Asn Met Ala Ser His Pro Val Ser Leu His
1               5                   10                  15

Ala

<210> SEQ ID NO 20
<211> LENGTH: 9
<212> TYPE: PRT
<213> ORGANISM: Homo sapiens

<400> SEQUENCE: 20

Val Ile Thr Leu Lys Asn Met Ala Ser
1               5

<210> SEQ ID NO 21
<211> LENGTH: 10
<212> TYPE: PRT
<213> ORGANISM: Homo sapiens

<400> SEQUENCE: 21

Val Ile Thr Leu Lys Asn Met Ala Ser His
1               5                   10

<210> SEQ ID NO 22
<211> LENGTH: 11
<212> TYPE: PRT
<213> ORGANISM: Homo sapiens

```
<400> SEQUENCE: 22

Val Ile Thr Leu Lys Asn Met Ala Ser His Pro
1               5                   10

<210> SEQ ID NO 23
<211> LENGTH: 12
<212> TYPE: PRT
<213> ORGANISM: Homo sapiens

<400> SEQUENCE: 23

Val Ile Thr Leu Lys Asn Met Ala Ser His Pro Val
1               5                   10

<210> SEQ ID NO 24
<211> LENGTH: 13
<212> TYPE: PRT
<213> ORGANISM: Homo sapiens

<400> SEQUENCE: 24

Val Ile Thr Leu Lys Asn Met Ala Ser His Pro Val Ser
1               5                   10

<210> SEQ ID NO 25
<211> LENGTH: 14
<212> TYPE: PRT
<213> ORGANISM: Homo sapiens

<400> SEQUENCE: 25

Val Ile Thr Leu Lys Asn Met Ala Ser His Pro Val Ser Leu
1               5                   10

<210> SEQ ID NO 26
<211> LENGTH: 15
<212> TYPE: PRT
<213> ORGANISM: Homo sapiens

<400> SEQUENCE: 26

Val Ile Thr Leu Lys Asn Met Ala Ser His Pro Val Ser Leu His
1               5                   10                  15

<210> SEQ ID NO 27
<211> LENGTH: 16
<212> TYPE: PRT
<213> ORGANISM: Homo sapiens

<400> SEQUENCE: 27

Val Ile Thr Leu Lys Asn Met Ala Ser His Pro Val Ser Leu His Ala
1               5                   10                  15

<210> SEQ ID NO 28
<211> LENGTH: 9
<212> TYPE: PRT
<213> ORGANISM: Homo sapiens

<400> SEQUENCE: 28

Ile Thr Leu Lys Asn Met Ala Ser His
1               5

<210> SEQ ID NO 29
<211> LENGTH: 10
<212> TYPE: PRT
<213> ORGANISM: Homo sapiens

<400> SEQUENCE: 29
```

```
Ile Thr Leu Lys Asn Met Ala Ser His Pro
1               5                   10

<210> SEQ ID NO 30
<211> LENGTH: 11
<212> TYPE: PRT
<213> ORGANISM: Homo sapiens

<400> SEQUENCE: 30

Ile Thr Leu Lys Asn Met Ala Ser His Pro Val
1               5                   10

<210> SEQ ID NO 31
<211> LENGTH: 12
<212> TYPE: PRT
<213> ORGANISM: Homo sapiens

<400> SEQUENCE: 31

Ile Thr Leu Lys Asn Met Ala Ser His Pro Val Ser
1               5                   10

<210> SEQ ID NO 32
<211> LENGTH: 13
<212> TYPE: PRT
<213> ORGANISM: Homo sapiens

<400> SEQUENCE: 32

Ile Thr Leu Lys Asn Met Ala Ser His Pro Val Ser Leu
1               5                   10

<210> SEQ ID NO 33
<211> LENGTH: 14
<212> TYPE: PRT
<213> ORGANISM: Homo sapiens

<400> SEQUENCE: 33

Ile Thr Leu Lys Asn Met Ala Ser His Pro Val Ser Leu His
1               5                   10

<210> SEQ ID NO 34
<211> LENGTH: 15
<212> TYPE: PRT
<213> ORGANISM: Homo sapiens

<400> SEQUENCE: 34

Ile Thr Leu Lys Asn Met Ala Ser His Pro Val Ser Leu His Ala
1               5                   10                  15

<210> SEQ ID NO 35
<211> LENGTH: 9
<212> TYPE: PRT
<213> ORGANISM: Homo sapiens

<400> SEQUENCE: 35

Thr Leu Lys Asn Met Ala Ser His Pro
1               5

<210> SEQ ID NO 36
<211> LENGTH: 10
<212> TYPE: PRT
<213> ORGANISM: Homo sapiens

<400> SEQUENCE: 36

Thr Leu Lys Asn Met Ala Ser His Pro Val
```

<210> SEQ ID NO 37
<211> LENGTH: 11
<212> TYPE: PRT
<213> ORGANISM: Homo sapiens

<400> SEQUENCE: 37

Thr Leu Lys Asn Met Ala Ser His Pro Val Ser
1               5                   10

<210> SEQ ID NO 38
<211> LENGTH: 12
<212> TYPE: PRT
<213> ORGANISM: Homo sapiens

<400> SEQUENCE: 38

Thr Leu Lys Asn Met Ala Ser His Pro Val Ser Leu
1               5                   10

<210> SEQ ID NO 39
<211> LENGTH: 13
<212> TYPE: PRT
<213> ORGANISM: Homo sapiens

<400> SEQUENCE: 39

Thr Leu Lys Asn Met Ala Ser His Pro Val Ser Leu His
1               5                   10

<210> SEQ ID NO 40
<211> LENGTH: 14
<212> TYPE: PRT
<213> ORGANISM: Homo sapiens

<400> SEQUENCE: 40

Thr Leu Lys Asn Met Ala Ser His Pro Val Ser Leu His Ala
1               5                   10

<210> SEQ ID NO 41
<211> LENGTH: 9
<212> TYPE: PRT
<213> ORGANISM: Homo sapiens

<400> SEQUENCE: 41

Leu Lys Asn Met Ala Ser His Pro Val
1               5

<210> SEQ ID NO 42
<211> LENGTH: 10
<212> TYPE: PRT
<213> ORGANISM: Homo sapiens

<400> SEQUENCE: 42

Leu Lys Asn Met Ala Ser His Pro Val Ser
1               5                   10

<210> SEQ ID NO 43
<211> LENGTH: 11
<212> TYPE: PRT
<213> ORGANISM: Homo sapiens

<400> SEQUENCE: 43

Leu Lys Asn Met Ala Ser His Pro Val Ser Leu
1               5                   10

```
<210> SEQ ID NO 44
<211> LENGTH: 12
<212> TYPE: PRT
<213> ORGANISM: Homo sapiens

<400> SEQUENCE: 44

Leu Lys Asn Met Ala Ser His Pro Val Ser Leu His
1               5                   10

<210> SEQ ID NO 45
<211> LENGTH: 13
<212> TYPE: PRT
<213> ORGANISM: Homo sapiens

<400> SEQUENCE: 45

Leu Lys Asn Met Ala Ser His Pro Val Ser Leu His Ala
1               5                   10

<210> SEQ ID NO 46
<211> LENGTH: 9
<212> TYPE: PRT
<213> ORGANISM: Homo sapiens

<400> SEQUENCE: 46

Lys Asn Met Ala Ser His Pro Val Ser
1               5

<210> SEQ ID NO 47
<211> LENGTH: 10
<212> TYPE: PRT
<213> ORGANISM: Homo sapiens

<400> SEQUENCE: 47

Lys Asn Met Ala Ser His Pro Val Ser Leu
1               5                   10

<210> SEQ ID NO 48
<211> LENGTH: 11
<212> TYPE: PRT
<213> ORGANISM: Homo sapiens

<400> SEQUENCE: 48

Lys Asn Met Ala Ser His Pro Val Ser Leu His
1               5                   10

<210> SEQ ID NO 49
<211> LENGTH: 12
<212> TYPE: PRT
<213> ORGANISM: Homo sapiens

<400> SEQUENCE: 49

Lys Asn Met Ala Ser His Pro Val Ser Leu His Ala
1               5                   10

<210> SEQ ID NO 50
<211> LENGTH: 9
<212> TYPE: PRT
<213> ORGANISM: Homo sapiens

<400> SEQUENCE: 50

Asn Met Ala Ser His Pro Val Ser Leu
1               5

<210> SEQ ID NO 51
```

```
<211> LENGTH: 10
<212> TYPE: PRT
<213> ORGANISM: Homo sapiens

<400> SEQUENCE: 51

Asn Met Ala Ser His Pro Val Ser Leu His
1               5                   10

<210> SEQ ID NO 52
<211> LENGTH: 11
<212> TYPE: PRT
<213> ORGANISM: Homo sapiens

<400> SEQUENCE: 52

Asn Met Ala Ser His Pro Val Ser Leu His Ala
1               5                   10

<210> SEQ ID NO 53
<211> LENGTH: 9
<212> TYPE: PRT
<213> ORGANISM: Homo sapiens

<400> SEQUENCE: 53

Met Ala Ser His Pro Val Ser Leu His
1               5

<210> SEQ ID NO 54
<211> LENGTH: 10
<212> TYPE: PRT
<213> ORGANISM: Homo sapiens

<400> SEQUENCE: 54

Met Ala Ser His Pro Val Ser Leu His Ala
1               5                   10

<210> SEQ ID NO 55
<211> LENGTH: 9
<212> TYPE: PRT
<213> ORGANISM: Homo sapiens

<400> SEQUENCE: 55

Ala Ser His Pro Val Ser Leu His Ala
1               5

<210> SEQ ID NO 56
<211> LENGTH: 9
<212> TYPE: PRT
<213> ORGANISM: Homo sapiens

<400> SEQUENCE: 56

Ala Trp Pro Lys Met His Thr Val Asn
1               5

<210> SEQ ID NO 57
<211> LENGTH: 10
<212> TYPE: PRT
<213> ORGANISM: Homo sapiens

<400> SEQUENCE: 57

Ala Trp Pro Lys Met His Thr Val Asn Gly
1               5                   10

<210> SEQ ID NO 58
<211> LENGTH: 11
<212> TYPE: PRT
```

-continued

<213> ORGANISM: Homo sapiens

<400> SEQUENCE: 58

Ala Trp Pro Lys Met His Thr Val Asn Gly Tyr
1               5                   10

<210> SEQ ID NO 59
<211> LENGTH: 12
<212> TYPE: PRT
<213> ORGANISM: Homo sapiens

<400> SEQUENCE: 59

Ala Trp Pro Lys Met His Thr Val Asn Gly Tyr Val
1               5                   10

<210> SEQ ID NO 60
<211> LENGTH: 13
<212> TYPE: PRT
<213> ORGANISM: Homo sapiens

<400> SEQUENCE: 60

Ala Trp Pro Lys Met His Thr Val Asn Gly Tyr Val Asn
1               5                   10

<210> SEQ ID NO 61
<211> LENGTH: 14
<212> TYPE: PRT
<213> ORGANISM: Homo sapiens

<400> SEQUENCE: 61

Ala Trp Pro Lys Met His Thr Val Asn Gly Tyr Val Asn Arg
1               5                   10

<210> SEQ ID NO 62
<211> LENGTH: 15
<212> TYPE: PRT
<213> ORGANISM: Homo sapiens

<400> SEQUENCE: 62

Ala Trp Pro Lys Met His Thr Val Asn Gly Tyr Val Asn Arg Ser
1               5                   10                  15

<210> SEQ ID NO 63
<211> LENGTH: 16
<212> TYPE: PRT
<213> ORGANISM: Homo sapiens

<400> SEQUENCE: 63

Ala Trp Pro Lys Met His Thr Val Asn Gly Tyr Val Asn Arg Ser Leu
1               5                   10                  15

<210> SEQ ID NO 64
<211> LENGTH: 17
<212> TYPE: PRT
<213> ORGANISM: Homo sapiens

<400> SEQUENCE: 64

Ala Trp Pro Lys Met His Thr Val Asn Gly Tyr Val Asn Arg Ser Leu
1               5                   10                  15

Pro

<210> SEQ ID NO 65
<211> LENGTH: 18
<212> TYPE: PRT

<213> ORGANISM: Homo sapiens

<400> SEQUENCE: 65

Ala Trp Pro Lys Met His Thr Val Asn Gly Tyr Val Asn Arg Ser Leu
1               5                   10                  15

Pro Gly

<210> SEQ ID NO 66
<211> LENGTH: 19
<212> TYPE: PRT
<213> ORGANISM: Homo sapiens

<400> SEQUENCE: 66

Ala Trp Pro Lys Met His Thr Val Asn Gly Tyr Val Asn Arg Ser Leu
1               5                   10                  15

Pro Gly Leu

<210> SEQ ID NO 67
<211> LENGTH: 20
<212> TYPE: PRT
<213> ORGANISM: Homo sapiens

<400> SEQUENCE: 67

Ala Trp Pro Lys Met His Thr Val Asn Gly Tyr Val Asn Arg Ser Leu
1               5                   10                  15

Pro Gly Leu Ile
            20

<210> SEQ ID NO 68
<211> LENGTH: 21
<212> TYPE: PRT
<213> ORGANISM: Homo sapiens

<400> SEQUENCE: 68

Ala Trp Pro Lys Met His Thr Val Asn Gly Tyr Val Asn Arg Ser Leu
1               5                   10                  15

Pro Gly Leu Ile Gly
            20

<210> SEQ ID NO 69
<211> LENGTH: 9
<212> TYPE: PRT
<213> ORGANISM: Homo sapiens

<400> SEQUENCE: 69

Trp Pro Lys Met His Thr Val Asn Gly
1               5

<210> SEQ ID NO 70
<211> LENGTH: 10
<212> TYPE: PRT
<213> ORGANISM: Homo sapiens

<400> SEQUENCE: 70

Trp Pro Lys Met His Thr Val Asn Gly Tyr
1               5                   10

<210> SEQ ID NO 71
<211> LENGTH: 11
<212> TYPE: PRT
<213> ORGANISM: Homo sapiens

<400> SEQUENCE: 71

```
Trp Pro Lys Met His Thr Val Asn Gly Tyr Val
1               5                   10

<210> SEQ ID NO 72
<211> LENGTH: 12
<212> TYPE: PRT
<213> ORGANISM: Homo sapiens

<400> SEQUENCE: 72

Trp Pro Lys Met His Thr Val Asn Gly Tyr Val Asn
1               5                   10

<210> SEQ ID NO 73
<211> LENGTH: 13
<212> TYPE: PRT
<213> ORGANISM: Homo sapiens

<400> SEQUENCE: 73

Trp Pro Lys Met His Thr Val Asn Gly Tyr Val Asn Arg
1               5                   10

<210> SEQ ID NO 74
<211> LENGTH: 14
<212> TYPE: PRT
<213> ORGANISM: Homo sapiens

<400> SEQUENCE: 74

Trp Pro Lys Met His Thr Val Asn Gly Tyr Val Asn Arg Ser
1               5                   10

<210> SEQ ID NO 75
<211> LENGTH: 15
<212> TYPE: PRT
<213> ORGANISM: Homo sapiens

<400> SEQUENCE: 75

Trp Pro Lys Met His Thr Val Asn Gly Tyr Val Asn Arg Ser Leu
1               5                   10                  15

<210> SEQ ID NO 76
<211> LENGTH: 16
<212> TYPE: PRT
<213> ORGANISM: Homo sapiens

<400> SEQUENCE: 76

Trp Pro Lys Met His Thr Val Asn Gly Tyr Val Asn Arg Ser Leu Pro
1               5                   10                  15

<210> SEQ ID NO 77
<211> LENGTH: 17
<212> TYPE: PRT
<213> ORGANISM: Homo sapiens

<400> SEQUENCE: 77

Trp Pro Lys Met His Thr Val Asn Gly Tyr Val Asn Arg Ser Leu Pro
1               5                   10                  15
Gly

<210> SEQ ID NO 78
<211> LENGTH: 18
<212> TYPE: PRT
<213> ORGANISM: Homo sapiens

<400> SEQUENCE: 78
```

Trp Pro Lys Met His Thr Val Asn Gly Tyr Val Asn Arg Ser Leu Pro
1               5                   10                  15

Gly Leu

<210> SEQ ID NO 79
<211> LENGTH: 19
<212> TYPE: PRT
<213> ORGANISM: Homo sapiens

<400> SEQUENCE: 79

Trp Pro Lys Met His Thr Val Asn Gly Tyr Val Asn Arg Ser Leu Pro
1               5                   10                  15

Gly Leu Ile

<210> SEQ ID NO 80
<211> LENGTH: 20
<212> TYPE: PRT
<213> ORGANISM: Homo sapiens

<400> SEQUENCE: 80

Trp Pro Lys Met His Thr Val Asn Gly Tyr Val Asn Arg Ser Leu Pro
1               5                   10                  15

Gly Leu Ile Gly
            20

<210> SEQ ID NO 81
<211> LENGTH: 9
<212> TYPE: PRT
<213> ORGANISM: Homo sapiens

<400> SEQUENCE: 81

Pro Lys Met His Thr Val Asn Gly Tyr
1               5

<210> SEQ ID NO 82
<211> LENGTH: 10
<212> TYPE: PRT
<213> ORGANISM: Homo sapiens

<400> SEQUENCE: 82

Pro Lys Met His Thr Val Asn Gly Tyr Val
1               5                   10

<210> SEQ ID NO 83
<211> LENGTH: 11
<212> TYPE: PRT
<213> ORGANISM: Homo sapiens

<400> SEQUENCE: 83

Pro Lys Met His Thr Val Asn Gly Tyr Val Asn
1               5                   10

<210> SEQ ID NO 84
<211> LENGTH: 12
<212> TYPE: PRT
<213> ORGANISM: Homo sapiens

<400> SEQUENCE: 84

Pro Lys Met His Thr Val Asn Gly Tyr Val Asn Arg
1               5                   10

<210> SEQ ID NO 85

```
<211> LENGTH: 13
<212> TYPE: PRT
<213> ORGANISM: Homo sapiens

<400> SEQUENCE: 85

Pro Lys Met His Thr Val Asn Gly Tyr Val Asn Arg Ser
1               5                   10

<210> SEQ ID NO 86
<211> LENGTH: 14
<212> TYPE: PRT
<213> ORGANISM: Homo sapiens

<400> SEQUENCE: 86

Pro Lys Met His Thr Val Asn Gly Tyr Val Asn Arg Ser Leu
1               5                   10

<210> SEQ ID NO 87
<211> LENGTH: 15
<212> TYPE: PRT
<213> ORGANISM: Homo sapiens

<400> SEQUENCE: 87

Pro Lys Met His Thr Val Asn Gly Tyr Val Asn Arg Ser Leu Pro
1               5                   10                  15

<210> SEQ ID NO 88
<211> LENGTH: 16
<212> TYPE: PRT
<213> ORGANISM: Homo sapiens

<400> SEQUENCE: 88

Pro Lys Met His Thr Val Asn Gly Tyr Val Asn Arg Ser Leu Pro Gly
1               5                   10                  15

<210> SEQ ID NO 89
<211> LENGTH: 17
<212> TYPE: PRT
<213> ORGANISM: Homo sapiens

<400> SEQUENCE: 89

Pro Lys Met His Thr Val Asn Gly Tyr Val Asn Arg Ser Leu Pro Gly
1               5                   10                  15

Leu

<210> SEQ ID NO 90
<211> LENGTH: 18
<212> TYPE: PRT
<213> ORGANISM: Homo sapiens

<400> SEQUENCE: 90

Pro Lys Met His Thr Val Asn Gly Tyr Val Asn Arg Ser Leu Pro Gly
1               5                   10                  15

Leu Ile

<210> SEQ ID NO 91
<211> LENGTH: 19
<212> TYPE: PRT
<213> ORGANISM: Homo sapiens

<400> SEQUENCE: 91

Pro Lys Met His Thr Val Asn Gly Tyr Val Asn Arg Ser Leu Pro Gly
1               5                   10                  15
```

Leu Ile Gly

<210> SEQ ID NO 92
<211> LENGTH: 9
<212> TYPE: PRT
<213> ORGANISM: Homo sapiens

<400> SEQUENCE: 92

Lys Met His Thr Val Asn Gly Tyr Val
1               5

<210> SEQ ID NO 93
<211> LENGTH: 10
<212> TYPE: PRT
<213> ORGANISM: Homo sapiens

<400> SEQUENCE: 93

Lys Met His Thr Val Asn Gly Tyr Val Asn
1               5                   10

<210> SEQ ID NO 94
<211> LENGTH: 11
<212> TYPE: PRT
<213> ORGANISM: Homo sapiens

<400> SEQUENCE: 94

Lys Met His Thr Val Asn Gly Tyr Val Asn Arg
1               5                   10

<210> SEQ ID NO 95
<211> LENGTH: 12
<212> TYPE: PRT
<213> ORGANISM: Homo sapiens

<400> SEQUENCE: 95

Lys Met His Thr Val Asn Gly Tyr Val Asn Arg Ser
1               5                   10

<210> SEQ ID NO 96
<211> LENGTH: 13
<212> TYPE: PRT
<213> ORGANISM: Homo sapiens

<400> SEQUENCE: 96

Lys Met His Thr Val Asn Gly Tyr Val Asn Arg Ser Leu
1               5                   10

<210> SEQ ID NO 97
<211> LENGTH: 14
<212> TYPE: PRT
<213> ORGANISM: Homo sapiens

<400> SEQUENCE: 97

Lys Met His Thr Val Asn Gly Tyr Val Asn Arg Ser Leu Pro
1               5                   10

<210> SEQ ID NO 98
<211> LENGTH: 15
<212> TYPE: PRT
<213> ORGANISM: Homo sapiens

<400> SEQUENCE: 98

Lys Met His Thr Val Asn Gly Tyr Val Asn Arg Ser Leu Pro Gly
1               5                   10                  15

```
<210> SEQ ID NO 99
<211> LENGTH: 16
<212> TYPE: PRT
<213> ORGANISM: Homo sapiens

<400> SEQUENCE: 99

Lys Met His Thr Val Asn Gly Tyr Val Asn Arg Ser Leu Pro Gly Leu
1               5                   10                  15

<210> SEQ ID NO 100
<211> LENGTH: 17
<212> TYPE: PRT
<213> ORGANISM: Homo sapiens

<400> SEQUENCE: 100

Lys Met His Thr Val Asn Gly Tyr Val Asn Arg Ser Leu Pro Gly Leu
1               5                   10                  15

Ile

<210> SEQ ID NO 101
<211> LENGTH: 18
<212> TYPE: PRT
<213> ORGANISM: Homo sapiens

<400> SEQUENCE: 101

Lys Met His Thr Val Asn Gly Tyr Val Asn Arg Ser Leu Pro Gly Leu
1               5                   10                  15

Ile Gly

<210> SEQ ID NO 102
<211> LENGTH: 9
<212> TYPE: PRT
<213> ORGANISM: Homo sapiens

<400> SEQUENCE: 102

Met His Thr Val Asn Gly Tyr Val Asn
1               5

<210> SEQ ID NO 103
<211> LENGTH: 10
<212> TYPE: PRT
<213> ORGANISM: Homo sapiens

<400> SEQUENCE: 103

Met His Thr Val Asn Gly Tyr Val Asn Arg
1               5                   10

<210> SEQ ID NO 104
<211> LENGTH: 11
<212> TYPE: PRT
<213> ORGANISM: Homo sapiens

<400> SEQUENCE: 104

Met His Thr Val Asn Gly Tyr Val Asn Arg Ser
1               5                   10

<210> SEQ ID NO 105
<211> LENGTH: 12
<212> TYPE: PRT
<213> ORGANISM: Homo sapiens

<400> SEQUENCE: 105

Met His Thr Val Asn Gly Tyr Val Asn Arg Ser Leu
```

```
1               5                  10
```

<210> SEQ ID NO 106
<211> LENGTH: 13
<212> TYPE: PRT
<213> ORGANISM: Homo sapiens

<400> SEQUENCE: 106

```
Met His Thr Val Asn Gly Tyr Val Asn Arg Ser Leu Pro
1               5                  10
```

<210> SEQ ID NO 107
<211> LENGTH: 14
<212> TYPE: PRT
<213> ORGANISM: Homo sapiens

<400> SEQUENCE: 107

```
Met His Thr Val Asn Gly Tyr Val Asn Arg Ser Leu Pro Gly
1               5                  10
```

<210> SEQ ID NO 108
<211> LENGTH: 15
<212> TYPE: PRT
<213> ORGANISM: Homo sapiens

<400> SEQUENCE: 108

```
Met His Thr Val Asn Gly Tyr Val Asn Arg Ser Leu Pro Gly Leu
1               5                  10                  15
```

<210> SEQ ID NO 109
<211> LENGTH: 16
<212> TYPE: PRT
<213> ORGANISM: Homo sapiens

<400> SEQUENCE: 109

```
Met His Thr Val Asn Gly Tyr Val Asn Arg Ser Leu Pro Gly Leu Ile
1               5                  10                  15
```

<210> SEQ ID NO 110
<211> LENGTH: 17
<212> TYPE: PRT
<213> ORGANISM: Homo sapiens

<400> SEQUENCE: 110

```
Met His Thr Val Asn Gly Tyr Val Asn Arg Ser Leu Pro Gly Leu Ile
1               5                  10                  15
Gly
```

<210> SEQ ID NO 111
<211> LENGTH: 9
<212> TYPE: PRT
<213> ORGANISM: Homo sapiens

<400> SEQUENCE: 111

```
His Thr Val Asn Gly Tyr Val Asn Arg
1               5
```

<210> SEQ ID NO 112
<211> LENGTH: 10
<212> TYPE: PRT
<213> ORGANISM: Homo sapiens

<400> SEQUENCE: 112

His Thr Val Asn Gly Tyr Val Asn Arg Ser

```
1               5                   10
```

<210> SEQ ID NO 113
<211> LENGTH: 11
<212> TYPE: PRT
<213> ORGANISM: Homo sapiens

<400> SEQUENCE: 113

```
His Thr Val Asn Gly Tyr Val Asn Arg Ser Leu
1               5                   10
```

<210> SEQ ID NO 114
<211> LENGTH: 12
<212> TYPE: PRT
<213> ORGANISM: Homo sapiens

<400> SEQUENCE: 114

```
His Thr Val Asn Gly Tyr Val Asn Arg Ser Leu Pro
1               5                   10
```

<210> SEQ ID NO 115
<211> LENGTH: 13
<212> TYPE: PRT
<213> ORGANISM: Homo sapiens

<400> SEQUENCE: 115

```
His Thr Val Asn Gly Tyr Val Asn Arg Ser Leu Pro Gly
1               5                   10
```

<210> SEQ ID NO 116
<211> LENGTH: 14
<212> TYPE: PRT
<213> ORGANISM: Homo sapiens

<400> SEQUENCE: 116

```
His Thr Val Asn Gly Tyr Val Asn Arg Ser Leu Pro Gly Leu
1               5                   10
```

<210> SEQ ID NO 117
<211> LENGTH: 15
<212> TYPE: PRT
<213> ORGANISM: Homo sapiens

<400> SEQUENCE: 117

```
His Thr Val Asn Gly Tyr Val Asn Arg Ser Leu Pro Gly Leu Ile
1               5                   10                  15
```

<210> SEQ ID NO 118
<211> LENGTH: 16
<212> TYPE: PRT
<213> ORGANISM: Homo sapiens

<400> SEQUENCE: 118

```
His Thr Val Asn Gly Tyr Val Asn Arg Ser Leu Pro Gly Leu Ile Gly
1               5                   10                  15
```

<210> SEQ ID NO 119
<211> LENGTH: 9
<212> TYPE: PRT
<213> ORGANISM: Homo sapiens

<400> SEQUENCE: 119

```
Thr Val Asn Gly Tyr Val Asn Arg Ser
1               5
```

<210> SEQ ID NO 120
<211> LENGTH: 10
<212> TYPE: PRT
<213> ORGANISM: Homo sapiens

<400> SEQUENCE: 120

Thr Val Asn Gly Tyr Val Asn Arg Ser Leu
1               5                   10

<210> SEQ ID NO 121
<211> LENGTH: 11
<212> TYPE: PRT
<213> ORGANISM: Homo sapiens

<400> SEQUENCE: 121

Thr Val Asn Gly Tyr Val Asn Arg Ser Leu Pro
1               5                   10

<210> SEQ ID NO 122
<211> LENGTH: 12
<212> TYPE: PRT
<213> ORGANISM: Homo sapiens

<400> SEQUENCE: 122

Thr Val Asn Gly Tyr Val Asn Arg Ser Leu Pro Gly
1               5                   10

<210> SEQ ID NO 123
<211> LENGTH: 13
<212> TYPE: PRT
<213> ORGANISM: Homo sapiens

<400> SEQUENCE: 123

Thr Val Asn Gly Tyr Val Asn Arg Ser Leu Pro Gly Leu
1               5                   10

<210> SEQ ID NO 124
<211> LENGTH: 14
<212> TYPE: PRT
<213> ORGANISM: Homo sapiens

<400> SEQUENCE: 124

Thr Val Asn Gly Tyr Val Asn Arg Ser Leu Pro Gly Leu Ile
1               5                   10

<210> SEQ ID NO 125
<211> LENGTH: 15
<212> TYPE: PRT
<213> ORGANISM: Homo sapiens

<400> SEQUENCE: 125

Thr Val Asn Gly Tyr Val Asn Arg Ser Leu Pro Gly Leu Ile Gly
1               5                   10                  15

<210> SEQ ID NO 126
<211> LENGTH: 9
<212> TYPE: PRT
<213> ORGANISM: Homo sapiens

<400> SEQUENCE: 126

Val Asn Gly Tyr Val Asn Arg Ser Leu
1               5

<210> SEQ ID NO 127

```
<211> LENGTH: 10
<212> TYPE: PRT
<213> ORGANISM: Homo sapiens

<400> SEQUENCE: 127

Val Asn Gly Tyr Val Asn Arg Ser Leu Pro
1               5                   10

<210> SEQ ID NO 128
<211> LENGTH: 11
<212> TYPE: PRT
<213> ORGANISM: Homo sapiens

<400> SEQUENCE: 128

Val Asn Gly Tyr Val Asn Arg Ser Leu Pro Gly
1               5                   10

<210> SEQ ID NO 129
<211> LENGTH: 12
<212> TYPE: PRT
<213> ORGANISM: Homo sapiens

<400> SEQUENCE: 129

Val Asn Gly Tyr Val Asn Arg Ser Leu Pro Gly Leu
1               5                   10

<210> SEQ ID NO 130
<211> LENGTH: 13
<212> TYPE: PRT
<213> ORGANISM: Homo sapiens

<400> SEQUENCE: 130

Val Asn Gly Tyr Val Asn Arg Ser Leu Pro Gly Leu Ile
1               5                   10

<210> SEQ ID NO 131
<211> LENGTH: 14
<212> TYPE: PRT
<213> ORGANISM: Homo sapiens

<400> SEQUENCE: 131

Val Asn Gly Tyr Val Asn Arg Ser Leu Pro Gly Leu Ile Gly
1               5                   10

<210> SEQ ID NO 132
<211> LENGTH: 9
<212> TYPE: PRT
<213> ORGANISM: Homo sapiens

<400> SEQUENCE: 132

Asn Gly Tyr Val Asn Arg Ser Leu Pro
1               5

<210> SEQ ID NO 133
<211> LENGTH: 10
<212> TYPE: PRT
<213> ORGANISM: Homo sapiens

<400> SEQUENCE: 133

Asn Gly Tyr Val Asn Arg Ser Leu Pro Gly
1               5                   10

<210> SEQ ID NO 134
<211> LENGTH: 11
<212> TYPE: PRT
```

-continued

<213> ORGANISM: Homo sapiens

<400> SEQUENCE: 134

Asn Gly Tyr Val Asn Arg Ser Leu Pro Gly Leu
1               5                   10

<210> SEQ ID NO 135
<211> LENGTH: 12
<212> TYPE: PRT
<213> ORGANISM: Homo sapiens

<400> SEQUENCE: 135

Asn Gly Tyr Val Asn Arg Ser Leu Pro Gly Leu Ile
1               5                   10

<210> SEQ ID NO 136
<211> LENGTH: 13
<212> TYPE: PRT
<213> ORGANISM: Homo sapiens

<400> SEQUENCE: 136

Asn Gly Tyr Val Asn Arg Ser Leu Pro Gly Leu Ile Gly
1               5                   10

<210> SEQ ID NO 137
<211> LENGTH: 9
<212> TYPE: PRT
<213> ORGANISM: Homo sapiens

<400> SEQUENCE: 137

Gly Tyr Val Asn Arg Ser Leu Pro Gly
1               5

<210> SEQ ID NO 138
<211> LENGTH: 10
<212> TYPE: PRT
<213> ORGANISM: Homo sapiens

<400> SEQUENCE: 138

Gly Tyr Val Asn Arg Ser Leu Pro Gly Leu
1               5                   10

<210> SEQ ID NO 139
<211> LENGTH: 11
<212> TYPE: PRT
<213> ORGANISM: Homo sapiens

<400> SEQUENCE: 139

Gly Tyr Val Asn Arg Ser Leu Pro Gly Leu Ile
1               5                   10

<210> SEQ ID NO 140
<211> LENGTH: 12
<212> TYPE: PRT
<213> ORGANISM: Homo sapiens

<400> SEQUENCE: 140

Gly Tyr Val Asn Arg Ser Leu Pro Gly Leu Ile Gly
1               5                   10

<210> SEQ ID NO 141
<211> LENGTH: 9
<212> TYPE: PRT
<213> ORGANISM: Homo sapiens

```
<400> SEQUENCE: 141

Tyr Val Asn Arg Ser Leu Pro Gly Leu
1               5

<210> SEQ ID NO 142
<211> LENGTH: 10
<212> TYPE: PRT
<213> ORGANISM: Homo sapiens

<400> SEQUENCE: 142

Tyr Val Asn Arg Ser Leu Pro Gly Leu Ile
1               5                   10

<210> SEQ ID NO 143
<211> LENGTH: 11
<212> TYPE: PRT
<213> ORGANISM: Homo sapiens

<400> SEQUENCE: 143

Tyr Val Asn Arg Ser Leu Pro Gly Leu Ile Gly
1               5                   10

<210> SEQ ID NO 144
<211> LENGTH: 9
<212> TYPE: PRT
<213> ORGANISM: Homo sapiens

<400> SEQUENCE: 144

Val Asn Arg Ser Leu Pro Gly Leu Ile
1               5

<210> SEQ ID NO 145
<211> LENGTH: 10
<212> TYPE: PRT
<213> ORGANISM: Homo sapiens

<400> SEQUENCE: 145

Val Asn Arg Ser Leu Pro Gly Leu Ile Gly
1               5                   10

<210> SEQ ID NO 146
<211> LENGTH: 9
<212> TYPE: PRT
<213> ORGANISM: Homo sapiens

<400> SEQUENCE: 146

Asn Arg Ser Leu Pro Gly Leu Ile Gly
1               5

<210> SEQ ID NO 147
<211> LENGTH: 9
<212> TYPE: PRT
<213> ORGANISM: Homo sapiens

<400> SEQUENCE: 147

Gly Glu Val Gly Asp Thr Leu Leu Ile
1               5

<210> SEQ ID NO 148
<211> LENGTH: 10
<212> TYPE: PRT
<213> ORGANISM: Homo sapiens

<400> SEQUENCE: 148
```

```
Gly Glu Val Gly Asp Thr Leu Leu Ile Ile
1               5                   10
```

<210> SEQ ID NO 149
<211> LENGTH: 11
<212> TYPE: PRT
<213> ORGANISM: Homo sapiens

<400> SEQUENCE: 149

```
Gly Glu Val Gly Asp Thr Leu Leu Ile Ile Phe
1               5                   10
```

<210> SEQ ID NO 150
<211> LENGTH: 12
<212> TYPE: PRT
<213> ORGANISM: Homo sapiens

<400> SEQUENCE: 150

```
Gly Glu Val Gly Asp Thr Leu Leu Ile Ile Phe Lys
1               5                   10
```

<210> SEQ ID NO 151
<211> LENGTH: 13
<212> TYPE: PRT
<213> ORGANISM: Homo sapiens

<400> SEQUENCE: 151

```
Gly Glu Val Gly Asp Thr Leu Leu Ile Ile Phe Lys Asn
1               5                   10
```

<210> SEQ ID NO 152
<211> LENGTH: 14
<212> TYPE: PRT
<213> ORGANISM: Homo sapiens

<400> SEQUENCE: 152

```
Gly Glu Val Gly Asp Thr Leu Leu Ile Ile Phe Lys Asn Gln
1               5                   10
```

<210> SEQ ID NO 153
<211> LENGTH: 15
<212> TYPE: PRT
<213> ORGANISM: Homo sapiens

<400> SEQUENCE: 153

```
Gly Glu Val Gly Asp Thr Leu Leu Ile Ile Phe Lys Asn Gln Ala
1               5                   10                  15
```

<210> SEQ ID NO 154
<211> LENGTH: 16
<212> TYPE: PRT
<213> ORGANISM: Homo sapiens

<400> SEQUENCE: 154

```
Gly Glu Val Gly Asp Thr Leu Leu Ile Ile Phe Lys Asn Gln Ala Ser
1               5                   10                  15
```

<210> SEQ ID NO 155
<211> LENGTH: 17
<212> TYPE: PRT
<213> ORGANISM: Homo sapiens

<400> SEQUENCE: 155

```
Gly Glu Val Gly Asp Thr Leu Leu Ile Ile Phe Lys Asn Gln Ala Ser
1               5                   10                  15
```

Arg

<210> SEQ ID NO 156
<211> LENGTH: 18
<212> TYPE: PRT
<213> ORGANISM: Homo sapiens

<400> SEQUENCE: 156

Gly Glu Val Gly Asp Thr Leu Leu Ile Ile Phe Lys Asn Gln Ala Ser
1               5                   10                  15

Arg Pro

<210> SEQ ID NO 157
<211> LENGTH: 19
<212> TYPE: PRT
<213> ORGANISM: Homo sapiens

<400> SEQUENCE: 157

Gly Glu Val Gly Asp Thr Leu Leu Ile Ile Phe Lys Asn Gln Ala Ser
1               5                   10                  15

Arg Pro Tyr

<210> SEQ ID NO 158
<211> LENGTH: 20
<212> TYPE: PRT
<213> ORGANISM: Homo sapiens

<400> SEQUENCE: 158

Gly Glu Val Gly Asp Thr Leu Leu Ile Ile Phe Lys Asn Gln Ala Ser
1               5                   10                  15

Arg Pro Tyr Asn
            20

<210> SEQ ID NO 159
<211> LENGTH: 21
<212> TYPE: PRT
<213> ORGANISM: Homo sapiens

<400> SEQUENCE: 159

Gly Glu Val Gly Asp Thr Leu Leu Ile Ile Phe Lys Asn Gln Ala Ser
1               5                   10                  15

Arg Pro Tyr Asn Ile
            20

<210> SEQ ID NO 160
<211> LENGTH: 9
<212> TYPE: PRT
<213> ORGANISM: Homo sapiens

<400> SEQUENCE: 160

Glu Val Gly Asp Thr Leu Leu Ile Ile
1               5

<210> SEQ ID NO 161
<211> LENGTH: 10
<212> TYPE: PRT
<213> ORGANISM: Homo sapiens

<400> SEQUENCE: 161

Glu Val Gly Asp Thr Leu Leu Ile Ile Phe
1               5                   10

```
<210> SEQ ID NO 162
<211> LENGTH: 11
<212> TYPE: PRT
<213> ORGANISM: Homo sapiens

<400> SEQUENCE: 162

Glu Val Gly Asp Thr Leu Leu Ile Ile Phe Lys
1               5                   10

<210> SEQ ID NO 163
<211> LENGTH: 12
<212> TYPE: PRT
<213> ORGANISM: Homo sapiens

<400> SEQUENCE: 163

Glu Val Gly Asp Thr Leu Leu Ile Ile Phe Lys Asn
1               5                   10

<210> SEQ ID NO 164
<211> LENGTH: 13
<212> TYPE: PRT
<213> ORGANISM: Homo sapiens

<400> SEQUENCE: 164

Glu Val Gly Asp Thr Leu Leu Ile Ile Phe Lys Asn Gln
1               5                   10

<210> SEQ ID NO 165
<211> LENGTH: 14
<212> TYPE: PRT
<213> ORGANISM: Homo sapiens

<400> SEQUENCE: 165

Glu Val Gly Asp Thr Leu Leu Ile Ile Phe Lys Asn Gln Ala
1               5                   10

<210> SEQ ID NO 166
<211> LENGTH: 15
<212> TYPE: PRT
<213> ORGANISM: Homo sapiens

<400> SEQUENCE: 166

Glu Val Gly Asp Thr Leu Leu Ile Ile Phe Lys Asn Gln Ala Ser
1               5                   10                  15

<210> SEQ ID NO 167
<211> LENGTH: 16
<212> TYPE: PRT
<213> ORGANISM: Homo sapiens

<400> SEQUENCE: 167

Glu Val Gly Asp Thr Leu Leu Ile Ile Phe Lys Asn Gln Ala Ser Arg
1               5                   10                  15

<210> SEQ ID NO 168
<211> LENGTH: 17
<212> TYPE: PRT
<213> ORGANISM: Homo sapiens

<400> SEQUENCE: 168

Glu Val Gly Asp Thr Leu Leu Ile Ile Phe Lys Asn Gln Ala Ser Arg
1               5                   10                  15

Pro
```

<210> SEQ ID NO 169
<211> LENGTH: 18
<212> TYPE: PRT
<213> ORGANISM: Homo sapiens

<400> SEQUENCE: 169

Glu Val Gly Asp Thr Leu Leu Ile Ile Phe Lys Asn Gln Ala Ser Arg
1               5                   10                  15

Pro Tyr

<210> SEQ ID NO 170
<211> LENGTH: 19
<212> TYPE: PRT
<213> ORGANISM: Homo sapiens

<400> SEQUENCE: 170

Glu Val Gly Asp Thr Leu Leu Ile Ile Phe Lys Asn Gln Ala Ser Arg
1               5                   10                  15

Pro Tyr Asn

<210> SEQ ID NO 171
<211> LENGTH: 20
<212> TYPE: PRT
<213> ORGANISM: Homo sapiens

<400> SEQUENCE: 171

Glu Val Gly Asp Thr Leu Leu Ile Ile Phe Lys Asn Gln Ala Ser Arg
1               5                   10                  15

Pro Tyr Asn Ile
            20

<210> SEQ ID NO 172
<211> LENGTH: 9
<212> TYPE: PRT
<213> ORGANISM: Homo sapiens

<400> SEQUENCE: 172

Val Gly Asp Thr Leu Leu Ile Ile Phe
1               5

<210> SEQ ID NO 173
<211> LENGTH: 10
<212> TYPE: PRT
<213> ORGANISM: Homo sapiens

<400> SEQUENCE: 173

Val Gly Asp Thr Leu Leu Ile Ile Phe Lys
1               5                   10

<210> SEQ ID NO 174
<211> LENGTH: 11
<212> TYPE: PRT
<213> ORGANISM: Homo sapiens

<400> SEQUENCE: 174

Val Gly Asp Thr Leu Leu Ile Ile Phe Lys Asn
1               5                   10

<210> SEQ ID NO 175
<211> LENGTH: 12
<212> TYPE: PRT
<213> ORGANISM: Homo sapiens

```
<400> SEQUENCE: 175

Val Gly Asp Thr Leu Leu Ile Ile Phe Lys Asn Gln
1               5                   10

<210> SEQ ID NO 176
<211> LENGTH: 13
<212> TYPE: PRT
<213> ORGANISM: Homo sapiens

<400> SEQUENCE: 176

Val Gly Asp Thr Leu Leu Ile Ile Phe Lys Asn Gln Ala
1               5                   10

<210> SEQ ID NO 177
<211> LENGTH: 14
<212> TYPE: PRT
<213> ORGANISM: Homo sapiens

<400> SEQUENCE: 177

Val Gly Asp Thr Leu Leu Ile Ile Phe Lys Asn Gln Ala Ser
1               5                   10

<210> SEQ ID NO 178
<211> LENGTH: 15
<212> TYPE: PRT
<213> ORGANISM: Homo sapiens

<400> SEQUENCE: 178

Val Gly Asp Thr Leu Leu Ile Ile Phe Lys Asn Gln Ala Ser Arg
1               5                   10                  15

<210> SEQ ID NO 179
<211> LENGTH: 16
<212> TYPE: PRT
<213> ORGANISM: Homo sapiens

<400> SEQUENCE: 179

Val Gly Asp Thr Leu Leu Ile Ile Phe Lys Asn Gln Ala Ser Arg Pro
1               5                   10                  15

<210> SEQ ID NO 180
<211> LENGTH: 17
<212> TYPE: PRT
<213> ORGANISM: Homo sapiens

<400> SEQUENCE: 180

Val Gly Asp Thr Leu Leu Ile Ile Phe Lys Asn Gln Ala Ser Arg Pro
1               5                   10                  15

Tyr

<210> SEQ ID NO 181
<211> LENGTH: 18
<212> TYPE: PRT
<213> ORGANISM: Homo sapiens

<400> SEQUENCE: 181

Val Gly Asp Thr Leu Leu Ile Ile Phe Lys Asn Gln Ala Ser Arg Pro
1               5                   10                  15

Tyr Asn

<210> SEQ ID NO 182
<211> LENGTH: 19
<212> TYPE: PRT
```

<213> ORGANISM: Homo sapiens

<400> SEQUENCE: 182

Val Gly Asp Thr Leu Leu Ile Ile Phe Lys Asn Gln Ala Ser Arg Pro
1               5                   10                  15

Tyr Asn Ile

<210> SEQ ID NO 183
<211> LENGTH: 9
<212> TYPE: PRT
<213> ORGANISM: Homo sapiens

<400> SEQUENCE: 183

Gly Asp Thr Leu Leu Ile Ile Phe Lys
1               5

<210> SEQ ID NO 184
<211> LENGTH: 10
<212> TYPE: PRT
<213> ORGANISM: Homo sapiens

<400> SEQUENCE: 184

Gly Asp Thr Leu Leu Ile Ile Phe Lys Asn
1               5                   10

<210> SEQ ID NO 185
<211> LENGTH: 11
<212> TYPE: PRT
<213> ORGANISM: Homo sapiens

<400> SEQUENCE: 185

Gly Asp Thr Leu Leu Ile Ile Phe Lys Asn Gln
1               5                   10

<210> SEQ ID NO 186
<211> LENGTH: 12
<212> TYPE: PRT
<213> ORGANISM: Homo sapiens

<400> SEQUENCE: 186

Gly Asp Thr Leu Leu Ile Ile Phe Lys Asn Gln Ala
1               5                   10

<210> SEQ ID NO 187
<211> LENGTH: 13
<212> TYPE: PRT
<213> ORGANISM: Homo sapiens

<400> SEQUENCE: 187

Gly Asp Thr Leu Leu Ile Ile Phe Lys Asn Gln Ala Ser
1               5                   10

<210> SEQ ID NO 188
<211> LENGTH: 14
<212> TYPE: PRT
<213> ORGANISM: Homo sapiens

<400> SEQUENCE: 188

Gly Asp Thr Leu Leu Ile Ile Phe Lys Asn Gln Ala Ser Arg
1               5                   10

<210> SEQ ID NO 189
<211> LENGTH: 15
<212> TYPE: PRT

<213> ORGANISM: Homo sapiens

<400> SEQUENCE: 189

Gly Asp Thr Leu Leu Ile Ile Phe Lys Asn Gln Ala Ser Arg Pro
1               5                   10                  15

<210> SEQ ID NO 190
<211> LENGTH: 16
<212> TYPE: PRT
<213> ORGANISM: Homo sapiens

<400> SEQUENCE: 190

Gly Asp Thr Leu Leu Ile Ile Phe Lys Asn Gln Ala Ser Arg Pro Tyr
1               5                   10                  15

<210> SEQ ID NO 191
<211> LENGTH: 17
<212> TYPE: PRT
<213> ORGANISM: Homo sapiens

<400> SEQUENCE: 191

Gly Asp Thr Leu Leu Ile Ile Phe Lys Asn Gln Ala Ser Arg Pro Tyr
1               5                   10                  15

Asn

<210> SEQ ID NO 192
<211> LENGTH: 18
<212> TYPE: PRT
<213> ORGANISM: Homo sapiens

<400> SEQUENCE: 192

Gly Asp Thr Leu Leu Ile Ile Phe Lys Asn Gln Ala Ser Arg Pro Tyr
1               5                   10                  15

Asn Ile

<210> SEQ ID NO 193
<211> LENGTH: 9
<212> TYPE: PRT
<213> ORGANISM: Homo sapiens

<400> SEQUENCE: 193

Asp Thr Leu Leu Ile Ile Phe Lys Asn
1               5

<210> SEQ ID NO 194
<211> LENGTH: 10
<212> TYPE: PRT
<213> ORGANISM: Homo sapiens

<400> SEQUENCE: 194

Asp Thr Leu Leu Ile Ile Phe Lys Asn Gln
1               5                   10

<210> SEQ ID NO 195
<211> LENGTH: 11
<212> TYPE: PRT
<213> ORGANISM: Homo sapiens

<400> SEQUENCE: 195

Asp Thr Leu Leu Ile Ile Phe Lys Asn Gln Ala
1               5                   10

<210> SEQ ID NO 196

<211> LENGTH: 12
<212> TYPE: PRT
<213> ORGANISM: Homo sapiens

<400> SEQUENCE: 196

Asp Thr Leu Leu Ile Ile Phe Lys Asn Gln Ala Ser
1               5                   10

<210> SEQ ID NO 197
<211> LENGTH: 13
<212> TYPE: PRT
<213> ORGANISM: Homo sapiens

<400> SEQUENCE: 197

Asp Thr Leu Leu Ile Ile Phe Lys Asn Gln Ala Ser Arg
1               5                   10

<210> SEQ ID NO 198
<211> LENGTH: 14
<212> TYPE: PRT
<213> ORGANISM: Homo sapiens

<400> SEQUENCE: 198

Asp Thr Leu Leu Ile Ile Phe Lys Asn Gln Ala Ser Arg Pro
1               5                   10

<210> SEQ ID NO 199
<211> LENGTH: 15
<212> TYPE: PRT
<213> ORGANISM: Homo sapiens

<400> SEQUENCE: 199

Asp Thr Leu Leu Ile Ile Phe Lys Asn Gln Ala Ser Arg Pro Tyr
1               5                   10                  15

<210> SEQ ID NO 200
<211> LENGTH: 16
<212> TYPE: PRT
<213> ORGANISM: Homo sapiens

<400> SEQUENCE: 200

Asp Thr Leu Leu Ile Ile Phe Lys Asn Gln Ala Ser Arg Pro Tyr Asn
1               5                   10                  15

<210> SEQ ID NO 201
<211> LENGTH: 17
<212> TYPE: PRT
<213> ORGANISM: Homo sapiens

<400> SEQUENCE: 201

Asp Thr Leu Leu Ile Ile Phe Lys Asn Gln Ala Ser Arg Pro Tyr Asn
1               5                   10                  15

Ile

<210> SEQ ID NO 202
<211> LENGTH: 9
<212> TYPE: PRT
<213> ORGANISM: Homo sapiens

<400> SEQUENCE: 202

Thr Leu Leu Ile Ile Phe Lys Asn Gln
1               5

<210> SEQ ID NO 203

```
<211> LENGTH: 10
<212> TYPE: PRT
<213> ORGANISM: Homo sapiens

<400> SEQUENCE: 203

Thr Leu Leu Ile Ile Phe Lys Asn Gln Ala
1               5                   10

<210> SEQ ID NO 204
<211> LENGTH: 11
<212> TYPE: PRT
<213> ORGANISM: Homo sapiens

<400> SEQUENCE: 204

Thr Leu Leu Ile Ile Phe Lys Asn Gln Ala Ser
1               5                   10

<210> SEQ ID NO 205
<211> LENGTH: 12
<212> TYPE: PRT
<213> ORGANISM: Homo sapiens

<400> SEQUENCE: 205

Thr Leu Leu Ile Ile Phe Lys Asn Gln Ala Ser Arg
1               5                   10

<210> SEQ ID NO 206
<211> LENGTH: 13
<212> TYPE: PRT
<213> ORGANISM: Homo sapiens

<400> SEQUENCE: 206

Thr Leu Leu Ile Ile Phe Lys Asn Gln Ala Ser Arg Pro
1               5                   10

<210> SEQ ID NO 207
<211> LENGTH: 14
<212> TYPE: PRT
<213> ORGANISM: Homo sapiens

<400> SEQUENCE: 207

Thr Leu Leu Ile Ile Phe Lys Asn Gln Ala Ser Arg Pro Tyr
1               5                   10

<210> SEQ ID NO 208
<211> LENGTH: 15
<212> TYPE: PRT
<213> ORGANISM: Homo sapiens

<400> SEQUENCE: 208

Thr Leu Leu Ile Ile Phe Lys Asn Gln Ala Ser Arg Pro Tyr Asn
1               5                   10                  15

<210> SEQ ID NO 209
<211> LENGTH: 16
<212> TYPE: PRT
<213> ORGANISM: Homo sapiens

<400> SEQUENCE: 209

Thr Leu Leu Ile Ile Phe Lys Asn Gln Ala Ser Arg Pro Tyr Asn Ile
1               5                   10                  15

<210> SEQ ID NO 210
<211> LENGTH: 9
<212> TYPE: PRT
```

<213> ORGANISM: Homo sapiens

<400> SEQUENCE: 210

Leu Leu Ile Ile Phe Lys Asn Gln Ala
1               5

<210> SEQ ID NO 211
<211> LENGTH: 10
<212> TYPE: PRT
<213> ORGANISM: Homo sapiens

<400> SEQUENCE: 211

Leu Leu Ile Ile Phe Lys Asn Gln Ala Ser
1               5                   10

<210> SEQ ID NO 212
<211> LENGTH: 11
<212> TYPE: PRT
<213> ORGANISM: Homo sapiens

<400> SEQUENCE: 212

Leu Leu Ile Ile Phe Lys Asn Gln Ala Ser Arg
1               5                   10

<210> SEQ ID NO 213
<211> LENGTH: 12
<212> TYPE: PRT
<213> ORGANISM: Homo sapiens

<400> SEQUENCE: 213

Leu Leu Ile Ile Phe Lys Asn Gln Ala Ser Arg Pro
1               5                   10

<210> SEQ ID NO 214
<211> LENGTH: 13
<212> TYPE: PRT
<213> ORGANISM: Homo sapiens

<400> SEQUENCE: 214

Leu Leu Ile Ile Phe Lys Asn Gln Ala Ser Arg Pro Tyr
1               5                   10

<210> SEQ ID NO 215
<211> LENGTH: 14
<212> TYPE: PRT
<213> ORGANISM: Homo sapiens

<400> SEQUENCE: 215

Leu Leu Ile Ile Phe Lys Asn Gln Ala Ser Arg Pro Tyr Asn
1               5                   10

<210> SEQ ID NO 216
<211> LENGTH: 15
<212> TYPE: PRT
<213> ORGANISM: Homo sapiens

<400> SEQUENCE: 216

Leu Leu Ile Ile Phe Lys Asn Gln Ala Ser Arg Pro Tyr Asn Ile
1               5                   10                  15

<210> SEQ ID NO 217
<211> LENGTH: 9
<212> TYPE: PRT
<213> ORGANISM: Homo sapiens

```
<400> SEQUENCE: 217

Leu Ile Ile Phe Lys Asn Gln Ala Ser
1               5

<210> SEQ ID NO 218
<211> LENGTH: 10
<212> TYPE: PRT
<213> ORGANISM: Homo sapiens

<400> SEQUENCE: 218

Leu Ile Ile Phe Lys Asn Gln Ala Ser Arg
1               5                   10

<210> SEQ ID NO 219
<211> LENGTH: 11
<212> TYPE: PRT
<213> ORGANISM: Homo sapiens

<400> SEQUENCE: 219

Leu Ile Ile Phe Lys Asn Gln Ala Ser Arg Pro
1               5                   10

<210> SEQ ID NO 220
<211> LENGTH: 12
<212> TYPE: PRT
<213> ORGANISM: Homo sapiens

<400> SEQUENCE: 220

Leu Ile Ile Phe Lys Asn Gln Ala Ser Arg Pro Tyr
1               5                   10

<210> SEQ ID NO 221
<211> LENGTH: 13
<212> TYPE: PRT
<213> ORGANISM: Homo sapiens

<400> SEQUENCE: 221

Leu Ile Ile Phe Lys Asn Gln Ala Ser Arg Pro Tyr Asn
1               5                   10

<210> SEQ ID NO 222
<211> LENGTH: 14
<212> TYPE: PRT
<213> ORGANISM: Homo sapiens

<400> SEQUENCE: 222

Leu Ile Ile Phe Lys Asn Gln Ala Ser Arg Pro Tyr Asn Ile
1               5                   10

<210> SEQ ID NO 223
<211> LENGTH: 9
<212> TYPE: PRT
<213> ORGANISM: Homo sapiens

<400> SEQUENCE: 223

Ile Ile Phe Lys Asn Gln Ala Ser Arg
1               5

<210> SEQ ID NO 224
<211> LENGTH: 10
<212> TYPE: PRT
<213> ORGANISM: Homo sapiens

<400> SEQUENCE: 224
```

```
Ile Ile Phe Lys Asn Gln Ala Ser Arg Pro
1               5                   10
```

<210> SEQ ID NO 225
<211> LENGTH: 11
<212> TYPE: PRT
<213> ORGANISM: Homo sapiens

<400> SEQUENCE: 225

```
Ile Ile Phe Lys Asn Gln Ala Ser Arg Pro Tyr
1               5                   10
```

<210> SEQ ID NO 226
<211> LENGTH: 12
<212> TYPE: PRT
<213> ORGANISM: Homo sapiens

<400> SEQUENCE: 226

```
Ile Ile Phe Lys Asn Gln Ala Ser Arg Pro Tyr Asn
1               5                   10
```

<210> SEQ ID NO 227
<211> LENGTH: 13
<212> TYPE: PRT
<213> ORGANISM: Homo sapiens

<400> SEQUENCE: 227

```
Ile Ile Phe Lys Asn Gln Ala Ser Arg Pro Tyr Asn Ile
1               5                   10
```

<210> SEQ ID NO 228
<211> LENGTH: 9
<212> TYPE: PRT
<213> ORGANISM: Homo sapiens

<400> SEQUENCE: 228

```
Ile Phe Lys Asn Gln Ala Ser Arg Pro
1               5
```

<210> SEQ ID NO 229
<211> LENGTH: 10
<212> TYPE: PRT
<213> ORGANISM: Homo sapiens

<400> SEQUENCE: 229

```
Ile Phe Lys Asn Gln Ala Ser Arg Pro Tyr
1               5                   10
```

<210> SEQ ID NO 230
<211> LENGTH: 11
<212> TYPE: PRT
<213> ORGANISM: Homo sapiens

<400> SEQUENCE: 230

```
Ile Phe Lys Asn Gln Ala Ser Arg Pro Tyr Asn
1               5                   10
```

<210> SEQ ID NO 231
<211> LENGTH: 12
<212> TYPE: PRT
<213> ORGANISM: Homo sapiens

<400> SEQUENCE: 231

```
Ile Phe Lys Asn Gln Ala Ser Arg Pro Tyr Asn Ile
1               5                   10
```

```
<210> SEQ ID NO 232
<211> LENGTH: 9
<212> TYPE: PRT
<213> ORGANISM: Homo sapiens

<400> SEQUENCE: 232

Phe Lys Asn Gln Ala Ser Arg Pro Tyr
1               5

<210> SEQ ID NO 233
<211> LENGTH: 10
<212> TYPE: PRT
<213> ORGANISM: Homo sapiens

<400> SEQUENCE: 233

Phe Lys Asn Gln Ala Ser Arg Pro Tyr Asn
1               5                   10

<210> SEQ ID NO 234
<211> LENGTH: 11
<212> TYPE: PRT
<213> ORGANISM: Homo sapiens

<400> SEQUENCE: 234

Phe Lys Asn Gln Ala Ser Arg Pro Tyr Asn Ile
1               5                   10

<210> SEQ ID NO 235
<211> LENGTH: 9
<212> TYPE: PRT
<213> ORGANISM: Homo sapiens

<400> SEQUENCE: 235

Lys Asn Gln Ala Ser Arg Pro Tyr Asn
1               5

<210> SEQ ID NO 236
<211> LENGTH: 10
<212> TYPE: PRT
<213> ORGANISM: Homo sapiens

<400> SEQUENCE: 236

Lys Asn Gln Ala Ser Arg Pro Tyr Asn Ile
1               5                   10

<210> SEQ ID NO 237
<211> LENGTH: 9
<212> TYPE: PRT
<213> ORGANISM: Homo sapiens

<400> SEQUENCE: 237

Asn Gln Ala Ser Arg Pro Tyr Asn Ile
1               5

<210> SEQ ID NO 238
<211> LENGTH: 9
<212> TYPE: PRT
<213> ORGANISM: Homo sapiens

<400> SEQUENCE: 238

Pro Thr Lys Ser Asp Pro Arg Cys Leu
1               5
```

```
<210> SEQ ID NO 239
<211> LENGTH: 10
<212> TYPE: PRT
<213> ORGANISM: Homo sapiens

<400> SEQUENCE: 239

Pro Thr Lys Ser Asp Pro Arg Cys Leu Thr
1               5                   10

<210> SEQ ID NO 240
<211> LENGTH: 11
<212> TYPE: PRT
<213> ORGANISM: Homo sapiens

<400> SEQUENCE: 240

Pro Thr Lys Ser Asp Pro Arg Cys Leu Thr Arg
1               5                   10

<210> SEQ ID NO 241
<211> LENGTH: 12
<212> TYPE: PRT
<213> ORGANISM: Homo sapiens

<400> SEQUENCE: 241

Pro Thr Lys Ser Asp Pro Arg Cys Leu Thr Arg Tyr
1               5                   10

<210> SEQ ID NO 242
<211> LENGTH: 13
<212> TYPE: PRT
<213> ORGANISM: Homo sapiens

<400> SEQUENCE: 242

Pro Thr Lys Ser Asp Pro Arg Cys Leu Thr Arg Tyr Tyr
1               5                   10

<210> SEQ ID NO 243
<211> LENGTH: 14
<212> TYPE: PRT
<213> ORGANISM: Homo sapiens

<400> SEQUENCE: 243

Pro Thr Lys Ser Asp Pro Arg Cys Leu Thr Arg Tyr Tyr Ser
1               5                   10

<210> SEQ ID NO 244
<211> LENGTH: 15
<212> TYPE: PRT
<213> ORGANISM: Homo sapiens

<400> SEQUENCE: 244

Pro Thr Lys Ser Asp Pro Arg Cys Leu Thr Arg Tyr Tyr Ser Ser
1               5                   10                  15

<210> SEQ ID NO 245
<211> LENGTH: 16
<212> TYPE: PRT
<213> ORGANISM: Homo sapiens

<400> SEQUENCE: 245

Pro Thr Lys Ser Asp Pro Arg Cys Leu Thr Arg Tyr Tyr Ser Ser Phe
1               5                   10                  15

<210> SEQ ID NO 246
<211> LENGTH: 17
```

<212> TYPE: PRT
<213> ORGANISM: Homo sapiens

<400> SEQUENCE: 246

Pro Thr Lys Ser Asp Pro Arg Cys Leu Thr Arg Tyr Tyr Ser Ser Phe
1               5                   10                  15
Val

<210> SEQ ID NO 247
<211> LENGTH: 18
<212> TYPE: PRT
<213> ORGANISM: Homo sapiens

<400> SEQUENCE: 247

Pro Thr Lys Ser Asp Pro Arg Cys Leu Thr Arg Tyr Tyr Ser Ser Phe
1               5                   10                  15
Val Asn

<210> SEQ ID NO 248
<211> LENGTH: 19
<212> TYPE: PRT
<213> ORGANISM: Homo sapiens

<400> SEQUENCE: 248

Pro Thr Lys Ser Asp Pro Arg Cys Leu Thr Arg Tyr Tyr Ser Ser Phe
1               5                   10                  15
Val Asn Met

<210> SEQ ID NO 249
<211> LENGTH: 20
<212> TYPE: PRT
<213> ORGANISM: Homo sapiens

<400> SEQUENCE: 249

Pro Thr Lys Ser Asp Pro Arg Cys Leu Thr Arg Tyr Tyr Ser Ser Phe
1               5                   10                  15
Val Asn Met Glu
            20

<210> SEQ ID NO 250
<211> LENGTH: 21
<212> TYPE: PRT
<213> ORGANISM: Homo sapiens

<400> SEQUENCE: 250

Pro Thr Lys Ser Asp Pro Arg Cys Leu Thr Arg Tyr Tyr Ser Ser Phe
1               5                   10                  15
Val Asn Met Glu Arg
            20

<210> SEQ ID NO 251
<211> LENGTH: 9
<212> TYPE: PRT
<213> ORGANISM: Homo sapiens

<400> SEQUENCE: 251

Thr Lys Ser Asp Pro Arg Cys Leu Thr
1               5

<210> SEQ ID NO 252
<211> LENGTH: 10
<212> TYPE: PRT

<213> ORGANISM: Homo sapiens

<400> SEQUENCE: 252

Thr Lys Ser Asp Pro Arg Cys Leu Thr Arg
1               5                   10

<210> SEQ ID NO 253
<211> LENGTH: 11
<212> TYPE: PRT
<213> ORGANISM: Homo sapiens

<400> SEQUENCE: 253

Thr Lys Ser Asp Pro Arg Cys Leu Thr Arg Tyr
1               5                   10

<210> SEQ ID NO 254
<211> LENGTH: 12
<212> TYPE: PRT
<213> ORGANISM: Homo sapiens

<400> SEQUENCE: 254

Thr Lys Ser Asp Pro Arg Cys Leu Thr Arg Tyr Tyr
1               5                   10

<210> SEQ ID NO 255
<211> LENGTH: 13
<212> TYPE: PRT
<213> ORGANISM: Homo sapiens

<400> SEQUENCE: 255

Thr Lys Ser Asp Pro Arg Cys Leu Thr Arg Tyr Tyr Ser
1               5                   10

<210> SEQ ID NO 256
<211> LENGTH: 14
<212> TYPE: PRT
<213> ORGANISM: Homo sapiens

<400> SEQUENCE: 256

Thr Lys Ser Asp Pro Arg Cys Leu Thr Arg Tyr Tyr Ser Ser
1               5                   10

<210> SEQ ID NO 257
<211> LENGTH: 15
<212> TYPE: PRT
<213> ORGANISM: Homo sapiens

<400> SEQUENCE: 257

Thr Lys Ser Asp Pro Arg Cys Leu Thr Arg Tyr Tyr Ser Ser Phe
1               5                   10                  15

<210> SEQ ID NO 258
<211> LENGTH: 16
<212> TYPE: PRT
<213> ORGANISM: Homo sapiens

<400> SEQUENCE: 258

Thr Lys Ser Asp Pro Arg Cys Leu Thr Arg Tyr Tyr Ser Ser Phe Val
1               5                   10                  15

<210> SEQ ID NO 259
<211> LENGTH: 17
<212> TYPE: PRT
<213> ORGANISM: Homo sapiens

```
<400> SEQUENCE: 259

Thr Lys Ser Asp Pro Arg Cys Leu Thr Arg Tyr Tyr Ser Ser Phe Val
1               5                   10                  15

Asn

<210> SEQ ID NO 260
<211> LENGTH: 18
<212> TYPE: PRT
<213> ORGANISM: Homo sapiens

<400> SEQUENCE: 260

Thr Lys Ser Asp Pro Arg Cys Leu Thr Arg Tyr Tyr Ser Ser Phe Val
1               5                   10                  15

Asn Met

<210> SEQ ID NO 261
<211> LENGTH: 19
<212> TYPE: PRT
<213> ORGANISM: Homo sapiens

<400> SEQUENCE: 261

Thr Lys Ser Asp Pro Arg Cys Leu Thr Arg Tyr Tyr Ser Ser Phe Val
1               5                   10                  15

Asn Met Glu

<210> SEQ ID NO 262
<211> LENGTH: 20
<212> TYPE: PRT
<213> ORGANISM: Homo sapiens

<400> SEQUENCE: 262

Thr Lys Ser Asp Pro Arg Cys Leu Thr Arg Tyr Tyr Ser Ser Phe Val
1               5                   10                  15

Asn Met Glu Arg
            20

<210> SEQ ID NO 263
<211> LENGTH: 9
<212> TYPE: PRT
<213> ORGANISM: Homo sapiens

<400> SEQUENCE: 263

Lys Ser Asp Pro Arg Cys Leu Thr Arg
1               5

<210> SEQ ID NO 264
<211> LENGTH: 10
<212> TYPE: PRT
<213> ORGANISM: Homo sapiens

<400> SEQUENCE: 264

Lys Ser Asp Pro Arg Cys Leu Thr Arg Tyr
1               5                   10

<210> SEQ ID NO 265
<211> LENGTH: 11
<212> TYPE: PRT
<213> ORGANISM: Homo sapiens

<400> SEQUENCE: 265

Lys Ser Asp Pro Arg Cys Leu Thr Arg Tyr Tyr
1               5                   10
```

```
<210> SEQ ID NO 266
<211> LENGTH: 12
<212> TYPE: PRT
<213> ORGANISM: Homo sapiens

<400> SEQUENCE: 266

Lys Ser Asp Pro Arg Cys Leu Thr Arg Tyr Tyr Ser
1               5                   10

<210> SEQ ID NO 267
<211> LENGTH: 13
<212> TYPE: PRT
<213> ORGANISM: Homo sapiens

<400> SEQUENCE: 267

Lys Ser Asp Pro Arg Cys Leu Thr Arg Tyr Tyr Ser Ser
1               5                   10

<210> SEQ ID NO 268
<211> LENGTH: 14
<212> TYPE: PRT
<213> ORGANISM: Homo sapiens

<400> SEQUENCE: 268

Lys Ser Asp Pro Arg Cys Leu Thr Arg Tyr Tyr Ser Ser Phe
1               5                   10

<210> SEQ ID NO 269
<211> LENGTH: 15
<212> TYPE: PRT
<213> ORGANISM: Homo sapiens

<400> SEQUENCE: 269

Lys Ser Asp Pro Arg Cys Leu Thr Arg Tyr Tyr Ser Ser Phe Val
1               5                   10                  15

<210> SEQ ID NO 270
<211> LENGTH: 16
<212> TYPE: PRT
<213> ORGANISM: Homo sapiens

<400> SEQUENCE: 270

Lys Ser Asp Pro Arg Cys Leu Thr Arg Tyr Tyr Ser Ser Phe Val Asn
1               5                   10                  15

<210> SEQ ID NO 271
<211> LENGTH: 17
<212> TYPE: PRT
<213> ORGANISM: Homo sapiens

<400> SEQUENCE: 271

Lys Ser Asp Pro Arg Cys Leu Thr Arg Tyr Tyr Ser Ser Phe Val Asn
1               5                   10                  15

Met

<210> SEQ ID NO 272
<211> LENGTH: 18
<212> TYPE: PRT
<213> ORGANISM: Homo sapiens

<400> SEQUENCE: 272

Lys Ser Asp Pro Arg Cys Leu Thr Arg Tyr Tyr Ser Ser Phe Val Asn
1               5                   10                  15
```

Met Glu

<210> SEQ ID NO 273
<211> LENGTH: 19
<212> TYPE: PRT
<213> ORGANISM: Homo sapiens

<400> SEQUENCE: 273

Lys Ser Asp Pro Arg Cys Leu Thr Arg Tyr Tyr Ser Ser Phe Val Asn
1               5                   10                  15

Met Glu Arg

<210> SEQ ID NO 274
<211> LENGTH: 9
<212> TYPE: PRT
<213> ORGANISM: Homo sapiens

<400> SEQUENCE: 274

Ser Asp Pro Arg Cys Leu Thr Arg Tyr
1               5

<210> SEQ ID NO 275
<211> LENGTH: 10
<212> TYPE: PRT
<213> ORGANISM: Homo sapiens

<400> SEQUENCE: 275

Ser Asp Pro Arg Cys Leu Thr Arg Tyr Tyr
1               5                   10

<210> SEQ ID NO 276
<211> LENGTH: 11
<212> TYPE: PRT
<213> ORGANISM: Homo sapiens

<400> SEQUENCE: 276

Ser Asp Pro Arg Cys Leu Thr Arg Tyr Tyr Ser
1               5                   10

<210> SEQ ID NO 277
<211> LENGTH: 12
<212> TYPE: PRT
<213> ORGANISM: Homo sapiens

<400> SEQUENCE: 277

Ser Asp Pro Arg Cys Leu Thr Arg Tyr Tyr Ser Ser
1               5                   10

<210> SEQ ID NO 278
<211> LENGTH: 13
<212> TYPE: PRT
<213> ORGANISM: Homo sapiens

<400> SEQUENCE: 278

Ser Asp Pro Arg Cys Leu Thr Arg Tyr Tyr Ser Ser Phe
1               5                   10

<210> SEQ ID NO 279
<211> LENGTH: 14
<212> TYPE: PRT
<213> ORGANISM: Homo sapiens

<400> SEQUENCE: 279

Ser Asp Pro Arg Cys Leu Thr Arg Tyr Tyr Ser Ser Phe Val
1               5                   10

<210> SEQ ID NO 280
<211> LENGTH: 15
<212> TYPE: PRT
<213> ORGANISM: Homo sapiens

<400> SEQUENCE: 280

Ser Asp Pro Arg Cys Leu Thr Arg Tyr Tyr Ser Ser Phe Val Asn
1               5                   10                  15

<210> SEQ ID NO 281
<211> LENGTH: 16
<212> TYPE: PRT
<213> ORGANISM: Homo sapiens

<400> SEQUENCE: 281

Ser Asp Pro Arg Cys Leu Thr Arg Tyr Tyr Ser Ser Phe Val Asn Met
1               5                   10                  15

<210> SEQ ID NO 282
<211> LENGTH: 17
<212> TYPE: PRT
<213> ORGANISM: Homo sapiens

<400> SEQUENCE: 282

Ser Asp Pro Arg Cys Leu Thr Arg Tyr Tyr Ser Ser Phe Val Asn Met
1               5                   10                  15

Glu

<210> SEQ ID NO 283
<211> LENGTH: 18
<212> TYPE: PRT
<213> ORGANISM: Homo sapiens

<400> SEQUENCE: 283

Ser Asp Pro Arg Cys Leu Thr Arg Tyr Tyr Ser Ser Phe Val Asn Met
1               5                   10                  15

Glu Arg

<210> SEQ ID NO 284
<211> LENGTH: 9
<212> TYPE: PRT
<213> ORGANISM: Homo sapiens

<400> SEQUENCE: 284

Asp Pro Arg Cys Leu Thr Arg Tyr Tyr
1               5

<210> SEQ ID NO 285
<211> LENGTH: 10
<212> TYPE: PRT
<213> ORGANISM: Homo sapiens

<400> SEQUENCE: 285

Asp Pro Arg Cys Leu Thr Arg Tyr Tyr Ser
1               5                   10

<210> SEQ ID NO 286
<211> LENGTH: 11
<212> TYPE: PRT
<213> ORGANISM: Homo sapiens

<400> SEQUENCE: 286

Asp Pro Arg Cys Leu Thr Arg Tyr Tyr Ser Ser
1               5                   10

<210> SEQ ID NO 287
<211> LENGTH: 12
<212> TYPE: PRT
<213> ORGANISM: Homo sapiens

<400> SEQUENCE: 287

Asp Pro Arg Cys Leu Thr Arg Tyr Tyr Ser Ser Phe
1               5                   10

<210> SEQ ID NO 288
<211> LENGTH: 13
<212> TYPE: PRT
<213> ORGANISM: Homo sapiens

<400> SEQUENCE: 288

Asp Pro Arg Cys Leu Thr Arg Tyr Tyr Ser Ser Phe Val
1               5                   10

<210> SEQ ID NO 289
<211> LENGTH: 14
<212> TYPE: PRT
<213> ORGANISM: Homo sapiens

<400> SEQUENCE: 289

Asp Pro Arg Cys Leu Thr Arg Tyr Tyr Ser Ser Phe Val Asn
1               5                   10

<210> SEQ ID NO 290
<211> LENGTH: 15
<212> TYPE: PRT
<213> ORGANISM: Homo sapiens

<400> SEQUENCE: 290

Asp Pro Arg Cys Leu Thr Arg Tyr Tyr Ser Ser Phe Val Asn Met
1               5                   10                  15

<210> SEQ ID NO 291
<211> LENGTH: 16
<212> TYPE: PRT
<213> ORGANISM: Homo sapiens

<400> SEQUENCE: 291

Asp Pro Arg Cys Leu Thr Arg Tyr Tyr Ser Ser Phe Val Asn Met Glu
1               5                   10                  15

<210> SEQ ID NO 292
<211> LENGTH: 17
<212> TYPE: PRT
<213> ORGANISM: Homo sapiens

<400> SEQUENCE: 292

Asp Pro Arg Cys Leu Thr Arg Tyr Tyr Ser Ser Phe Val Asn Met Glu
1               5                   10                  15

Arg

<210> SEQ ID NO 293
<211> LENGTH: 9
<212> TYPE: PRT
<213> ORGANISM: Homo sapiens

```
<400> SEQUENCE: 293

Pro Arg Cys Leu Thr Arg Tyr Tyr Ser
1               5

<210> SEQ ID NO 294
<211> LENGTH: 10
<212> TYPE: PRT
<213> ORGANISM: Homo sapiens

<400> SEQUENCE: 294

Pro Arg Cys Leu Thr Arg Tyr Tyr Ser Ser
1               5                   10

<210> SEQ ID NO 295
<211> LENGTH: 11
<212> TYPE: PRT
<213> ORGANISM: Homo sapiens

<400> SEQUENCE: 295

Pro Arg Cys Leu Thr Arg Tyr Tyr Ser Ser Phe
1               5                   10

<210> SEQ ID NO 296
<211> LENGTH: 12
<212> TYPE: PRT
<213> ORGANISM: Homo sapiens

<400> SEQUENCE: 296

Pro Arg Cys Leu Thr Arg Tyr Tyr Ser Ser Phe Val
1               5                   10

<210> SEQ ID NO 297
<211> LENGTH: 13
<212> TYPE: PRT
<213> ORGANISM: Homo sapiens

<400> SEQUENCE: 297

Pro Arg Cys Leu Thr Arg Tyr Tyr Ser Ser Phe Val Asn
1               5                   10

<210> SEQ ID NO 298
<211> LENGTH: 14
<212> TYPE: PRT
<213> ORGANISM: Homo sapiens

<400> SEQUENCE: 298

Pro Arg Cys Leu Thr Arg Tyr Tyr Ser Ser Phe Val Asn Met
1               5                   10

<210> SEQ ID NO 299
<211> LENGTH: 15
<212> TYPE: PRT
<213> ORGANISM: Homo sapiens

<400> SEQUENCE: 299

Pro Arg Cys Leu Thr Arg Tyr Tyr Ser Ser Phe Val Asn Met Glu
1               5                   10                  15

<210> SEQ ID NO 300
<211> LENGTH: 16
<212> TYPE: PRT
<213> ORGANISM: Homo sapiens

<400> SEQUENCE: 300
```

Pro Arg Cys Leu Thr Arg Tyr Tyr Ser Ser Phe Val Asn Met Glu Arg
1               5                   10                  15

<210> SEQ ID NO 301
<211> LENGTH: 9
<212> TYPE: PRT
<213> ORGANISM: Homo sapiens

<400> SEQUENCE: 301

Arg Cys Leu Thr Arg Tyr Tyr Ser Ser
1               5

<210> SEQ ID NO 302
<211> LENGTH: 10
<212> TYPE: PRT
<213> ORGANISM: Homo sapiens

<400> SEQUENCE: 302

Arg Cys Leu Thr Arg Tyr Tyr Ser Ser Phe
1               5                   10

<210> SEQ ID NO 303
<211> LENGTH: 11
<212> TYPE: PRT
<213> ORGANISM: Homo sapiens

<400> SEQUENCE: 303

Arg Cys Leu Thr Arg Tyr Tyr Ser Ser Phe Val
1               5                   10

<210> SEQ ID NO 304
<211> LENGTH: 12
<212> TYPE: PRT
<213> ORGANISM: Homo sapiens

<400> SEQUENCE: 304

Arg Cys Leu Thr Arg Tyr Tyr Ser Ser Phe Val Asn
1               5                   10

<210> SEQ ID NO 305
<211> LENGTH: 13
<212> TYPE: PRT
<213> ORGANISM: Homo sapiens

<400> SEQUENCE: 305

Arg Cys Leu Thr Arg Tyr Tyr Ser Ser Phe Val Asn Met
1               5                   10

<210> SEQ ID NO 306
<211> LENGTH: 14
<212> TYPE: PRT
<213> ORGANISM: Homo sapiens

<400> SEQUENCE: 306

Arg Cys Leu Thr Arg Tyr Tyr Ser Ser Phe Val Asn Met Glu
1               5                   10

<210> SEQ ID NO 307
<211> LENGTH: 15
<212> TYPE: PRT
<213> ORGANISM: Homo sapiens

<400> SEQUENCE: 307

Arg Cys Leu Thr Arg Tyr Tyr Ser Ser Phe Val Asn Met Glu Arg
1               5                   10                  15

```
<210> SEQ ID NO 308
<211> LENGTH: 9
<212> TYPE: PRT
<213> ORGANISM: Homo sapiens

<400> SEQUENCE: 308

Cys Leu Thr Arg Tyr Tyr Ser Ser Phe
1               5

<210> SEQ ID NO 309
<211> LENGTH: 10
<212> TYPE: PRT
<213> ORGANISM: Homo sapiens

<400> SEQUENCE: 309

Cys Leu Thr Arg Tyr Tyr Ser Ser Phe Val
1               5                   10

<210> SEQ ID NO 310
<211> LENGTH: 11
<212> TYPE: PRT
<213> ORGANISM: Homo sapiens

<400> SEQUENCE: 310

Cys Leu Thr Arg Tyr Tyr Ser Ser Phe Val Asn
1               5                   10

<210> SEQ ID NO 311
<211> LENGTH: 12
<212> TYPE: PRT
<213> ORGANISM: Homo sapiens

<400> SEQUENCE: 311

Cys Leu Thr Arg Tyr Tyr Ser Ser Phe Val Asn Met
1               5                   10

<210> SEQ ID NO 312
<211> LENGTH: 13
<212> TYPE: PRT
<213> ORGANISM: Homo sapiens

<400> SEQUENCE: 312

Cys Leu Thr Arg Tyr Tyr Ser Ser Phe Val Asn Met Glu
1               5                   10

<210> SEQ ID NO 313
<211> LENGTH: 14
<212> TYPE: PRT
<213> ORGANISM: Homo sapiens

<400> SEQUENCE: 313

Cys Leu Thr Arg Tyr Tyr Ser Ser Phe Val Asn Met Glu Arg
1               5                   10

<210> SEQ ID NO 314
<211> LENGTH: 9
<212> TYPE: PRT
<213> ORGANISM: Homo sapiens

<400> SEQUENCE: 314

Leu Thr Arg Tyr Tyr Ser Ser Phe Val
1               5
```

<210> SEQ ID NO 315
<211> LENGTH: 10
<212> TYPE: PRT
<213> ORGANISM: Homo sapiens

<400> SEQUENCE: 315

Leu Thr Arg Tyr Tyr Ser Ser Phe Val Asn
1               5                   10

<210> SEQ ID NO 316
<211> LENGTH: 11
<212> TYPE: PRT
<213> ORGANISM: Homo sapiens

<400> SEQUENCE: 316

Leu Thr Arg Tyr Tyr Ser Ser Phe Val Asn Met
1               5                   10

<210> SEQ ID NO 317
<211> LENGTH: 12
<212> TYPE: PRT
<213> ORGANISM: Homo sapiens

<400> SEQUENCE: 317

Leu Thr Arg Tyr Tyr Ser Ser Phe Val Asn Met Glu
1               5                   10

<210> SEQ ID NO 318
<211> LENGTH: 13
<212> TYPE: PRT
<213> ORGANISM: Homo sapiens

<400> SEQUENCE: 318

Leu Thr Arg Tyr Tyr Ser Ser Phe Val Asn Met Glu Arg
1               5                   10

<210> SEQ ID NO 319
<211> LENGTH: 9
<212> TYPE: PRT
<213> ORGANISM: Homo sapiens

<400> SEQUENCE: 319

Thr Arg Tyr Tyr Ser Ser Phe Val Asn
1               5

<210> SEQ ID NO 320
<211> LENGTH: 10
<212> TYPE: PRT
<213> ORGANISM: Homo sapiens

<400> SEQUENCE: 320

Thr Arg Tyr Tyr Ser Ser Phe Val Asn Met
1               5                   10

<210> SEQ ID NO 321
<211> LENGTH: 11
<212> TYPE: PRT
<213> ORGANISM: Homo sapiens

<400> SEQUENCE: 321

Thr Arg Tyr Tyr Ser Ser Phe Val Asn Met Glu
1               5                   10

<210> SEQ ID NO 322
<211> LENGTH: 12

```
<212> TYPE: PRT
<213> ORGANISM: Homo sapiens

<400> SEQUENCE: 322

Thr Arg Tyr Tyr Ser Ser Phe Val Asn Met Glu Arg
1               5                   10

<210> SEQ ID NO 323
<211> LENGTH: 9
<212> TYPE: PRT
<213> ORGANISM: Homo sapiens

<400> SEQUENCE: 323

Arg Tyr Tyr Ser Ser Phe Val Asn Met
1               5

<210> SEQ ID NO 324
<211> LENGTH: 10
<212> TYPE: PRT
<213> ORGANISM: Homo sapiens

<400> SEQUENCE: 324

Arg Tyr Tyr Ser Ser Phe Val Asn Met Glu
1               5                   10

<210> SEQ ID NO 325
<211> LENGTH: 11
<212> TYPE: PRT
<213> ORGANISM: Homo sapiens

<400> SEQUENCE: 325

Arg Tyr Tyr Ser Ser Phe Val Asn Met Glu Arg
1               5                   10

<210> SEQ ID NO 326
<211> LENGTH: 9
<212> TYPE: PRT
<213> ORGANISM: Homo sapiens

<400> SEQUENCE: 326

Tyr Tyr Ser Ser Phe Val Asn Met Glu
1               5

<210> SEQ ID NO 327
<211> LENGTH: 10
<212> TYPE: PRT
<213> ORGANISM: Homo sapiens

<400> SEQUENCE: 327

Tyr Tyr Ser Ser Phe Val Asn Met Glu Arg
1               5                   10

<210> SEQ ID NO 328
<211> LENGTH: 9
<212> TYPE: PRT
<213> ORGANISM: Homo sapiens

<400> SEQUENCE: 328

Tyr Ser Ser Phe Val Asn Met Glu Arg
1               5

<210> SEQ ID NO 329
<211> LENGTH: 9
<212> TYPE: PRT
<213> ORGANISM: Homo sapiens
```

```
<400> SEQUENCE: 329

Gln Ala Asn Arg Ser Pro Leu Pro Ile
1               5

<210> SEQ ID NO 330
<211> LENGTH: 10
<212> TYPE: PRT
<213> ORGANISM: Homo sapiens

<400> SEQUENCE: 330

Gln Ala Asn Arg Ser Pro Leu Pro Ile Ala
1               5                   10

<210> SEQ ID NO 331
<211> LENGTH: 11
<212> TYPE: PRT
<213> ORGANISM: Homo sapiens

<400> SEQUENCE: 331

Gln Ala Asn Arg Ser Pro Leu Pro Ile Ala Lys
1               5                   10

<210> SEQ ID NO 332
<211> LENGTH: 12
<212> TYPE: PRT
<213> ORGANISM: Homo sapiens

<400> SEQUENCE: 332

Gln Ala Asn Arg Ser Pro Leu Pro Ile Ala Lys Val
1               5                   10

<210> SEQ ID NO 333
<211> LENGTH: 13
<212> TYPE: PRT
<213> ORGANISM: Homo sapiens

<400> SEQUENCE: 333

Gln Ala Asn Arg Ser Pro Leu Pro Ile Ala Lys Val Ser
1               5                   10

<210> SEQ ID NO 334
<211> LENGTH: 14
<212> TYPE: PRT
<213> ORGANISM: Homo sapiens

<400> SEQUENCE: 334

Gln Ala Asn Arg Ser Pro Leu Pro Ile Ala Lys Val Ser Ser
1               5                   10

<210> SEQ ID NO 335
<211> LENGTH: 15
<212> TYPE: PRT
<213> ORGANISM: Homo sapiens

<400> SEQUENCE: 335

Gln Ala Asn Arg Ser Pro Leu Pro Ile Ala Lys Val Ser Ser Phe
1               5                   10                  15

<210> SEQ ID NO 336
<211> LENGTH: 16
<212> TYPE: PRT
<213> ORGANISM: Homo sapiens

<400> SEQUENCE: 336
```

Gln Ala Asn Arg Ser Pro Leu Pro Ile Ala Lys Val Ser Ser Phe Pro
1               5                   10                  15

<210> SEQ ID NO 337
<211> LENGTH: 17
<212> TYPE: PRT
<213> ORGANISM: Homo sapiens

<400> SEQUENCE: 337

Gln Ala Asn Arg Ser Pro Leu Pro Ile Ala Lys Val Ser Ser Phe Pro
1               5                   10                  15

Ser

<210> SEQ ID NO 338
<211> LENGTH: 18
<212> TYPE: PRT
<213> ORGANISM: Homo sapiens

<400> SEQUENCE: 338

Gln Ala Asn Arg Ser Pro Leu Pro Ile Ala Lys Val Ser Ser Phe Pro
1               5                   10                  15

Ser Ile

<210> SEQ ID NO 339
<211> LENGTH: 19
<212> TYPE: PRT
<213> ORGANISM: Homo sapiens

<400> SEQUENCE: 339

Gln Ala Asn Arg Ser Pro Leu Pro Ile Ala Lys Val Ser Ser Phe Pro
1               5                   10                  15

Ser Ile Arg

<210> SEQ ID NO 340
<211> LENGTH: 20
<212> TYPE: PRT
<213> ORGANISM: Homo sapiens

<400> SEQUENCE: 340

Gln Ala Asn Arg Ser Pro Leu Pro Ile Ala Lys Val Ser Ser Phe Pro
1               5                   10                  15

Ser Ile Arg Pro
            20

<210> SEQ ID NO 341
<211> LENGTH: 21
<212> TYPE: PRT
<213> ORGANISM: Homo sapiens

<400> SEQUENCE: 341

Gln Ala Asn Arg Ser Pro Leu Pro Ile Ala Lys Val Ser Ser Phe Pro
1               5                   10                  15

Ser Ile Arg Pro Ile
            20

<210> SEQ ID NO 342
<211> LENGTH: 22
<212> TYPE: PRT
<213> ORGANISM: Homo sapiens

<400> SEQUENCE: 342

```
Gln Ala Asn Arg Ser Pro Leu Pro Ile Ala Lys Val Ser Ser Phe Pro
1               5                   10                  15

Ser Ile Arg Pro Ile Tyr
            20

<210> SEQ ID NO 343
<211> LENGTH: 23
<212> TYPE: PRT
<213> ORGANISM: Homo sapiens

<400> SEQUENCE: 343

Gln Ala Asn Arg Ser Pro Leu Pro Ile Ala Lys Val Ser Ser Phe Pro
1               5                   10                  15

Ser Ile Arg Pro Ile Tyr Leu
            20

<210> SEQ ID NO 344
<211> LENGTH: 24
<212> TYPE: PRT
<213> ORGANISM: Homo sapiens

<400> SEQUENCE: 344

Gln Ala Asn Arg Ser Pro Leu Pro Ile Ala Lys Val Ser Ser Phe Pro
1               5                   10                  15

Ser Ile Arg Pro Ile Tyr Leu Thr
            20

<210> SEQ ID NO 345
<211> LENGTH: 9
<212> TYPE: PRT
<213> ORGANISM: Homo sapiens

<400> SEQUENCE: 345

Ala Asn Arg Ser Pro Leu Pro Ile Ala
1               5

<210> SEQ ID NO 346
<211> LENGTH: 10
<212> TYPE: PRT
<213> ORGANISM: Homo sapiens

<400> SEQUENCE: 346

Ala Asn Arg Ser Pro Leu Pro Ile Ala Lys
1               5                   10

<210> SEQ ID NO 347
<211> LENGTH: 11
<212> TYPE: PRT
<213> ORGANISM: Homo sapiens

<400> SEQUENCE: 347

Ala Asn Arg Ser Pro Leu Pro Ile Ala Lys Val
1               5                   10

<210> SEQ ID NO 348
<211> LENGTH: 12
<212> TYPE: PRT
<213> ORGANISM: Homo sapiens

<400> SEQUENCE: 348

Ala Asn Arg Ser Pro Leu Pro Ile Ala Lys Val Ser
1               5                   10
```

<210> SEQ ID NO 349
<211> LENGTH: 13
<212> TYPE: PRT
<213> ORGANISM: Homo sapiens

<400> SEQUENCE: 349

Ala Asn Arg Ser Pro Leu Pro Ile Ala Lys Val Ser Ser
1               5                   10

<210> SEQ ID NO 350
<211> LENGTH: 14
<212> TYPE: PRT
<213> ORGANISM: Homo sapiens

<400> SEQUENCE: 350

Ala Asn Arg Ser Pro Leu Pro Ile Ala Lys Val Ser Ser Phe
1               5                   10

<210> SEQ ID NO 351
<211> LENGTH: 15
<212> TYPE: PRT
<213> ORGANISM: Homo sapiens

<400> SEQUENCE: 351

Ala Asn Arg Ser Pro Leu Pro Ile Ala Lys Val Ser Ser Phe Pro
1               5                   10                  15

<210> SEQ ID NO 352
<211> LENGTH: 16
<212> TYPE: PRT
<213> ORGANISM: Homo sapiens

<400> SEQUENCE: 352

Ala Asn Arg Ser Pro Leu Pro Ile Ala Lys Val Ser Ser Phe Pro Ser
1               5                   10                  15

<210> SEQ ID NO 353
<211> LENGTH: 17
<212> TYPE: PRT
<213> ORGANISM: Homo sapiens

<400> SEQUENCE: 353

Ala Asn Arg Ser Pro Leu Pro Ile Ala Lys Val Ser Ser Phe Pro Ser
1               5                   10                  15

Ile

<210> SEQ ID NO 354
<211> LENGTH: 18
<212> TYPE: PRT
<213> ORGANISM: Homo sapiens

<400> SEQUENCE: 354

Ala Asn Arg Ser Pro Leu Pro Ile Ala Lys Val Ser Ser Phe Pro Ser
1               5                   10                  15

Ile Arg

<210> SEQ ID NO 355
<211> LENGTH: 19
<212> TYPE: PRT
<213> ORGANISM: Homo sapiens

<400> SEQUENCE: 355

Ala Asn Arg Ser Pro Leu Pro Ile Ala Lys Val Ser Ser Phe Pro Ser
1               5                   10                  15

Ile Arg Pro

<210> SEQ ID NO 356
<211> LENGTH: 20
<212> TYPE: PRT
<213> ORGANISM: Homo sapiens

<400> SEQUENCE: 356

Ala Asn Arg Ser Pro Leu Pro Ile Ala Lys Val Ser Ser Phe Pro Ser
1               5                   10                  15

Ile Arg Pro Ile
            20

<210> SEQ ID NO 357
<211> LENGTH: 21
<212> TYPE: PRT
<213> ORGANISM: Homo sapiens

<400> SEQUENCE: 357

Ala Asn Arg Ser Pro Leu Pro Ile Ala Lys Val Ser Ser Phe Pro Ser
1               5                   10                  15

Ile Arg Pro Ile Tyr
            20

<210> SEQ ID NO 358
<211> LENGTH: 22
<212> TYPE: PRT
<213> ORGANISM: Homo sapiens

<400> SEQUENCE: 358

Ala Asn Arg Ser Pro Leu Pro Ile Ala Lys Val Ser Ser Phe Pro Ser
1               5                   10                  15

Ile Arg Pro Ile Tyr Leu
            20

<210> SEQ ID NO 359
<211> LENGTH: 23
<212> TYPE: PRT
<213> ORGANISM: Homo sapiens

<400> SEQUENCE: 359

Ala Asn Arg Ser Pro Leu Pro Ile Ala Lys Val Ser Ser Phe Pro Ser
1               5                   10                  15

Ile Arg Pro Ile Tyr Leu Thr
            20

<210> SEQ ID NO 360
<211> LENGTH: 9
<212> TYPE: PRT
<213> ORGANISM: Homo sapiens

<400> SEQUENCE: 360

Asn Arg Ser Pro Leu Pro Ile Ala Lys
1               5

<210> SEQ ID NO 361
<211> LENGTH: 10
<212> TYPE: PRT
<213> ORGANISM: Homo sapiens

<400> SEQUENCE: 361

Asn Arg Ser Pro Leu Pro Ile Ala Lys Val

```
1               5                   10
```

<210> SEQ ID NO 362
<211> LENGTH: 11
<212> TYPE: PRT
<213> ORGANISM: Homo sapiens

<400> SEQUENCE: 362

```
Asn Arg Ser Pro Leu Pro Ile Ala Lys Val Ser
1               5                   10
```

<210> SEQ ID NO 363
<211> LENGTH: 12
<212> TYPE: PRT
<213> ORGANISM: Homo sapiens

<400> SEQUENCE: 363

```
Asn Arg Ser Pro Leu Pro Ile Ala Lys Val Ser Ser
1               5                   10
```

<210> SEQ ID NO 364
<211> LENGTH: 13
<212> TYPE: PRT
<213> ORGANISM: Homo sapiens

<400> SEQUENCE: 364

```
Asn Arg Ser Pro Leu Pro Ile Ala Lys Val Ser Ser Phe
1               5                   10
```

<210> SEQ ID NO 365
<211> LENGTH: 14
<212> TYPE: PRT
<213> ORGANISM: Homo sapiens

<400> SEQUENCE: 365

```
Asn Arg Ser Pro Leu Pro Ile Ala Lys Val Ser Ser Phe Pro
1               5                   10
```

<210> SEQ ID NO 366
<211> LENGTH: 15
<212> TYPE: PRT
<213> ORGANISM: Homo sapiens

<400> SEQUENCE: 366

```
Asn Arg Ser Pro Leu Pro Ile Ala Lys Val Ser Ser Phe Pro Ser
1               5                   10                  15
```

<210> SEQ ID NO 367
<211> LENGTH: 16
<212> TYPE: PRT
<213> ORGANISM: Homo sapiens

<400> SEQUENCE: 367

```
Asn Arg Ser Pro Leu Pro Ile Ala Lys Val Ser Ser Phe Pro Ser Ile
1               5                   10                  15
```

<210> SEQ ID NO 368
<211> LENGTH: 17
<212> TYPE: PRT
<213> ORGANISM: Homo sapiens

<400> SEQUENCE: 368

```
Asn Arg Ser Pro Leu Pro Ile Ala Lys Val Ser Ser Phe Pro Ser Ile
1               5                   10                  15
```

Arg

<210> SEQ ID NO 369
<211> LENGTH: 18
<212> TYPE: PRT
<213> ORGANISM: Homo sapiens

<400> SEQUENCE: 369

Asn Arg Ser Pro Leu Pro Ile Ala Lys Val Ser Ser Phe Pro Ser Ile
1               5                   10                  15

Arg Pro

<210> SEQ ID NO 370
<211> LENGTH: 19
<212> TYPE: PRT
<213> ORGANISM: Homo sapiens

<400> SEQUENCE: 370

Asn Arg Ser Pro Leu Pro Ile Ala Lys Val Ser Ser Phe Pro Ser Ile
1               5                   10                  15

Arg Pro Ile

<210> SEQ ID NO 371
<211> LENGTH: 20
<212> TYPE: PRT
<213> ORGANISM: Homo sapiens

<400> SEQUENCE: 371

Asn Arg Ser Pro Leu Pro Ile Ala Lys Val Ser Ser Phe Pro Ser Ile
1               5                   10                  15

Arg Pro Ile Tyr
            20

<210> SEQ ID NO 372
<211> LENGTH: 21
<212> TYPE: PRT
<213> ORGANISM: Homo sapiens

<400> SEQUENCE: 372

Asn Arg Ser Pro Leu Pro Ile Ala Lys Val Ser Ser Phe Pro Ser Ile
1               5                   10                  15

Arg Pro Ile Tyr Leu
            20

<210> SEQ ID NO 373
<211> LENGTH: 22
<212> TYPE: PRT
<213> ORGANISM: Homo sapiens

<400> SEQUENCE: 373

Asn Arg Ser Pro Leu Pro Ile Ala Lys Val Ser Ser Phe Pro Ser Ile
1               5                   10                  15

Arg Pro Ile Tyr Leu Thr
            20

<210> SEQ ID NO 374
<211> LENGTH: 9
<212> TYPE: PRT
<213> ORGANISM: Homo sapiens

<400> SEQUENCE: 374

Arg Ser Pro Leu Pro Ile Ala Lys Val

```
<210> SEQ ID NO 375
<211> LENGTH: 10
<212> TYPE: PRT
<213> ORGANISM: Homo sapiens

<400> SEQUENCE: 375

Arg Ser Pro Leu Pro Ile Ala Lys Val Ser
1               5                   10

<210> SEQ ID NO 376
<211> LENGTH: 11
<212> TYPE: PRT
<213> ORGANISM: Homo sapiens

<400> SEQUENCE: 376

Arg Ser Pro Leu Pro Ile Ala Lys Val Ser Ser
1               5                   10

<210> SEQ ID NO 377
<211> LENGTH: 12
<212> TYPE: PRT
<213> ORGANISM: Homo sapiens

<400> SEQUENCE: 377

Arg Ser Pro Leu Pro Ile Ala Lys Val Ser Ser Phe
1               5                   10

<210> SEQ ID NO 378
<211> LENGTH: 13
<212> TYPE: PRT
<213> ORGANISM: Homo sapiens

<400> SEQUENCE: 378

Arg Ser Pro Leu Pro Ile Ala Lys Val Ser Ser Phe Pro
1               5                   10

<210> SEQ ID NO 379
<211> LENGTH: 14
<212> TYPE: PRT
<213> ORGANISM: Homo sapiens

<400> SEQUENCE: 379

Arg Ser Pro Leu Pro Ile Ala Lys Val Ser Ser Phe Pro Ser
1               5                   10

<210> SEQ ID NO 380
<211> LENGTH: 15
<212> TYPE: PRT
<213> ORGANISM: Homo sapiens

<400> SEQUENCE: 380

Arg Ser Pro Leu Pro Ile Ala Lys Val Ser Ser Phe Pro Ser Ile
1               5                   10                  15

<210> SEQ ID NO 381
<211> LENGTH: 16
<212> TYPE: PRT
<213> ORGANISM: Homo sapiens

<400> SEQUENCE: 381

Arg Ser Pro Leu Pro Ile Ala Lys Val Ser Ser Phe Pro Ser Ile Arg
1               5                   10                  15
```

<210> SEQ ID NO 382
<211> LENGTH: 17
<212> TYPE: PRT
<213> ORGANISM: Homo sapiens

<400> SEQUENCE: 382

Arg Ser Pro Leu Pro Ile Ala Lys Val Ser Ser Phe Pro Ser Ile Arg
1               5                   10                  15

Pro

<210> SEQ ID NO 383
<211> LENGTH: 18
<212> TYPE: PRT
<213> ORGANISM: Homo sapiens

<400> SEQUENCE: 383

Arg Ser Pro Leu Pro Ile Ala Lys Val Ser Ser Phe Pro Ser Ile Arg
1               5                   10                  15

Pro Ile

<210> SEQ ID NO 384
<211> LENGTH: 19
<212> TYPE: PRT
<213> ORGANISM: Homo sapiens

<400> SEQUENCE: 384

Arg Ser Pro Leu Pro Ile Ala Lys Val Ser Ser Phe Pro Ser Ile Arg
1               5                   10                  15

Pro Ile Tyr

<210> SEQ ID NO 385
<211> LENGTH: 20
<212> TYPE: PRT
<213> ORGANISM: Homo sapiens

<400> SEQUENCE: 385

Arg Ser Pro Leu Pro Ile Ala Lys Val Ser Ser Phe Pro Ser Ile Arg
1               5                   10                  15

Pro Ile Tyr Leu
            20

<210> SEQ ID NO 386
<211> LENGTH: 21
<212> TYPE: PRT
<213> ORGANISM: Homo sapiens

<400> SEQUENCE: 386

Arg Ser Pro Leu Pro Ile Ala Lys Val Ser Ser Phe Pro Ser Ile Arg
1               5                   10                  15

Pro Ile Tyr Leu Thr
            20

<210> SEQ ID NO 387
<211> LENGTH: 9
<212> TYPE: PRT
<213> ORGANISM: Homo sapiens

<400> SEQUENCE: 387

Ser Pro Leu Pro Ile Ala Lys Val Ser
1               5

```
<210> SEQ ID NO 388
<211> LENGTH: 10
<212> TYPE: PRT
<213> ORGANISM: Homo sapiens

<400> SEQUENCE: 388

Ser Pro Leu Pro Ile Ala Lys Val Ser Ser
1               5                   10

<210> SEQ ID NO 389
<211> LENGTH: 11
<212> TYPE: PRT
<213> ORGANISM: Homo sapiens

<400> SEQUENCE: 389

Ser Pro Leu Pro Ile Ala Lys Val Ser Ser Phe
1               5                   10

<210> SEQ ID NO 390
<211> LENGTH: 12
<212> TYPE: PRT
<213> ORGANISM: Homo sapiens

<400> SEQUENCE: 390

Ser Pro Leu Pro Ile Ala Lys Val Ser Ser Phe Pro
1               5                   10

<210> SEQ ID NO 391
<211> LENGTH: 13
<212> TYPE: PRT
<213> ORGANISM: Homo sapiens

<400> SEQUENCE: 391

Ser Pro Leu Pro Ile Ala Lys Val Ser Ser Phe Pro Ser
1               5                   10

<210> SEQ ID NO 392
<211> LENGTH: 14
<212> TYPE: PRT
<213> ORGANISM: Homo sapiens

<400> SEQUENCE: 392

Ser Pro Leu Pro Ile Ala Lys Val Ser Ser Phe Pro Ser Ile
1               5                   10

<210> SEQ ID NO 393
<211> LENGTH: 15
<212> TYPE: PRT
<213> ORGANISM: Homo sapiens

<400> SEQUENCE: 393

Ser Pro Leu Pro Ile Ala Lys Val Ser Ser Phe Pro Ser Ile Arg
1               5                   10                  15

<210> SEQ ID NO 394
<211> LENGTH: 16
<212> TYPE: PRT
<213> ORGANISM: Homo sapiens

<400> SEQUENCE: 394

Ser Pro Leu Pro Ile Ala Lys Val Ser Ser Phe Pro Ser Ile Arg Pro
1               5                   10                  15

<210> SEQ ID NO 395
<211> LENGTH: 17
```

```
<212> TYPE: PRT
<213> ORGANISM: Homo sapiens

<400> SEQUENCE: 395

Ser Pro Leu Pro Ile Ala Lys Val Ser Ser Phe Pro Ser Ile Arg Pro
1               5                   10                  15

Ile

<210> SEQ ID NO 396
<211> LENGTH: 18
<212> TYPE: PRT
<213> ORGANISM: Homo sapiens

<400> SEQUENCE: 396

Ser Pro Leu Pro Ile Ala Lys Val Ser Ser Phe Pro Ser Ile Arg Pro
1               5                   10                  15

Ile Tyr

<210> SEQ ID NO 397
<211> LENGTH: 19
<212> TYPE: PRT
<213> ORGANISM: Homo sapiens

<400> SEQUENCE: 397

Ser Pro Leu Pro Ile Ala Lys Val Ser Ser Phe Pro Ser Ile Arg Pro
1               5                   10                  15

Ile Tyr Leu

<210> SEQ ID NO 398
<211> LENGTH: 20
<212> TYPE: PRT
<213> ORGANISM: Homo sapiens

<400> SEQUENCE: 398

Ser Pro Leu Pro Ile Ala Lys Val Ser Ser Phe Pro Ser Ile Arg Pro
1               5                   10                  15

Ile Tyr Leu Thr
            20

<210> SEQ ID NO 399
<211> LENGTH: 9
<212> TYPE: PRT
<213> ORGANISM: Homo sapiens

<400> SEQUENCE: 399

Pro Leu Pro Ile Ala Lys Val Ser Ser
1               5

<210> SEQ ID NO 400
<211> LENGTH: 10
<212> TYPE: PRT
<213> ORGANISM: Homo sapiens

<400> SEQUENCE: 400

Pro Leu Pro Ile Ala Lys Val Ser Ser Phe
1               5                   10

<210> SEQ ID NO 401
<211> LENGTH: 11
<212> TYPE: PRT
<213> ORGANISM: Homo sapiens

<400> SEQUENCE: 401
```

Pro Leu Pro Ile Ala Lys Val Ser Ser Phe Pro
1               5                   10

<210> SEQ ID NO 402
<211> LENGTH: 12
<212> TYPE: PRT
<213> ORGANISM: Homo sapiens

<400> SEQUENCE: 402

Pro Leu Pro Ile Ala Lys Val Ser Ser Phe Pro Ser
1               5                   10

<210> SEQ ID NO 403
<211> LENGTH: 13
<212> TYPE: PRT
<213> ORGANISM: Homo sapiens

<400> SEQUENCE: 403

Pro Leu Pro Ile Ala Lys Val Ser Ser Phe Pro Ser Ile
1               5                   10

<210> SEQ ID NO 404
<211> LENGTH: 14
<212> TYPE: PRT
<213> ORGANISM: Homo sapiens

<400> SEQUENCE: 404

Pro Leu Pro Ile Ala Lys Val Ser Ser Phe Pro Ser Ile Arg
1               5                   10

<210> SEQ ID NO 405
<211> LENGTH: 15
<212> TYPE: PRT
<213> ORGANISM: Homo sapiens

<400> SEQUENCE: 405

Pro Leu Pro Ile Ala Lys Val Ser Ser Phe Pro Ser Ile Arg Pro
1               5                   10                  15

<210> SEQ ID NO 406
<211> LENGTH: 16
<212> TYPE: PRT
<213> ORGANISM: Homo sapiens

<400> SEQUENCE: 406

Pro Leu Pro Ile Ala Lys Val Ser Ser Phe Pro Ser Ile Arg Pro Ile
1               5                   10                  15

<210> SEQ ID NO 407
<211> LENGTH: 17
<212> TYPE: PRT
<213> ORGANISM: Homo sapiens

<400> SEQUENCE: 407

Pro Leu Pro Ile Ala Lys Val Ser Ser Phe Pro Ser Ile Arg Pro Ile
1               5                   10                  15

Tyr

<210> SEQ ID NO 408
<211> LENGTH: 18
<212> TYPE: PRT
<213> ORGANISM: Homo sapiens

<400> SEQUENCE: 408

Pro Leu Pro Ile Ala Lys Val Ser Ser Phe Pro Ser Ile Arg Pro Ile
1               5                   10                  15

Tyr Leu

<210> SEQ ID NO 409
<211> LENGTH: 19
<212> TYPE: PRT
<213> ORGANISM: Homo sapiens

<400> SEQUENCE: 409

Pro Leu Pro Ile Ala Lys Val Ser Ser Phe Pro Ser Ile Arg Pro Ile
1               5                   10                  15

Tyr Leu Thr

<210> SEQ ID NO 410
<211> LENGTH: 9
<212> TYPE: PRT
<213> ORGANISM: Homo sapiens

<400> SEQUENCE: 410

Leu Pro Ile Ala Lys Val Ser Ser Phe
1               5

<210> SEQ ID NO 411
<211> LENGTH: 10
<212> TYPE: PRT
<213> ORGANISM: Homo sapiens

<400> SEQUENCE: 411

Leu Pro Ile Ala Lys Val Ser Ser Phe Pro
1               5                   10

<210> SEQ ID NO 412
<211> LENGTH: 11
<212> TYPE: PRT
<213> ORGANISM: Homo sapiens

<400> SEQUENCE: 412

Leu Pro Ile Ala Lys Val Ser Ser Phe Pro Ser
1               5                   10

<210> SEQ ID NO 413
<211> LENGTH: 12
<212> TYPE: PRT
<213> ORGANISM: Homo sapiens

<400> SEQUENCE: 413

Leu Pro Ile Ala Lys Val Ser Ser Phe Pro Ser Ile
1               5                   10

<210> SEQ ID NO 414
<211> LENGTH: 13
<212> TYPE: PRT
<213> ORGANISM: Homo sapiens

<400> SEQUENCE: 414

Leu Pro Ile Ala Lys Val Ser Ser Phe Pro Ser Ile Arg
1               5                   10

<210> SEQ ID NO 415
<211> LENGTH: 14
<212> TYPE: PRT
<213> ORGANISM: Homo sapiens

<400> SEQUENCE: 415

Leu Pro Ile Ala Lys Val Ser Ser Phe Pro Ser Ile Arg Pro
1               5                   10

<210> SEQ ID NO 416
<211> LENGTH: 15
<212> TYPE: PRT
<213> ORGANISM: Homo sapiens

<400> SEQUENCE: 416

Leu Pro Ile Ala Lys Val Ser Ser Phe Pro Ser Ile Arg Pro Ile
1               5                   10                  15

<210> SEQ ID NO 417
<211> LENGTH: 16
<212> TYPE: PRT
<213> ORGANISM: Homo sapiens

<400> SEQUENCE: 417

Leu Pro Ile Ala Lys Val Ser Ser Phe Pro Ser Ile Arg Pro Ile Tyr
1               5                   10                  15

<210> SEQ ID NO 418
<211> LENGTH: 17
<212> TYPE: PRT
<213> ORGANISM: Homo sapiens

<400> SEQUENCE: 418

Leu Pro Ile Ala Lys Val Ser Ser Phe Pro Ser Ile Arg Pro Ile Tyr
1               5                   10                  15

Leu

<210> SEQ ID NO 419
<211> LENGTH: 18
<212> TYPE: PRT
<213> ORGANISM: Homo sapiens

<400> SEQUENCE: 419

Leu Pro Ile Ala Lys Val Ser Ser Phe Pro Ser Ile Arg Pro Ile Tyr
1               5                   10                  15

Leu Thr

<210> SEQ ID NO 420
<211> LENGTH: 9
<212> TYPE: PRT
<213> ORGANISM: Homo sapiens

<400> SEQUENCE: 420

Pro Ile Ala Lys Val Ser Ser Phe Pro
1               5

<210> SEQ ID NO 421
<211> LENGTH: 10
<212> TYPE: PRT
<213> ORGANISM: Homo sapiens

<400> SEQUENCE: 421

Pro Ile Ala Lys Val Ser Ser Phe Pro Ser
1               5                   10

<210> SEQ ID NO 422
<211> LENGTH: 11

```
<212> TYPE: PRT
<213> ORGANISM: Homo sapiens

<400> SEQUENCE: 422

Pro Ile Ala Lys Val Ser Ser Phe Pro Ser Ile
1               5                   10

<210> SEQ ID NO 423
<211> LENGTH: 12
<212> TYPE: PRT
<213> ORGANISM: Homo sapiens

<400> SEQUENCE: 423

Pro Ile Ala Lys Val Ser Ser Phe Pro Ser Ile Arg
1               5                   10

<210> SEQ ID NO 424
<211> LENGTH: 13
<212> TYPE: PRT
<213> ORGANISM: Homo sapiens

<400> SEQUENCE: 424

Pro Ile Ala Lys Val Ser Ser Phe Pro Ser Ile Arg Pro
1               5                   10

<210> SEQ ID NO 425
<211> LENGTH: 14
<212> TYPE: PRT
<213> ORGANISM: Homo sapiens

<400> SEQUENCE: 425

Pro Ile Ala Lys Val Ser Ser Phe Pro Ser Ile Arg Pro Ile
1               5                   10

<210> SEQ ID NO 426
<211> LENGTH: 15
<212> TYPE: PRT
<213> ORGANISM: Homo sapiens

<400> SEQUENCE: 426

Pro Ile Ala Lys Val Ser Ser Phe Pro Ser Ile Arg Pro Ile Tyr
1               5                   10                  15

<210> SEQ ID NO 427
<211> LENGTH: 16
<212> TYPE: PRT
<213> ORGANISM: Homo sapiens

<400> SEQUENCE: 427

Pro Ile Ala Lys Val Ser Ser Phe Pro Ser Ile Arg Pro Ile Tyr Leu
1               5                   10                  15

<210> SEQ ID NO 428
<211> LENGTH: 17
<212> TYPE: PRT
<213> ORGANISM: Homo sapiens

<400> SEQUENCE: 428

Pro Ile Ala Lys Val Ser Ser Phe Pro Ser Ile Arg Pro Ile Tyr Leu
1               5                   10                  15

Thr

<210> SEQ ID NO 429
<211> LENGTH: 9
```

```
<212> TYPE: PRT
<213> ORGANISM: Homo sapiens

<400> SEQUENCE: 429

Ile Ala Lys Val Ser Ser Phe Pro Ser
1               5

<210> SEQ ID NO 430
<211> LENGTH: 10
<212> TYPE: PRT
<213> ORGANISM: Homo sapiens

<400> SEQUENCE: 430

Ile Ala Lys Val Ser Ser Phe Pro Ser Ile
1               5                   10

<210> SEQ ID NO 431
<211> LENGTH: 11
<212> TYPE: PRT
<213> ORGANISM: Homo sapiens

<400> SEQUENCE: 431

Ile Ala Lys Val Ser Ser Phe Pro Ser Ile Arg
1               5                   10

<210> SEQ ID NO 432
<211> LENGTH: 12
<212> TYPE: PRT
<213> ORGANISM: Homo sapiens

<400> SEQUENCE: 432

Ile Ala Lys Val Ser Ser Phe Pro Ser Ile Arg Pro
1               5                   10

<210> SEQ ID NO 433
<211> LENGTH: 13
<212> TYPE: PRT
<213> ORGANISM: Homo sapiens

<400> SEQUENCE: 433

Ile Ala Lys Val Ser Ser Phe Pro Ser Ile Arg Pro Ile
1               5                   10

<210> SEQ ID NO 434
<211> LENGTH: 14
<212> TYPE: PRT
<213> ORGANISM: Homo sapiens

<400> SEQUENCE: 434

Ile Ala Lys Val Ser Ser Phe Pro Ser Ile Arg Pro Ile Tyr
1               5                   10

<210> SEQ ID NO 435
<211> LENGTH: 15
<212> TYPE: PRT
<213> ORGANISM: Homo sapiens

<400> SEQUENCE: 435

Ile Ala Lys Val Ser Ser Phe Pro Ser Ile Arg Pro Ile Tyr Leu
1               5                   10                  15

<210> SEQ ID NO 436
<211> LENGTH: 16
<212> TYPE: PRT
<213> ORGANISM: Homo sapiens
```

<400> SEQUENCE: 436

Ile Ala Lys Val Ser Ser Phe Pro Ser Ile Arg Pro Ile Tyr Leu Thr
1               5                   10                  15

<210> SEQ ID NO 437
<211> LENGTH: 9
<212> TYPE: PRT
<213> ORGANISM: Homo sapiens

<400> SEQUENCE: 437

Ala Lys Val Ser Ser Phe Pro Ser Ile
1               5

<210> SEQ ID NO 438
<211> LENGTH: 10
<212> TYPE: PRT
<213> ORGANISM: Homo sapiens

<400> SEQUENCE: 438

Ala Lys Val Ser Ser Phe Pro Ser Ile Arg
1               5                   10

<210> SEQ ID NO 439
<211> LENGTH: 11
<212> TYPE: PRT
<213> ORGANISM: Homo sapiens

<400> SEQUENCE: 439

Ala Lys Val Ser Ser Phe Pro Ser Ile Arg Pro
1               5                   10

<210> SEQ ID NO 440
<211> LENGTH: 12
<212> TYPE: PRT
<213> ORGANISM: Homo sapiens

<400> SEQUENCE: 440

Ala Lys Val Ser Ser Phe Pro Ser Ile Arg Pro Ile
1               5                   10

<210> SEQ ID NO 441
<211> LENGTH: 13
<212> TYPE: PRT
<213> ORGANISM: Homo sapiens

<400> SEQUENCE: 441

Ala Lys Val Ser Ser Phe Pro Ser Ile Arg Pro Ile Tyr
1               5                   10

<210> SEQ ID NO 442
<211> LENGTH: 14
<212> TYPE: PRT
<213> ORGANISM: Homo sapiens

<400> SEQUENCE: 442

Ala Lys Val Ser Ser Phe Pro Ser Ile Arg Pro Ile Tyr Leu
1               5                   10

<210> SEQ ID NO 443
<211> LENGTH: 15
<212> TYPE: PRT
<213> ORGANISM: Homo sapiens

<400> SEQUENCE: 443

Ala Lys Val Ser Ser Phe Pro Ser Ile Arg Pro Ile Tyr Leu Thr
1               5                   10                  15

<210> SEQ ID NO 444
<211> LENGTH: 9
<212> TYPE: PRT
<213> ORGANISM: Homo sapiens

<400> SEQUENCE: 444

Lys Val Ser Ser Phe Pro Ser Ile Arg
1               5

<210> SEQ ID NO 445
<211> LENGTH: 10
<212> TYPE: PRT
<213> ORGANISM: Homo sapiens

<400> SEQUENCE: 445

Lys Val Ser Ser Phe Pro Ser Ile Arg Pro
1               5                   10

<210> SEQ ID NO 446
<211> LENGTH: 11
<212> TYPE: PRT
<213> ORGANISM: Homo sapiens

<400> SEQUENCE: 446

Lys Val Ser Ser Phe Pro Ser Ile Arg Pro Ile
1               5                   10

<210> SEQ ID NO 447
<211> LENGTH: 12
<212> TYPE: PRT
<213> ORGANISM: Homo sapiens

<400> SEQUENCE: 447

Lys Val Ser Ser Phe Pro Ser Ile Arg Pro Ile Tyr
1               5                   10

<210> SEQ ID NO 448
<211> LENGTH: 13
<212> TYPE: PRT
<213> ORGANISM: Homo sapiens

<400> SEQUENCE: 448

Lys Val Ser Ser Phe Pro Ser Ile Arg Pro Ile Tyr Leu
1               5                   10

<210> SEQ ID NO 449
<211> LENGTH: 14
<212> TYPE: PRT
<213> ORGANISM: Homo sapiens

<400> SEQUENCE: 449

Lys Val Ser Ser Phe Pro Ser Ile Arg Pro Ile Tyr Leu Thr
1               5                   10

<210> SEQ ID NO 450
<211> LENGTH: 9
<212> TYPE: PRT
<213> ORGANISM: Homo sapiens

<400> SEQUENCE: 450

Val Ser Ser Phe Pro Ser Ile Arg Pro

```
1               5
```

<210> SEQ ID NO 451
<211> LENGTH: 10
<212> TYPE: PRT
<213> ORGANISM: Homo sapiens

<400> SEQUENCE: 451

```
Val Ser Ser Phe Pro Ser Ile Arg Pro Ile
1               5                   10
```

<210> SEQ ID NO 452
<211> LENGTH: 11
<212> TYPE: PRT
<213> ORGANISM: Homo sapiens

<400> SEQUENCE: 452

```
Val Ser Ser Phe Pro Ser Ile Arg Pro Ile Tyr
1               5                   10
```

<210> SEQ ID NO 453
<211> LENGTH: 12
<212> TYPE: PRT
<213> ORGANISM: Homo sapiens

<400> SEQUENCE: 453

```
Val Ser Ser Phe Pro Ser Ile Arg Pro Ile Tyr Leu
1               5                   10
```

<210> SEQ ID NO 454
<211> LENGTH: 13
<212> TYPE: PRT
<213> ORGANISM: Homo sapiens

<400> SEQUENCE: 454

```
Val Ser Ser Phe Pro Ser Ile Arg Pro Ile Tyr Leu Thr
1               5                   10
```

<210> SEQ ID NO 455
<211> LENGTH: 9
<212> TYPE: PRT
<213> ORGANISM: Homo sapiens

<400> SEQUENCE: 455

```
Ser Ser Phe Pro Ser Ile Arg Pro Ile
1               5
```

<210> SEQ ID NO 456
<211> LENGTH: 10
<212> TYPE: PRT
<213> ORGANISM: Homo sapiens

<400> SEQUENCE: 456

```
Ser Ser Phe Pro Ser Ile Arg Pro Ile Tyr
1               5                   10
```

<210> SEQ ID NO 457
<211> LENGTH: 11
<212> TYPE: PRT
<213> ORGANISM: Homo sapiens

<400> SEQUENCE: 457

```
Ser Ser Phe Pro Ser Ile Arg Pro Ile Tyr Leu
1               5                   10
```

<210> SEQ ID NO 458
<211> LENGTH: 12
<212> TYPE: PRT
<213> ORGANISM: Homo sapiens

<400> SEQUENCE: 458

Ser Ser Phe Pro Ser Ile Arg Pro Ile Tyr Leu Thr
1               5                   10

<210> SEQ ID NO 459
<211> LENGTH: 9
<212> TYPE: PRT
<213> ORGANISM: Homo sapiens

<400> SEQUENCE: 459

Ser Phe Pro Ser Ile Arg Pro Ile Tyr
1               5

<210> SEQ ID NO 460
<211> LENGTH: 10
<212> TYPE: PRT
<213> ORGANISM: Homo sapiens

<400> SEQUENCE: 460

Ser Phe Pro Ser Ile Arg Pro Ile Tyr Leu
1               5                   10

<210> SEQ ID NO 461
<211> LENGTH: 11
<212> TYPE: PRT
<213> ORGANISM: Homo sapiens

<400> SEQUENCE: 461

Ser Phe Pro Ser Ile Arg Pro Ile Tyr Leu Thr
1               5                   10

<210> SEQ ID NO 462
<211> LENGTH: 9
<212> TYPE: PRT
<213> ORGANISM: Homo sapiens

<400> SEQUENCE: 462

Phe Pro Ser Ile Arg Pro Ile Tyr Leu
1               5

<210> SEQ ID NO 463
<211> LENGTH: 10
<212> TYPE: PRT
<213> ORGANISM: Homo sapiens

<400> SEQUENCE: 463

Phe Pro Ser Ile Arg Pro Ile Tyr Leu Thr
1               5                   10

<210> SEQ ID NO 464
<211> LENGTH: 9
<212> TYPE: PRT
<213> ORGANISM: Homo sapiens

<400> SEQUENCE: 464

Pro Ser Ile Arg Pro Ile Tyr Leu Thr
1               5

<210> SEQ ID NO 465

```
<211> LENGTH: 9
<212> TYPE: PRT
<213> ORGANISM: Homo sapiens

<400> SEQUENCE: 465

Glu Val Glu Asp Asn Ile Met Val Thr
1               5

<210> SEQ ID NO 466
<211> LENGTH: 10
<212> TYPE: PRT
<213> ORGANISM: Homo sapiens

<400> SEQUENCE: 466

Glu Val Glu Asp Asn Ile Met Val Thr Phe
1               5                   10

<210> SEQ ID NO 467
<211> LENGTH: 11
<212> TYPE: PRT
<213> ORGANISM: Homo sapiens

<400> SEQUENCE: 467

Glu Val Glu Asp Asn Ile Met Val Thr Phe Arg
1               5                   10

<210> SEQ ID NO 468
<211> LENGTH: 12
<212> TYPE: PRT
<213> ORGANISM: Homo sapiens

<400> SEQUENCE: 468

Glu Val Glu Asp Asn Ile Met Val Thr Phe Arg Asn
1               5                   10

<210> SEQ ID NO 469
<211> LENGTH: 13
<212> TYPE: PRT
<213> ORGANISM: Homo sapiens

<400> SEQUENCE: 469

Glu Val Glu Asp Asn Ile Met Val Thr Phe Arg Asn Gln
1               5                   10

<210> SEQ ID NO 470
<211> LENGTH: 14
<212> TYPE: PRT
<213> ORGANISM: Homo sapiens

<400> SEQUENCE: 470

Glu Val Glu Asp Asn Ile Met Val Thr Phe Arg Asn Gln Ala
1               5                   10

<210> SEQ ID NO 471
<211> LENGTH: 15
<212> TYPE: PRT
<213> ORGANISM: Homo sapiens

<400> SEQUENCE: 471

Glu Val Glu Asp Asn Ile Met Val Thr Phe Arg Asn Gln Ala Ser
1               5                   10                  15

<210> SEQ ID NO 472
<211> LENGTH: 16
<212> TYPE: PRT
```

-continued

<213> ORGANISM: Homo sapiens

<400> SEQUENCE: 472

Glu Val Glu Asp Asn Ile Met Val Thr Phe Arg Asn Gln Ala Ser Arg
1               5                   10                  15

<210> SEQ ID NO 473
<211> LENGTH: 17
<212> TYPE: PRT
<213> ORGANISM: Homo sapiens

<400> SEQUENCE: 473

Glu Val Glu Asp Asn Ile Met Val Thr Phe Arg Asn Gln Ala Ser Arg
1               5                   10                  15

Pro

<210> SEQ ID NO 474
<211> LENGTH: 18
<212> TYPE: PRT
<213> ORGANISM: Homo sapiens

<400> SEQUENCE: 474

Glu Val Glu Asp Asn Ile Met Val Thr Phe Arg Asn Gln Ala Ser Arg
1               5                   10                  15

Pro Tyr

<210> SEQ ID NO 475
<211> LENGTH: 19
<212> TYPE: PRT
<213> ORGANISM: Homo sapiens

<400> SEQUENCE: 475

Glu Val Glu Asp Asn Ile Met Val Thr Phe Arg Asn Gln Ala Ser Arg
1               5                   10                  15

Pro Tyr Ser

<210> SEQ ID NO 476
<211> LENGTH: 20
<212> TYPE: PRT
<213> ORGANISM: Homo sapiens

<400> SEQUENCE: 476

Glu Val Glu Asp Asn Ile Met Val Thr Phe Arg Asn Gln Ala Ser Arg
1               5                   10                  15

Pro Tyr Ser Phe
            20

<210> SEQ ID NO 477
<211> LENGTH: 21
<212> TYPE: PRT
<213> ORGANISM: Homo sapiens

<400> SEQUENCE: 477

Glu Val Glu Asp Asn Ile Met Val Thr Phe Arg Asn Gln Ala Ser Arg
1               5                   10                  15

Pro Tyr Ser Phe Tyr
            20

<210> SEQ ID NO 478
<211> LENGTH: 9
<212> TYPE: PRT
<213> ORGANISM: Homo sapiens

<400> SEQUENCE: 478

Val Glu Asp Asn Ile Met Val Thr Phe
1               5

<210> SEQ ID NO 479
<211> LENGTH: 10
<212> TYPE: PRT
<213> ORGANISM: Homo sapiens

<400> SEQUENCE: 479

Val Glu Asp Asn Ile Met Val Thr Phe Arg
1               5                   10

<210> SEQ ID NO 480
<211> LENGTH: 11
<212> TYPE: PRT
<213> ORGANISM: Homo sapiens

<400> SEQUENCE: 480

Val Glu Asp Asn Ile Met Val Thr Phe Arg Asn
1               5                   10

<210> SEQ ID NO 481
<211> LENGTH: 12
<212> TYPE: PRT
<213> ORGANISM: Homo sapiens

<400> SEQUENCE: 481

Val Glu Asp Asn Ile Met Val Thr Phe Arg Asn Gln
1               5                   10

<210> SEQ ID NO 482
<211> LENGTH: 13
<212> TYPE: PRT
<213> ORGANISM: Homo sapiens

<400> SEQUENCE: 482

Val Glu Asp Asn Ile Met Val Thr Phe Arg Asn Gln Ala
1               5                   10

<210> SEQ ID NO 483
<211> LENGTH: 14
<212> TYPE: PRT
<213> ORGANISM: Homo sapiens

<400> SEQUENCE: 483

Val Glu Asp Asn Ile Met Val Thr Phe Arg Asn Gln Ala Ser
1               5                   10

<210> SEQ ID NO 484
<211> LENGTH: 15
<212> TYPE: PRT
<213> ORGANISM: Homo sapiens

<400> SEQUENCE: 484

Val Glu Asp Asn Ile Met Val Thr Phe Arg Asn Gln Ala Ser Arg
1               5                   10                  15

<210> SEQ ID NO 485
<211> LENGTH: 16
<212> TYPE: PRT
<213> ORGANISM: Homo sapiens

<400> SEQUENCE: 485

Val Glu Asp Asn Ile Met Val Thr Phe Arg Asn Gln Ala Ser Arg Pro
1               5                   10                  15

<210> SEQ ID NO 486
<211> LENGTH: 17
<212> TYPE: PRT
<213> ORGANISM: Homo sapiens

<400> SEQUENCE: 486

Val Glu Asp Asn Ile Met Val Thr Phe Arg Asn Gln Ala Ser Arg Pro
1               5                   10                  15

Tyr

<210> SEQ ID NO 487
<211> LENGTH: 18
<212> TYPE: PRT
<213> ORGANISM: Homo sapiens

<400> SEQUENCE: 487

Val Glu Asp Asn Ile Met Val Thr Phe Arg Asn Gln Ala Ser Arg Pro
1               5                   10                  15

Tyr Ser

<210> SEQ ID NO 488
<211> LENGTH: 19
<212> TYPE: PRT
<213> ORGANISM: Homo sapiens

<400> SEQUENCE: 488

Val Glu Asp Asn Ile Met Val Thr Phe Arg Asn Gln Ala Ser Arg Pro
1               5                   10                  15

Tyr Ser Phe

<210> SEQ ID NO 489
<211> LENGTH: 20
<212> TYPE: PRT
<213> ORGANISM: Homo sapiens

<400> SEQUENCE: 489

Val Glu Asp Asn Ile Met Val Thr Phe Arg Asn Gln Ala Ser Arg Pro
1               5                   10                  15

Tyr Ser Phe Tyr
            20

<210> SEQ ID NO 490
<211> LENGTH: 9
<212> TYPE: PRT
<213> ORGANISM: Homo sapiens

<400> SEQUENCE: 490

Glu Asp Asn Ile Met Val Thr Phe Arg
1               5

<210> SEQ ID NO 491
<211> LENGTH: 10
<212> TYPE: PRT
<213> ORGANISM: Homo sapiens

<400> SEQUENCE: 491

Glu Asp Asn Ile Met Val Thr Phe Arg Asn
1               5                   10

<210> SEQ ID NO 492
<211> LENGTH: 11
<212> TYPE: PRT
<213> ORGANISM: Homo sapiens

<400> SEQUENCE: 492

Glu Asp Asn Ile Met Val Thr Phe Arg Asn Gln
1               5                   10

<210> SEQ ID NO 493
<211> LENGTH: 12
<212> TYPE: PRT
<213> ORGANISM: Homo sapiens

<400> SEQUENCE: 493

Glu Asp Asn Ile Met Val Thr Phe Arg Asn Gln Ala
1               5                   10

<210> SEQ ID NO 494
<211> LENGTH: 13
<212> TYPE: PRT
<213> ORGANISM: Homo sapiens

<400> SEQUENCE: 494

Glu Asp Asn Ile Met Val Thr Phe Arg Asn Gln Ala Ser
1               5                   10

<210> SEQ ID NO 495
<211> LENGTH: 14
<212> TYPE: PRT
<213> ORGANISM: Homo sapiens

<400> SEQUENCE: 495

Glu Asp Asn Ile Met Val Thr Phe Arg Asn Gln Ala Ser Arg
1               5                   10

<210> SEQ ID NO 496
<211> LENGTH: 15
<212> TYPE: PRT
<213> ORGANISM: Homo sapiens

<400> SEQUENCE: 496

Glu Asp Asn Ile Met Val Thr Phe Arg Asn Gln Ala Ser Arg Pro
1               5                   10                  15

<210> SEQ ID NO 497
<211> LENGTH: 16
<212> TYPE: PRT
<213> ORGANISM: Homo sapiens

<400> SEQUENCE: 497

Glu Asp Asn Ile Met Val Thr Phe Arg Asn Gln Ala Ser Arg Pro Tyr
1               5                   10                  15

<210> SEQ ID NO 498
<211> LENGTH: 17
<212> TYPE: PRT
<213> ORGANISM: Homo sapiens

<400> SEQUENCE: 498

Glu Asp Asn Ile Met Val Thr Phe Arg Asn Gln Ala Ser Arg Pro Tyr
1               5                   10                  15
Ser

```
<210> SEQ ID NO 499
<211> LENGTH: 18
<212> TYPE: PRT
<213> ORGANISM: Homo sapiens

<400> SEQUENCE: 499

Glu Asp Asn Ile Met Val Thr Phe Arg Asn Gln Ala Ser Arg Pro Tyr
1               5                   10                  15

Ser Phe

<210> SEQ ID NO 500
<211> LENGTH: 19
<212> TYPE: PRT
<213> ORGANISM: Homo sapiens

<400> SEQUENCE: 500

Glu Asp Asn Ile Met Val Thr Phe Arg Asn Gln Ala Ser Arg Pro Tyr
1               5                   10                  15

Ser Phe Tyr

<210> SEQ ID NO 501
<211> LENGTH: 9
<212> TYPE: PRT
<213> ORGANISM: Homo sapiens

<400> SEQUENCE: 501

Asp Asn Ile Met Val Thr Phe Arg Asn
1               5

<210> SEQ ID NO 502
<211> LENGTH: 10
<212> TYPE: PRT
<213> ORGANISM: Homo sapiens

<400> SEQUENCE: 502

Asp Asn Ile Met Val Thr Phe Arg Asn Gln
1               5                   10

<210> SEQ ID NO 503
<211> LENGTH: 11
<212> TYPE: PRT
<213> ORGANISM: Homo sapiens

<400> SEQUENCE: 503

Asp Asn Ile Met Val Thr Phe Arg Asn Gln Ala
1               5                   10

<210> SEQ ID NO 504
<211> LENGTH: 12
<212> TYPE: PRT
<213> ORGANISM: Homo sapiens

<400> SEQUENCE: 504

Asp Asn Ile Met Val Thr Phe Arg Asn Gln Ala Ser
1               5                   10

<210> SEQ ID NO 505
<211> LENGTH: 13
<212> TYPE: PRT
<213> ORGANISM: Homo sapiens

<400> SEQUENCE: 505

Asp Asn Ile Met Val Thr Phe Arg Asn Gln Ala Ser Arg
```

```
1               5                   10
```

<210> SEQ ID NO 506
<211> LENGTH: 14
<212> TYPE: PRT
<213> ORGANISM: Homo sapiens

<400> SEQUENCE: 506

```
Asp Asn Ile Met Val Thr Phe Arg Asn Gln Ala Ser Arg Pro
1               5                   10
```

<210> SEQ ID NO 507
<211> LENGTH: 15
<212> TYPE: PRT
<213> ORGANISM: Homo sapiens

<400> SEQUENCE: 507

```
Asp Asn Ile Met Val Thr Phe Arg Asn Gln Ala Ser Arg Pro Tyr
1               5                   10                  15
```

<210> SEQ ID NO 508
<211> LENGTH: 16
<212> TYPE: PRT
<213> ORGANISM: Homo sapiens

<400> SEQUENCE: 508

```
Asp Asn Ile Met Val Thr Phe Arg Asn Gln Ala Ser Arg Pro Tyr Ser
1               5                   10                  15
```

<210> SEQ ID NO 509
<211> LENGTH: 17
<212> TYPE: PRT
<213> ORGANISM: Homo sapiens

<400> SEQUENCE: 509

```
Asp Asn Ile Met Val Thr Phe Arg Asn Gln Ala Ser Arg Pro Tyr Ser
1               5                   10                  15

Phe
```

<210> SEQ ID NO 510
<211> LENGTH: 18
<212> TYPE: PRT
<213> ORGANISM: Homo sapiens

<400> SEQUENCE: 510

```
Asp Asn Ile Met Val Thr Phe Arg Asn Gln Ala Ser Arg Pro Tyr Ser
1               5                   10                  15

Phe Tyr
```

<210> SEQ ID NO 511
<211> LENGTH: 9
<212> TYPE: PRT
<213> ORGANISM: Homo sapiens

<400> SEQUENCE: 511

```
Asn Ile Met Val Thr Phe Arg Asn Gln
1               5
```

<210> SEQ ID NO 512
<211> LENGTH: 10
<212> TYPE: PRT
<213> ORGANISM: Homo sapiens

<400> SEQUENCE: 512

Asn Ile Met Val Thr Phe Arg Asn Gln Ala
1               5                   10

<210> SEQ ID NO 513
<211> LENGTH: 11
<212> TYPE: PRT
<213> ORGANISM: Homo sapiens

<400> SEQUENCE: 513

Asn Ile Met Val Thr Phe Arg Asn Gln Ala Ser
1               5                   10

<210> SEQ ID NO 514
<211> LENGTH: 12
<212> TYPE: PRT
<213> ORGANISM: Homo sapiens

<400> SEQUENCE: 514

Asn Ile Met Val Thr Phe Arg Asn Gln Ala Ser Arg
1               5                   10

<210> SEQ ID NO 515
<211> LENGTH: 13
<212> TYPE: PRT
<213> ORGANISM: Homo sapiens

<400> SEQUENCE: 515

Asn Ile Met Val Thr Phe Arg Asn Gln Ala Ser Arg Pro
1               5                   10

<210> SEQ ID NO 516
<211> LENGTH: 14
<212> TYPE: PRT
<213> ORGANISM: Homo sapiens

<400> SEQUENCE: 516

Asn Ile Met Val Thr Phe Arg Asn Gln Ala Ser Arg Pro Tyr
1               5                   10

<210> SEQ ID NO 517
<211> LENGTH: 15
<212> TYPE: PRT
<213> ORGANISM: Homo sapiens

<400> SEQUENCE: 517

Asn Ile Met Val Thr Phe Arg Asn Gln Ala Ser Arg Pro Tyr Ser
1               5                   10                  15

<210> SEQ ID NO 518
<211> LENGTH: 16
<212> TYPE: PRT
<213> ORGANISM: Homo sapiens

<400> SEQUENCE: 518

Asn Ile Met Val Thr Phe Arg Asn Gln Ala Ser Arg Pro Tyr Ser Phe
1               5                   10                  15

<210> SEQ ID NO 519
<211> LENGTH: 17
<212> TYPE: PRT
<213> ORGANISM: Homo sapiens

<400> SEQUENCE: 519

Asn Ile Met Val Thr Phe Arg Asn Gln Ala Ser Arg Pro Tyr Ser Phe

```
1               5                  10                 15
Tyr

<210> SEQ ID NO 520
<211> LENGTH: 9
<212> TYPE: PRT
<213> ORGANISM: Homo sapiens

<400> SEQUENCE: 520

Ile Met Val Thr Phe Arg Asn Gln Ala
1               5

<210> SEQ ID NO 521
<211> LENGTH: 10
<212> TYPE: PRT
<213> ORGANISM: Homo sapiens

<400> SEQUENCE: 521

Ile Met Val Thr Phe Arg Asn Gln Ala Ser
1               5                  10

<210> SEQ ID NO 522
<211> LENGTH: 11
<212> TYPE: PRT
<213> ORGANISM: Homo sapiens

<400> SEQUENCE: 522

Ile Met Val Thr Phe Arg Asn Gln Ala Ser Arg
1               5                  10

<210> SEQ ID NO 523
<211> LENGTH: 12
<212> TYPE: PRT
<213> ORGANISM: Homo sapiens

<400> SEQUENCE: 523

Ile Met Val Thr Phe Arg Asn Gln Ala Ser Arg Pro
1               5                  10

<210> SEQ ID NO 524
<211> LENGTH: 13
<212> TYPE: PRT
<213> ORGANISM: Homo sapiens

<400> SEQUENCE: 524

Ile Met Val Thr Phe Arg Asn Gln Ala Ser Arg Pro Tyr
1               5                  10

<210> SEQ ID NO 525
<211> LENGTH: 14
<212> TYPE: PRT
<213> ORGANISM: Homo sapiens

<400> SEQUENCE: 525

Ile Met Val Thr Phe Arg Asn Gln Ala Ser Arg Pro Tyr Ser
1               5                  10

<210> SEQ ID NO 526
<211> LENGTH: 15
<212> TYPE: PRT
<213> ORGANISM: Homo sapiens

<400> SEQUENCE: 526

Ile Met Val Thr Phe Arg Asn Gln Ala Ser Arg Pro Tyr Ser Phe
```

-continued

```
1               5                   10                  15

<210> SEQ ID NO 527
<211> LENGTH: 16
<212> TYPE: PRT
<213> ORGANISM: Homo sapiens

<400> SEQUENCE: 527

Ile Met Val Thr Phe Arg Asn Gln Ala Ser Arg Pro Tyr Ser Phe Tyr
1               5                   10                  15

<210> SEQ ID NO 528
<211> LENGTH: 9
<212> TYPE: PRT
<213> ORGANISM: Homo sapiens

<400> SEQUENCE: 528

Met Val Thr Phe Arg Asn Gln Ala Ser
1               5

<210> SEQ ID NO 529
<211> LENGTH: 10
<212> TYPE: PRT
<213> ORGANISM: Homo sapiens

<400> SEQUENCE: 529

Met Val Thr Phe Arg Asn Gln Ala Ser Arg
1               5                   10

<210> SEQ ID NO 530
<211> LENGTH: 11
<212> TYPE: PRT
<213> ORGANISM: Homo sapiens

<400> SEQUENCE: 530

Met Val Thr Phe Arg Asn Gln Ala Ser Arg Pro
1               5                   10

<210> SEQ ID NO 531
<211> LENGTH: 12
<212> TYPE: PRT
<213> ORGANISM: Homo sapiens

<400> SEQUENCE: 531

Met Val Thr Phe Arg Asn Gln Ala Ser Arg Pro Tyr
1               5                   10

<210> SEQ ID NO 532
<211> LENGTH: 13
<212> TYPE: PRT
<213> ORGANISM: Homo sapiens

<400> SEQUENCE: 532

Met Val Thr Phe Arg Asn Gln Ala Ser Arg Pro Tyr Ser
1               5                   10

<210> SEQ ID NO 533
<211> LENGTH: 14
<212> TYPE: PRT
<213> ORGANISM: Homo sapiens

<400> SEQUENCE: 533

Met Val Thr Phe Arg Asn Gln Ala Ser Arg Pro Tyr Ser Phe
1               5                   10
```

<210> SEQ ID NO 534
<211> LENGTH: 15
<212> TYPE: PRT
<213> ORGANISM: Homo sapiens

<400> SEQUENCE: 534

Met Val Thr Phe Arg Asn Gln Ala Ser Arg Pro Tyr Ser Phe Tyr
1               5                   10                  15

<210> SEQ ID NO 535
<211> LENGTH: 9
<212> TYPE: PRT
<213> ORGANISM: Homo sapiens

<400> SEQUENCE: 535

Val Thr Phe Arg Asn Gln Ala Ser Arg
1               5

<210> SEQ ID NO 536
<211> LENGTH: 10
<212> TYPE: PRT
<213> ORGANISM: Homo sapiens

<400> SEQUENCE: 536

Val Thr Phe Arg Asn Gln Ala Ser Arg Pro
1               5                   10

<210> SEQ ID NO 537
<211> LENGTH: 11
<212> TYPE: PRT
<213> ORGANISM: Homo sapiens

<400> SEQUENCE: 537

Val Thr Phe Arg Asn Gln Ala Ser Arg Pro Tyr
1               5                   10

<210> SEQ ID NO 538
<211> LENGTH: 12
<212> TYPE: PRT
<213> ORGANISM: Homo sapiens

<400> SEQUENCE: 538

Val Thr Phe Arg Asn Gln Ala Ser Arg Pro Tyr Ser
1               5                   10

<210> SEQ ID NO 539
<211> LENGTH: 13
<212> TYPE: PRT
<213> ORGANISM: Homo sapiens

<400> SEQUENCE: 539

Val Thr Phe Arg Asn Gln Ala Ser Arg Pro Tyr Ser Phe
1               5                   10

<210> SEQ ID NO 540
<211> LENGTH: 14
<212> TYPE: PRT
<213> ORGANISM: Homo sapiens

<400> SEQUENCE: 540

Val Thr Phe Arg Asn Gln Ala Ser Arg Pro Tyr Ser Phe Tyr
1               5                   10

<210> SEQ ID NO 541

```
<211> LENGTH: 9
<212> TYPE: PRT
<213> ORGANISM: Homo sapiens

<400> SEQUENCE: 541

Thr Phe Arg Asn Gln Ala Ser Arg Pro
1               5

<210> SEQ ID NO 542
<211> LENGTH: 10
<212> TYPE: PRT
<213> ORGANISM: Homo sapiens

<400> SEQUENCE: 542

Thr Phe Arg Asn Gln Ala Ser Arg Pro Tyr
1               5                   10

<210> SEQ ID NO 543
<211> LENGTH: 11
<212> TYPE: PRT
<213> ORGANISM: Homo sapiens

<400> SEQUENCE: 543

Thr Phe Arg Asn Gln Ala Ser Arg Pro Tyr Ser
1               5                   10

<210> SEQ ID NO 544
<211> LENGTH: 12
<212> TYPE: PRT
<213> ORGANISM: Homo sapiens

<400> SEQUENCE: 544

Thr Phe Arg Asn Gln Ala Ser Arg Pro Tyr Ser Phe
1               5                   10

<210> SEQ ID NO 545
<211> LENGTH: 13
<212> TYPE: PRT
<213> ORGANISM: Homo sapiens

<400> SEQUENCE: 545

Thr Phe Arg Asn Gln Ala Ser Arg Pro Tyr Ser Phe Tyr
1               5                   10

<210> SEQ ID NO 546
<211> LENGTH: 9
<212> TYPE: PRT
<213> ORGANISM: Homo sapiens

<400> SEQUENCE: 546

Phe Arg Asn Gln Ala Ser Arg Pro Tyr
1               5

<210> SEQ ID NO 547
<211> LENGTH: 10
<212> TYPE: PRT
<213> ORGANISM: Homo sapiens

<400> SEQUENCE: 547

Phe Arg Asn Gln Ala Ser Arg Pro Tyr Ser
1               5                   10

<210> SEQ ID NO 548
<211> LENGTH: 11
<212> TYPE: PRT
```

<213> ORGANISM: Homo sapiens

<400> SEQUENCE: 548

Phe Arg Asn Gln Ala Ser Arg Pro Tyr Ser Phe
1               5                   10

<210> SEQ ID NO 549
<211> LENGTH: 12
<212> TYPE: PRT
<213> ORGANISM: Homo sapiens

<400> SEQUENCE: 549

Phe Arg Asn Gln Ala Ser Arg Pro Tyr Ser Phe Tyr
1               5                   10

<210> SEQ ID NO 550
<211> LENGTH: 9
<212> TYPE: PRT
<213> ORGANISM: Homo sapiens

<400> SEQUENCE: 550

Arg Asn Gln Ala Ser Arg Pro Tyr Ser
1               5

<210> SEQ ID NO 551
<211> LENGTH: 10
<212> TYPE: PRT
<213> ORGANISM: Homo sapiens

<400> SEQUENCE: 551

Arg Asn Gln Ala Ser Arg Pro Tyr Ser Phe
1               5                   10

<210> SEQ ID NO 552
<211> LENGTH: 11
<212> TYPE: PRT
<213> ORGANISM: Homo sapiens

<400> SEQUENCE: 552

Arg Asn Gln Ala Ser Arg Pro Tyr Ser Phe Tyr
1               5                   10

<210> SEQ ID NO 553
<211> LENGTH: 9
<212> TYPE: PRT
<213> ORGANISM: Homo sapiens

<400> SEQUENCE: 553

Asn Gln Ala Ser Arg Pro Tyr Ser Phe
1               5

<210> SEQ ID NO 554
<211> LENGTH: 10
<212> TYPE: PRT
<213> ORGANISM: Homo sapiens

<400> SEQUENCE: 554

Asn Gln Ala Ser Arg Pro Tyr Ser Phe Tyr
1               5                   10

<210> SEQ ID NO 555
<211> LENGTH: 9
<212> TYPE: PRT
<213> ORGANISM: Homo sapiens

```
<400> SEQUENCE: 555

Gln Ala Ser Arg Pro Tyr Ser Phe Tyr
1               5

<210> SEQ ID NO 556
<211> LENGTH: 9
<212> TYPE: PRT
<213> ORGANISM: Homo sapiens

<400> SEQUENCE: 556

Leu His Ala Gly Met Ser Thr Leu Phe
1               5

<210> SEQ ID NO 557
<211> LENGTH: 10
<212> TYPE: PRT
<213> ORGANISM: Homo sapiens

<400> SEQUENCE: 557

Leu His Ala Gly Met Ser Thr Leu Phe Leu
1               5                   10

<210> SEQ ID NO 558
<211> LENGTH: 11
<212> TYPE: PRT
<213> ORGANISM: Homo sapiens

<400> SEQUENCE: 558

Leu His Ala Gly Met Ser Thr Leu Phe Leu Val
1               5                   10

<210> SEQ ID NO 559
<211> LENGTH: 12
<212> TYPE: PRT
<213> ORGANISM: Homo sapiens

<400> SEQUENCE: 559

Leu His Ala Gly Met Ser Thr Leu Phe Leu Val Tyr
1               5                   10

<210> SEQ ID NO 560
<211> LENGTH: 13
<212> TYPE: PRT
<213> ORGANISM: Homo sapiens

<400> SEQUENCE: 560

Leu His Ala Gly Met Ser Thr Leu Phe Leu Val Tyr Ser
1               5                   10

<210> SEQ ID NO 561
<211> LENGTH: 14
<212> TYPE: PRT
<213> ORGANISM: Homo sapiens

<400> SEQUENCE: 561

Leu His Ala Gly Met Ser Thr Leu Phe Leu Val Tyr Ser Asn
1               5                   10

<210> SEQ ID NO 562
<211> LENGTH: 15
<212> TYPE: PRT
<213> ORGANISM: Homo sapiens

<400> SEQUENCE: 562
```

```
Leu His Ala Gly Met Ser Thr Leu Phe Leu Val Tyr Ser Asn Lys
1               5                   10                  15

<210> SEQ ID NO 563
<211> LENGTH: 16
<212> TYPE: PRT
<213> ORGANISM: Homo sapiens

<400> SEQUENCE: 563

Leu His Ala Gly Met Ser Thr Leu Phe Leu Val Tyr Ser Asn Lys Cys
1               5                   10                  15

<210> SEQ ID NO 564
<211> LENGTH: 17
<212> TYPE: PRT
<213> ORGANISM: Homo sapiens

<400> SEQUENCE: 564

Leu His Ala Gly Met Ser Thr Leu Phe Leu Val Tyr Ser Asn Lys Cys
1               5                   10                  15

Gln

<210> SEQ ID NO 565
<211> LENGTH: 18
<212> TYPE: PRT
<213> ORGANISM: Homo sapiens

<400> SEQUENCE: 565

Leu His Ala Gly Met Ser Thr Leu Phe Leu Val Tyr Ser Asn Lys Cys
1               5                   10                  15

Gln Thr

<210> SEQ ID NO 566
<211> LENGTH: 19
<212> TYPE: PRT
<213> ORGANISM: Homo sapiens

<400> SEQUENCE: 566

Leu His Ala Gly Met Ser Thr Leu Phe Leu Val Tyr Ser Asn Lys Cys
1               5                   10                  15

Gln Thr Pro

<210> SEQ ID NO 567
<211> LENGTH: 20
<212> TYPE: PRT
<213> ORGANISM: Homo sapiens

<400> SEQUENCE: 567

Leu His Ala Gly Met Ser Thr Leu Phe Leu Val Tyr Ser Asn Lys Cys
1               5                   10                  15

Gln Thr Pro Leu
            20

<210> SEQ ID NO 568
<211> LENGTH: 21
<212> TYPE: PRT
<213> ORGANISM: Homo sapiens

<400> SEQUENCE: 568

Leu His Ala Gly Met Ser Thr Leu Phe Leu Val Tyr Ser Asn Lys Cys
1               5                   10                  15

Gln Thr Pro Leu Gly
```

```
                   20

<210> SEQ ID NO 569
<211> LENGTH: 9
<212> TYPE: PRT
<213> ORGANISM: Homo sapiens

<400> SEQUENCE: 569

His Ala Gly Met Ser Thr Leu Phe Leu
1               5

<210> SEQ ID NO 570
<211> LENGTH: 10
<212> TYPE: PRT
<213> ORGANISM: Homo sapiens

<400> SEQUENCE: 570

His Ala Gly Met Ser Thr Leu Phe Leu Val
1               5                  10

<210> SEQ ID NO 571
<211> LENGTH: 11
<212> TYPE: PRT
<213> ORGANISM: Homo sapiens

<400> SEQUENCE: 571

His Ala Gly Met Ser Thr Leu Phe Leu Val Tyr
1               5                  10

<210> SEQ ID NO 572
<211> LENGTH: 12
<212> TYPE: PRT
<213> ORGANISM: Homo sapiens

<400> SEQUENCE: 572

His Ala Gly Met Ser Thr Leu Phe Leu Val Tyr Ser
1               5                  10

<210> SEQ ID NO 573
<211> LENGTH: 13
<212> TYPE: PRT
<213> ORGANISM: Homo sapiens

<400> SEQUENCE: 573

His Ala Gly Met Ser Thr Leu Phe Leu Val Tyr Ser Asn
1               5                  10

<210> SEQ ID NO 574
<211> LENGTH: 14
<212> TYPE: PRT
<213> ORGANISM: Homo sapiens

<400> SEQUENCE: 574

His Ala Gly Met Ser Thr Leu Phe Leu Val Tyr Ser Asn Lys
1               5                  10

<210> SEQ ID NO 575
<211> LENGTH: 15
<212> TYPE: PRT
<213> ORGANISM: Homo sapiens

<400> SEQUENCE: 575

His Ala Gly Met Ser Thr Leu Phe Leu Val Tyr Ser Asn Lys Cys
1               5                  10                  15
```

<210> SEQ ID NO 576
<211> LENGTH: 16
<212> TYPE: PRT
<213> ORGANISM: Homo sapiens

<400> SEQUENCE: 576

His Ala Gly Met Ser Thr Leu Phe Leu Val Tyr Ser Asn Lys Cys Gln
1               5                   10                  15

<210> SEQ ID NO 577
<211> LENGTH: 17
<212> TYPE: PRT
<213> ORGANISM: Homo sapiens

<400> SEQUENCE: 577

His Ala Gly Met Ser Thr Leu Phe Leu Val Tyr Ser Asn Lys Cys Gln
1               5                   10                  15

Thr

<210> SEQ ID NO 578
<211> LENGTH: 18
<212> TYPE: PRT
<213> ORGANISM: Homo sapiens

<400> SEQUENCE: 578

His Ala Gly Met Ser Thr Leu Phe Leu Val Tyr Ser Asn Lys Cys Gln
1               5                   10                  15

Thr Pro

<210> SEQ ID NO 579
<211> LENGTH: 19
<212> TYPE: PRT
<213> ORGANISM: Homo sapiens

<400> SEQUENCE: 579

His Ala Gly Met Ser Thr Leu Phe Leu Val Tyr Ser Asn Lys Cys Gln
1               5                   10                  15

Thr Pro Leu

<210> SEQ ID NO 580
<211> LENGTH: 20
<212> TYPE: PRT
<213> ORGANISM: Homo sapiens

<400> SEQUENCE: 580

His Ala Gly Met Ser Thr Leu Phe Leu Val Tyr Ser Asn Lys Cys Gln
1               5                   10                  15

Thr Pro Leu Gly
            20

<210> SEQ ID NO 581
<211> LENGTH: 9
<212> TYPE: PRT
<213> ORGANISM: Homo sapiens

<400> SEQUENCE: 581

Ala Gly Met Ser Thr Leu Phe Leu Val
1               5

<210> SEQ ID NO 582
<211> LENGTH: 10
<212> TYPE: PRT

<213> ORGANISM: Homo sapiens

<400> SEQUENCE: 582

Ala Gly Met Ser Thr Leu Phe Leu Val Tyr
1               5                   10

<210> SEQ ID NO 583
<211> LENGTH: 11
<212> TYPE: PRT
<213> ORGANISM: Homo sapiens

<400> SEQUENCE: 583

Ala Gly Met Ser Thr Leu Phe Leu Val Tyr Ser
1               5                   10

<210> SEQ ID NO 584
<211> LENGTH: 12
<212> TYPE: PRT
<213> ORGANISM: Homo sapiens

<400> SEQUENCE: 584

Ala Gly Met Ser Thr Leu Phe Leu Val Tyr Ser Asn
1               5                   10

<210> SEQ ID NO 585
<211> LENGTH: 13
<212> TYPE: PRT
<213> ORGANISM: Homo sapiens

<400> SEQUENCE: 585

Ala Gly Met Ser Thr Leu Phe Leu Val Tyr Ser Asn Lys
1               5                   10

<210> SEQ ID NO 586
<211> LENGTH: 14
<212> TYPE: PRT
<213> ORGANISM: Homo sapiens

<400> SEQUENCE: 586

Ala Gly Met Ser Thr Leu Phe Leu Val Tyr Ser Asn Lys Cys
1               5                   10

<210> SEQ ID NO 587
<211> LENGTH: 15
<212> TYPE: PRT
<213> ORGANISM: Homo sapiens

<400> SEQUENCE: 587

Ala Gly Met Ser Thr Leu Phe Leu Val Tyr Ser Asn Lys Cys Gln
1               5                   10                  15

<210> SEQ ID NO 588
<211> LENGTH: 16
<212> TYPE: PRT
<213> ORGANISM: Homo sapiens

<400> SEQUENCE: 588

Ala Gly Met Ser Thr Leu Phe Leu Val Tyr Ser Asn Lys Cys Gln Thr
1               5                   10                  15

<210> SEQ ID NO 589
<211> LENGTH: 17
<212> TYPE: PRT
<213> ORGANISM: Homo sapiens

```
<400> SEQUENCE: 589

Ala Gly Met Ser Thr Leu Phe Leu Val Tyr Ser Asn Lys Cys Gln Thr
1               5                   10                  15

Pro

<210> SEQ ID NO 590
<211> LENGTH: 18
<212> TYPE: PRT
<213> ORGANISM: Homo sapiens

<400> SEQUENCE: 590

Ala Gly Met Ser Thr Leu Phe Leu Val Tyr Ser Asn Lys Cys Gln Thr
1               5                   10                  15

Pro Leu

<210> SEQ ID NO 591
<211> LENGTH: 19
<212> TYPE: PRT
<213> ORGANISM: Homo sapiens

<400> SEQUENCE: 591

Ala Gly Met Ser Thr Leu Phe Leu Val Tyr Ser Asn Lys Cys Gln Thr
1               5                   10                  15

Pro Leu Gly

<210> SEQ ID NO 592
<211> LENGTH: 9
<212> TYPE: PRT
<213> ORGANISM: Homo sapiens

<400> SEQUENCE: 592

Gly Met Ser Thr Leu Phe Leu Val Tyr
1               5

<210> SEQ ID NO 593
<211> LENGTH: 10
<212> TYPE: PRT
<213> ORGANISM: Homo sapiens

<400> SEQUENCE: 593

Gly Met Ser Thr Leu Phe Leu Val Tyr Ser
1               5                   10

<210> SEQ ID NO 594
<211> LENGTH: 11
<212> TYPE: PRT
<213> ORGANISM: Homo sapiens

<400> SEQUENCE: 594

Gly Met Ser Thr Leu Phe Leu Val Tyr Ser Asn
1               5                   10

<210> SEQ ID NO 595
<211> LENGTH: 12
<212> TYPE: PRT
<213> ORGANISM: Homo sapiens

<400> SEQUENCE: 595

Gly Met Ser Thr Leu Phe Leu Val Tyr Ser Asn Lys
1               5                   10

<210> SEQ ID NO 596
```

<210> SEQ ID NO 596
<211> LENGTH: 13
<212> TYPE: PRT
<213> ORGANISM: Homo sapiens

<400> SEQUENCE: 596

Gly Met Ser Thr Leu Phe Leu Val Tyr Ser Asn Lys Cys
1               5                   10

<210> SEQ ID NO 597
<211> LENGTH: 14
<212> TYPE: PRT
<213> ORGANISM: Homo sapiens

<400> SEQUENCE: 597

Gly Met Ser Thr Leu Phe Leu Val Tyr Ser Asn Lys Cys Gln
1               5                   10

<210> SEQ ID NO 598
<211> LENGTH: 15
<212> TYPE: PRT
<213> ORGANISM: Homo sapiens

<400> SEQUENCE: 598

Gly Met Ser Thr Leu Phe Leu Val Tyr Ser Asn Lys Cys Gln Thr
1               5                   10                  15

<210> SEQ ID NO 599
<211> LENGTH: 16
<212> TYPE: PRT
<213> ORGANISM: Homo sapiens

<400> SEQUENCE: 599

Gly Met Ser Thr Leu Phe Leu Val Tyr Ser Asn Lys Cys Gln Thr Pro
1               5                   10                  15

<210> SEQ ID NO 600
<211> LENGTH: 17
<212> TYPE: PRT
<213> ORGANISM: Homo sapiens

<400> SEQUENCE: 600

Gly Met Ser Thr Leu Phe Leu Val Tyr Ser Asn Lys Cys Gln Thr Pro
1               5                   10                  15

Leu

<210> SEQ ID NO 601
<211> LENGTH: 18
<212> TYPE: PRT
<213> ORGANISM: Homo sapiens

<400> SEQUENCE: 601

Gly Met Ser Thr Leu Phe Leu Val Tyr Ser Asn Lys Cys Gln Thr Pro
1               5                   10                  15

Leu Gly

<210> SEQ ID NO 602
<211> LENGTH: 9
<212> TYPE: PRT
<213> ORGANISM: Homo sapiens

<400> SEQUENCE: 602

Met Ser Thr Leu Phe Leu Val Tyr Ser
1               5

<210> SEQ ID NO 603
<211> LENGTH: 10
<212> TYPE: PRT
<213> ORGANISM: Homo sapiens

<400> SEQUENCE: 603

Met Ser Thr Leu Phe Leu Val Tyr Ser Asn
1               5                   10

<210> SEQ ID NO 604
<211> LENGTH: 11
<212> TYPE: PRT
<213> ORGANISM: Homo sapiens

<400> SEQUENCE: 604

Met Ser Thr Leu Phe Leu Val Tyr Ser Asn Lys
1               5                   10

<210> SEQ ID NO 605
<211> LENGTH: 12
<212> TYPE: PRT
<213> ORGANISM: Homo sapiens

<400> SEQUENCE: 605

Met Ser Thr Leu Phe Leu Val Tyr Ser Asn Lys Cys
1               5                   10

<210> SEQ ID NO 606
<211> LENGTH: 13
<212> TYPE: PRT
<213> ORGANISM: Homo sapiens

<400> SEQUENCE: 606

Met Ser Thr Leu Phe Leu Val Tyr Ser Asn Lys Cys Gln
1               5                   10

<210> SEQ ID NO 607
<211> LENGTH: 14
<212> TYPE: PRT
<213> ORGANISM: Homo sapiens

<400> SEQUENCE: 607

Met Ser Thr Leu Phe Leu Val Tyr Ser Asn Lys Cys Gln Thr
1               5                   10

<210> SEQ ID NO 608
<211> LENGTH: 15
<212> TYPE: PRT
<213> ORGANISM: Homo sapiens

<400> SEQUENCE: 608

Met Ser Thr Leu Phe Leu Val Tyr Ser Asn Lys Cys Gln Thr Pro
1               5                   10                  15

<210> SEQ ID NO 609
<211> LENGTH: 16
<212> TYPE: PRT
<213> ORGANISM: Homo sapiens

<400> SEQUENCE: 609

Met Ser Thr Leu Phe Leu Val Tyr Ser Asn Lys Cys Gln Thr Pro Leu
1               5                   10                  15

<210> SEQ ID NO 610

<211> LENGTH: 17
<212> TYPE: PRT
<213> ORGANISM: Homo sapiens

<400> SEQUENCE: 610

Met Ser Thr Leu Phe Leu Val Tyr Ser Asn Lys Cys Gln Thr Pro Leu
1               5                   10                  15

Gly

<210> SEQ ID NO 611
<211> LENGTH: 9
<212> TYPE: PRT
<213> ORGANISM: Homo sapiens

<400> SEQUENCE: 611

Ser Thr Leu Phe Leu Val Tyr Ser Asn
1               5

<210> SEQ ID NO 612
<211> LENGTH: 10
<212> TYPE: PRT
<213> ORGANISM: Homo sapiens

<400> SEQUENCE: 612

Ser Thr Leu Phe Leu Val Tyr Ser Asn Lys
1               5                   10

<210> SEQ ID NO 613
<211> LENGTH: 11
<212> TYPE: PRT
<213> ORGANISM: Homo sapiens

<400> SEQUENCE: 613

Ser Thr Leu Phe Leu Val Tyr Ser Asn Lys Cys
1               5                   10

<210> SEQ ID NO 614
<211> LENGTH: 12
<212> TYPE: PRT
<213> ORGANISM: Homo sapiens

<400> SEQUENCE: 614

Ser Thr Leu Phe Leu Val Tyr Ser Asn Lys Cys Gln
1               5                   10

<210> SEQ ID NO 615
<211> LENGTH: 13
<212> TYPE: PRT
<213> ORGANISM: Homo sapiens

<400> SEQUENCE: 615

Ser Thr Leu Phe Leu Val Tyr Ser Asn Lys Cys Gln Thr
1               5                   10

<210> SEQ ID NO 616
<211> LENGTH: 14
<212> TYPE: PRT
<213> ORGANISM: Homo sapiens

<400> SEQUENCE: 616

Ser Thr Leu Phe Leu Val Tyr Ser Asn Lys Cys Gln Thr Pro
1               5                   10

<210> SEQ ID NO 617

```
<211> LENGTH: 15
<212> TYPE: PRT
<213> ORGANISM: Homo sapiens

<400> SEQUENCE: 617

Ser Thr Leu Phe Leu Val Tyr Ser Asn Lys Cys Gln Thr Pro Leu
1               5                   10                  15

<210> SEQ ID NO 618
<211> LENGTH: 16
<212> TYPE: PRT
<213> ORGANISM: Homo sapiens

<400> SEQUENCE: 618

Ser Thr Leu Phe Leu Val Tyr Ser Asn Lys Cys Gln Thr Pro Leu Gly
1               5                   10                  15

<210> SEQ ID NO 619
<211> LENGTH: 9
<212> TYPE: PRT
<213> ORGANISM: Homo sapiens

<400> SEQUENCE: 619

Thr Leu Phe Leu Val Tyr Ser Asn Lys
1               5

<210> SEQ ID NO 620
<211> LENGTH: 10
<212> TYPE: PRT
<213> ORGANISM: Homo sapiens

<400> SEQUENCE: 620

Thr Leu Phe Leu Val Tyr Ser Asn Lys Cys
1               5                   10

<210> SEQ ID NO 621
<211> LENGTH: 11
<212> TYPE: PRT
<213> ORGANISM: Homo sapiens

<400> SEQUENCE: 621

Thr Leu Phe Leu Val Tyr Ser Asn Lys Cys Gln
1               5                   10

<210> SEQ ID NO 622
<211> LENGTH: 12
<212> TYPE: PRT
<213> ORGANISM: Homo sapiens

<400> SEQUENCE: 622

Thr Leu Phe Leu Val Tyr Ser Asn Lys Cys Gln Thr
1               5                   10

<210> SEQ ID NO 623
<211> LENGTH: 13
<212> TYPE: PRT
<213> ORGANISM: Homo sapiens

<400> SEQUENCE: 623

Thr Leu Phe Leu Val Tyr Ser Asn Lys Cys Gln Thr Pro
1               5                   10

<210> SEQ ID NO 624
<211> LENGTH: 14
<212> TYPE: PRT
```

<213> ORGANISM: Homo sapiens

<400> SEQUENCE: 624

Thr Leu Phe Leu Val Tyr Ser Asn Lys Cys Gln Thr Pro Leu
1               5                   10

<210> SEQ ID NO 625
<211> LENGTH: 15
<212> TYPE: PRT
<213> ORGANISM: Homo sapiens

<400> SEQUENCE: 625

Thr Leu Phe Leu Val Tyr Ser Asn Lys Cys Gln Thr Pro Leu Gly
1               5                   10                  15

<210> SEQ ID NO 626
<211> LENGTH: 9
<212> TYPE: PRT
<213> ORGANISM: Homo sapiens

<400> SEQUENCE: 626

Leu Phe Leu Val Tyr Ser Asn Lys Cys
1               5

<210> SEQ ID NO 627
<211> LENGTH: 10
<212> TYPE: PRT
<213> ORGANISM: Homo sapiens

<400> SEQUENCE: 627

Leu Phe Leu Val Tyr Ser Asn Lys Cys Gln
1               5                   10

<210> SEQ ID NO 628
<211> LENGTH: 11
<212> TYPE: PRT
<213> ORGANISM: Homo sapiens

<400> SEQUENCE: 628

Leu Phe Leu Val Tyr Ser Asn Lys Cys Gln Thr
1               5                   10

<210> SEQ ID NO 629
<211> LENGTH: 12
<212> TYPE: PRT
<213> ORGANISM: Homo sapiens

<400> SEQUENCE: 629

Leu Phe Leu Val Tyr Ser Asn Lys Cys Gln Thr Pro
1               5                   10

<210> SEQ ID NO 630
<211> LENGTH: 13
<212> TYPE: PRT
<213> ORGANISM: Homo sapiens

<400> SEQUENCE: 630

Leu Phe Leu Val Tyr Ser Asn Lys Cys Gln Thr Pro Leu
1               5                   10

<210> SEQ ID NO 631
<211> LENGTH: 14
<212> TYPE: PRT
<213> ORGANISM: Homo sapiens

```
<400> SEQUENCE: 631

Leu Phe Leu Val Tyr Ser Asn Lys Cys Gln Thr Pro Leu Gly
1               5                   10

<210> SEQ ID NO 632
<211> LENGTH: 9
<212> TYPE: PRT
<213> ORGANISM: Homo sapiens

<400> SEQUENCE: 632

Phe Leu Val Tyr Ser Asn Lys Cys Gln
1               5

<210> SEQ ID NO 633
<211> LENGTH: 10
<212> TYPE: PRT
<213> ORGANISM: Homo sapiens

<400> SEQUENCE: 633

Phe Leu Val Tyr Ser Asn Lys Cys Gln Thr
1               5                   10

<210> SEQ ID NO 634
<211> LENGTH: 11
<212> TYPE: PRT
<213> ORGANISM: Homo sapiens

<400> SEQUENCE: 634

Phe Leu Val Tyr Ser Asn Lys Cys Gln Thr Pro
1               5                   10

<210> SEQ ID NO 635
<211> LENGTH: 12
<212> TYPE: PRT
<213> ORGANISM: Homo sapiens

<400> SEQUENCE: 635

Phe Leu Val Tyr Ser Asn Lys Cys Gln Thr Pro Leu
1               5                   10

<210> SEQ ID NO 636
<211> LENGTH: 13
<212> TYPE: PRT
<213> ORGANISM: Homo sapiens

<400> SEQUENCE: 636

Phe Leu Val Tyr Ser Asn Lys Cys Gln Thr Pro Leu Gly
1               5                   10

<210> SEQ ID NO 637
<211> LENGTH: 9
<212> TYPE: PRT
<213> ORGANISM: Homo sapiens

<400> SEQUENCE: 637

Leu Val Tyr Ser Asn Lys Cys Gln Thr
1               5

<210> SEQ ID NO 638
<211> LENGTH: 10
<212> TYPE: PRT
<213> ORGANISM: Homo sapiens

<400> SEQUENCE: 638
```

```
Leu Val Tyr Ser Asn Lys Cys Gln Thr Pro
1               5                   10
```

<210> SEQ ID NO 639
<211> LENGTH: 11
<212> TYPE: PRT
<213> ORGANISM: Homo sapiens

<400> SEQUENCE: 639

```
Leu Val Tyr Ser Asn Lys Cys Gln Thr Pro Leu
1               5                   10
```

<210> SEQ ID NO 640
<211> LENGTH: 12
<212> TYPE: PRT
<213> ORGANISM: Homo sapiens

<400> SEQUENCE: 640

```
Leu Val Tyr Ser Asn Lys Cys Gln Thr Pro Leu Gly
1               5                   10
```

<210> SEQ ID NO 641
<211> LENGTH: 9
<212> TYPE: PRT
<213> ORGANISM: Homo sapiens

<400> SEQUENCE: 641

```
Val Tyr Ser Asn Lys Cys Gln Thr Pro
1               5
```

<210> SEQ ID NO 642
<211> LENGTH: 10
<212> TYPE: PRT
<213> ORGANISM: Homo sapiens

<400> SEQUENCE: 642

```
Val Tyr Ser Asn Lys Cys Gln Thr Pro Leu
1               5                   10
```

<210> SEQ ID NO 643
<211> LENGTH: 11
<212> TYPE: PRT
<213> ORGANISM: Homo sapiens

<400> SEQUENCE: 643

```
Val Tyr Ser Asn Lys Cys Gln Thr Pro Leu Gly
1               5                   10
```

<210> SEQ ID NO 644
<211> LENGTH: 9
<212> TYPE: PRT
<213> ORGANISM: Homo sapiens

<400> SEQUENCE: 644

```
Tyr Ser Asn Lys Cys Gln Thr Pro Leu
1               5
```

<210> SEQ ID NO 645
<211> LENGTH: 10
<212> TYPE: PRT
<213> ORGANISM: Homo sapiens

<400> SEQUENCE: 645

```
Tyr Ser Asn Lys Cys Gln Thr Pro Leu Gly
1               5                   10
```

```
<210> SEQ ID NO 646
<211> LENGTH: 9
<212> TYPE: PRT
<213> ORGANISM: Homo sapiens

<400> SEQUENCE: 646

Ser Asn Lys Cys Gln Thr Pro Leu Gly
1               5

<210> SEQ ID NO 647
<211> LENGTH: 9
<212> TYPE: PRT
<213> ORGANISM: Homo sapiens

<400> SEQUENCE: 647

Asn Pro Pro Ile Ile Ala Arg Tyr Ile
1               5

<210> SEQ ID NO 648
<211> LENGTH: 10
<212> TYPE: PRT
<213> ORGANISM: Homo sapiens

<400> SEQUENCE: 648

Asn Pro Pro Ile Ile Ala Arg Tyr Ile Arg
1               5                   10

<210> SEQ ID NO 649
<211> LENGTH: 11
<212> TYPE: PRT
<213> ORGANISM: Homo sapiens

<400> SEQUENCE: 649

Asn Pro Pro Ile Ile Ala Arg Tyr Ile Arg Leu
1               5                   10

<210> SEQ ID NO 650
<211> LENGTH: 12
<212> TYPE: PRT
<213> ORGANISM: Homo sapiens

<400> SEQUENCE: 650

Asn Pro Pro Ile Ile Ala Arg Tyr Ile Arg Leu His
1               5                   10

<210> SEQ ID NO 651
<211> LENGTH: 13
<212> TYPE: PRT
<213> ORGANISM: Homo sapiens

<400> SEQUENCE: 651

Asn Pro Pro Ile Ile Ala Arg Tyr Ile Arg Leu His Pro
1               5                   10

<210> SEQ ID NO 652
<211> LENGTH: 14
<212> TYPE: PRT
<213> ORGANISM: Homo sapiens

<400> SEQUENCE: 652

Asn Pro Pro Ile Ile Ala Arg Tyr Ile Arg Leu His Pro Thr
1               5                   10
```

```
<210> SEQ ID NO 653
<211> LENGTH: 15
<212> TYPE: PRT
<213> ORGANISM: Homo sapiens

<400> SEQUENCE: 653

Asn Pro Pro Ile Ile Ala Arg Tyr Ile Arg Leu His Pro Thr His
1               5                   10                  15

<210> SEQ ID NO 654
<211> LENGTH: 16
<212> TYPE: PRT
<213> ORGANISM: Homo sapiens

<400> SEQUENCE: 654

Asn Pro Pro Ile Ile Ala Arg Tyr Ile Arg Leu His Pro Thr His Tyr
1               5                   10                  15

<210> SEQ ID NO 655
<211> LENGTH: 17
<212> TYPE: PRT
<213> ORGANISM: Homo sapiens

<400> SEQUENCE: 655

Asn Pro Pro Ile Ile Ala Arg Tyr Ile Arg Leu His Pro Thr His Tyr
1               5                   10                  15

Ser

<210> SEQ ID NO 656
<211> LENGTH: 18
<212> TYPE: PRT
<213> ORGANISM: Homo sapiens

<400> SEQUENCE: 656

Asn Pro Pro Ile Ile Ala Arg Tyr Ile Arg Leu His Pro Thr His Tyr
1               5                   10                  15

Ser Ile

<210> SEQ ID NO 657
<211> LENGTH: 19
<212> TYPE: PRT
<213> ORGANISM: Homo sapiens

<400> SEQUENCE: 657

Asn Pro Pro Ile Ile Ala Arg Tyr Ile Arg Leu His Pro Thr His Tyr
1               5                   10                  15

Ser Ile Arg

<210> SEQ ID NO 658
<211> LENGTH: 20
<212> TYPE: PRT
<213> ORGANISM: Homo sapiens

<400> SEQUENCE: 658

Asn Pro Pro Ile Ile Ala Arg Tyr Ile Arg Leu His Pro Thr His Tyr
1               5                   10                  15

Ser Ile Arg Ser
20

<210> SEQ ID NO 659
<211> LENGTH: 21
<212> TYPE: PRT
<213> ORGANISM: Homo sapiens
```

<400> SEQUENCE: 659

Asn Pro Pro Ile Ile Ala Arg Tyr Ile Arg Leu His Pro Thr His Tyr
1               5                   10                  15

Ser Ile Arg Ser Thr
        20

<210> SEQ ID NO 660
<211> LENGTH: 9
<212> TYPE: PRT
<213> ORGANISM: Homo sapiens

<400> SEQUENCE: 660

Pro Pro Ile Ile Ala Arg Tyr Ile Arg
1               5

<210> SEQ ID NO 661
<211> LENGTH: 10
<212> TYPE: PRT
<213> ORGANISM: Homo sapiens

<400> SEQUENCE: 661

Pro Pro Ile Ile Ala Arg Tyr Ile Arg Leu
1               5                   10

<210> SEQ ID NO 662
<211> LENGTH: 11
<212> TYPE: PRT
<213> ORGANISM: Homo sapiens

<400> SEQUENCE: 662

Pro Pro Ile Ile Ala Arg Tyr Ile Arg Leu His
1               5                   10

<210> SEQ ID NO 663
<211> LENGTH: 12
<212> TYPE: PRT
<213> ORGANISM: Homo sapiens

<400> SEQUENCE: 663

Pro Pro Ile Ile Ala Arg Tyr Ile Arg Leu His Pro
1               5                   10

<210> SEQ ID NO 664
<211> LENGTH: 13
<212> TYPE: PRT
<213> ORGANISM: Homo sapiens

<400> SEQUENCE: 664

Pro Pro Ile Ile Ala Arg Tyr Ile Arg Leu His Pro Thr
1               5                   10

<210> SEQ ID NO 665
<211> LENGTH: 14
<212> TYPE: PRT
<213> ORGANISM: Homo sapiens

<400> SEQUENCE: 665

Pro Pro Ile Ile Ala Arg Tyr Ile Arg Leu His Pro Thr His
1               5                   10

<210> SEQ ID NO 666
<211> LENGTH: 15
<212> TYPE: PRT

<213> ORGANISM: Homo sapiens

<400> SEQUENCE: 666

Pro Pro Ile Ile Ala Arg Tyr Ile Arg Leu His Pro Thr His Tyr
1               5                   10                  15

<210> SEQ ID NO 667
<211> LENGTH: 16
<212> TYPE: PRT
<213> ORGANISM: Homo sapiens

<400> SEQUENCE: 667

Pro Pro Ile Ile Ala Arg Tyr Ile Arg Leu His Pro Thr His Tyr Ser
1               5                   10                  15

<210> SEQ ID NO 668
<211> LENGTH: 17
<212> TYPE: PRT
<213> ORGANISM: Homo sapiens

<400> SEQUENCE: 668

Pro Pro Ile Ile Ala Arg Tyr Ile Arg Leu His Pro Thr His Tyr Ser
1               5                   10                  15

Ile

<210> SEQ ID NO 669
<211> LENGTH: 18
<212> TYPE: PRT
<213> ORGANISM: Homo sapiens

<400> SEQUENCE: 669

Pro Pro Ile Ile Ala Arg Tyr Ile Arg Leu His Pro Thr His Tyr Ser
1               5                   10                  15

Ile Arg

<210> SEQ ID NO 670
<211> LENGTH: 19
<212> TYPE: PRT
<213> ORGANISM: Homo sapiens

<400> SEQUENCE: 670

Pro Pro Ile Ile Ala Arg Tyr Ile Arg Leu His Pro Thr His Tyr Ser
1               5                   10                  15

Ile Arg Ser

<210> SEQ ID NO 671
<211> LENGTH: 20
<212> TYPE: PRT
<213> ORGANISM: Homo sapiens

<400> SEQUENCE: 671

Pro Pro Ile Ile Ala Arg Tyr Ile Arg Leu His Pro Thr His Tyr Ser
1               5                   10                  15

Ile Arg Ser Thr
            20

<210> SEQ ID NO 672
<211> LENGTH: 9
<212> TYPE: PRT
<213> ORGANISM: Homo sapiens

<400> SEQUENCE: 672

Pro Ile Ala Arg Tyr Ile Arg Leu
1               5

<210> SEQ ID NO 673
<211> LENGTH: 10
<212> TYPE: PRT
<213> ORGANISM: Homo sapiens

<400> SEQUENCE: 673

Pro Ile Ile Ala Arg Tyr Ile Arg Leu His
1               5                   10

<210> SEQ ID NO 674
<211> LENGTH: 11
<212> TYPE: PRT
<213> ORGANISM: Homo sapiens

<400> SEQUENCE: 674

Pro Ile Ile Ala Arg Tyr Ile Arg Leu His Pro
1               5                   10

<210> SEQ ID NO 675
<211> LENGTH: 12
<212> TYPE: PRT
<213> ORGANISM: Homo sapiens

<400> SEQUENCE: 675

Pro Ile Ile Ala Arg Tyr Ile Arg Leu His Pro Thr
1               5                   10

<210> SEQ ID NO 676
<211> LENGTH: 13
<212> TYPE: PRT
<213> ORGANISM: Homo sapiens

<400> SEQUENCE: 676

Pro Ile Ile Ala Arg Tyr Ile Arg Leu His Pro Thr His
1               5                   10

<210> SEQ ID NO 677
<211> LENGTH: 14
<212> TYPE: PRT
<213> ORGANISM: Homo sapiens

<400> SEQUENCE: 677

Pro Ile Ile Ala Arg Tyr Ile Arg Leu His Pro Thr His Tyr
1               5                   10

<210> SEQ ID NO 678
<211> LENGTH: 15
<212> TYPE: PRT
<213> ORGANISM: Homo sapiens

<400> SEQUENCE: 678

Pro Ile Ile Ala Arg Tyr Ile Arg Leu His Pro Thr His Tyr Ser
1               5                   10                  15

<210> SEQ ID NO 679
<211> LENGTH: 16
<212> TYPE: PRT
<213> ORGANISM: Homo sapiens

<400> SEQUENCE: 679

Pro Ile Ile Ala Arg Tyr Ile Arg Leu His Pro Thr His Tyr Ser Ile
1               5                   10                  15

<210> SEQ ID NO 680
<211> LENGTH: 17
<212> TYPE: PRT
<213> ORGANISM: Homo sapiens

<400> SEQUENCE: 680

Pro Ile Ile Ala Arg Tyr Ile Arg Leu His Pro Thr His Tyr Ser Ile
1               5                   10                  15

Arg

<210> SEQ ID NO 681
<211> LENGTH: 18
<212> TYPE: PRT
<213> ORGANISM: Homo sapiens

<400> SEQUENCE: 681

Pro Ile Ile Ala Arg Tyr Ile Arg Leu His Pro Thr His Tyr Ser Ile
1               5                   10                  15

Arg Ser

<210> SEQ ID NO 682
<211> LENGTH: 19
<212> TYPE: PRT
<213> ORGANISM: Homo sapiens

<400> SEQUENCE: 682

Pro Ile Ile Ala Arg Tyr Ile Arg Leu His Pro Thr His Tyr Ser Ile
1               5                   10                  15

Arg Ser Thr

<210> SEQ ID NO 683
<211> LENGTH: 9
<212> TYPE: PRT
<213> ORGANISM: Homo sapiens

<400> SEQUENCE: 683

Ile Ile Ala Arg Tyr Ile Arg Leu His
1               5

<210> SEQ ID NO 684
<211> LENGTH: 10
<212> TYPE: PRT
<213> ORGANISM: Homo sapiens

<400> SEQUENCE: 684

Ile Ile Ala Arg Tyr Ile Arg Leu His Pro
1               5                   10

<210> SEQ ID NO 685
<211> LENGTH: 11
<212> TYPE: PRT
<213> ORGANISM: Homo sapiens

<400> SEQUENCE: 685

Ile Ile Ala Arg Tyr Ile Arg Leu His Pro Thr
1               5                   10

<210> SEQ ID NO 686
<211> LENGTH: 12
<212> TYPE: PRT
<213> ORGANISM: Homo sapiens

<400> SEQUENCE: 686

Ile Ile Ala Arg Tyr Ile Arg Leu His Pro Thr His
1               5                   10

<210> SEQ ID NO 687
<211> LENGTH: 13
<212> TYPE: PRT
<213> ORGANISM: Homo sapiens

<400> SEQUENCE: 687

Ile Ile Ala Arg Tyr Ile Arg Leu His Pro Thr His Tyr
1               5                   10

<210> SEQ ID NO 688
<211> LENGTH: 14
<212> TYPE: PRT
<213> ORGANISM: Homo sapiens

<400> SEQUENCE: 688

Ile Ile Ala Arg Tyr Ile Arg Leu His Pro Thr His Tyr Ser
1               5                   10

<210> SEQ ID NO 689
<211> LENGTH: 15
<212> TYPE: PRT
<213> ORGANISM: Homo sapiens

<400> SEQUENCE: 689

Ile Ile Ala Arg Tyr Ile Arg Leu His Pro Thr His Tyr Ser Ile
1               5                   10                  15

<210> SEQ ID NO 690
<211> LENGTH: 16
<212> TYPE: PRT
<213> ORGANISM: Homo sapiens

<400> SEQUENCE: 690

Ile Ile Ala Arg Tyr Ile Arg Leu His Pro Thr His Tyr Ser Ile Arg
1               5                   10                  15

<210> SEQ ID NO 691
<211> LENGTH: 17
<212> TYPE: PRT
<213> ORGANISM: Homo sapiens

<400> SEQUENCE: 691

Ile Ile Ala Arg Tyr Ile Arg Leu His Pro Thr His Tyr Ser Ile Arg
1               5                   10                  15

Ser

<210> SEQ ID NO 692
<211> LENGTH: 18
<212> TYPE: PRT
<213> ORGANISM: Homo sapiens

<400> SEQUENCE: 692

Ile Ile Ala Arg Tyr Ile Arg Leu His Pro Thr His Tyr Ser Ile Arg
1               5                   10                  15

Ser Thr

<210> SEQ ID NO 693
<211> LENGTH: 9
<212> TYPE: PRT

<213> ORGANISM: Homo sapiens

<400> SEQUENCE: 693

Ile Ala Arg Tyr Ile Arg Leu His Pro
1               5

<210> SEQ ID NO 694
<211> LENGTH: 10
<212> TYPE: PRT
<213> ORGANISM: Homo sapiens

<400> SEQUENCE: 694

Ile Ala Arg Tyr Ile Arg Leu His Pro Thr
1               5                   10

<210> SEQ ID NO 695
<211> LENGTH: 11
<212> TYPE: PRT
<213> ORGANISM: Homo sapiens

<400> SEQUENCE: 695

Ile Ala Arg Tyr Ile Arg Leu His Pro Thr His
1               5                   10

<210> SEQ ID NO 696
<211> LENGTH: 12
<212> TYPE: PRT
<213> ORGANISM: Homo sapiens

<400> SEQUENCE: 696

Ile Ala Arg Tyr Ile Arg Leu His Pro Thr His Tyr
1               5                   10

<210> SEQ ID NO 697
<211> LENGTH: 13
<212> TYPE: PRT
<213> ORGANISM: Homo sapiens

<400> SEQUENCE: 697

Ile Ala Arg Tyr Ile Arg Leu His Pro Thr His Tyr Ser
1               5                   10

<210> SEQ ID NO 698
<211> LENGTH: 14
<212> TYPE: PRT
<213> ORGANISM: Homo sapiens

<400> SEQUENCE: 698

Ile Ala Arg Tyr Ile Arg Leu His Pro Thr His Tyr Ser Ile
1               5                   10

<210> SEQ ID NO 699
<211> LENGTH: 15
<212> TYPE: PRT
<213> ORGANISM: Homo sapiens

<400> SEQUENCE: 699

Ile Ala Arg Tyr Ile Arg Leu His Pro Thr His Tyr Ser Ile Arg
1               5                   10                  15

<210> SEQ ID NO 700
<211> LENGTH: 16
<212> TYPE: PRT
<213> ORGANISM: Homo sapiens

```
<400> SEQUENCE: 700

Ile Ala Arg Tyr Ile Arg Leu His Pro Thr His Tyr Ser Ile Arg Ser
1               5                   10                  15

<210> SEQ ID NO 701
<211> LENGTH: 17
<212> TYPE: PRT
<213> ORGANISM: Homo sapiens

<400> SEQUENCE: 701

Ile Ala Arg Tyr Ile Arg Leu His Pro Thr His Tyr Ser Ile Arg Ser
1               5                   10                  15
Thr

<210> SEQ ID NO 702
<211> LENGTH: 9
<212> TYPE: PRT
<213> ORGANISM: Homo sapiens

<400> SEQUENCE: 702

Ala Arg Tyr Ile Arg Leu His Pro Thr
1               5

<210> SEQ ID NO 703
<211> LENGTH: 10
<212> TYPE: PRT
<213> ORGANISM: Homo sapiens

<400> SEQUENCE: 703

Ala Arg Tyr Ile Arg Leu His Pro Thr His
1               5                   10

<210> SEQ ID NO 704
<211> LENGTH: 11
<212> TYPE: PRT
<213> ORGANISM: Homo sapiens

<400> SEQUENCE: 704

Ala Arg Tyr Ile Arg Leu His Pro Thr His Tyr
1               5                   10

<210> SEQ ID NO 705
<211> LENGTH: 12
<212> TYPE: PRT
<213> ORGANISM: Homo sapiens

<400> SEQUENCE: 705

Ala Arg Tyr Ile Arg Leu His Pro Thr His Tyr Ser
1               5                   10

<210> SEQ ID NO 706
<211> LENGTH: 13
<212> TYPE: PRT
<213> ORGANISM: Homo sapiens

<400> SEQUENCE: 706

Ala Arg Tyr Ile Arg Leu His Pro Thr His Tyr Ser Ile
1               5                   10

<210> SEQ ID NO 707
<211> LENGTH: 14
<212> TYPE: PRT
<213> ORGANISM: Homo sapiens
```

```
<400> SEQUENCE: 707

Ala Arg Tyr Ile Arg Leu His Pro Thr His Tyr Ser Ile Arg
1               5                   10

<210> SEQ ID NO 708
<211> LENGTH: 15
<212> TYPE: PRT
<213> ORGANISM: Homo sapiens

<400> SEQUENCE: 708

Ala Arg Tyr Ile Arg Leu His Pro Thr His Tyr Ser Ile Arg Ser
1               5                   10                  15

<210> SEQ ID NO 709
<211> LENGTH: 16
<212> TYPE: PRT
<213> ORGANISM: Homo sapiens

<400> SEQUENCE: 709

Ala Arg Tyr Ile Arg Leu His Pro Thr His Tyr Ser Ile Arg Ser Thr
1               5                   10                  15

<210> SEQ ID NO 710
<211> LENGTH: 9
<212> TYPE: PRT
<213> ORGANISM: Homo sapiens

<400> SEQUENCE: 710

Arg Tyr Ile Arg Leu His Pro Thr His
1               5

<210> SEQ ID NO 711
<211> LENGTH: 10
<212> TYPE: PRT
<213> ORGANISM: Homo sapiens

<400> SEQUENCE: 711

Arg Tyr Ile Arg Leu His Pro Thr His Tyr
1               5                   10

<210> SEQ ID NO 712
<211> LENGTH: 11
<212> TYPE: PRT
<213> ORGANISM: Homo sapiens

<400> SEQUENCE: 712

Arg Tyr Ile Arg Leu His Pro Thr His Tyr Ser
1               5                   10

<210> SEQ ID NO 713
<211> LENGTH: 12
<212> TYPE: PRT
<213> ORGANISM: Homo sapiens

<400> SEQUENCE: 713

Arg Tyr Ile Arg Leu His Pro Thr His Tyr Ser Ile
1               5                   10

<210> SEQ ID NO 714
<211> LENGTH: 13
<212> TYPE: PRT
<213> ORGANISM: Homo sapiens

<400> SEQUENCE: 714
```

Arg Tyr Ile Arg Leu His Pro Thr His Tyr Ser Ile Arg
1               5                   10

<210> SEQ ID NO 715
<211> LENGTH: 14
<212> TYPE: PRT
<213> ORGANISM: Homo sapiens

<400> SEQUENCE: 715

Arg Tyr Ile Arg Leu His Pro Thr His Tyr Ser Ile Arg Ser
1               5                   10

<210> SEQ ID NO 716
<211> LENGTH: 15
<212> TYPE: PRT
<213> ORGANISM: Homo sapiens

<400> SEQUENCE: 716

Arg Tyr Ile Arg Leu His Pro Thr His Tyr Ser Ile Arg Ser Thr
1               5                   10                  15

<210> SEQ ID NO 717
<211> LENGTH: 9
<212> TYPE: PRT
<213> ORGANISM: Homo sapiens

<400> SEQUENCE: 717

Tyr Ile Arg Leu His Pro Thr His Tyr
1               5

<210> SEQ ID NO 718
<211> LENGTH: 10
<212> TYPE: PRT
<213> ORGANISM: Homo sapiens

<400> SEQUENCE: 718

Tyr Ile Arg Leu His Pro Thr His Tyr Ser
1               5                   10

<210> SEQ ID NO 719
<211> LENGTH: 11
<212> TYPE: PRT
<213> ORGANISM: Homo sapiens

<400> SEQUENCE: 719

Tyr Ile Arg Leu His Pro Thr His Tyr Ser Ile
1               5                   10

<210> SEQ ID NO 720
<211> LENGTH: 12
<212> TYPE: PRT
<213> ORGANISM: Homo sapiens

<400> SEQUENCE: 720

Tyr Ile Arg Leu His Pro Thr His Tyr Ser Ile Arg
1               5                   10

<210> SEQ ID NO 721
<211> LENGTH: 13
<212> TYPE: PRT
<213> ORGANISM: Homo sapiens

<400> SEQUENCE: 721

Tyr Ile Arg Leu His Pro Thr His Tyr Ser Ile Arg Ser
1               5                   10

<210> SEQ ID NO 722
<211> LENGTH: 14
<212> TYPE: PRT
<213> ORGANISM: Homo sapiens

<400> SEQUENCE: 722

Tyr Ile Arg Leu His Pro Thr His Tyr Ser Ile Arg Ser Thr
1               5                   10

<210> SEQ ID NO 723
<211> LENGTH: 9
<212> TYPE: PRT
<213> ORGANISM: Homo sapiens

<400> SEQUENCE: 723

Ile Arg Leu His Pro Thr His Tyr Ser
1               5

<210> SEQ ID NO 724
<211> LENGTH: 10
<212> TYPE: PRT
<213> ORGANISM: Homo sapiens

<400> SEQUENCE: 724

Ile Arg Leu His Pro Thr His Tyr Ser Ile
1               5                   10

<210> SEQ ID NO 725
<211> LENGTH: 11
<212> TYPE: PRT
<213> ORGANISM: Homo sapiens

<400> SEQUENCE: 725

Ile Arg Leu His Pro Thr His Tyr Ser Ile Arg
1               5                   10

<210> SEQ ID NO 726
<211> LENGTH: 12
<212> TYPE: PRT
<213> ORGANISM: Homo sapiens

<400> SEQUENCE: 726

Ile Arg Leu His Pro Thr His Tyr Ser Ile Arg Ser
1               5                   10

<210> SEQ ID NO 727
<211> LENGTH: 13
<212> TYPE: PRT
<213> ORGANISM: Homo sapiens

<400> SEQUENCE: 727

Ile Arg Leu His Pro Thr His Tyr Ser Ile Arg Ser Thr
1               5                   10

<210> SEQ ID NO 728
<211> LENGTH: 9
<212> TYPE: PRT
<213> ORGANISM: Homo sapiens

<400> SEQUENCE: 728

Arg Leu His Pro Thr His Tyr Ser Ile
1               5

<210> SEQ ID NO 729
<211> LENGTH: 10
<212> TYPE: PRT
<213> ORGANISM: Homo sapiens

<400> SEQUENCE: 729

Arg Leu His Pro Thr His Tyr Ser Ile Arg
1               5                   10

<210> SEQ ID NO 730
<211> LENGTH: 11
<212> TYPE: PRT
<213> ORGANISM: Homo sapiens

<400> SEQUENCE: 730

Arg Leu His Pro Thr His Tyr Ser Ile Arg Ser
1               5                   10

<210> SEQ ID NO 731
<211> LENGTH: 12
<212> TYPE: PRT
<213> ORGANISM: Homo sapiens

<400> SEQUENCE: 731

Arg Leu His Pro Thr His Tyr Ser Ile Arg Ser Thr
1               5                   10

<210> SEQ ID NO 732
<211> LENGTH: 9
<212> TYPE: PRT
<213> ORGANISM: Homo sapiens

<400> SEQUENCE: 732

Leu His Pro Thr His Tyr Ser Ile Arg
1               5

<210> SEQ ID NO 733
<211> LENGTH: 10
<212> TYPE: PRT
<213> ORGANISM: Homo sapiens

<400> SEQUENCE: 733

Leu His Pro Thr His Tyr Ser Ile Arg Ser
1               5                   10

<210> SEQ ID NO 734
<211> LENGTH: 11
<212> TYPE: PRT
<213> ORGANISM: Homo sapiens

<400> SEQUENCE: 734

Leu His Pro Thr His Tyr Ser Ile Arg Ser Thr
1               5                   10

<210> SEQ ID NO 735
<211> LENGTH: 9
<212> TYPE: PRT
<213> ORGANISM: Homo sapiens

<400> SEQUENCE: 735

His Pro Thr His Tyr Ser Ile Arg Ser
1               5

<210> SEQ ID NO 736
<211> LENGTH: 10

<212> TYPE: PRT
<213> ORGANISM: Homo sapiens

<400> SEQUENCE: 736

His Pro Thr His Tyr Ser Ile Arg Ser Thr
1               5                   10

<210> SEQ ID NO 737
<211> LENGTH: 9
<212> TYPE: PRT
<213> ORGANISM: Homo sapiens

<400> SEQUENCE: 737

Pro Thr His Tyr Ser Ile Arg Ser Thr
1               5

<210> SEQ ID NO 738
<211> LENGTH: 19
<212> TYPE: PRT
<213> ORGANISM: Homo sapiens

<400> SEQUENCE: 738

Thr Val Val Ile Thr Leu Lys Asn Met Ala Ser His Pro Val Ser Leu
1               5                   10                  15

His Ala Val

<210> SEQ ID NO 739
<211> LENGTH: 20
<212> TYPE: PRT
<213> ORGANISM: Homo sapiens

<400> SEQUENCE: 739

Thr Val Val Ile Thr Leu Lys Asn Met Ala Ser His Pro Val Ser Leu
1               5                   10                  15

His Ala Val Gly
            20

<210> SEQ ID NO 740
<211> LENGTH: 21
<212> TYPE: PRT
<213> ORGANISM: Homo sapiens

<400> SEQUENCE: 740

Thr Val Val Ile Thr Leu Lys Asn Met Ala Ser His Pro Val Ser Leu
1               5                   10                  15

His Ala Val Gly Val
            20

<210> SEQ ID NO 741
<211> LENGTH: 18
<212> TYPE: PRT
<213> ORGANISM: Homo sapiens

<400> SEQUENCE: 741

Val Val Ile Thr Leu Lys Asn Met Ala Ser His Pro Val Ser Leu His
1               5                   10                  15

Ala Val

<210> SEQ ID NO 742
<211> LENGTH: 19
<212> TYPE: PRT
<213> ORGANISM: Homo sapiens

```
<400> SEQUENCE: 742

Val Val Ile Thr Leu Lys Asn Met Ala Ser His Pro Val Ser Leu His
1               5                   10                  15

Ala Val Gly

<210> SEQ ID NO 743
<211> LENGTH: 20
<212> TYPE: PRT
<213> ORGANISM: Homo sapiens

<400> SEQUENCE: 743

Val Val Ile Thr Leu Lys Asn Met Ala Ser His Pro Val Ser Leu His
1               5                   10                  15

Ala Val Gly Val
            20

<210> SEQ ID NO 744
<211> LENGTH: 17
<212> TYPE: PRT
<213> ORGANISM: Homo sapiens

<400> SEQUENCE: 744

Val Ile Thr Leu Lys Asn Met Ala Ser His Pro Val Ser Leu His Ala
1               5                   10                  15

Val

<210> SEQ ID NO 745
<211> LENGTH: 18
<212> TYPE: PRT
<213> ORGANISM: Homo sapiens

<400> SEQUENCE: 745

Val Ile Thr Leu Lys Asn Met Ala Ser His Pro Val Ser Leu His Ala
1               5                   10                  15

Val Gly

<210> SEQ ID NO 746
<211> LENGTH: 19
<212> TYPE: PRT
<213> ORGANISM: Homo sapiens

<400> SEQUENCE: 746

Val Ile Thr Leu Lys Asn Met Ala Ser His Pro Val Ser Leu His Ala
1               5                   10                  15

Val Gly Val

<210> SEQ ID NO 747
<211> LENGTH: 16
<212> TYPE: PRT
<213> ORGANISM: Homo sapiens

<400> SEQUENCE: 747

Ile Thr Leu Lys Asn Met Ala Ser His Pro Val Ser Leu His Ala Val
1               5                   10                  15

<210> SEQ ID NO 748
<211> LENGTH: 17
<212> TYPE: PRT
<213> ORGANISM: Homo sapiens

<400> SEQUENCE: 748
```

```
Ile Thr Leu Lys Asn Met Ala Ser His Pro Val Ser Leu His Ala Val
1               5                   10                  15

Gly

<210> SEQ ID NO 749
<211> LENGTH: 18
<212> TYPE: PRT
<213> ORGANISM: Homo sapiens

<400> SEQUENCE: 749

Ile Thr Leu Lys Asn Met Ala Ser His Pro Val Ser Leu His Ala Val
1               5                   10                  15

Gly Val

<210> SEQ ID NO 750
<211> LENGTH: 15
<212> TYPE: PRT
<213> ORGANISM: Homo sapiens

<400> SEQUENCE: 750

Thr Leu Lys Asn Met Ala Ser His Pro Val Ser Leu His Ala Val
1               5                   10                  15

<210> SEQ ID NO 751
<211> LENGTH: 16
<212> TYPE: PRT
<213> ORGANISM: Homo sapiens

<400> SEQUENCE: 751

Thr Leu Lys Asn Met Ala Ser His Pro Val Ser Leu His Ala Val Gly
1               5                   10                  15

<210> SEQ ID NO 752
<211> LENGTH: 17
<212> TYPE: PRT
<213> ORGANISM: Homo sapiens

<400> SEQUENCE: 752

Thr Leu Lys Asn Met Ala Ser His Pro Val Ser Leu His Ala Val Gly
1               5                   10                  15

Val

<210> SEQ ID NO 753
<211> LENGTH: 14
<212> TYPE: PRT
<213> ORGANISM: Homo sapiens

<400> SEQUENCE: 753

Leu Lys Asn Met Ala Ser His Pro Val Ser Leu His Ala Val
1               5                   10

<210> SEQ ID NO 754
<211> LENGTH: 15
<212> TYPE: PRT
<213> ORGANISM: Homo sapiens

<400> SEQUENCE: 754

Leu Lys Asn Met Ala Ser His Pro Val Ser Leu His Ala Val Gly
1               5                   10                  15

<210> SEQ ID NO 755
<211> LENGTH: 16
<212> TYPE: PRT
```

```
<213> ORGANISM: Homo sapiens

<400> SEQUENCE: 755

Leu Lys Asn Met Ala Ser His Pro Val Ser Leu His Ala Val Gly Val
1               5                   10                  15

<210> SEQ ID NO 756
<211> LENGTH: 13
<212> TYPE: PRT
<213> ORGANISM: Homo sapiens

<400> SEQUENCE: 756

Lys Asn Met Ala Ser His Pro Val Ser Leu His Ala Val
1               5                   10

<210> SEQ ID NO 757
<211> LENGTH: 14
<212> TYPE: PRT
<213> ORGANISM: Homo sapiens

<400> SEQUENCE: 757

Lys Asn Met Ala Ser His Pro Val Ser Leu His Ala Val Gly
1               5                   10

<210> SEQ ID NO 758
<211> LENGTH: 15
<212> TYPE: PRT
<213> ORGANISM: Homo sapiens

<400> SEQUENCE: 758

Lys Asn Met Ala Ser His Pro Val Ser Leu His Ala Val Gly Val
1               5                   10                  15

<210> SEQ ID NO 759
<211> LENGTH: 12
<212> TYPE: PRT
<213> ORGANISM: Homo sapiens

<400> SEQUENCE: 759

Asn Met Ala Ser His Pro Val Ser Leu His Ala Val
1               5                   10

<210> SEQ ID NO 760
<211> LENGTH: 13
<212> TYPE: PRT
<213> ORGANISM: Homo sapiens

<400> SEQUENCE: 760

Asn Met Ala Ser His Pro Val Ser Leu His Ala Val Gly
1               5                   10

<210> SEQ ID NO 761
<211> LENGTH: 14
<212> TYPE: PRT
<213> ORGANISM: Homo sapiens

<400> SEQUENCE: 761

Asn Met Ala Ser His Pro Val Ser Leu His Ala Val Gly Val
1               5                   10

<210> SEQ ID NO 762
<211> LENGTH: 11
<212> TYPE: PRT
<213> ORGANISM: Homo sapiens
```

-continued

```
<400> SEQUENCE: 762

Met Ala Ser His Pro Val Ser Leu His Ala Val
1               5                   10

<210> SEQ ID NO 763
<211> LENGTH: 12
<212> TYPE: PRT
<213> ORGANISM: Homo sapiens

<400> SEQUENCE: 763

Met Ala Ser His Pro Val Ser Leu His Ala Val Gly
1               5                   10

<210> SEQ ID NO 764
<211> LENGTH: 13
<212> TYPE: PRT
<213> ORGANISM: Homo sapiens

<400> SEQUENCE: 764

Met Ala Ser His Pro Val Ser Leu His Ala Val Gly Val
1               5                   10

<210> SEQ ID NO 765
<211> LENGTH: 10
<212> TYPE: PRT
<213> ORGANISM: Homo sapiens

<400> SEQUENCE: 765

Ala Ser His Pro Val Ser Leu His Ala Val
1               5                   10

<210> SEQ ID NO 766
<211> LENGTH: 11
<212> TYPE: PRT
<213> ORGANISM: Homo sapiens

<400> SEQUENCE: 766

Ala Ser His Pro Val Ser Leu His Ala Val Gly
1               5                   10

<210> SEQ ID NO 767
<211> LENGTH: 12
<212> TYPE: PRT
<213> ORGANISM: Homo sapiens

<400> SEQUENCE: 767

Ala Ser His Pro Val Ser Leu His Ala Val Gly Val
1               5                   10

<210> SEQ ID NO 768
<211> LENGTH: 9
<212> TYPE: PRT
<213> ORGANISM: Homo sapiens

<400> SEQUENCE: 768

Ser His Pro Val Ser Leu His Ala Val
1               5

<210> SEQ ID NO 769
<211> LENGTH: 10
<212> TYPE: PRT
<213> ORGANISM: Homo sapiens

<400> SEQUENCE: 769
```

```
Ser His Pro Val Ser Leu His Ala Val Gly
1               5                   10

<210> SEQ ID NO 770
<211> LENGTH: 11
<212> TYPE: PRT
<213> ORGANISM: Homo sapiens

<400> SEQUENCE: 770

Ser His Pro Val Ser Leu His Ala Val Gly Val
1               5                   10

<210> SEQ ID NO 771
<211> LENGTH: 9
<212> TYPE: PRT
<213> ORGANISM: Homo sapiens

<400> SEQUENCE: 771

His Pro Val Ser Leu His Ala Val Gly
1               5

<210> SEQ ID NO 772
<211> LENGTH: 10
<212> TYPE: PRT
<213> ORGANISM: Homo sapiens

<400> SEQUENCE: 772

His Pro Val Ser Leu His Ala Val Gly Val
1               5                   10

<210> SEQ ID NO 773
<211> LENGTH: 9
<212> TYPE: PRT
<213> ORGANISM: Homo sapiens

<400> SEQUENCE: 773

Pro Val Ser Leu His Ala Val Gly Val
1               5
```